(12) United States Patent
Zhao et al.

(10) Patent No.: US 10,934,336 B2
(45) Date of Patent: Mar. 2, 2021

(54) USE OF GENE EDITING TO GENERATE UNIVERSAL TCR RE-DIRECTED T CELLS FOR ADOPTIVE IMMUNOTHERAPY

(71) Applicant: THE TRUSTEES OF THE UNIVERSITY OF PENNSYLVANIA, Philadelphia, PA (US)

(72) Inventors: Yangbing Zhao, Lumberton, NJ (US); Xiaojun Liu, Wallingford, PA (US); Wei Pan, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 15/951,904

(22) Filed: Apr. 12, 2018

(65) Prior Publication Data
US 2019/0055297 A1 Feb. 21, 2019

Related U.S. Application Data

(60) Provisional application No. 62/485,166, filed on Apr. 13, 2017.

(51) Int. Cl.
| | | |
|---|---|---|
| *C07K 14/705* | (2006.01) | |
| *A61P 35/00* | (2006.01) | |
| *A61K 31/65* | (2006.01) | |
| *A61K 35/17* | (2015.01) | |
| *C07K 14/725* | (2006.01) | |
| *C07K 19/00* | (2006.01) | |
| *A61K 38/17* | (2006.01) | |

(52) U.S. Cl.
CPC .......... *C07K 14/7051* (2013.01); *A61K 31/65* (2013.01); *A61K 35/17* (2013.01); *A61K 38/177* (2013.01); *A61P 35/00* (2018.01); *C07K 14/705* (2013.01); *C07K 19/00* (2013.01); *C07K 2319/03* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,399,346 A | 3/1995 | Anderson et al. | |
| 5,580,859 A | 12/1996 | Felgner et al. | |
| 5,589,466 A | 12/1996 | Felgner et al. | |
| 6,080,840 A | 6/2000 | Slanetz et al. | |
| 6,326,193 B1 | 12/2001 | Liu et al. | |
| 2015/0216948 A1 | 8/2015 | Hanenberg et al. | |
| 2016/0264665 A1* | 9/2016 | Lim | C07K 14/71 |
| 2016/0348073 A1 | 12/2016 | Meissner et al. | |
| 2017/0016025 A1 | 1/2017 | Poirot et al. | |
| 2017/0152297 A1* | 6/2017 | Jensen | C07K 14/71 |
| 2018/0044424 A1* | 2/2018 | June | C07K 14/5443 |
| 2018/0185434 A1* | 7/2018 | Borrello | C12N 15/8201 |
| 2018/0362975 A1* | 12/2018 | Chen | A61P 35/02 |
| 2018/0371052 A1* | 12/2018 | Ma | C07K 14/70521 |
| 2019/0055297 A1* | 2/2019 | Zhao | A61K 35/17 |

FOREIGN PATENT DOCUMENTS

| | | | |
|---|---|---|---|
| WO | 0129058 A1 | 4/2001 | |
| WO | 0196584 A2 | 12/2001 | |
| WO | 2015161276 A2 | 10/2015 | |
| WO | 2016069282 A1 | 5/2016 | |
| WO | 2016122738 A1 | 8/2016 | |
| WO | 2016154176 A1 | 9/2016 | |
| WO | WO-2018156818 A1 * | 8/2018 | C12N 15/85 |

OTHER PUBLICATIONS

Sakemura et al. (2016) Cancer Immunol Res; 4(8); 658-668.*
Riviere et al. (2017) Molecular Therapy 25(5): 1117-1124.*
Liu et al. (2017) Protein Cell 8(12): 861-877.*
Zhen et al. (2017) Immunotherapy 9(5): 401-410.*
Kobold et al. (2015) JNCI J Natl Cancer Inst (2015) 107(8): djv146 (p. 1-10).*
PCT/US2018/027291—International Search Report and Written Opinion dated Aug. 6, 2018.
Chothia, et al., "The outline structure of the T-cell alpha-beta receptor", EMBO J. 7:3745-3755, 1988.
Cohen, et al., "Recognition of Fresh Human Tumor by Human Peripheral Blood Lymphocytes Transduced with a Bicistronic Retroviral Vector Encoding a Murine Anti-p53 TCR", 2005, J Immunol 175:5799-5808.
Cong, et al., "Multiplex Genome Engineering Using CRISPR/Cas Systems", Science, vol. 339, No. 6021, 2013, pp. 819-823.
Das, et al., "Tet-On Systems for Doxycycline-inducible Gene Expression.", Curr Gene Ther. 2016;16(3):156-67. (Jun. 1, 2016).
Davodeau, et al., "Secretion of Disculfide-linked Human T-cell Receptor gamma-delta Heterodimers.", 1993, J. Biol Chem 268(21):15455-15460.
Garboczi, et al., "Assembly, specific binding, and crystallization of a human TCR-alphabeta wit an antigenic Tax peptide from human T lymphotropic virus type 1 and the class I MHX molwxulw HLA-A2.", 1996, The Journal of Immunology 157(12):5403-5410. Abstract.
Garboczi, et al., "Structure of the complex between human T-cell receptor, viral peptide and HLA-A2.", 1996, Nature 384:134-141 (Abstract).
Golden, et al., "High-level production of a secreted heterodimeric alpha-beta murine T-cell receptor in *Escherichia coli.*", 1997, Journal of Immunological Methods 206(1-2):163-169 (Abstract).
Heinz, et al., "Retroviral and transposon-based tet-regulated all-in-one vectors with reduced background expression and improved dynamic range.", Hum Gene Ther. Feb. 2011;22(2):166-76. doi: 10.1089/hum2010.099.
Hoseini, et al., "Inducible T-cell receptor expression in precursor T-cells for leukemia control.", Leukemia. Jul. 2015; 29(7): 1530-1542.

(Continued)

*Primary Examiner* — Ilia I Ouspenski
(74) *Attorney, Agent, or Firm* — Saul Ewing Arnstein & Lehr LLP; Kathryn Doyle

(57) ABSTRACT

The present invention includes compositions and methods for a modified immune cell or precursor cell thereof comprising an inducible expression system. Also provided are gene edited modified immune cells suitable for T cell therapy. Methods of treatment using modified immune cells of the present invention are also provided.

22 Claims, 49 Drawing Sheets
Specification includes a Sequence Listing.

(56) References Cited

OTHER PUBLICATIONS

Jiang, et al., "CRISPR-assisted editing of bacterial genomes.", Nat Biotechnol. Mar. 2013;31(3):233-9.
Jinek, et al., "A programmable dual RNA-guided DNA endonuclease in adaptive bacterial immunity.", 2012, Science 337:816-821.
Jores, et al., "Resolution of hypervariable regions in T-cell receptor beta chains by a modified Wu-Kabat index of amino acid diversity.", Proc. Nat'l Acad. Sci. U.S.A. 87:9138, 1990.
June, "Remote Controlled CARs: Towards a Safer Therapy for Leukemia.", 2016, Cancer Immunol Res 2016;4:643.
Kouranova, et al., "CRISPRs for Optimal Targeting: Delivery of CRISPR Components as DNA, RNA, and Protein Into Cultured Cells and Single-Cell Embryos.", Hum Gene Ther. Jun. 2016;27(6):464-75. doi: 0.1089/hum.2016.009. Epub May 12, 2016.
Li, et al., "Directed evolution of human T-cell receptors with picomolar affinities by phage display.", Nat Biotechnol. Mar. 2005;23(3):349-54 (Abstract).
Liu, et al., "A Chimeric Switch-Receptor Targeting PD1 Aguments the Efficacy of Second-Generation Cart Cells in Advanced Solid Tumors.", 2016, Cancer Research 76(6):1578-1590 (Mar. 15, 2016).
Liu, et al., "Sequence features associated with the cleavage efficiency of CRISPR/Cas9 system.", Sci Rep. Jan. 27, 2016;6:19675. doi: 10.1038/srep19675.
Loew, et al., "Improved Tet-responsive promoters with minimized background expression.", BMC Biotechnol. Nov. 24, 2010;10:81. doi: 10.1186/1472-6750-10-81.
Mali, et al., "RNA-Guided Human Genome Engineering via Cas9.", Science. Feb. 15, 2013;339(6121):823-6.
Parkhurst, et al., "Characterization of Genetically Modified T-Cell Receptors that Recognize the CEA:691-699 Peptide in the Context of HLA-A2.1 on Human Colorectal Cancer Cells.", 2009, Clin Cancer Res 15:169-180.
Ren, et al. "Multiplex Genome Editing to Generate Universal CAR T Cells Resistant to PD1 Inhibition." 2017, Clin Cancer Research 23(9):2255-2266.
Reuss, et al., "TCR-engineered T cells: A model of inducible TCR expression to dissect the interrelationship between two TCRs.", Eur J Immunol, 2014, 44:265-274.
Rosenberg, et al., "Use of Tumor-Infiltrating Lymphocytes and Interleukin-2 in the Immunotherapy of Patients with Metastatic Melanoma", New Eng. J. of Med. 319:1676-1680, 1988.
Sakemura, "A Tet-On Inducible System for Controlling CD19-Chimeric Antigen Receptor Expression upon Drug Administration.", 2016, Cancer Immunol Res. 4(8):658-688 (Jun. 21, 2016).
Slaymaker, et al., "Rationally engineered Cas9 nucleases with improved specificity.", 2016, Science 351:84-88.

\* cited by examiner

| gRNA | KO efficiency | RNA yield | Highest MM | Score |
|---|---|---|---|---|
| CIITA2-4 | 69.7 | 118 | 1.3 | 74 |
| CIITA3-1 | 65.0 | 62 | 1 | 86 |
| CIITA3-3 | 26.6 | 6 | 1.4 | 81 |
| CIITA4-1 | 73.4 | 146 | 1.4 | 72 |
| CIITA5-1 | 57.8 | 78 | 1.4 | 82 |
| CIITA6-2 | 9.2 | 74 | 1.6 | 68 |
| CIITA7-1 | 9.0 | 44 | 1.3 | 87 |
| CIITA7-4 | 44.5 | 145 | 0.7 | 84 |
| CIITA8-1 | 77.3 | 65 | 0.9 | 81 |
| CIITA8-4 | 38.7 | 63 | 1.3 | 77 |
| CIITA9-1 | -0.8 | 36 | 0.9 | 86 |
| CIITA10-1 | 43.0 | 97 | 1.3 | 78 |
| CIITA11-2 | 33.8 | 109 | 1.3 | 95 |
| CIITA11-3 | 35.2 | 98 | 0.8 | 92 |
| CIITA12-3 | 81.7 | 76 | 1.4 | 69 |
| CIITA13-1 | 7.6 | 8 | 0.8 | 90 |
| CIITA13-2 | 85.8 | 19 | 0.8 | 86 |
| CIITA14-2 | 91.0 | 33 | 0.8 | 88 |
| CIITA15-1 | 82.0 | 105 | 0.7 | 89 |
| CIITA16-1 | 19.5 | 123 | 1.5 | 94 |
| CIITA17-1 | 74.6 | 19 | 0.7 | 94 |
| CIITA17-2 | 11.5 | 48 | 0.8 | 91 |
| CIITA18-1 | 8.8 | 10 | 0.8 | 92 |
| CIITA19-1 | 0.8 | 20 | 1.5 | 79 |
| No | 0.0 | | | |

FIG. 4C

| EP# | gRNA name |
|---|---|
| A1 | PD1.1-1 |
| A2 | PD1.1-2 |
| A3 | PD1.1-3 |
| A4 | PD1.1-4 |
| A5 | PD1.1-5 |
| A6 | PD1.21-1 |
| A7 | PD1.21-2 |
| A8 | PD1.21-3 |
| A9 | PD1.21-4 |
| A10 | PD1.21-5 |
| A11 | PD1.21-6 |
| A12 | PD1.21-7 |
| B1 | PD1.21-8 |
| B2 | PD1.21-9 |
| B3 | PD1.21-10 |
| B4 | PD1.22-1 |
| B5 | PD1.22-2 |
| B6 | PD1.22-3 |
| B7 | PD1.22-4 |
| B8 | PD1.3-1 |
| B9 | PD1.3-2 |
| B10 | PD1.5-1 |
| B11 | PD1.5-2 |
| B12 | PD1.5-3 |
| C5 | NO RNA |
| C6 | NO RNA |

FIG. 5C

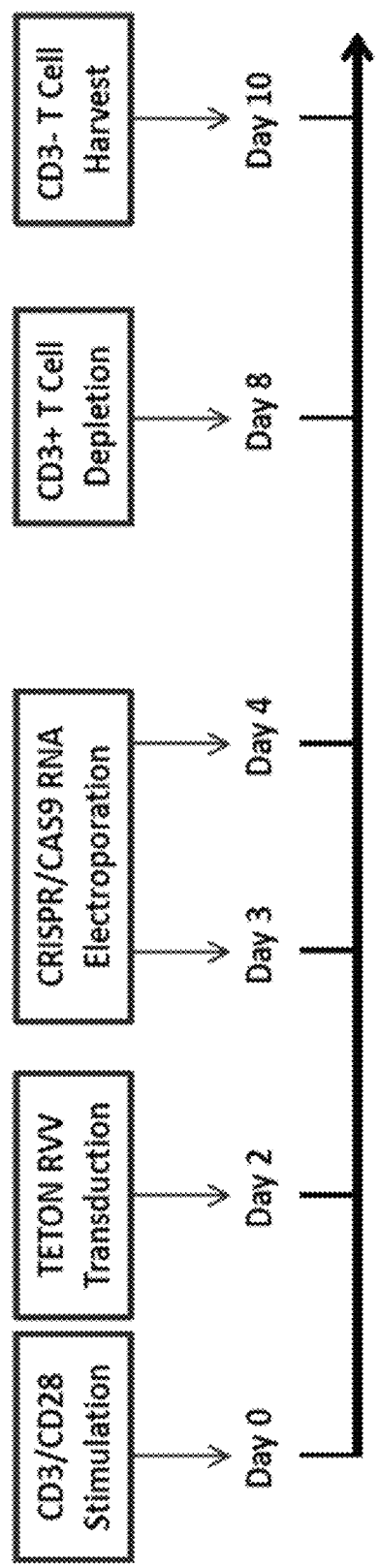
FIG. 17
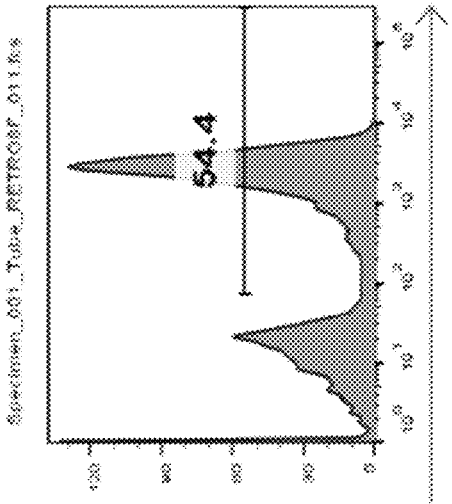
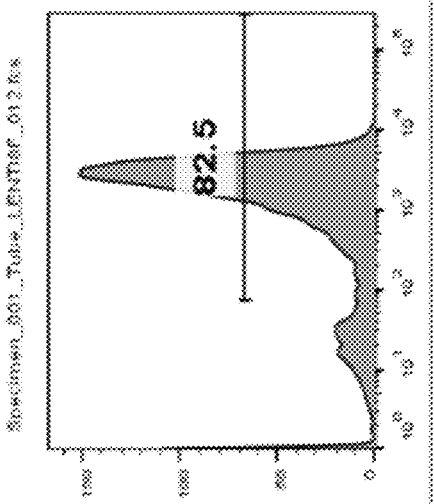
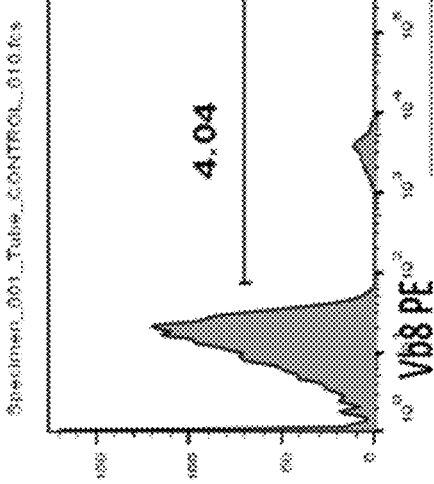
FIG. 18

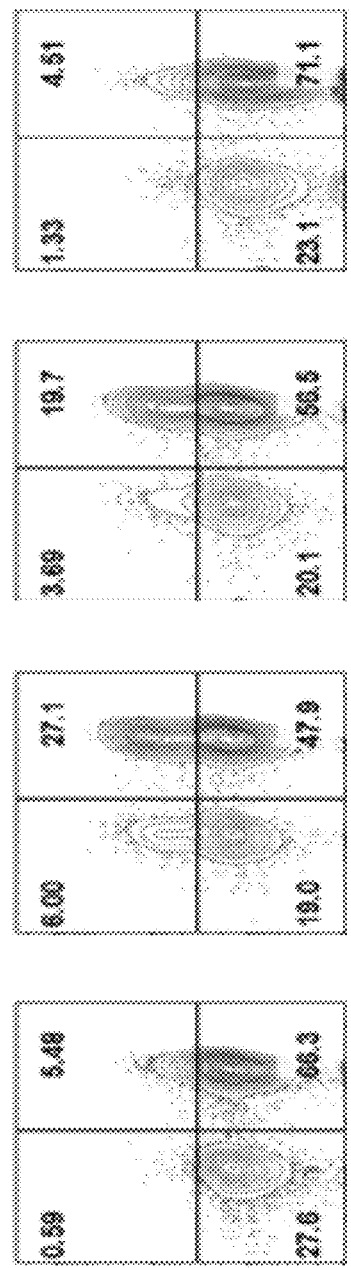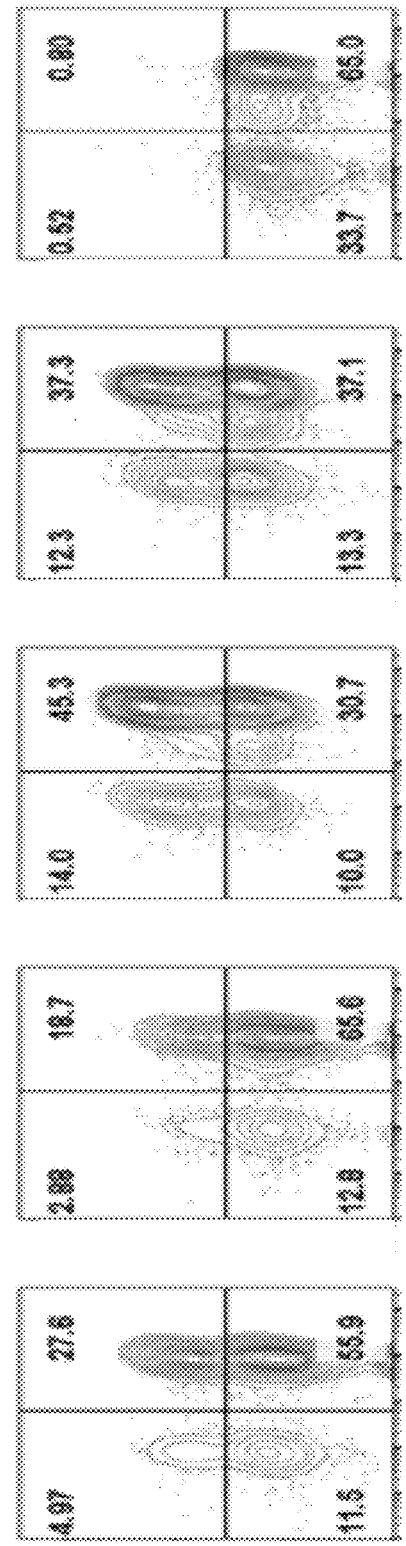
FIG. 24A

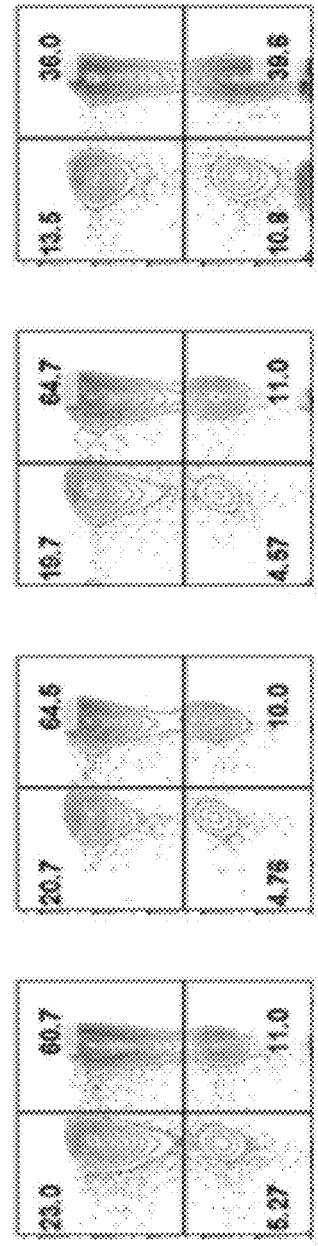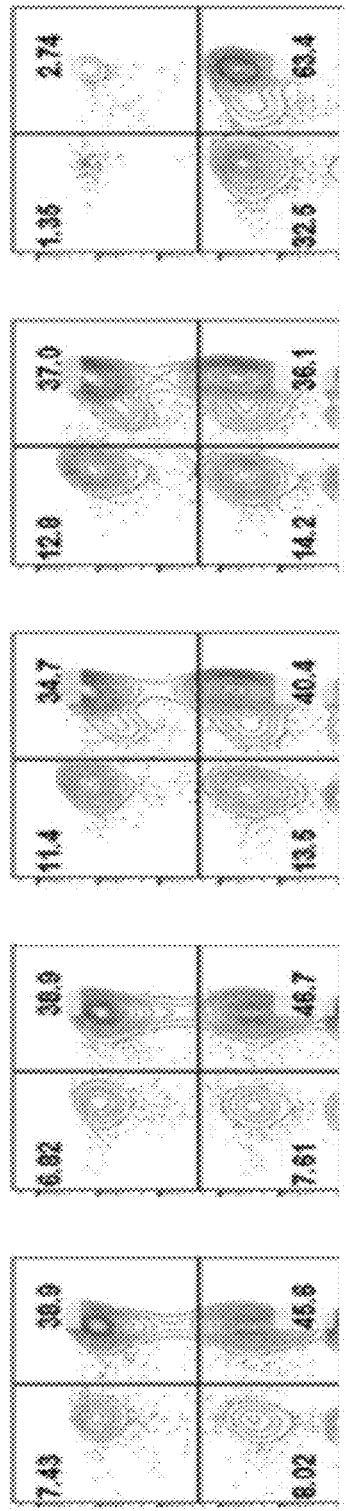
FIG. 24B

FIG. 24C

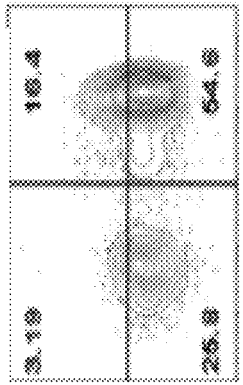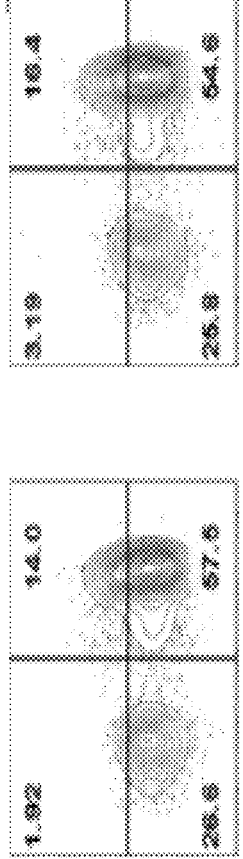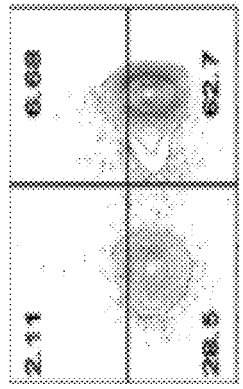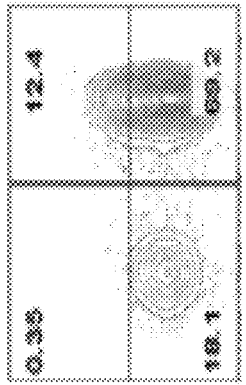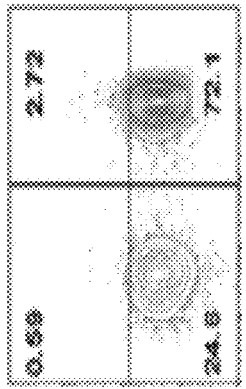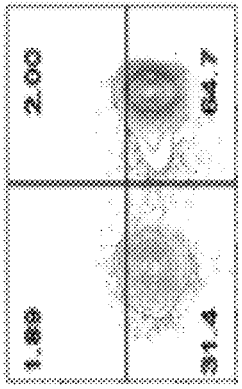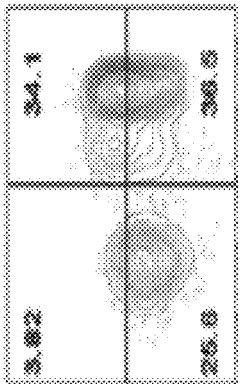
FIG. 25A

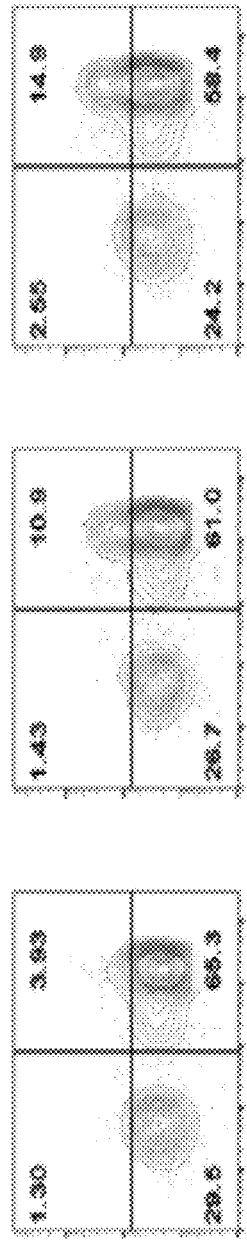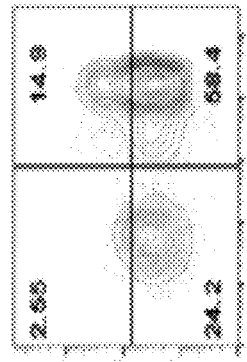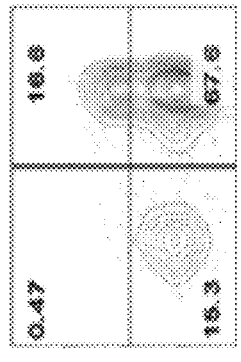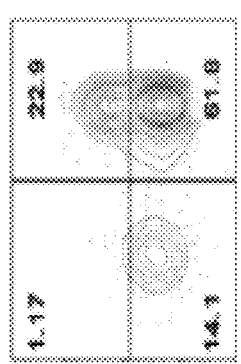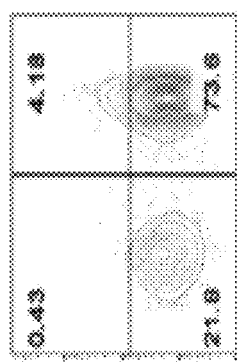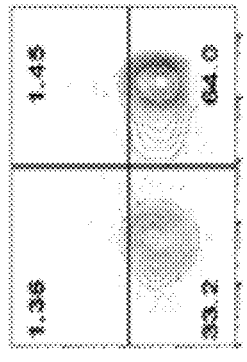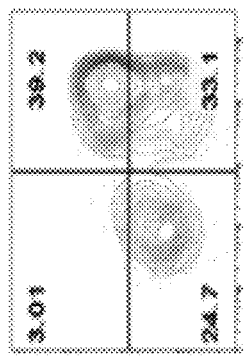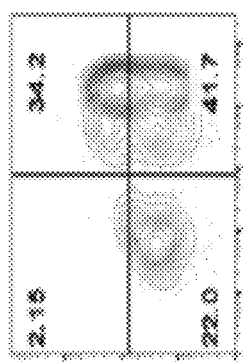
FIG. 25B

FIG. 25C

| gRNA# | TRBC gRNA Name | TRBC gRNA sequence | gRNA# | CIITA gRNA Name | CIITA gRNA sequence | gRNA# | PD1 gRNA Name | PD1 gRNA sequence |
|---|---|---|---|---|---|---|---|---|
| 1 | TRBC1.1 | CAAGACAGCGACCTGGGT | 1 | CIITA2-4 | CTCCAGGTAGCCACTTCTA | 1 | PD1.1.1 | TGTAGCACGGCCAGAGCGAC |
| 2 | TRBC1.2 | GGGTCAAACAGCAACGACTT | 2 | CIITA3-1 | GCTGAACTGGTCGGAGTTGA | 2 | PD1.1.2 | CGTCTGGGCGGTGCTACAAC |
| 3 | TRBC1.3 | TGAACAGCGACACCTGCGG | 3 | CIITA3-3 | TCAACTGCGACCAGTCAGC | 3 | PD1.1.3 | GTCTGGGCGGTGCTACAACT |
| 4 | TRBC1.4 | TGGCTCAAACAGCAACGACT | 4 | CIITA4-1 | GGGAGTCCTGGAAGACATAC | 4 | PD1.1.4 | AGGGCCCTGGCCAGTCGTC |
| 5 | TRBC1.5 | TCTCTGAAGATCCGTAGAAC | 5 | CIITA5-1 | CTCTACCGATCACTTCATC | 5 | PD1.1.5 | CACGGCGAGAGATGAGTGGCC |
| 6 | TRBC2.2 | GGGTCTGGGAAGAATGAGAG | 6 | CIITA6-2 | AGGTCTGCCGGAAGCTCTC | 6 | PD1.21.1 | ATGTGGAAGTCACGCCCGTT |
| 7 | TRBC2.3 | TGACAGCGGAAGTGGTTGCG | 7 | CIITA7-1 | CGGTTTTCTCAGGCGATC | 7 | PD1.21.2 | CATGGGAAGTCACGCCCGT |
| 8 | TRBC2.4 | AGTTCAGTTCACGGCTCT | 8 | CIITA7-4 | GGCTCCTGGTTGAACAGCGC | 8 | PD1.21.3 | CACGAAGCTTCGATGTGT |
| 9 | TRBC2.5 | CTCTGCTTCTGATGGCTCAA | 9 | CIITA8-1 | CAAACTGGATGGGTCCTA | 9 | PD1.21.4 | CGGAGAAGCTTGTGCTAAAC |
| 10 | TRBC2.6 | AGTTAAGTCCAGTGGTGG | 10 | CIITA8-4 | CAGGCAGTCAACGAGGAAC | 10 | PD1.21.5 | CCTGTCGTGGGACGGAAG |
| 11 | TRBC2.7 | ACTGGACTTGACAGCGGAAG | 11 | CIITA9-1 | CCAAACATCTCAGACCGGCC | 11 | PD1.21.6 | CCCTTCGGTCACCACGAAC |
| 12 | TRBC2.8 | TGACAGCCGGAAGTGGTTGC | 12 | CIITA10-1 | CTCTCCAGTCGCCGGCATT | 12 | PD1.21.7 | AGGGCGCAGCTTGTCCGTC |
| 13 | TRBC2.9 | GAGAGTGGAAGTGCTTGCGG | 13 | CIITA11-2 | ACGTATGGTGCCGAGCCCGC | 13 | PD1.21.8 | GCCCTGCTCGTGGTGACCGA |
| 14 | TRBC2.10 | TGAACAGTGGATGGCTCAG | 14 | CIITA11-3 | GAGCGGTAGAACTGCTCAA | 14 | PD1.21.9 | CCCTTCGGTCACCACGAGCA |
| 15 | TRBC2.11 | CGTAGAACTGGACTTGACAG | 15 | CIITA12-3 | GAGTCTGCACAAGCTTTCCC | 15 | PD1.21.10 | CCCTGCTCGTGGTGACGAA |
| 16 | TRBC2.12 | ATGACGAGTGGACGCAGGAT | 16 | CIITA13-1 | TTCTTAGGTCCCGAACAGC | 16 | PD1.22.1 | GCGTGACTTCCACATGAGCG |
| 17 | TRBC2.13 | CTTGACAGCGGAAGTGGTTG | 17 | CIITA13-2 | TCTTTAGGTCCCGAACAGCA | 17 | PD1.22.2 | AGGTGCCGTGTATTGGGC |
| 18 | TRBC2.14 | GCTGTCAAGTCCAGTTCTAC | 18 | CIITA14-2 | CAAACTGGTGCGGATCCTA | 18 | PD1.22.3 | ACTTCAATGTGGTGGTC |
| 19 | TRBC3.1 | AGGGTCTGGGCGCGTGACATC | 19 | CIITA15-1 | GAGAACAAGATGGGGACGA | 19 | PD1.22.4 | GGTGCGGCTGTCATTGGCC |
| 20 | TRBC3.2 | GGGTCGGGCCCTGACATC | 20 | CIITA16-1 | GGGTGCCTACAAACTGCCG | 20 | PD1.3.1 | ACCTGCTGGTTGTGT |
| 21 | TRBC3.3 | ATGCCGATTGGACACAGGT | 21 | CIITA17-1 | AATAACTGCATCTGCGACGT | 21 | PD1.3.2 | AGGGTTTGGAACTGGCCGG |
| 22 | TRBC3.4 | GAGACGAATGAACTCAGTT | 22 | CIITA17-2 | CAATAACAGTCATCTGGACG | 22 | PD1.5.1 | ATGTGTTTCCTAGCGGAAT |
| 23 | TRBC3.5 | GATCGTCAGCGCCGAGCCT | 23 | CIITA18-1 | TACAACAAGTTCACGGCTGC | 23 | PD1.5.2 | TCAGTGGCTGGGACTCCGA |
| 24 | TRBC3.6 | AGATCCGTACGCGAAGGGC | 24 | CIITA19-1 | TCCGTGAATCCTGTTGTTGC | 24 | PD1.5.3 | CATGTCTTTCCTAGCGGAA |

FIG. 26

| gRNA# | gRNA Name | B2M gRNA sequence | gRNA# | gRNA Name | TRAC gRNA sequence |
|---|---|---|---|---|---|
| 1 | B2M1-1 | GAGTAGCGCGAGCACAGCTA | 1 | TRAC1-1 | GAGAATCAAAATCGGTGAAT |
| 2 | B2M1-2 | CGCGAGCACAGCTAAGGCCA | 2 | TRAC1-4 | TGTGCTAGACATGAGGTCTA |
| 3 | B2M1-3 | CTCGGCTACTCTCTCTTTC | 3 | TRAC1-5 | AAAGTCAGATTTGTTGCTCC |
| 4 | B2M2-1 | AAGTCAACTTCAATGTCGGA | 4 | TRAC1-9 | AGAGTCTCTCAGCTGGTACA |
| 5 | B2M2-2 | CGTGAGTAAACCTGAATCTT | 5 | TRAC1-13 | AGCTGGTACACGGCAGGGTC |
| 6 | B2M2-3 | ACCCAGACACATAGCAATTC | 6 | TRAC1-16 | ACAAAACTGTCTAGACATG |
| 7 | B2M2-4 | TTCCTGAATTGCTATGTGTC | 7 | TRAC2-1 | CTCGACCAGCTTGACATCAC |
| 8 | B2M2-5 | CAGTAAGTCAACTTCAATGT | 8 | TRAC2-2 | AAGTTCCTGTGATGTCAAGC |
| 9 | B2M2-6 | TCCTGAATTGCTATGTGTCT | 9 | TRAC3-1 | TTCGAACCAATCACTGAC |
| 10 | B2M2-8 | GGCATACTCATCTTTTCAG | 10 | TRAC3-2 | TAATCTGCTCATGACGGTG |
| 11 | B2M3-1 | ACAGCCCAAGATAGTTAAGT | 11 | TRAC3-3 | GATTAAACCGGCCACTTTC |
| 12 | B2M3-2 | CACAGCCCAAGATAGTTAAG | 12 | TRAC3-4 | CGTCATGAGCAGATTAAACC |
|  |  |  | 13 | TRAC3-5 | TAAACCGGCCACTTTCAGG |

FIG. 27

| Clone# | gRNA |
|---|---|
| L1 | CIITA13-2 |
| L2 | CIITA14-2 |
| L3 | CIITA15-1 |
| L4 | CIITA17-1 |
| L5 | B2M 1-2 |
| L6 | B2M 2-6 |
| L7 | B2M 2-8 |
| L8 | PD1.1-3 |
| L9 | PD1.21-5 |
| L10 | PD1.21-9 |
| L11 | TRBC12-12 |
| L12 | TRAC1-9 |
| L13 | TRAC2-1 |
| L14 | TRAC3-1 |
| L15 | TRAC3-3 |
| L16 | TRAC3-4 |
| L17 | TRAC-3-5 |

FIG. 28

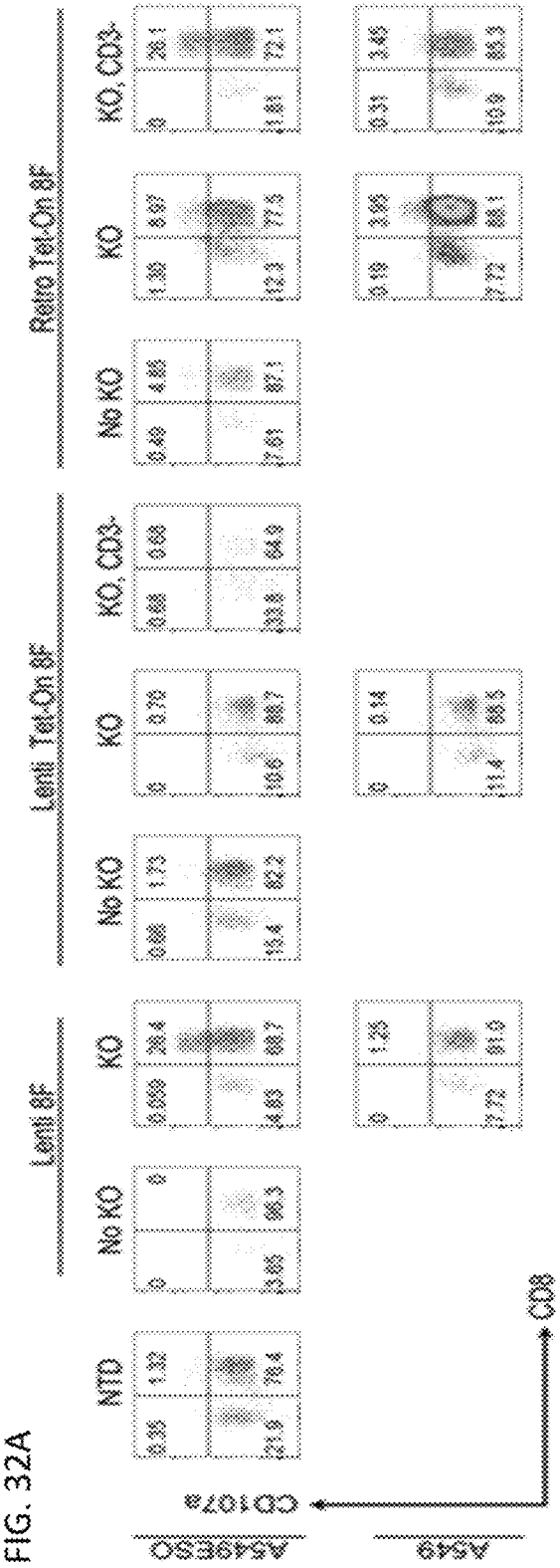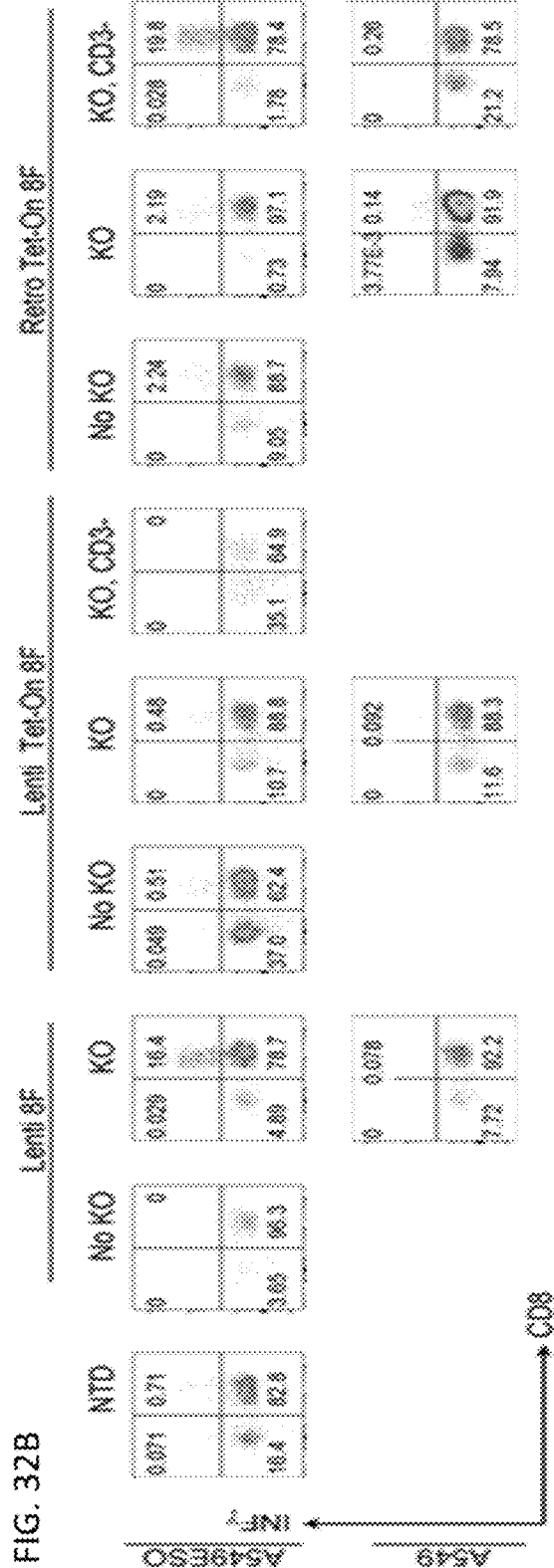
FIG. 32A
FIG. 32B

SEQUENCE LISTING

```
<160> NUMBER OF SEQ ID NOS: 140

<210> SEQ ID NO 1
<211> LENGTH: 20
<212> TYPE: DNA
<213> ORGANISM: Artificial sequence
<220> FEATURE:
<223> OTHER INFORMATION: gRNA

<400> SEQUENCE: 1
caaacacagc gacctcgggt                                              20

<210> SEQ ID NO 2
<211> LENGTH: 20
<212> TYPE: DNA
<213> ORGANISM: Artificial sequence
<220> FEATURE:
<223> OTHER INFORMATION: gRNA

<400> SEQUENCE: 2
ggctcaaaca cagcgacctc                                              20

<210> SEQ ID NO 3
<211> LENGTH: 20
<212> TYPE: DNA
<213> ORGANISM: Artificial sequence
<220> FEATURE:
<223> OTHER INFORMATION: gRNA

<400> SEQUENCE: 3
tcaaacacag cgacctcggg                                              20

<210> SEQ ID NO 4
<211> LENGTH: 20
<212> TYPE: DNA
<213> ORGANISM: Artificial sequence
<220> FEATURE:
<223> OTHER INFORMATION: gRNA

<400> SEQUENCE: 4
tggctcaaac acagcgacct                                              20

<210> SEQ ID NO 5
<211> LENGTH: 20
<212> TYPE: DNA
<213> ORGANISM: Artificial sequence
<220> FEATURE:
<223> OTHER INFORMATION: gRNA
```

<400> SEQUENCE: 5
tctccgagag cccgtagaac                                       20

<210> SEQ ID NO 6
<211> LENGTH: 20
<212> TYPE: DNA
<213> ORGANISM: Artificial sequence
<220> FEATURE:
<223> OTHER INFORMATION: gRNA

<400> SEQUENCE: 6
ggctctcgga gaatgacgag                                       20

<210> SEQ ID NO 7
<211> LENGTH: 20
<212> TYPE: DNA
<213> ORGANISM: Artificial sequence
<220> FEATURE:
<223> OTHER INFORMATION: gRNA

<400> SEQUENCE: 7
tgacagcgga agtggttgcg                                       20

<210> SEQ ID NO 8
<211> LENGTH: 20
<212> TYPE: DNA
<213> ORGANISM: Artificial sequence
<220> FEATURE:
<223> OTHER INFORMATION: gRNA

<400> SEQUENCE: 8
agtccagttc tacgggctct                                       20

<210> SEQ ID NO 9
<211> LENGTH: 20
<212> TYPE: DNA
<213> ORGANISM: Artificial sequence
<220> FEATURE:
<223> OTHER INFORMATION: gRNA

<400> SEQUENCE: 9
cgctgtcaag tccagttcta                                       20

<210> SEQ ID NO 10
<211> LENGTH: 20
<212> TYPE: DNA
<213> ORGANISM: Artificial sequence
<220> FEATURE:
<223> OTHER INFORMATION: gRNA

<400> SEQUENCE: 10
agctcagctc cacgtggtcg                                       20

<210> SEQ ID NO 11
<211> LENGTH: 20
<212> TYPE: DNA
<213> ORGANISM: Artificial sequence
<220> FEATURE:
<223> OTHER INFORMATION: gRNA

<400> SEQUENCE: 11
actggacttg acagcggaag                                       20

```
<210> SEQ ID NO 12
<211> LENGTH: 20
<212> TYPE: DNA
<213> ORGANISM: Artificial sequence
<220> FEATURE:
<223> OTHER INFORMATION: gRNA

<400> SEQUENCE: 12
ttgacagcgg aagtggttgc                                               20

<210> SEQ ID NO 13
<211> LENGTH: 20
<212> TYPE: DNA
<213> ORGANISM: Artificial sequence
<220> FEATURE:
<223> OTHER INFORMATION: gRNA

<400> SEQUENCE: 13
gacagcggaa gtggttgcgg                                               20

<210> SEQ ID NO 14
<211> LENGTH: 20
<212> TYPE: DNA
<213> ORGANISM: Artificial sequence
<220> FEATURE:
<223> OTHER INFORMATION: gRNA

<400> SEQUENCE: 14
tgacgagtgg acccaggata                                               20

<210> SEQ ID NO 15
<211> LENGTH: 20
<212> TYPE: DNA
<213> ORGANISM: Artificial sequence
<220> FEATURE:
<223> OTHER INFORMATION: gRNA

<400> SEQUENCE: 15
cgtagaactg gacttgacag                                               20

<210> SEQ ID NO 16
<211> LENGTH: 20
<212> TYPE: DNA
<213> ORGANISM: Artificial sequence
<220> FEATURE:
<223> OTHER INFORMATION: gRNA

<400> SEQUENCE: 16
atgacgagtg gacccaggat                                               20

<210> SEQ ID NO 17
<211> LENGTH: 20
<212> TYPE: DNA
<213> ORGANISM: Artificial sequence
<220> FEATURE:
<223> OTHER INFORMATION: gRNA

<400> SEQUENCE: 17
cttgacagcg gaagtggttg                                               20

<210> SEQ ID NO 18
<211> LENGTH: 20
<212> TYPE: DNA
<213> ORGANISM: Artificial sequence
<220> FEATURE:
<223> OTHER INFORMATION: gRNA
```

```
<400> SEQUENCE: 18
gctgtcaagt ccagttctac                                               20

<210> SEQ ID NO 19
<211> LENGTH: 20
<212> TYPE: DNA
<213> ORGANISM: Artificial sequence
<220> FEATURE:
<223> OTHER INFORMATION: gRNA

<400> SEQUENCE: 19
aggcctcggc gctgacgatc                                               20

<210> SEQ ID NO 20
<211> LENGTH: 20
<212> TYPE: DNA
<213> ORGANISM: Artificial sequence
<220> FEATURE:
<223> OTHER INFORMATION: gRNA

<400> SEQUENCE: 20
ggcctcggcg ctgacgatct                                               20

<210> SEQ ID NO 21
<211> LENGTH: 20
<212> TYPE: DNA
<213> ORGANISM: Artificial sequence
<220> FEATURE:
<223> OTHER INFORMATION: gRNA

<400> SEQUENCE: 21
cacccagatc gtcagcgccg                                               20

<210> SEQ ID NO 22
<211> LENGTH: 20
<212> TYPE: DNA
<213> ORGANISM: Artificial sequence
<220> FEATURE:
<223> OTHER INFORMATION: gRNA

<400> SEQUENCE: 22
gacgatctgg gtgacgggtt                                               20

<210> SEQ ID NO 23
<211> LENGTH: 20
<212> TYPE: DNA
<213> ORGANISM: Artificial sequence
<220> FEATURE:
<223> OTHER INFORMATION: gRNA

<400> SEQUENCE: 23
gatcgtcagc gccgaggcct                                               20

<210> SEQ ID NO 24
<211> LENGTH: 20
<212> TYPE: DNA
<213> ORGANISM: Artificial sequence
<220> FEATURE:
<223> OTHER INFORMATION: gRNA

<400> SEQUENCE: 24
agatcgtcag cgccgaggcc                                               20
```

```
<210> SEQ ID NO 25
<211> LENGTH: 20
<212> TYPE: DNA
<213> ORGANISM: Artificial sequence
<220> FEATURE:
<223> OTHER INFORMATION: gRNA

<400> SEQUENCE: 25
ctccaggtag ccaccttcta                                              20

<210> SEQ ID NO 26
<211> LENGTH: 20
<212> TYPE: DNA
<213> ORGANISM: Artificial sequence
<220> FEATURE:
<223> OTHER INFORMATION: gRNA

<400> SEQUENCE: 26
gctgaactgg tcgcagttga                                              20

<210> SEQ ID NO 27
<211> LENGTH: 20
<212> TYPE: DNA
<213> ORGANISM: Artificial sequence
<220> FEATURE:
<223> OTHER INFORMATION: gRNA

<400> SEQUENCE: 27
tcaactgcga ccagttcagc                                              20

<210> SEQ ID NO 28
<211> LENGTH: 20
<212> TYPE: DNA
<213> ORGANISM: Artificial sequence
<220> FEATURE:
<223> OTHER INFORMATION: gRNA

<400> SEQUENCE: 28
gggagtcctg gaagacatac                                              20

<210> SEQ ID NO 29
<211> LENGTH: 20
<212> TYPE: DNA
<213> ORGANISM: Artificial sequence
<220> FEATURE:
<223> OTHER INFORMATION: gRNA

<400> SEQUENCE: 29
ctctcaccga tcacttcatc                                              20

<210> SEQ ID NO 30
<211> LENGTH: 20
<212> TYPE: DNA
<213> ORGANISM: Artificial sequence
<220> FEATURE:
<223> OTHER INFORMATION: gRNA

<400> SEQUENCE: 30
aggtctgccg gaagctcctc                                              20

<210> SEQ ID NO 31
<211> LENGTH: 20
<212> TYPE: DNA
<213> ORGANISM: Artificial sequence
<220> FEATURE:
<223> OTHER INFORMATION: gRNA
```

<400> SEQUENCE: 31
cggttttctc caggcgcatc                                           20

<210> SEQ ID NO 32
<211> LENGTH: 20
<212> TYPE: DNA
<213> ORGANISM: Artificial sequence
<220> FEATURE:
<223> OTHER INFORMATION: gRNA

<400> SEQUENCE: 32
ggctcctggt tgaacagcgc                                           20

<210> SEQ ID NO 33
<211> LENGTH: 20
<212> TYPE: DNA
<213> ORGANISM: Artificial sequence
<220> FEATURE:
<223> OTHER INFORMATION: gRNA

<400> SEQUENCE: 33
caaactggat gggtccctca                                           20

<210> SEQ ID NO 34
<211> LENGTH: 20
<212> TYPE: DNA
<213> ORGANISM: Artificial sequence
<220> FEATURE:
<223> OTHER INFORMATION: gRNA

<400> SEQUENCE: 34
caggcagctc aacgaggaac                                           20

<210> SEQ ID NO 35
<211> LENGTH: 20
<212> TYPE: DNA
<213> ORGANISM: Artificial sequence
<220> FEATURE:
<223> OTHER INFORMATION: gRNA

<400> SEQUENCE: 35
ccaacatctc cagaccggcc                                           20

<210> SEQ ID NO 36
<211> LENGTH: 20
<212> TYPE: DNA
<213> ORGANISM: Artificial sequence
<220> FEATURE:
<223> OTHER INFORMATION: gRNA

<400> SEQUENCE: 36
ctctccagct gccgggcatt                                           20

<210> SEQ ID NO 37
<211> LENGTH: 20
<212> TYPE: DNA
<213> ORGANISM: Artificial sequence
<220> FEATURE:
<223> OTHER INFORMATION: gRNA

<400> SEQUENCE: 37
acgtatggtg ccgagcccgc                                           20

```
<210> SEQ ID NO 38
<211> LENGTH: 20
<212> TYPE: DNA
<213> ORGANISM: Artificial sequence
<220> FEATURE:
<223> OTHER INFORMATION: gRNA

<400> SEQUENCE: 38
gagcggtaga actgctccac                                          20

<210> SEQ ID NO 39
<211> LENGTH: 20
<212> TYPE: DNA
<213> ORGANISM: Artificial sequence
<220> FEATURE:
<223> OTHER INFORMATION: gRNA

<400> SEQUENCE: 39
gagtctgcac aagctttccc                                          20

<210> SEQ ID NO 40
<211> LENGTH: 20
<212> TYPE: DNA
<213> ORGANISM: Artificial sequence
<220> FEATURE:
<223> OTHER INFORMATION: gRNA

<400> SEQUENCE: 40
ttctttaggt cccgaacagc                                          20

<210> SEQ ID NO 41
<211> LENGTH: 20
<212> TYPE: DNA
<213> ORGANISM: Artificial sequence
<220> FEATURE:
<223> OTHER INFORMATION: gRNA

<400> SEQUENCE: 41
tctttaggtc ccgaacagca                                          20

<210> SEQ ID NO 42
<211> LENGTH: 20
<212> TYPE: DNA
<213> ORGANISM: Artificial sequence
<220> FEATURE:
<223> OTHER INFORMATION: gRNA

<400> SEQUENCE: 42
caaactggtg cggatcctca                                          20

<210> SEQ ID NO 43
<211> LENGTH: 20
<212> TYPE: DNA
<213> ORGANISM: Artificial sequence
<220> FEATURE:
<223> OTHER INFORMATION: gRNA

<400> SEQUENCE: 43
gagaacaaga tcggggacga                                          20

<210> SEQ ID NO 44
<211> LENGTH: 20
<212> TYPE: DNA
<213> ORGANISM: Artificial sequence
<220> FEATURE:
<223> OTHER INFORMATION: gRNA
```

```
<400> SEQUENCE: 44
gggtgcctac aaactcgccg                                              20

<210> SEQ ID NO 45
<211> LENGTH: 20
<212> TYPE: DNA
<213> ORGANISM: Artificial sequence
<220> FEATURE:
<223> OTHER INFORMATION: gRNA

<400> SEQUENCE: 45
aataactgca tctgcgacgt                                              20

<210> SEQ ID NO 46
<211> LENGTH: 20
<212> TYPE: DNA
<213> ORGANISM: Artificial sequence
<220> FEATURE:
<223> OTHER INFORMATION: gRNA

<400> SEQUENCE: 46
caataactgc atctgcgacg                                              20

<210> SEQ ID NO 47
<211> LENGTH: 20
<212> TYPE: DNA
<213> ORGANISM: Artificial sequence
<220> FEATURE:
<223> OTHER INFORMATION: gRNA

<400> SEQUENCE: 47
tacaacaagt tcacggctgc                                              20

<210> SEQ ID NO 48
<211> LENGTH: 20
<212> TYPE: DNA
<213> ORGANISM: Artificial sequence
<220> FEATURE:
<223> OTHER INFORMATION: gRNA

<400> SEQUENCE: 48
tccgtgaatc ctgttgttgc                                              20

<210> SEQ ID NO 49
<211> LENGTH: 20
<212> TYPE: DNA
<213> ORGANISM: Artificial sequence
<220> FEATURE:
<223> OTHER INFORMATION: gRNA

<400> SEQUENCE: 49
tgtagcaccg cccagacgac                                              20

<210> SEQ ID NO 50
<211> LENGTH: 20
<212> TYPE: DNA
<213> ORGANISM: Artificial sequence
<220> FEATURE:
<223> OTHER INFORMATION: gRNA

<400> SEQUENCE: 50
cgtctgggcg gtgctacaac                                              20
```

```
<210> SEQ ID NO 51
<211> LENGTH: 20
<212> TYPE: DNA
<213> ORGANISM: Artificial sequence
<220> FEATURE:
<223> OTHER INFORMATION: gRNA

<400> SEQUENCE: 51
gtctgggcgg tgctacaact                                              20

<210> SEQ ID NO 52
<211> LENGTH: 20
<212> TYPE: DNA
<213> ORGANISM: Artificial sequence
<220> FEATURE:
<223> OTHER INFORMATION: gRNA

<400> SEQUENCE: 52
aggcgccctg gccagtcgtc                                              20

<210> SEQ ID NO 53
<211> LENGTH: 20
<212> TYPE: DNA
<213> ORGANISM: Artificial sequence
<220> FEATURE:
<223> OTHER INFORMATION: gRNA

<400> SEQUENCE: 53
caccgcccag acgactggcc                                              20

<210> SEQ ID NO 54
<211> LENGTH: 20
<212> TYPE: DNA
<213> ORGANISM: Artificial sequence
<220> FEATURE:
<223> OTHER INFORMATION: gRNA

<400> SEQUENCE: 54
atgtggaagt cacgcccgtt                                              20

<210> SEQ ID NO 55
<211> LENGTH: 20
<212> TYPE: DNA
<213> ORGANISM: Artificial sequence
<220> FEATURE:
<223> OTHER INFORMATION: gRNA

<400> SEQUENCE: 55
catgtggaag tcacgcccgt                                              20

<210> SEQ ID NO 56
<211> LENGTH: 20
<212> TYPE: DNA
<213> ORGANISM: Artificial sequence
<220> FEATURE:
<223> OTHER INFORMATION: gRNA

<400> SEQUENCE: 56
cacgaagctc tccgatgtgt                                              20

<210> SEQ ID NO 57
<211> LENGTH: 20
<212> TYPE: DNA
<213> ORGANISM: Artificial sequence
<220> FEATURE:
<223> OTHER INFORMATION: gRNA
```

<400> SEQUENCE: 57
cggagagctt cgtgctaaac                                               20

<210> SEQ ID NO 58
<211> LENGTH: 20
<212> TYPE: DNA
<213> ORGANISM: Artificial sequence
<220> FEATURE:
<223> OTHER INFORMATION: gRNA

<400> SEQUENCE: 58
cctgctcgtg gtgaccgaag                                               20

<210> SEQ ID NO 59
<211> LENGTH: 20
<212> TYPE: DNA
<213> ORGANISM: Artificial sequence
<220> FEATURE:
<223> OTHER INFORMATION: gRNA

<400> SEQUENCE: 59
ccccttcggt caccacgagc                                               20

<210> SEQ ID NO 60
<211> LENGTH: 20
<212> TYPE: DNA
<213> ORGANISM: Artificial sequence
<220> FEATURE:
<223> OTHER INFORMATION: gRNA

<400> SEQUENCE: 60
aggcggccag cttgtccgtc                                               20

<210> SEQ ID NO 61
<211> LENGTH: 20
<212> TYPE: DNA
<213> ORGANISM: Artificial sequence
<220> FEATURE:
<223> OTHER INFORMATION: gRNA

<400> SEQUENCE: 61
gccctgctcg tggtgaccga                                               20

<210> SEQ ID NO 62
<211> LENGTH: 20
<212> TYPE: DNA
<213> ORGANISM: Artificial sequence
<220> FEATURE:
<223> OTHER INFORMATION: gRNA

<400> SEQUENCE: 62
cccttcggtc accacgagca                                               20

<210> SEQ ID NO 63
<211> LENGTH: 20
<212> TYPE: DNA
<213> ORGANISM: Artificial sequence
<220> FEATURE:
<223> OTHER INFORMATION: gRNA

<400> SEQUENCE: 63
ccctgctcgt ggtgaccgaa                                               20

```
<210> SEQ ID NO 64
<211> LENGTH: 20
<212> TYPE: DNA
<213> ORGANISM: Artificial sequence
<220> FEATURE:
<223> OTHER INFORMATION: gRNA

<400> SEQUENCE: 64
gcgtgacttc cacatgagcg                                                 20

<210> SEQ ID NO 65
<211> LENGTH: 20
<212> TYPE: DNA
<213> ORGANISM: Artificial sequence
<220> FEATURE:
<223> OTHER INFORMATION: gRNA

<400> SEQUENCE: 65
aggtgccgct gtcattgcgc                                                 20

<210> SEQ ID NO 66
<211> LENGTH: 20
<212> TYPE: DNA
<213> ORGANISM: Artificial sequence
<220> FEATURE:
<223> OTHER INFORMATION: gRNA

<400> SEQUENCE: 66
acttccacat gagcgtggtc                                                 20

<210> SEQ ID NO 67
<211> LENGTH: 20
<212> TYPE: DNA
<213> ORGANISM: Artificial sequence
<220> FEATURE:
<223> OTHER INFORMATION: gRNA

<400> SEQUENCE: 67
ggtgccgctg tcattgcgcc                                                 20

<210> SEQ ID NO 68
<211> LENGTH: 20
<212> TYPE: DNA
<213> ORGANISM: Artificial sequence
<220> FEATURE:
<223> OTHER INFORMATION: gRNA

<400> SEQUENCE: 68
accctggtgg ttggtgtcgt                                                 20

<210> SEQ ID NO 69
<211> LENGTH: 20
<212> TYPE: DNA
<213> ORGANISM: Artificial sequence
<220> FEATURE:
<223> OTHER INFORMATION: gRNA

<400> SEQUENCE: 69
agggtttgga actggccggc                                                 20

<210> SEQ ID NO 70
<211> LENGTH: 20
<212> TYPE: DNA
<213> ORGANISM: Artificial sequence
<220> FEATURE:
<223> OTHER INFORMATION: gRNA
```

<400> SEQUENCE: 70
attgtctttc ctagcggaat                                              20

<210> SEQ ID NO 71
<211> LENGTH: 20
<212> TYPE: DNA
<213> ORGANISM: Artificial sequence
<220> FEATURE:
<223> OTHER INFORMATION: gRNA

<400> SEQUENCE: 71
tcagtggctg ggcactccga                                              20

<210> SEQ ID NO 72
<211> LENGTH: 20
<212> TYPE: DNA
<213> ORGANISM: Artificial sequence
<220> FEATURE:
<223> OTHER INFORMATION: gRNA

<400> SEQUENCE: 72
cattgtcttt cctagcggaa                                              20

<210> SEQ ID NO 73
<211> LENGTH: 20
<212> TYPE: DNA
<213> ORGANISM: Artificial sequence
<220> FEATURE:
<223> OTHER INFORMATION: gRNA

<400> SEQUENCE: 73
gagtagcgcg agcacagcta                                              20

<210> SEQ ID NO 74
<211> LENGTH: 20
<212> TYPE: DNA
<213> ORGANISM: Artificial sequence
<220> FEATURE:
<223> OTHER INFORMATION: gRNA

<400> SEQUENCE: 74
cgcgagcaca gctaaggcca                                              20

<210> SEQ ID NO 75
<211> LENGTH: 20
<212> TYPE: DNA
<213> ORGANISM: Artificial sequence
<220> FEATURE:
<223> OTHER INFORMATION: gRNA

<400> SEQUENCE: 75
ctcgcgctac tctctctttc                                              20

<210> SEQ ID NO 76
<211> LENGTH: 20
<212> TYPE: DNA
<213> ORGANISM: Artificial sequence
<220> FEATURE:
<223> OTHER INFORMATION: gRNA

<400> SEQUENCE: 76
aagtcaactt caatgtcgga                                              20

```
<210> SEQ ID NO 77
<211> LENGTH: 20
<212> TYPE: DNA
<213> ORGANISM: Artificial sequence
<220> FEATURE:
<223> OTHER INFORMATION: gRNA

<400> SEQUENCE: 77
cgtgagtaaa cctgaatctt                                               20

<210> SEQ ID NO 78
<211> LENGTH: 20
<212> TYPE: DNA
<213> ORGANISM: Artificial sequence
<220> FEATURE:
<223> OTHER INFORMATION: gRNA

<400> SEQUENCE: 78
acccagacac atagcaattc                                               20

<210> SEQ ID NO 79
<211> LENGTH: 20
<212> TYPE: DNA
<213> ORGANISM: Artificial sequence
<220> FEATURE:
<223> OTHER INFORMATION: gRNA

<400> SEQUENCE: 79
ttcctgaatt gctatgtgtc                                               20

<210> SEQ ID NO 80
<211> LENGTH: 20
<212> TYPE: DNA
<213> ORGANISM: Artificial sequence
<220> FEATURE:
<223> OTHER INFORMATION: gRNA

<400> SEQUENCE: 80
cagtaagtca acttcaatgt                                               20

<210> SEQ ID NO 81
<211> LENGTH: 20
<212> TYPE: DNA
<213> ORGANISM: Artificial sequence
<220> FEATURE:
<223> OTHER INFORMATION: gRNA

<400> SEQUENCE: 81
tcctgaattg ctatgtgtct                                               20

<210> SEQ ID NO 82
<211> LENGTH: 20
<212> TYPE: DNA
<213> ORGANISM: Artificial sequence
<220> FEATURE:
<223> OTHER INFORMATION: gRNA

<400> SEQUENCE: 82
ggcatactca tcttttttcag                                              20

<210> SEQ ID NO 83
<211> LENGTH: 20
<212> TYPE: DNA
<213> ORGANISM: Artificial sequence
<220> FEATURE:
<223> OTHER INFORMATION: gRNA
```

<400> SEQUENCE: 83
acagcccaag atagttaagt                                              20

<210> SEQ ID NO 84
<211> LENGTH: 20
<212> TYPE: DNA
<213> ORGANISM: Artificial sequence
<220> FEATURE:
<223> OTHER INFORMATION: gRNA

<400> SEQUENCE: 84
cacagcccaa gatagttaag                                              20

<210> SEQ ID NO 85
<211> LENGTH: 20
<212> TYPE: DNA
<213> ORGANISM: Artificial sequence
<220> FEATURE:
<223> OTHER INFORMATION: gRNA

<400> SEQUENCE: 85
gagaatcaaa atcggtgaat                                              20

<210> SEQ ID NO 86
<211> LENGTH: 20
<212> TYPE: DNA
<213> ORGANISM: Artificial sequence
<220> FEATURE:
<223> OTHER INFORMATION: gRNA

<400> SEQUENCE: 86
tgtgctagac atgaggtcta                                              20

<210> SEQ ID NO 87
<211> LENGTH: 20
<212> TYPE: DNA
<213> ORGANISM: Artificial sequence
<220> FEATURE:
<223> OTHER INFORMATION: gRNA

<400> SEQUENCE: 87
aaagtcagat ttgttgctcc                                              20

<210> SEQ ID NO 88
<211> LENGTH: 20
<212> TYPE: DNA
<213> ORGANISM: Artificial sequence
<220> FEATURE:
<223> OTHER INFORMATION: gRNA

<400> SEQUENCE: 88
agagtctctc agctggtaca                                              20

<210> SEQ ID NO 89
<211> LENGTH: 20
<212> TYPE: DNA
<213> ORGANISM: Artificial sequence
<220> FEATURE:
<223> OTHER INFORMATION: gRNA

<400> SEQUENCE: 89
agctggtaca cggcagggtc                                              20

```
<210> SEQ ID NO 90
<211> LENGTH: 20
<212> TYPE: DNA
<213> ORGANISM: Artificial sequence
<220> FEATURE:
<223> OTHER INFORMATION: gRNA

<400> SEQUENCE: 90
acaaaactgt gctagacatg                                              20

<210> SEQ ID NO 91
<211> LENGTH: 20
<212> TYPE: DNA
<213> ORGANISM: Artificial sequence
<220> FEATURE:
<223> OTHER INFORMATION: gRNA

<400> SEQUENCE: 91
ctcgaccagc ttgacatcac                                              20

<210> SEQ ID NO 92
<211> LENGTH: 20
<212> TYPE: DNA
<213> ORGANISM: Artificial sequence
<220> FEATURE:
<223> OTHER INFORMATION: gRNA

<400> SEQUENCE: 92
aagttcctgt gatgtcaagc                                              20

<210> SEQ ID NO 93
<211> LENGTH: 20
<212> TYPE: DNA
<213> ORGANISM: Artificial sequence
<220> FEATURE:
<223> OTHER INFORMATION: gRNA

<400> SEQUENCE: 93
ttcggaaccc aatcactgac                                              20

<210> SEQ ID NO 94
<211> LENGTH: 20
<212> TYPE: DNA
<213> ORGANISM: Artificial sequence
<220> FEATURE:
<223> OTHER INFORMATION: gRNA

<400> SEQUENCE: 94
ttaatctgct catgacgctg                                              20

<210> SEQ ID NO 95
<211> LENGTH: 20
<212> TYPE: DNA
<213> ORGANISM: Artificial sequence
<220> FEATURE:
<223> OTHER INFORMATION: gRNA

<400> SEQUENCE: 95
gattaaaccc ggccactttc                                              20

<210> SEQ ID NO 96
<211> LENGTH: 20
<212> TYPE: DNA
<213> ORGANISM: Artificial sequence
<220> FEATURE:
<223> OTHER INFORMATION: gRNA
```

```
<400> SEQUENCE: 96
cgtcatgagc agattaaacc                                              20

<210> SEQ ID NO 97
<211> LENGTH: 20
<212> TYPE: DNA
<213> ORGANISM: Artificial sequence
<220> FEATURE:
<223> OTHER INFORMATION: gRNA

<400> SEQUENCE: 97
taaacccggc cactttcagg                                              20

<210> SEQ ID NO 98
<211> LENGTH: 9
<212> TYPE: PRT
<213> ORGANISM: Artificial sequence
<220> FEATURE:
<223> OTHER INFORMATION: NY-ESO epitope

<400> SEQUENCE: 98

Ser Leu Leu Met Trp Ile Thr Gln Cys
1               5

<210> SEQ ID NO 99
<211> LENGTH: 5
<212> TYPE: PRT
<213> ORGANISM: Artificial sequence
<220> FEATURE:
<223> OTHER INFORMATION: linker
<220> FEATURE:
<221> NAME/KEY: misc_feature
<222> LOCATION: (1)..(5)
<223> OTHER INFORMATION: can be repeated n times, where n is an integer
      of at least 1

<400> SEQUENCE: 99

Gly Ser Gly Gly Ser
1               5

<210> SEQ ID NO 100
<211> LENGTH: 4
<212> TYPE: PRT
<213> ORGANISM: Artificial sequence
<220> FEATURE:
<223> OTHER INFORMATION: linker
<220> FEATURE:
<221> NAME/KEY: misc_feature
<222> LOCATION: (1)..(4)
<223> OTHER INFORMATION: can be repeated n times, where n is an integer
      of at least 1

<400> SEQUENCE: 100

Gly Gly Gly Ser
1

<210> SEQ ID NO 101
<211> LENGTH: 5
<212> TYPE: PRT
<213> ORGANISM: Artificial sequence
<220> FEATURE:
<223> OTHER INFORMATION: linker
<220> FEATURE:
<221> NAME/KEY: misc_feature
<222> LOCATION: (1)..(5)
<223> OTHER INFORMATION: can be repeated n times, where n is an integer
      of at least 1
```

```
<400> SEQUENCE: 101

Gly Gly Gly Gly Ser
1               5

<210> SEQ ID NO 102
<211> LENGTH: 4
<212> TYPE: PRT
<213> ORGANISM: Artificial sequence
<220> FEATURE:
<223> OTHER INFORMATION: linker

<400> SEQUENCE: 102

Gly Gly Ser Gly
1

<210> SEQ ID NO 103
<211> LENGTH: 5
<212> TYPE: PRT
<213> ORGANISM: Artificial sequence
<220> FEATURE:
<223> OTHER INFORMATION: linker

<400> SEQUENCE: 103

Gly Gly Ser Gly Gly
1               5

<210> SEQ ID NO 104
<211> LENGTH: 5
<212> TYPE: PRT
<213> ORGANISM: Artificial sequence
<220> FEATURE:
<223> OTHER INFORMATION: linker

<400> SEQUENCE: 104

Gly Ser Gly Ser Gly
1               5

<210> SEQ ID NO 105
<211> LENGTH: 5
<212> TYPE: PRT
<213> ORGANISM: Artificial sequence
<220> FEATURE:
<223> OTHER INFORMATION: linker

<400> SEQUENCE: 105

Gly Ser Gly Gly Gly
1               5

<210> SEQ ID NO 106
<211> LENGTH: 5
<212> TYPE: PRT
<213> ORGANISM: Artificial sequence
<220> FEATURE:
<223> OTHER INFORMATION: linker

<400> SEQUENCE: 106

Gly Gly Gly Ser Gly
1               5

<210> SEQ ID NO 107
<211> LENGTH: 5
<212> TYPE: PRT
<213> ORGANISM: Artificial sequence
<220> FEATURE:
<223> OTHER INFORMATION: linker
```

```
<400> SEQUENCE: 107

Gly Ser Ser Ser Gly
1               5

<210> SEQ ID NO 108
<211> LENGTH: 5
<212> TYPE: PRT
<213> ORGANISM: Artificial sequence
<220> FEATURE:
<223> OTHER INFORMATION: linker

<400> SEQUENCE: 108

Gly Gly Gly Gly Ser
1               5

<210> SEQ ID NO 109
<211> LENGTH: 15
<212> TYPE: PRT
<213> ORGANISM: Artificial sequence
<220> FEATURE:
<223> OTHER INFORMATION: linker

<400> SEQUENCE: 109

Gly Gly Gly Gly Ser Gly Gly Gly Gly Ser Gly Gly Gly Gly Ser
1               5                   10                  15

<210> SEQ ID NO 110
<211> LENGTH: 15
<212> TYPE: PRT
<213> ORGANISM: Artificial sequence
<220> FEATURE:
<223> OTHER INFORMATION: linker

<400> SEQUENCE: 110

Gly Gly Gly Gly Ser Gly Gly Gly Gly Ser Gly Gly Gly Gly Ser
1               5                   10                  15

<210> SEQ ID NO 111
<211> LENGTH: 45
<212> TYPE: DNA
<213> ORGANISM: Artificial sequence
<220> FEATURE:
<223> OTHER INFORMATION: linker

<400> SEQUENCE: 111
ggtggcggtg gctcgggcgg tggtgggtcg ggtggcggcg gatct             45

<210> SEQ ID NO 112
<211> LENGTH: 5
<212> TYPE: PRT
<213> ORGANISM: Artificial sequence
<220> FEATURE:
<223> OTHER INFORMATION: hinge

<400> SEQUENCE: 112

Asp Lys Thr His Thr
1               5

<210> SEQ ID NO 113
<211> LENGTH: 4
<212> TYPE: PRT
<213> ORGANISM: Artificial sequence
<220> FEATURE:
<223> OTHER INFORMATION: hinge
```

```
<400> SEQUENCE: 113

Cys Pro Pro Cys
1

<210> SEQ ID NO 114
<211> LENGTH: 15
<212> TYPE: PRT
<213> ORGANISM: Artificial sequence
<220> FEATURE:
<223> OTHER INFORMATION: hinge

<400> SEQUENCE: 114

Cys Pro Glu Pro Lys Ser Cys Asp Thr Pro Pro Cys Pro Arg
1               5                  10                  15

<210> SEQ ID NO 115
<211> LENGTH: 12
<212> TYPE: PRT
<213> ORGANISM: Artificial sequence
<220> FEATURE:
<223> OTHER INFORMATION: hinge

<400> SEQUENCE: 115

Glu Leu Lys Thr Pro Leu Gly Asp Thr Thr His Thr
1               5                  10

<210> SEQ ID NO 116
<211> LENGTH: 10
<212> TYPE: PRT
<213> ORGANISM: Artificial sequence
<220> FEATURE:
<223> OTHER INFORMATION: hinge

<400> SEQUENCE: 116

Lys Ser Cys Asp Lys Thr His Thr Cys Pro
1               5                  10

<210> SEQ ID NO 117
<211> LENGTH: 7
<212> TYPE: PRT
<213> ORGANISM: Artificial sequence
<220> FEATURE:
<223> OTHER INFORMATION: hinge

<400> SEQUENCE: 117

Lys Cys Cys Val Asp Cys Pro
1               5

<210> SEQ ID NO 118
<211> LENGTH: 7
<212> TYPE: PRT
<213> ORGANISM: Artificial sequence
<220> FEATURE:
<223> OTHER INFORMATION: hinge

<400> SEQUENCE: 118

Lys Tyr Gly Pro Pro Cys Pro
1               5

<210> SEQ ID NO 119
<211> LENGTH: 15
<212> TYPE: PRT
<213> ORGANISM: Artificial sequence
<220> FEATURE:
<223> OTHER INFORMATION: hinge
```

```
<400> SEQUENCE: 119

Glu Pro Lys Ser Cys Asp Lys Thr His Thr Cys Pro Pro Cys Pro
1               5                   10                  15

<210> SEQ ID NO 120
<211> LENGTH: 12
<212> TYPE: PRT
<213> ORGANISM: Artificial sequence
<220> FEATURE:
<223> OTHER INFORMATION: hinge

<400> SEQUENCE: 120

Glu Arg Lys Cys Cys Val Glu Cys Pro Pro Cys Pro
1               5                   10

<210> SEQ ID NO 121
<211> LENGTH: 17
<212> TYPE: PRT
<213> ORGANISM: Artificial sequence
<220> FEATURE:
<223> OTHER INFORMATION: hinge

<400> SEQUENCE: 121

Glu Leu Lys Thr Pro Leu Gly Asp Thr Thr His Thr Cys Pro Arg Cys
1               5                   10                  15

Pro

<210> SEQ ID NO 122
<211> LENGTH: 12
<212> TYPE: PRT
<213> ORGANISM: Artificial sequence
<220> FEATURE:
<223> OTHER INFORMATION: hinge

<400> SEQUENCE: 122

Ser Pro Asn Met Val Pro His Ala His His Ala Gln
1               5                   10

<210> SEQ ID NO 123
<211> LENGTH: 15
<212> TYPE: PRT
<213> ORGANISM: Artificial sequence
<220> FEATURE:
<223> OTHER INFORMATION: hinge

<400> SEQUENCE: 123

Glu Pro Lys Ser Cys Asp Lys Thr Tyr Thr Cys Pro Pro Cys Pro
1               5                   10                  15

<210> SEQ ID NO 124
<211> LENGTH: 238
<212> TYPE: PRT
<213> ORGANISM: Artificial sequence
<220> FEATURE:
<223> OTHER INFORMATION: TGFBR-IL12RB1 receptor

<400> SEQUENCE: 124

Met Glu Ala Ala Val Ala Ala Pro Arg Pro Arg Leu Leu Leu Val
1               5                   10                  15

Leu Ala Ala Ala Ala Ala Ala Ala Ala Leu Leu Pro Gly Ala Thr
                20                  25                  30

Ala Leu Gln Cys Phe Cys His Leu Cys Thr Lys Asp Asn Phe Thr Cys
                35                  40                  45
```

| | | | | | | | | | | | |
|---|---|---|---|---|---|---|---|---|---|---|---|
| Val | Thr | Asp | Gly | Leu | Cys | Phe | Val | Ser | Val | Thr | Glu | Thr | Thr | Asp | Lys |
| | 50 | | | | 55 | | | | | 60 | |

Val Ile His Asn Ser Met Cys Ile Ala Glu Ile Asp Leu Ile Pro Arg
 65              70              75              80

Asp Arg Pro Phe Val Cys Ala Pro Ser Ser Lys Thr Gly Ser Val Thr
                 85              90              95

Thr Thr Tyr Cys Cys Asn Gln Asp His Cys Asn Lys Ile Glu Leu Pro
            100             105             110

Thr Thr Val Lys Ser Ser Pro Gly Leu Gly Pro Val Glu Leu Ala Ala
             115             120             125

Val Ile Ala Gly Pro Val Cys Phe Val Cys Ile Ser Leu Met Leu Met
130             135             140

Val Tyr Ile Arg Ala Ala Arg His Leu Cys Pro Pro Leu Pro Thr Pro
145             150             155             160

Cys Ala Ser Ser Ala Ile Glu Phe Pro Gly Gly Lys Glu Thr Trp Gln
                165             170             175

Trp Ile Asn Pro Val Asp Phe Gln Glu Glu Ala Ser Leu Gln Glu Ala
             180             185             190

Leu Val Val Glu Met Ser Trp Asp Lys Gly Glu Arg Thr Glu Pro Leu
             195             200             205

Glu Lys Thr Glu Leu Pro Glu Gly Ala Pro Glu Leu Ala Leu Asp Thr
210             215             220

Glu Leu Ser Leu Glu Asp Gly Asp Arg Cys Lys Ala Lys Met
225             230             235

<210> SEQ ID NO 125
<211> LENGTH: 714
<212> TYPE: DNA
<213> ORGANISM: Artificial sequence
<220> FEATURE:
<223> OTHER INFORMATION: TGFBR-IL12RB1 receptor

<400> SEQUENCE: 125

```
atggaggcgg cggtcgctgc tccgcgtccc cggctgctcc tcctcgtgct ggcggcggcg      60
gcggcggcgg cggcggcgct gctcccgggg gcgacggcgt acagtgtttt ctgccacctc     120
tgtacaaaag acaattttac ttgtgtgaca gatgggctct gctttgtctc tgtcacagag     180
accacagaca agttatacaa caacagcatg tgtatagctg aaattgactt aattcctcga     240
gataggccgt ttgtatgtgc accctcttca aaaactgggt ctgtgactac aacatattgc     300
tgcaatcagg accattgcaa taaaatagaa cttccaacta ctgtaaagtc atcacctggc     360
cttggtcctg tggaactggc agctgtcatt gctggaccag tgtgcttcgt ctgcatctca     420
ctcatgttga tggtctatat cagggccgca cggcacctgt gcccgccgct gcccacaccc     480
tgtgccagct ccgccattga gttccctgga gggaaggaga cttggcagtg gatcaaccca     540
gtggacttcc aggaagaggc atccctgcag gaggccctgg tggtagagat gtcctgggac     600
aaaggcgaga ggactgagcc tctcgagaag acagagctac tgagggtgc  ccctgagctg     660 gccctggata cagagttgtc cttggaggat ggagacaggt gcaaggccaa gatg            714
```

<210> SEQ ID NO 126
<211> LENGTH: 403
<212> TYPE: PRT
<213> ORGANISM: Artificial sequence
<220> FEATURE:
<223> OTHER INFORMATION: TGFBR-IL12RB2 receptor

<400> SEQUENCE: 126

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
                35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Gln Gln Lys Val Phe
            180                 185                 190

Val Leu Leu Ala Ala Leu Arg Pro Gln Trp Cys Ser Arg Glu Ile Pro
        195                 200                 205

Asp Pro Ala Asn Ser Thr Cys Ala Lys Lys Tyr Pro Ile Ala Glu Glu
        210                 215                 220

Lys Thr Gln Leu Pro Leu Asp Arg Leu Leu Ile Asp Trp Pro Thr Pro
225                 230                 235                 240

Glu Asp Pro Glu Pro Leu Val Ile Ser Glu Val Leu His Gln Val Thr
                245                 250                 255

Pro Val Phe Arg His Pro Pro Cys Ser Asn Trp Pro Gln Arg Glu Lys
            260                 265                 270

Gly Ile Gln Gly His Gln Ala Ser Glu Lys Asp Met Met His Ser Ala
        275                 280                 285

Ser Ser Pro Pro Pro Arg Ala Leu Gln Ala Glu Ser Arg Gln Leu
290                 295                 300

Val Asp Leu Tyr Lys Val Leu Glu Ser Arg Gly Ser Asp Pro Lys Pro
305                 310                 315                 320

Glu Asn Pro Ala Cys Pro Trp Thr Val Leu Pro Ala Gly Asp Leu Pro
                325                 330                 335

Thr His Asp Gly Tyr Leu Pro Ser Asn Ile Asp Asp Leu Pro Ser His
            340                 345                 350

Glu Ala Pro Leu Ala Asp Ser Leu Glu Glu Leu Glu Pro Gln His Ile
        355                 360                 365

Ser Leu Ser Val Phe Pro Ser Ser Leu His Pro Leu Thr Phe Ser
        370                 375                 380

Cys Gly Asp Lys Leu Thr Leu Asp Gln Leu Lys Met Arg Cys Asp Ser
385                 390                 395                 400

Leu Met Leu
```

```
<210> SEQ ID NO 127
<211> LENGTH: 1209
<212> TYPE: DNA
<213> ORGANISM: Artificial sequence
<220> FEATURE:
<223> OTHER INFORMATION: TGFBR-IL12RB2 receptor

<400> SEQUENCE: 127
atgggtcggg ggctgctcag gggcctgtgg ccgctgcaca tcgtcctgtg gacgcgtatc      60
gccagcacga tcccaccgca cgttcagaag tcggttaata cgacatgat agtcactgac     120
aacaacggtg cagtcaagtt tccacaactg tgtaaatttt gtgatgtgag attttccacc    180
tgtgacaacc agaaatcctg catgagcaac tgcagcatca cctccatctg tgagaagcca    240
caggaagtct gtgtggctgt atggagaaag aatgacgaga cataacact agagacagtt     300
tgccatgacc ccaagctccc ctaccatgac tttattctgg aagatgctgc ttctccaaag    360
tgcattatga aggaaaaaaa aaagcctggt gagactttct tcatgtgttc ctgtagctct    420
gatgagtgca atgacaacat catcttctca gaagaatata acaccagcaa tcctgacttg    480
ttgctagtca tatttcaagt gacaggcatc agcctcctgc caccactggg agttgccata    540
tctgtcatca tcatcttcta ccagcaaaag gtgtttgttc cctagcagc cctcagacct     600
cagtggtgta gcagagaaat tccagatcca gcaaatagca cttgcgctaa gaaatatccc    660
attgcagagg agaagacaca gctgcccttg gacaggctcc tgatagactg gcccacgcct    720
gaagatcctg aaccgctggt catcagtgaa gtccttcatc aagtgacccc agttttcaga    780
catccccct gctccaactg gccacaaagg gaaaaaggaa tccaaggtca tcaggcctct    840
gagaaagaca tgatgcacag tgcctcaagc ccaccacctc aagagctctc caagctgag    900
agcagacaac tggtggatct gtacaaggtg ctggagagca ggggctccga cccaaagcca    960
gaaaacccag cctgtccctg gacggtgctc ccagcaggtg accttcccac ccatgatggc   1020
tacttaccct ccaacataga tgacctcccc tcacatgagg cacctctcgc tgactctctg   1080
gaagaactgg agcctcagca catctccctt tctgttttcc cctcaagttc tcttcaccca   1140
ctcaccttct cctgtggtga taagctgact ctggatcagt taaagatgag gtgtgactcc   1200
ctcatgctc                                                           1209

<210> SEQ ID NO 128
<211> LENGTH: 238
<212> TYPE: PRT
<213> ORGANISM: Artificial sequence
<220> FEATURE:
<223> OTHER INFORMATION: PD1-CTM-CD28 receptor

<400> SEQUENCE: 128

Met Gln Ile Pro Gln Ala Pro Trp Pro Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95
```

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Phe Trp Val Leu Val Val
                165                 170                 175

Val Gly Gly Val Leu Ala Cys Tyr Ser Leu Leu Val Thr Val Ala Phe
            180                 185                 190

Ile Ile Phe Trp Val Arg Ser Lys Arg Ser Arg Leu Leu His Ser Asp
        195                 200                 205

Tyr Met Asn Met Thr Pro Arg Arg Pro Gly Pro Thr Arg Lys His Tyr
    210                 215                 220

Gln Pro Tyr Ala Pro Pro Arg Asp Phe Ala Ala Tyr Arg Ser
225                 230                 235

<210> SEQ ID NO 129
<211> LENGTH: 714
<212> TYPE: DNA
<213> ORGANISM: Artificial sequence
<220> FEATURE:
<223> OTHER INFORMATION: PD1-CTM-CD28 receptor

<400> SEQUENCE: 129
atgcagatcc cacaggcgcc ctggccagtc gtctgggcgg tgctacaact gggctggcgg      60
ccaggatggt tcttagactc cccagacagg ccctggaacc ccccaccctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg gggccatctc cctggccccc aaggcgcaga tcaaagagag cctgcgggca     420
gagctcaggg tgacagagag aagggcagaa gtgcccacag cccacccag ccctcacccc     480 aggccagccg gccagttcca aaccctggtg ttttgggtgc tggtggtggt tggtggagtc     540
ctggcttgct atagcttgct agtaacagtg gcctttatta ttttctgggt gaggagtaag     600
aggagcaggc tcctgcacag tgactacatg aacatgactc ccgccgccc gggcccacc      660 cgcaagcatt accagcccta tgccccacca cgcgacttcg cagcctatcg ctcc          714

<210> SEQ ID NO 130
<211> LENGTH: 232
<212> TYPE: PRT
<213> ORGANISM: Artificial sequence
<220> FEATURE:
<223> OTHER INFORMATION: PD1-PTM-CD28 receptor

<400> SEQUENCE: 130

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

```
Asn Ala Thr Phe Thr Cys Ser Phe Ser Asn Thr Ser Glu Ser Phe Val
     50                  55                  60

Leu Asn Trp Tyr Arg Met Ser Pro Ser Asn Gln Thr Asp Lys Leu Ala
 65              70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
             100                 105                 110

Ala Arg Arg Asn Asp Ser Gly Thr Tyr Leu Cys Gly Ala Ile Ser Leu
         115                 120                 125

Ala Pro Lys Leu Gln Ile Lys Glu Ser Leu Arg Ala Glu Leu Arg Val
     130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                 165                 170                 175

Leu Leu Gly Ser Leu Val Leu Leu Val Trp Val Leu Ala Val Ile Arg
             180                 185                 190

Ser Lys Arg Ser Arg Leu Leu His Ser Asp Tyr Met Asn Met Thr Pro
         195                 200                 205

Arg Arg Pro Gly Pro Thr Arg Lys His Tyr Gln Pro Tyr Ala Pro Pro
     210                 215                 220

Arg Asp Phe Ala Ala Tyr Arg Ser
225                 230
```

<210> SEQ ID NO 131
<211> LENGTH: 696
<212> TYPE: DNA
<213> ORGANISM: Artificial sequence
<220> FEATURE:
<223> OTHER INFORMATION: PD1-PTM-CD28 receptor

<400> SEQUENCE: 131

```
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agcccagca accagacgga caagctggcc      240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg ggccatctc cctggccccc aaggcgcaga tcaaagagag cctgcgggca     420
gagctcaggg tgacagagag aagggcagaa gtgcccacag cccaccccag ccctcacccc     480
aggccagccg gccagttcca aaccctggtg gttggtgtcg tgggcggcct gctgggcagc     540
ctggtgctgc tagtctgggt cctggccgtc atcaggagta gaggagcag gctcctgcac     600
agtgactaca tgaacatgac tccccgccgc cccgggccca cccgcaagca ttaccagccc     660
tatgccccac cacgcgactt cgcagcctat cgctcc                               696
```

<210> SEQ ID NO 132
<211> LENGTH: 232
<212> TYPE: PRT
<213> ORGANISM: Artificial sequence
<220> FEATURE:
<223> OTHER INFORMATION: PD1A132L-PTM-CD28 receptor

<400> SEQUENCE: 132

```
Met Gln Ile Pro Gln Ala Pro Trp Pro Val Val Trp Ala Val Leu Gln
1               5                   10                  15
Leu Gly Trp Arg Pro Gly Trp Phe Leu Asp Ser Pro Asp Arg Pro Trp
            20                  25                  30
Asn Pro Pro Thr Phe Ser Pro Ala Leu Leu Val Val Thr Glu Gly Asp
        35                  40                  45
Asn Ala Thr Phe Thr Cys Ser Phe Ser Asn Thr Ser Glu Ser Phe Val
    50                  55                  60
Leu Asn Trp Tyr Arg Met Ser Pro Ser Asn Gln Thr Asp Lys Leu Ala
65                  70                  75                  80
Ala Phe Pro Glu Asp Arg Ser Gln Pro Gly Gln Asp Cys Arg Phe Arg
                85                  90                  95
Val Thr Gln Leu Pro Asn Gly Arg Asp Phe His Met Ser Val Val Arg
            100                 105                 110
Ala Arg Arg Asn Asp Ser Gly Thr Tyr Leu Cys Gly Ala Ile Ser Leu
        115                 120                 125
Ala Pro Lys Leu Gln Ile Lys Glu Ser Leu Arg Ala Glu Leu Arg Val
    130                 135                 140
Thr Glu Arg Arg Ala Glu Val Pro Thr Ala His Pro Ser Pro Ser Pro
145                 150                 155                 160
Arg Pro Ala Gly Gln Phe Gln Thr Leu Val Val Gly Val Val Gly Gly
                165                 170                 175
Leu Leu Gly Ser Leu Val Leu Leu Val Trp Val Leu Ala Val Ile Arg
            180                 185                 190
Ser Lys Arg Ser Arg Leu Leu His Ser Asp Tyr Met Asn Met Thr Pro
        195                 200                 205
Arg Arg Pro Gly Pro Thr Arg Lys His Tyr Gln Pro Tyr Ala Pro Pro
    210                 215                 220
Arg Asp Phe Ala Ala Tyr Arg Ser
225                 230
```

<210> SEQ ID NO 133
<211> LENGTH: 693
<212> TYPE: DNA
<213> ORGANISM: Artificial sequence
<220> FEATURE:
<223> OTHER INFORMATION: PD1A132L-PTM-CD28 receptor

<400> SEQUENCE: 133

```
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcaggccc ggcgcaatga cagcggcacc     360
tacctctgtg gggccatctc cctggccccc aagctgcaga tcaaagagag cctgcgggca     420
gagctcaggg tgacagagag aagggcagaa gtgcccacag cccacccag ccctcacccc      480
aggccagccg ccagttcca aaccctggtg gttggtgtcg tgggcggcct gctgggcagc     540
ctggtgctgc tagtctgggt cctggccgtc atcaggagta agaggagcag gctcctgcac     600
```

```
agtgactaca tgaacatgac tccccgccgc cccgggccca cccgcaagca ttaccagccc      660
tatgccccac cacgcgactt cgcagcctat cgc                                  693
```

<210> SEQ ID NO 134
<211> LENGTH: 4
<212> TYPE: PRT
<213> ORGANISM: Artificial sequence
<220> FEATURE:
<223> OTHER INFORMATION: furin cleavage site
<220> FEATURE:
<221> NAME/KEY: misc_feature
<222> LOCATION: (2)..(2)
<223> OTHER INFORMATION: Xaa can be any naturally occurring amino acid

<400> SEQUENCE: 134

Arg Xaa Lys Arg
1

<210> SEQ ID NO 135
<211> LENGTH: 4
<212> TYPE: PRT
<213> ORGANISM: Artificial sequence
<220> FEATURE:
<223> OTHER INFORMATION: furin cleavage site
<220> FEATURE:
<221> NAME/KEY: misc_feature
<222> LOCATION: (2)..(2)
<223> OTHER INFORMATION: Xaa can be any naturally occurring amino acid

<400> SEQUENCE: 135

Arg Xaa Arg Arg
1

<210> SEQ ID NO 136
<211> LENGTH: 5
<212> TYPE: PRT
<213> ORGANISM: Artificial sequence
<220> FEATURE:
<223> OTHER INFORMATION: furin cleavage site
<220> FEATURE:
<221> NAME/KEY: misc_feature
<222> LOCATION: (1)..(1)
<223> OTHER INFORMATION: Xaa is K or R
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa is K or R

<400> SEQUENCE: 136

Xaa Arg Xaa Xaa Arg
1               5

<210> SEQ ID NO 137
<211> LENGTH: 4
<212> TYPE: PRT
<213> ORGANISM: Artificial sequence
<220> FEATURE:
<223> OTHER INFORMATION: furin cleavage site
<220> FEATURE:
<221> NAME/KEY: misc_feature
<222> LOCATION: (2)..(3)
<223> OTHER INFORMATION: Xaa can be any naturally occurring amino acid

<400> SEQUENCE: 137

Arg Xaa Xaa Arg
1

```
<210> SEQ ID NO 138
<211> LENGTH: 4
<212> TYPE: PRT
<213> ORGANISM: Artificial sequence
<220> FEATURE:
<223> OTHER INFORMATION: furin cleavage site

<400> SEQUENCE: 138

Arg Gln Lys Arg
1

<210> SEQ ID NO 139
<211> LENGTH: 96
<212> TYPE: DNA
<213> ORGANISM: Artificial sequence
<220> FEATURE:
<223> OTHER INFORMATION: F-GS2-T2A linker

<400> SEQUENCE: 139
cgtgcgaaga ggggcggcgg gggctccggc gggggaggca gtgagggccg cggctccctg      60
ctgacctgcg gagatgtaga agagaaccca ggcccc                                96

<210> SEQ ID NO 140
<211> LENGTH: 32
<212> TYPE: PRT
<213> ORGANISM: Artificial sequence
<220> FEATURE:
<223> OTHER INFORMATION: F-GS2-T2A linker

<400> SEQUENCE: 140

Arg Ala Lys Arg Gly Gly Gly Gly Ser Gly Gly Gly Gly Ser Glu Gly
1               5                   10                  15

Arg Gly Ser Leu Leu Thr Cys Gly Asp Val Glu Glu Asn Pro Gly Pro
            20                  25                  30
```

USE OF GENE EDITING TO GENERATE UNIVERSAL TCR RE-DIRECTED T CELLS FOR ADOPTIVE IMMUNOTHERAPY

CROSS-REFERENCE TO RELATED APPLICATION

The present application is entitled to priority under 35 U.S.C. § 119(e) to U.S. Provisional Patent Application No. 62/485,166, filed Apr. 13, 2017, which is hereby incorporated by reference in its entirety herein.

BACKGROUND OF THE INVENTION

Cell-based immunotherapy is receiving increasing attention as a viable approach for treating cancer. For example, T cells that have been genetically engineered to target CD19 have been used successfully in the clinic for the treatment of certain B cell leukemias. With this clinical success, there is now increased attention on immune cell therapy for treating solid tumor cancers. However, to be successful, immune cell must address a number of technical challenges including the immune cell dysfunction that may arise from exposure to the immunosuppressive conditions of the tumor microenvironment (so-called "T cell exhaustion"). In disease settings such as solid tumors, characteristics of exhaustion include continuous enhancement of T cell dysfunction due to persistent antigen exposure, an increased expression of multiple inhibitory receptors, the progressive loss of effector cytokine secretion, an altered cell metabolism and a markedly different transcriptional profile. T cell exhaustion is often associated with inefficient control of persisting infections and tumors, but revitalization of exhausted T cells can reinvigorate immunity.

Furthermore, while the use of allogeneic immune cells (e.g., chimeric antigen receptor (CAR) or T cell receptor (TCR) modified T cells) as universal effector cells provides an alternative to and potentially improves current cell therapy against cancers and infectious diseases, the endogenous TCR/CD3 complexes present on these immune cells may cause graft versus host disease (GVHD) if not depleted from the final T cell products. However, it is not possible to separate CD3+ T cells that express endogenous TCR (which can cause GVHD) from CD3+ T cells that express transferred TCR and CD3+ T cells that express both endogenous TCR and transgenic TCR. Moreover, although TCR ablated CD3 negative T cells can be stimulated and expanded using multiple strategies (WO2016069283), these re-stimulated CD3 negative T cells are difficult to transduce, which renders unfeasible the generation of universal T cells by transducing re-stimulated sorted CD3 negative gene edited T cells. Furthermore, using re-stimulated T cells potentially reduces the treatment efficacy, complicates the manufacturing process, and increases the cost.

A need exists for novel immune cell therapeutics that address these issues. The present invention satisfies this need.

SUMMARY OF THE INVENTION

Provided herein are genetically modified immune cells (e.g., isolated T cells) which are capable of inducibly expressing an exogenous receptor (e.g., a chimeric antigen receptor (CAR) or a transgenic T cell receptor (TCR)) under selected conditions.

In certain aspects, the disclosure provides a genetically modified immune cell comprising an exogenous nucleic acid encoding an exogenous receptor, wherein the exogenous receptor selectively binds to a tumor antigen expressed on a tumor, the cell further comprising an inducible gene expression system, wherein when an induction agent is administered to the cell, the gene expression system is induced and the exogenous receptor is expressed on the surface of the immune cell.

In certain embodiments, the inducible gene expression system comprises: (a) a first nucleic acid comprising a constitutive promoter operably linked to a nucleic acid sequence encoding a transactivator protein; and (b) a second nucleic acid comprising an inducible promoter operably linked to a nucleic acid sequence encoding the exogenous receptor, wherein the second nucleic acid is in reverse orientation to the first nucleic acid.

In certain embodiments, the transactivator protein is a reverse Tet repressor (rTetR). In certain embodiments, the transactivator protein is a reverse tetracycline-controlled transactivator protein (rtTA). In certain embodiments, the transactivator protein is a Tet-On 3G transactivator protein. In other embodiments, the inducible promoter comprises a Tet operator sequence. In other embodiments, the inducible promoter comprises one or more repeats of the Tet operator sequence. In other embodiments, the inducible promoter is a TRE3GS promoter.

In other embodiments, the constitutive promoter drives constitutive expression of the transactivator protein. In one embodiment, the constitutive promoter is a human constitutive promoter, e.g., a human phosphoglycerate kinase 1 (PGK1) promoter or a human elongation factor 1 alpha (EF1α) promoter.

In other embodiments, the induction agent is tetracycline or a derivative thereof, e.g., doxycycline.

In certain embodiments, the inducible gene expression system encodes a reverse Tet transactivator (rtTA) fusion protein and comprises at least one promoter fused downstream of at least one Tet-operator sequence.

In certain aspects the genetically modified immune cells comprise a tetracycline (Tet)-On inducible gene expression system, wherein the Tet-On inducible gene expression system comprises a reverse Tet transactivator (rtTA) fusion protein and at least one promoter fused downstream of at least one Tet-operator sequence.

In certain embodiments, the disclosure provides an isolated nucleic acid encoding an exogenous receptor (e.g., a chimeric antigen receptor (CAR) or transgenic T cell receptor (TCR)), the expression of which is under the control of a tetracycline (Tet)-On inducible gene expression system, wherein the Tet-On inducible gene expression system comprises a reverse Tet transactivator (rtTA) fusion protein and at least one promoter fused downstream of at least one Tet-operator sequence.

In other embodiments, the disclosure provides a genetically modified T cell comprising an exogenous nucleic acid encoding an exogenous receptor (e.g., a chimeric antigen receptor (CAR) or transgenic TCR) under the control of a tetracycline (Tet)-On inducible gene expression system, wherein the Tet-On inducible gene expression system comprises a reverse Tet transactivator (rtTA) fusion protein and at least one promoter fused downstream of at least one Tet-operator sequence, wherein when doxycycline (Dox) is administered to the cell, the gene expression system is induced and the TCR is expressed.

In other embodiments, the inducible promoter induces expression of the exogenous TCR or CAR is in a dose-dependent manner with respect to the amount of the induction agent present. In certain embodiments, withdrawal of the induction agent results in a reduction in the expression of the exogeneous receptor.

In certain embodiments, the exogenous receptor is a T cell receptor (TCR), e.g., wild-type TCR, a high affinity TCR, or a chimeric TCR. In certain embodiments, the exogenous TCR comprises at least one disulfide bond. In certain embodiments, the exogenous TCR comprises a TCR alpha chain and a TCR beta chain.

In certain embodiments, the exogenous receptor is a chimeric antigen receptor (CAR). In one embodiment, the CAR comprises an antigen-binding domain, a transmembrane domain, and an intracellular domain. In one embodiment, the antigen-binding domain is selected from the group consisting of an antibody, an scFv, and a Fab. In one embodiment, the CAR further comprising a hinge domain. Exemplary hinge domains include a Fc fragment of an antibody, a hinge region of an antibody, a CH2 region of an antibody, a CH3 region of an antibody, an artificial hinge domain, a hinge comprising an amino acid sequence of CD8, or any combination thereof. In certain embodiments, the transmembrane domain is selected from the group consisting of an artificial hydrophobic sequence and transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, CD134, CD137, and CD154. In other embodiments, the intracellular domain comprises at least one co-stimulatory domain selected from the group consisting of co-stimulatory domains of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS, NKG2C, and B7-H3. In other embodiments, the intracellular domain comprises an intracellular domain selected from the group consisting of cytoplasmic signaling domains of a human CD3 zeta chain, FcγRIII, FcεRI, a cytoplasmic tail of an Fc receptor, an immunoreceptor tyrosine-based activation motif (ITAM) bearing cytoplasmic receptors, TCR zeta, FcR gamma, FcR beta, CD3 gamma, CD3 delta, CD3 epsilon, CD5, CD22, CD79a, CD79b, and CD66d.

In certain embodiments, the immune cell is a genetically modified T cell. In other embodiments, the cell is an allogeneic cell. In other embodiments, the cell is an autologous cell. In other embodiments, the cell is a human cell.

In yet other embodiments, the modified immune cell further comprises an insertion and/or deletion in one or more gene loci each encoding an endogenous immune protein, wherein the insertion and/or deletion is capable of down-regulating expression of the endogenous immune protein. In certain embodiments, the insertion and/or deletion is the result of gene editing, e.g., CRISPR/Cas9 gene editing. In certain embodiments, expression of the endogenous immune protein is upregulated or downregulated in the presence of the tumor. In certain embodiments, the endogenous immune protein is selected from the group consisting of TRAC, TRBC, B2M, and CIITA. In other embodiments, the endogenous immune protein is an immune checkpoint protein, e.g., PD1 or PDL1.

In certain embodiments, the immune cell further comprises a switch receptor. Exemplary switch receptors include PD1-CTM-CD28, PD1-PTM-CD28, and PD1$^{A132L}$-PTM-CD28. In other embodiments, the switch receptor is TGFβR-IL12Rβ1 or TGFβR-IL12Rβ2.

In certain embodiments, the genetically modified immune cell (e.g., T cell) further comprises at least one gene that has undergone gene editing (i.e., is gene edited). In certain embodiments, the gene editing is performed using the CRISPR/Cas9 system.

In certain aspects the genetically modified immune cell comprises a tetracycline (Tet)-On inducible gene expression system, wherein the Tet-On inducible gene expression system comprises a reverse Tet transactivator (rtTA) fusion protein and at least one promoter fused downstream of at least one Tet-operator sequence.

In certain embodiments, the disclosure provides an isolated nucleic acid encoding an exogenous receptor (e.g., a chimeric antigen receptor (CAR) or transgenic T cell receptor (TCR)), the expression of which is under the control of a tetracycline (Tet)-On inducible gene expression system, wherein the Tet-On inducible gene expression system comprises a reverse Tet transactivator (rtTA) fusion protein and at least one promoter fused downstream of at least one Tet-operator sequence. In other embodiments, the disclosure provides a genetically modified T cell comprising an exogenous nucleic acid encoding an exogenous receptor (e.g., a chimeric antigen receptor (CAR) or transgenic TCR) under the control of a tetracycline (Tet)-On inducible gene expression system, wherein the Tet-On inducible gene expression system comprises a reverse Tet transactivator (rtTA) fusion protein and at least one promoter fused downstream of at least one Tet-operator sequence, wherein when doxycycline (Dox) is administered to the cell, the gene expression system is induced and the TCR is expressed.

In other aspects, the disclosure provides a method of generating a genetically modified immune cell, the method comprising introducing into the immune cell a nucleic acid comprising an exogenous nucleic acid encoding an exogenous receptor under the control of an inducible expression system, wherein the exogenous receptor selectively binds to a tumor antigen expressed on a tumor, wherein when an induction agent is administered to the cell, the gene expression system is induced and the exogenous receptor is expressed on the surface of the immune cell.

In certain embodiments, the inducible expression system comprises: (a) first nucleic acid comprising a constitutive promoter operably linked to a nucleic acid sequence encoding a transactivator protein; and (b) a second nucleic acid comprising an inducible promoter operably linked to a nucleic acid sequence encoding an exogenous receptor which selectively binds to a tumor antigen expressed on a tumor, wherein the second nucleic acid is in reverse orientation to the first nucleic acid.

In certain embodiments, the nucleic acid is introduced by viral transduction. In certain embodiments, the viral transduction comprises contacting the cell with a viral vector comprising the nucleic acid. In certain embodiments, the viral vector is a retroviral vector.

In certain embodiments, the nucleic acid encoding a switch receptor is introduced by viral transduction. In certain embodiments, the viral transduction comprises contacting the cell with a viral vector comprising the nucleic acid encoding a switch receptor.

In certain embodiments, the method further comprises introducing into the immune cell one or more polypeptides and/or nucleic acids capable of downregulating expression of one or more endogenous immune proteins. In certain embodiments, the one or more polypeptides and/or nucleic acids capable of downregulating expression comprises a CRISPR system. In certain embodiments, the CRISPR system comprises a CRISPR nuclease and a guide RNA. In certain embodiments, the guide RNA comprises a guide sequence that is complementary so as to bind with target sequence of an endogenous gene. In certain embodiments, the CRISPR nuclease and the guide RNA comprise a ribonucleoprotein (RNP) complex.

In certain embodiments, the expression of the endogenous immune protein is upregulated or downregulated in the presence of the tumor. In certain embodiments, the endogenous immune protein is selected from the group consisting of TRAC, TRBC, B2M, and CIITA. In certain embodiments, the target sequence is within the TRAC gene and wherein the guide RNA comprises a nucleic acid sequence set forth in any one of SEQ ID NOs: 85-97. In certain embodiments, the target sequence is within the TRBC gene and wherein the guide RNA comprises a nucleic acid sequence set forth in any one of SEQ ID NOs: 1-24. In certain embodiments, the target sequence is within the B2M gene and wherein the guide RNA comprises a nucleic acid sequence set forth in any one of SEQ ID NOs: 73-84. In certain embodiments, the target sequence is within the CIITA gene and wherein the guide RNA comprises a nucleic acid sequence set forth in any one of SEQ ID NOs: 25-48. In certain embodiments, the endogenous immune protein is an immune checkpoint protein, e.g., PD1 or PDL1. In certain embodiments, the target sequence is within the PD1 gene and wherein the guide RNA comprises a nucleic acid sequence set forth in any one of SEQ ID NOs: 49-72.

In other aspects, the disclosure provides a method for adoptive cell transfer therapy comprising administering to a subject in need thereof a population of immune cells comprising a modified immune cell (e.g., T cell) of the disclosure.

In other aspects, the disclosure provides a method of generating a population of modified T cells, the method comprising: a) stimulating a population of isolated T cells, thereby generating a population of stimulated T cells; b) introducing into the population of stimulated T cells a nucleic acid comprising an inducible TCR expression system, thereby generating a population of modified T cells; c) introducing into the population of modified T cells one or more polypeptides and/or nucleic acids capable of downregulating expression of an endogenous immune protein selected, thereby generating a population of gene edited modified T cells; d) depleting CD3+ T cells from the population of gene edited modified T cells and isolating a population of CD3− gene edited modified T cells; and e) contacting the population of CD3− gene edited modified T cells with an induction agent to induce expression of the exogenous TCR, thereby generating a population of modified T cells.

In certain embodiments, the step of stimulating a population of isolated T cells comprises contacting the population of isolated T cells with an anti-CD3 antibody and/or an anti-CD28 antibody. In one embodiment, the anti-CD3 antibody and/or the anti-CD28 antibody is coated on a magnetic bead. In another embodiment, the step of depleting CD3+ T cells from the population of gene edited modified T cells comprises removing the anti-CD3 antibody and/or the anti-CD28 antibody. In another embodiment, the step of depleting CD3+ T cells from the population of gene edited modified T cells comprises removing the anti-CD3 antibody and/or the anti-CD28 antibody coated magnetic bead.

In other embodiments, the method further comprises introducing into the population of stimulated T cells a nucleic acid encoding a switch receptor.

In another aspect, the invention provides a method for generating a genetically modified immune cell (e.g., T cell) comprising an exogenous receptor (e.g., a CAR or a transgenic TCR), the method comprising: (a) stimulating a population of immune cells (e.g., T cells) with CD3 and/or CD28, (b) transducing the immune cells with a Tet-On gene inducible gene expression system capable of inducibly expressing the exogenous receptor, wherein the Tet-On inducible gene expression system comprises a reverse Tet transactivator (rtTA) fusion protein and at least one promoter fused downstream of at least one Tet-operator sequence, (c) electroporating the immune cells with Cas9 RNA or Cas9 protein and a guide RNA, (d) depleting CD3+ T cells, (e) harvesting CD3− T cells, and (e) administering doxycycline to the immune cells to induce expression of the exogenous receptor on the immune cells.

In other aspects, the disclosure provides a pharmaceutical composition comprising the modified immune cells generated by the methods of the disclosure and a pharmaceutically acceptable carrier.

In other aspects, the disclosure provides a method of treating a tumor cancer in a subject in need thereof, the method comprising administering to the subject a pharmaceutical composition of the disclosure. In other embodiments, the method further comprises administering an inducing agent to the subject, thereby inducing expression of the exogenous receptor in the subject. In certain embodiments, the immune cell is contacted with the inducing agent prior to administration of the immune cell to the subject.

In other aspects, the disclosure provides a method of preventing T cell exhaustion in a subject in need thereof, the method comprising administering to the subject the pharmaceutical composition of the disclosure and an inducing agent, wherein the inducing agent induces expression of the exogenous receptor at a tumor site in the subject. In one embodiment, the immune cell is contacted with the inducing agent prior to administration of the immune cell to the subject. In other embodiments, the method further comprises the step of continual administration of the induction agent to the subject to induce expression of the exogenous receptor at a tumor site within the subject.

In other embodiments, the method further comprises the step of withholding administration of the induction agent to the subject to reduce expression of the exogenous receptor within the subject, thereby preventing T cell exhaustion. In other embodiments, the method further comprises the step of re-administering the induction agent to the subject to induce expression of the exogenous receptor within the subject. In certain embodiments, the inducing agent is tetracycline, doxycycline or an analog thereof.

In other aspects, the disclosure provides a method of treating a disease or condition in a subject in need thereof comprising administering to the subject a population of modified immune cells comprising the modified immune cell (T cell) of the disclosure. In certain embodiments, the disease or condition is selected from the group consisting of an infectious disease, an autoimmune disease and a cancer. In certain exemplary embodiment, the subject is a human. In other embodiments, the method further comprises administering a secondary treatment.

In other aspects, the disclosure provides a method of treating a disease or condition in a subject in need thereof comprising administering to the subject a genetically modified allogeneic immune cell (e.g., T cell) comprising an exogenous nucleic acid encoding an exogenous receptor (e.g., CAR or transgenic TCR) comprising a tetracycline (Tet)-On inducible gene expression system, wherein the Tet-On inducible gene expression system comprises a reverse Tet transactivator (rtTA) fusion protein and at least one promoter fused downstream of at least one Tet-operator sequence, wherein when doxycycline (Dox) is administered to the cell, the gene expression system is induced and the exogenous receptor is expressed.

In yet other aspects, the disclosure provides a method of treating a disease or condition in a subject in need thereof comprising administering to the subject a genetically modified autologous immune cell (e.g., T-cell) comprising an exogenous nucleic acid encoding an exogenous receptor (e.g., a transgenic TCR or a CAR) comprising a tetracycline (Tet)-On inducible gene expression system, wherein the Tet-On inducible gene expression system comprises a reverse Tet transactivator (rtTA) fusion protein and at least one promoter fused downstream of at least one Tet-operator sequence, wherein when doxycycline (Dox) is administered to the cell, the gene expression system is induced and the exogenous receptor is expressed.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIGS. 4A-4C are a series of plots and a table illustrating CIITA gene disruption efficiency in T cells screened by electroporation of CRISPR/CAS9 RNA for gRNAs targeting CIITA.

FIGS. 5A-5C are a series of plots and a table illustrating PD-1 gene disruption efficiency in T cells screened by electroporation of CRISPR/CAS9 RNA for gRNAs targeting PD-1.

FIG. 17 is a schematic of the universal TCR T cell production. CD3/CD28 Dynabead stimulated T cells were transduced by pRetoX-TetONE.8.TCR (TETON RVV) on day 2. Day 3 and day 4, the transduced T cells were electroporated with CRISPR/CAS9 RNA. CD3+ T cells were depleted on day 8 and T cells harvested on day 10.

FIG. 18 is a series of plots illustrating NY-ESO-1 TCR (vb8) expression of lentiviral vector pTRP.8F.TCR transduced T cells (LVV T cells) and pRetoX-TetONE.8.TCR transduced T cells that were cultured in the presence of different concentration of 100 ng/ml Dox for 24 hours (RVV TETONE T cells).

FIGS. 24A-24C are a series of plots illustrating transgenic TCR (vb8) and NY-ESO-1 tetramer detection of: 1.) lenti-viral vector transduced, CRISPR gene edited T cells; 2.) TETONE retroviral vector transduced, CRISPR gene edited T cells before CD3 depletion after Dox induction and 3.) TETONE retroviral vector transduced, CRISPR gene edited and CD3 depleted T cells after Dox induction. 8F LVV, pTRP.8F.TCR; TETONE.8F, pRetroX.TetONE.8F.TCR; KO2, TRAC and TRBC gene disruption; KO4, TRAC, TRBC, B2M and CIITA gene disruption; No TD, non-transduction.

FIGS. 25A-25C are a series of plots illustrating CD107a up-regulation of the universal NY-ESO-1 TCR T cells. NY-ESO-1/HLA-A2 positive tumor lines A549-ESO and Nalm6-ESO (A549 was used as negative control) were used to stimulate the following T cells for 4 h for CD107a assay: 1.) lentiviral vector transduced, CRISPR gene edited; 2.) TETONE retroviral vector transduced, CRISPR gene edited T cells before CD3 depletion after Dox induction and 3.) TETONE retroviral vector transduced, CRISPR gene edited and CD3 depleted T cells after Dox induction. 8F LVV, pTRP.8F.TCR; TETONE.8F, pRetroX.TetONE.8F.TCR; KO2, TRAC and TRBC gene disruption; KO4, TRAC, TRBC, B2M and CIITA gene disruption; No TD, non-transduction; No KO, non-gene editing.

FIG. 26 is a table showing gRNA sequences for TRBC (left columns), CIITA (middle columns) and PD-1 (right columns). gRNAs 1-24 for TRBC (left columns) correspond to SEQ ID NOs: 1-24; gRNAs 1-24 for CIITA (middle columns) correspond to SEQ ID NOs: 25-48; and gRNAs 1-24 for PD1 (right columns) correspond to SEQ ID NOs: 49-72.

FIG. 27 is a table showing gRNA sequences for B2M (left columns) and TRAC (right columns). gRNAs 1-12 for B2M (left columns) correspond to SEQ ID NOs: 73-84; and gRNAs 1-13 of TRAC (right columns) correspond to SEQ ID NOs: 85-97.

FIG. 28 is a table showing selected gRNAs for cloning.

FIGS. 32A-32F depict plots showing expression of CD107a (FIGS. 32A and 32D), IFNγ (FIGS. 32B and 32E), and TNFα (FIGS. 32C and 32F) in TILs as indicated after coculture with A549 or A549ESO.

DETAILED DESCRIPTION OF THE INVENTION

Definitions

Figure 1:
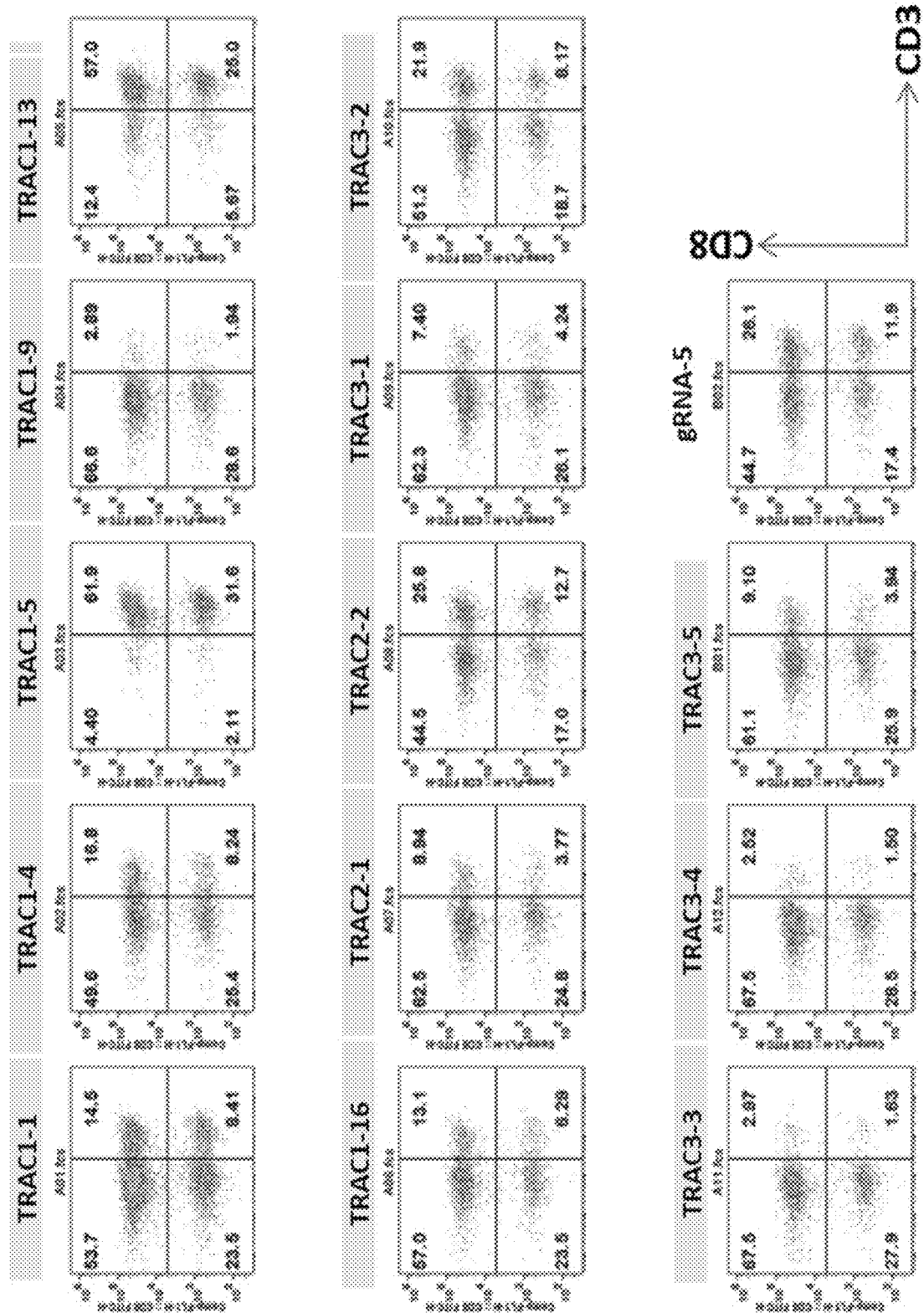
FIG. 1 is a series of plots illustrating TRAC gene disruption efficiency in T cells screened by electroporation of CRISPR/CAS9 RNA for gRNAs targeting TRAC.
Figure 2A:
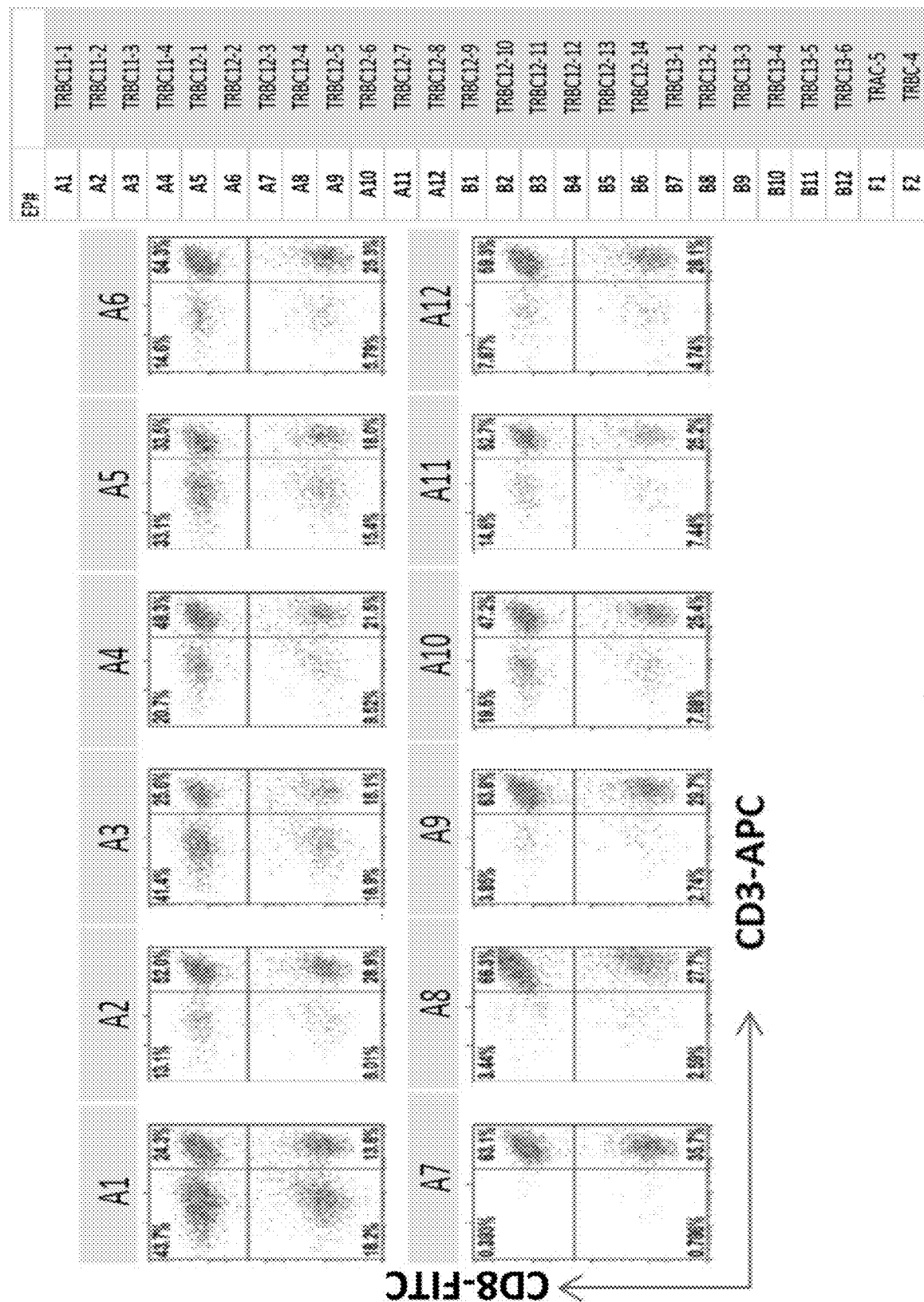
FIGS. 2A-2B are a series of plots and a table illustrating TRBC gene disruption efficiency in T cells screened by electroporation of CRISPR/CAS9 RNA for gRNAs targeting TRBC.
Figure 2B:
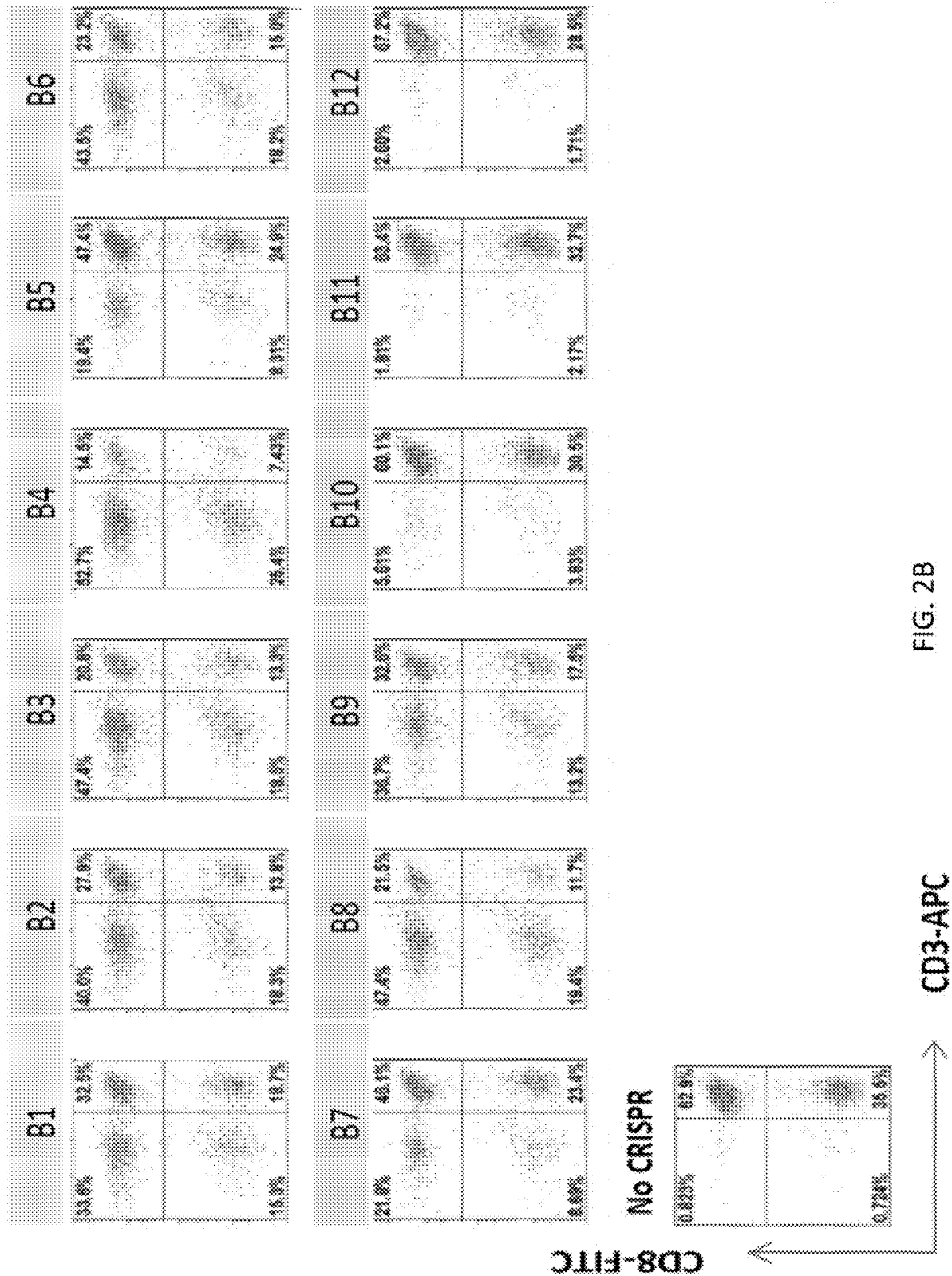
Figure 3:
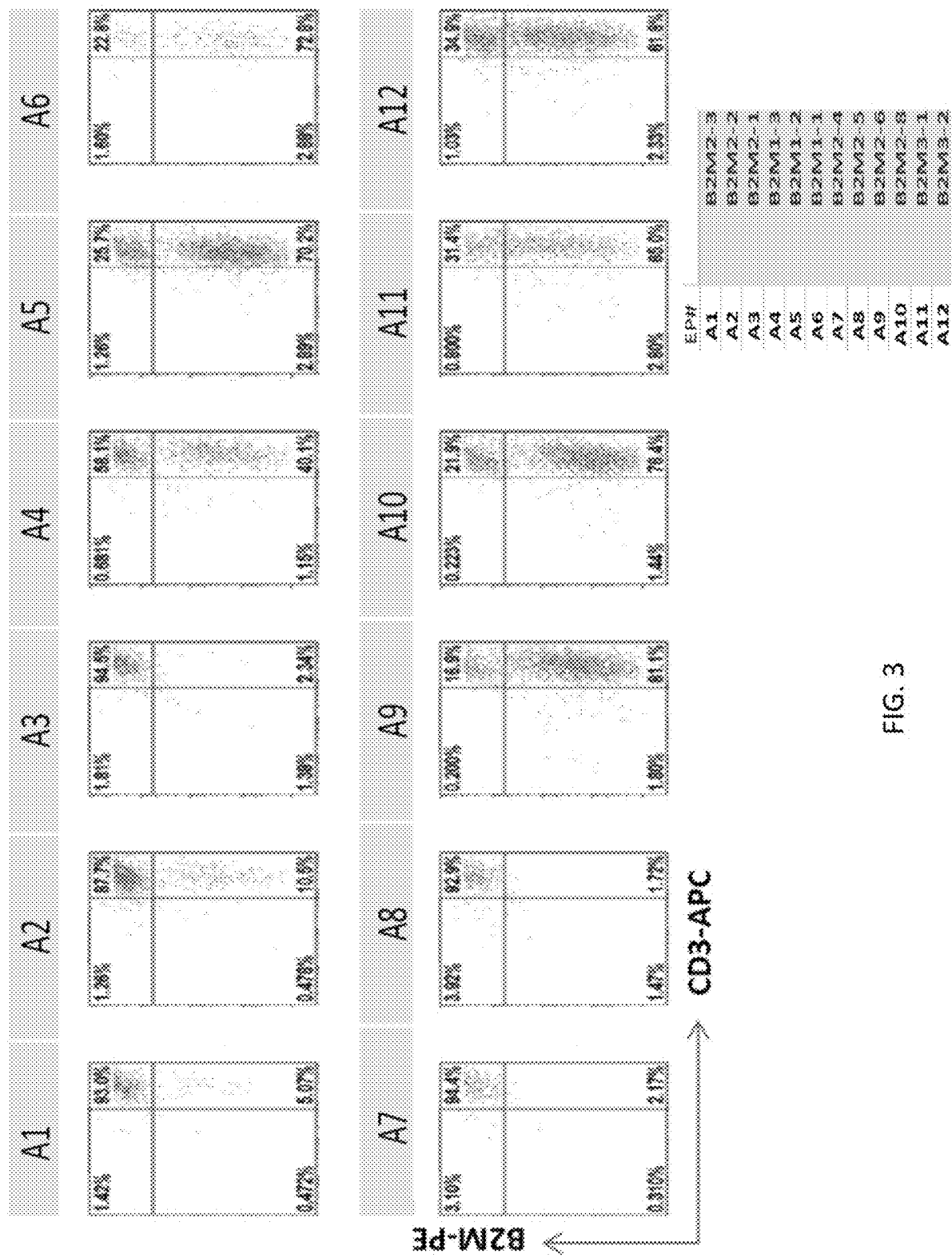
FIG. 3 is a series of plots and a table illustrating B2M gene disruption efficiency in T cells screened by electroporation of CRISPR/CAS9 RNA for gRNAs targeting B2M.
Figure 4A:
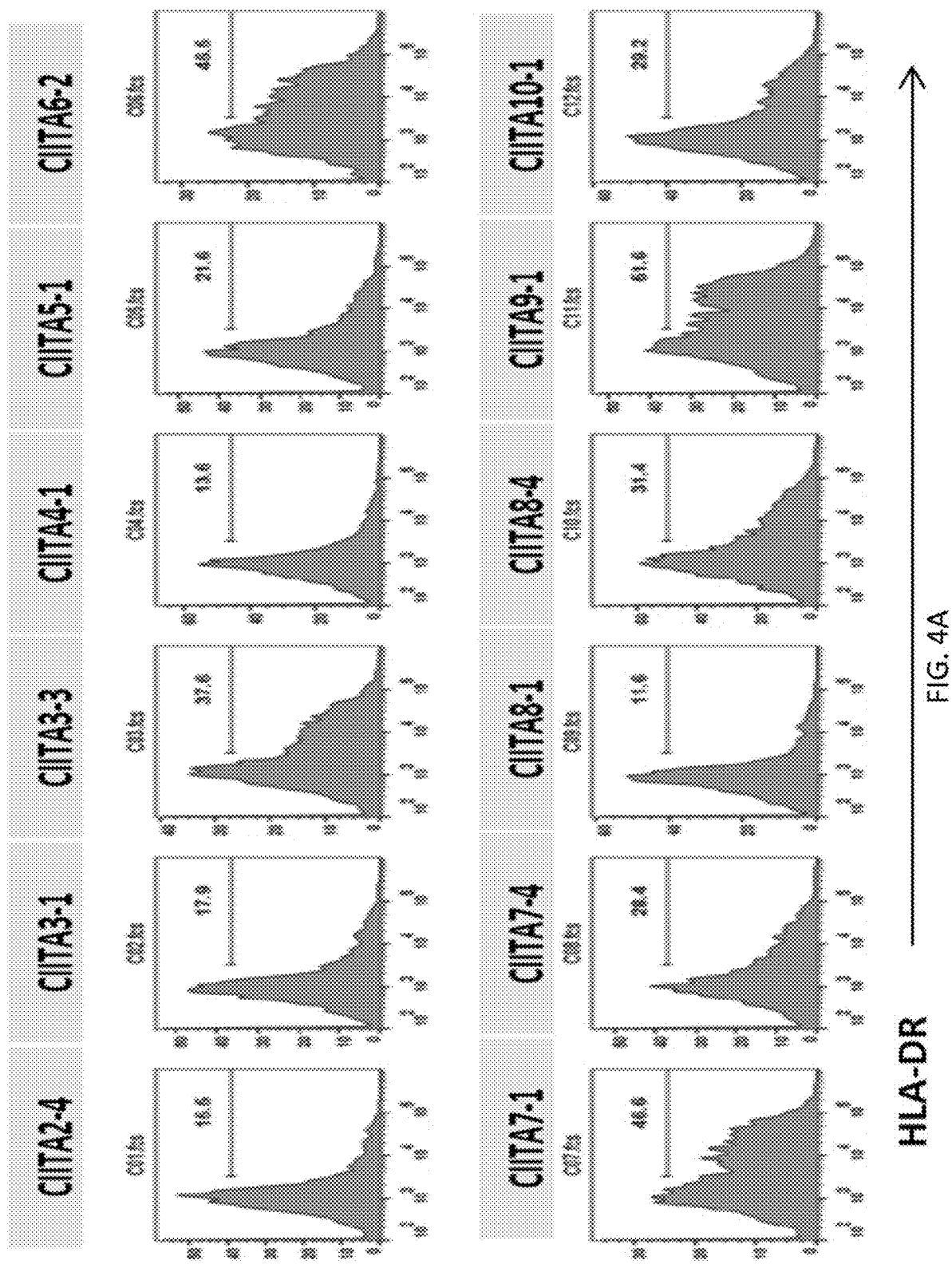
Figure 4B:
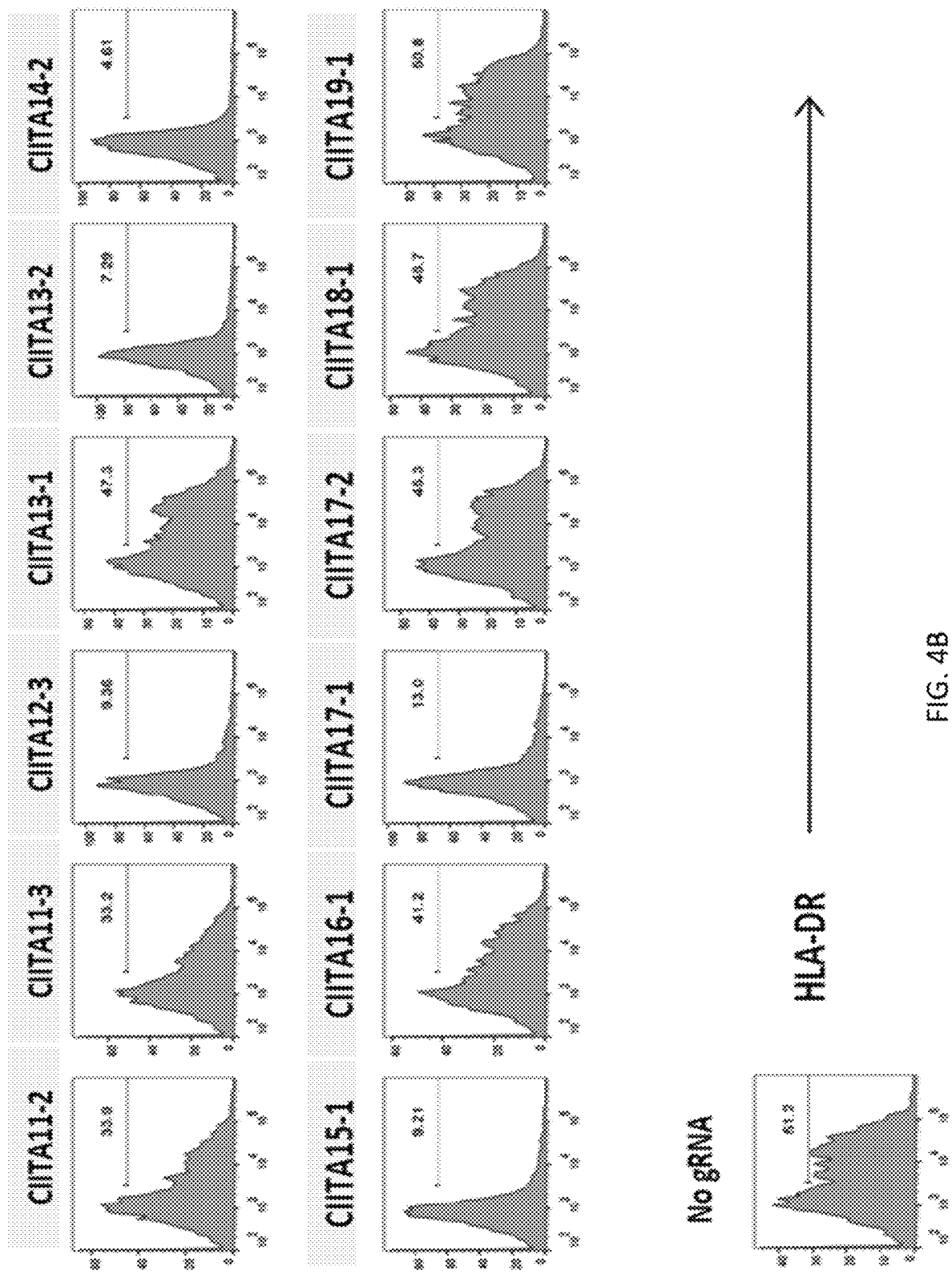
Figure 5A:
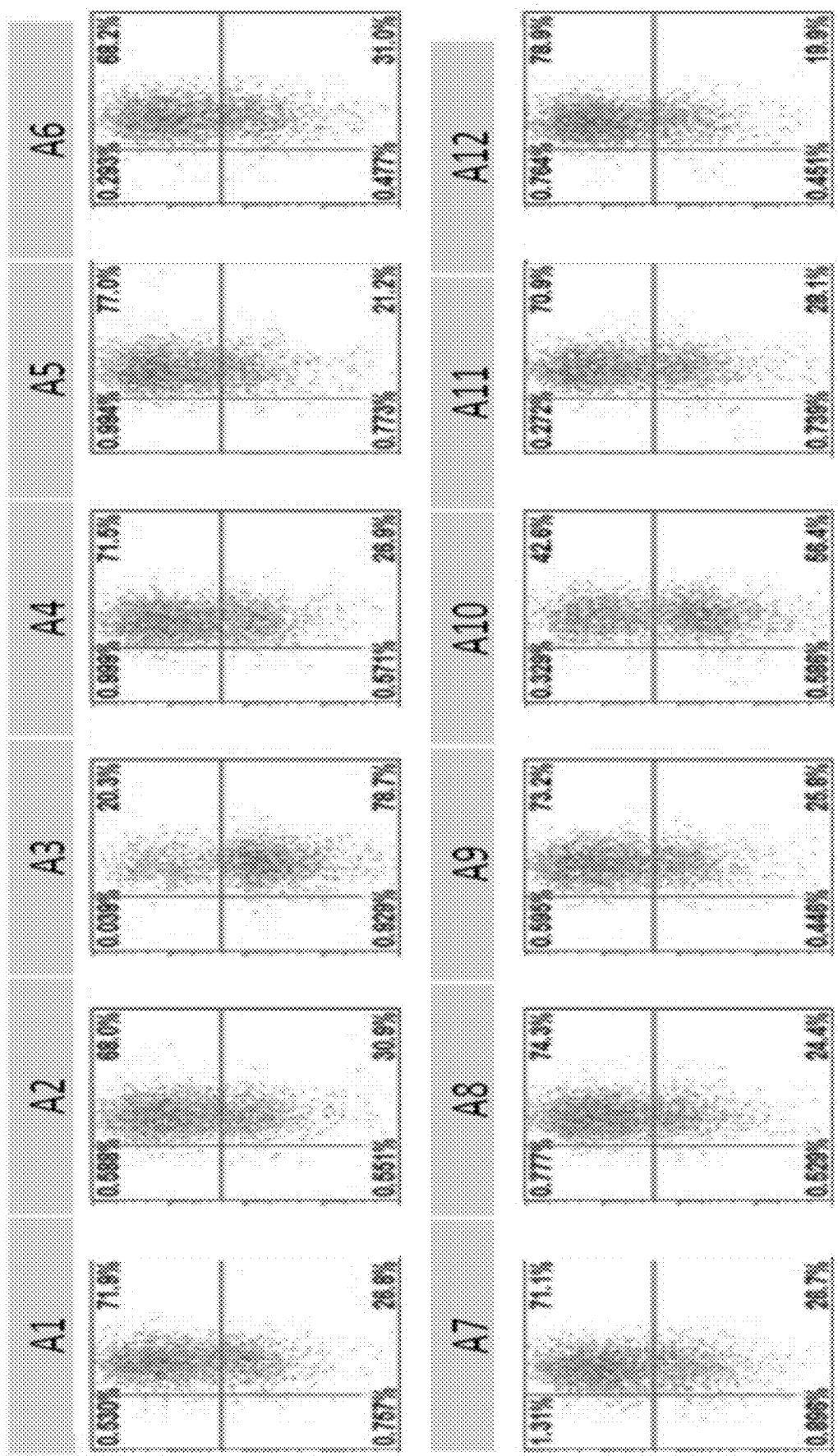
Figure 5B:
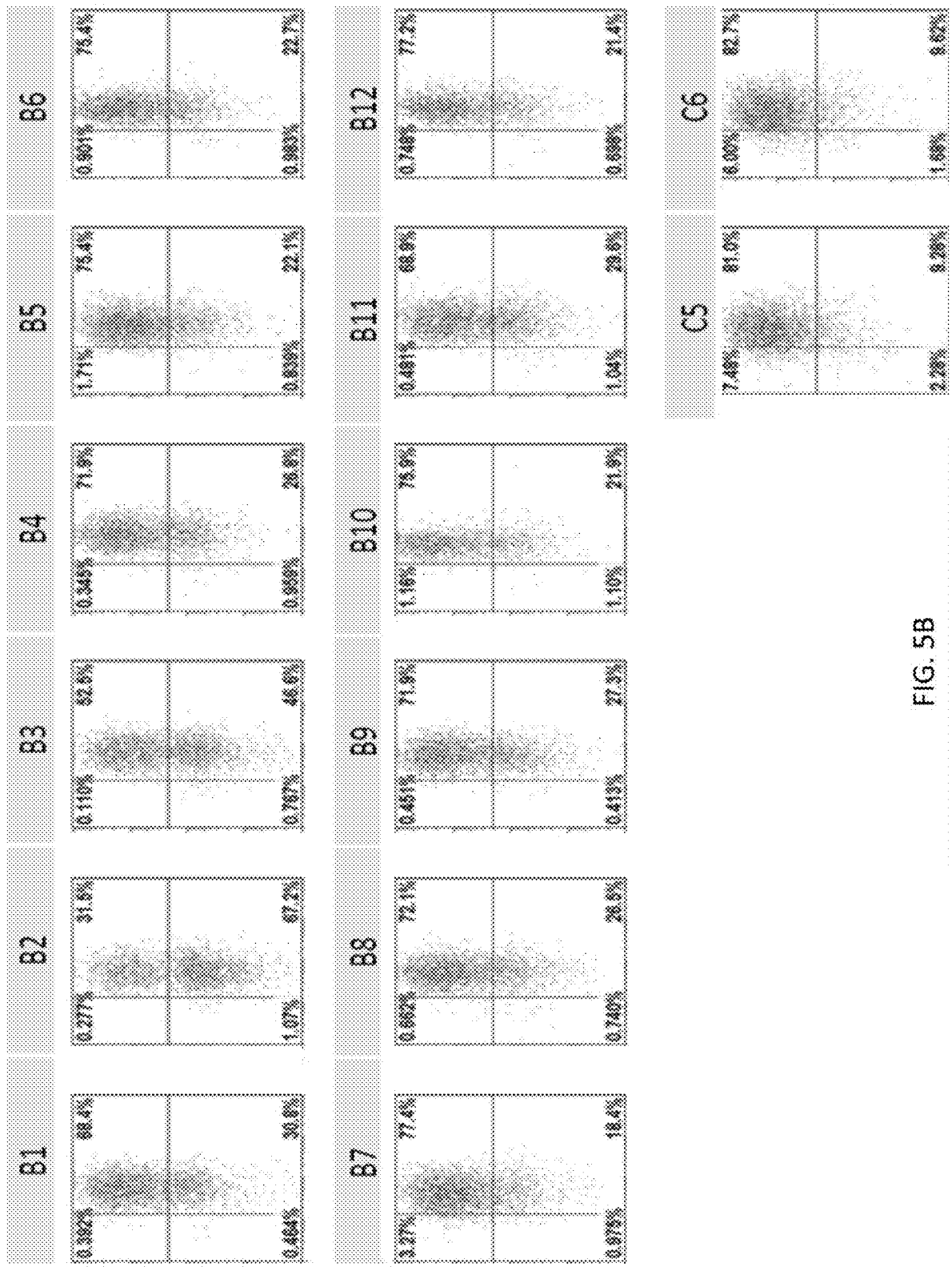

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

"Allogeneic" refers to a graft derived from a different animal of the same species.

"Alloantigen" refers to an antigen present only in some individuals of a species and capable of inducing the production of an alloantibody by individuals which lack it.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

"Allogeneic" refers to any material derived from a different animal of the same species.

The term "chimeric antigen receptor" or "CAR," as used herein, refers to an artificial T cell receptor that is engineered to be expressed on an immune effector cell and specifically bind an antigen. CARS may be used as a therapy with adoptive cell transfer. I' cells are removed from a patient and modified so that they express the receptors specific to a particular form of antigen. In some embodiments, the CAR has specificity to a selected target. CARs may also comprise an intracellular activation domain, a transmembrane domain and an extracellular domain comprising an antigen binding region. In some aspects, CARs comprise an extracellular domain comprising an anti-HLA binding domain fused to CD8 hinge domain, a CD28 transmembrane and intracellular domain, and a CD3-zeta domain.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. Preferably, the epitope is about 4-18 amino acids, more preferably about 5-16 amino acids, and even more most preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide of the present invention can be an epitope.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a cellular response to an antigen that occurs when lymphocytes identify antigenic molecules as foreign and induce the formation of antibodies and/or activate lymphocytes to remove the antigen.

The term "immunostimulatory" is used herein to refer to increasing overall immune response.

The term "immunosuppressive" is used herein to refer to reducing overall immune response.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "self-antigen" as used herein is defined as an antigen that is expressed by a host cell or tissue. Self-antigens may be tumor antigens, but in certain embodiments, are expressed in both normal and tumor cells. A skilled artisan would readily understand that a self-antigen may be overexpressed in a cell.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic add to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta cell.

The term "therapeutic" as used herein means a treatment and/or prophylaxis. A therapeutic effect is obtained by suppression, remission, or eradication of a disease state.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver. A transplant can also refer to any material that is to be administered to a host. For example, a transplant can refer to a nucleic acid or a protein.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

"Xenogeneic" refers to any material derived from an animal of a different species.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention includes compositions and methods for modified T cells as universal effector cells. Doxycycline is used to treat many different bacterial infections, such as acne, urinary tract infections, intestinal infections, eye infections, gonorrhea, *chlamydia*, periodontitis (gum disease), and others. The tetracycline (Tet)-On system is an inducible gene expression system for mammalian cells, in which the reverse Tet transactivator (rtTA) fusion protein, which is composed of the doxycycline-binding Tet-repressor mutant protein and the C terminal activator domain from the herpes simplex virus VP16 protein, is engineered to control gene expression with doxycycline (Dox). In the presence of Dox, rtTA activates the minimal promoters that are fused downstream of an array of seven repeated Tet-operator sequences (Loew et al. (2010) *BMC biotechnology* 10, 81). A one-vector system has recently been developed (Heinz et al. (2011) *Human gene therapy* 22, 166-176), which has enabled easy transduction of a gene of interest into primary immune cells (Sakemura et al. (2016) *Cancer Immunol Res* 4, 658-668). Using this inducible gene expression system, the an exogenous receptor (e.g., a transgenic TCR or CAR) is expressed only when the inducer (Dox) is present. In certain embodiments, this facilitates depletion of CD3+ non-gene edited T cells that cause GVHD when the T cells are used in allogeneic settings, leaving the TCR transduced and non-endogenous TCR expressed T cells in the final T cell products.

In certain exemplary embodiments, CRISPR/gRNAs were first screened for five gene loci: TRAC, TABC, B2M, CIITA and PD-1 for high efficient gene disruptions. Utilizing a tetracycline-inducible gene expression system, a strategy was successfully developed that could efficiently deplete endogenous TCR derived, non-gene edited CD3+ T cells from the final products that only contain the TCR transduced and non-endogenous TCR expressed. T cells. Moreover, the transgenic TCR could be efficiently expressed with high transduction efficiency when induced by providing Dox in the cultures. The anti-tumor activities of the Dox induced TCR expressing T cells were more potent than the T cells that were transduced with regular non-Tet lentiviral vector, due to the absence of endogenous TCR expression in the T cell products, thus providing universal TCR T cells that can be applied for future clinical use in treating patients with cancers or infectious diseases. Further, using tetracycline (Tet)-On system to control the expression of the transgenic TCR renders the TCR expression regulatable, ensuring the safety of the products when introduced into a subject.

Notwithstanding the working examples provided herewith, one of skill in the art will appreciate that the Tet-On inducible system disclosed herein can be used for regulating the expression of a non-endogenous receptor (e.g., an exogenous TCR or CAR). In particular, the Tet-On inducible system described in the present invention can readily be employed by those of skill in the art to regulate the temporal or spatial expression of the desired receptor on the surface of the immune cell. In particular, the inducible expression system may permit the periodic expression of the receptor on the surface of the immune cell, thereby counteracting the effects of T-cell exhaustion and the tumor microenvironment.

Inducible Expression System

In disease settings, T cells are exposed to persistent antigen and/or inflammatory signals. This scenario is often associated with the deterioration of T cell function: a state called 'exhaustion'. Exhausted T cells lose robust effector functions, express multiple inhibitory receptors and are defined by an altered transcriptional profile. T cell exhaustion is often associated with inefficient control of persisting infections and tumors, but revitalization of exhausted T cells can reinvigorate immunity.

The present invention provides an inducible expression system for expressing an exogenous receptor, e.g., T cell receptor (TCR) or chimeric antigen receptor (CAR) in an immune cell. It was found that TCR redirected T cells generated using an inducible expression system of the present invention provides superior efficacy. In the presence of an induction agent (i.e., inducer), the inducible expression system drives expression of the exogenous receptor (e.g., TCR or CAR). In an induced system, withdrawal of the induction agent may reduce and/or halt expression of the TCR or CAR. Upon re-introduction of the induction agent, the system can then be re-induced and restart the expression of the TCR or CAR. The inducible system of the present invention may solve the problem of T cell exhaustion experienced by current T cell therapies. For example, an administered T cell can be induced to express a TCR or CAR for a certain period of time within a subject in need thereof. Continuous expression of the TCR or CAR may cause T cell exhaustion. As such, withdrawal of the induction agent (e.g., by normal metabolic processes) may prevent exhaustion from occurring, and subsequent reintroduction of the induction agent can revitalize T cell function.

In some embodiments, an inducible expression system of the present invention may also provide tunable control of the expression of a TCR or CAR in a modified T cell. As used herein, the term "tunable control" refers to the ability to control the expression level of a TCR or CAR. For example, the level of induced expression of a TCR or CAR may depend on the amount of induction agent that is present. For example, the presence of a higher amount of induction agent can induce higher levels of expression of a TCR or CAR as compared to the presence of a lower amount of induction agent. As such, the inducible or tunable expression of a TCR or CAR is dose-dependent with respect to the amount of induction agent present.

In some embodiments, an inducible TCR or CAR expression system of the present invention comprises: a first nucleic acid comprising a constitutive promoter operably linked to a nucleic acid sequence encoding a transactivator protein; and a second nucleic acid comprising an inducible promoter operably linked to a nucleic acid sequencing encoding a TCR or CAR. The first nucleic acid and the second nucleic acid may reside on separate expression constructs. In an exemplary embodiment, the first nucleic acid and the second nucleic acid reside within the same expression construct. In an exemplary embodiment, the direction of the first nucleic acid is in reverse orientation of the second nucleic acid (i.e., the second nucleic acid is in reverse orientation to the first nucleic acid). In such an embodiment, the inducible expression system is said to be within a bidirectional expression construct.

Any constitutive promoter may be used in an inducible TCR or CAR expression system of the present invention. The constitutive promoter is operably linked to a downstream nucleic acid sequence encoding a transactivator protein (i.e., the constitutive promoter is upstream of the nucleic acid sequence encoding a transactivator protein), and provides for constitutive expression of the transactivator protein. In some embodiments, the constitutive promoter is a human constitutive promoter. Examples of constitutive promoters are described elsewhere herein. In an exemplary embodiment, the constitutive promoter is a human phosphoglycerate kinase 1 promoter. In some embodiments, the constitutive promoter is a human elongation factor 1 alpha promoter.

In some embodiments, the transactivator protein is a transactivator protein that activates expression in the presence of an induction agent. In one embodiment, the transactivator protein is a modified tetracycline repressor (TetR). In one embodiment, the transactivator protein is a reverse Tet repressor (rTetR). In one embodiment, the transactivator protein is a reverse tetracycline-controlled transactivator protein (rtTA). In an exemplary embodiment, the transactivator protein is a Tet-On 3G transactivator protein.

The inducible promoter is operably linked to a downstream nucleic acid sequence encoding a TCR or CAR (i.e., the inducible promoter is upstream of the nucleic acid sequence encoding a TCR or CAR), and provides for inducible expression of the TCR or CAR. In some embodiments, the inducible promoter comprises a tet operator sequence. In some embodiments, the inducible promoter comprises a minimal promoter. In some embodiments, the inducible promoter comprises a Tet operator sequence upstream of a minimal promoter. In some embodiments, the inducible promoter comprises one or more Tet operator sequences (i.e., several repeats of a Tet operator sequence) upstream of a minimal promoter. In such an embodiment, the inducible promoter may also be referred to as a tetracycline response element (IRE). In an exemplary embodiment, the inducible promoter is a TRE3GS promoter.

In an inducible system of the present invention, the transactivator protein is capable of binding and activating an inducible promoter only when the transactivator protein is bound by an induction agent. In some embodiments, the transactivator protein is selected from a modified TetR, a rTetR, a rtTA and a Tet-On 3G transactivator protein, the inducible promoter comprises a Tet operator sequence; and the induction agent is tetracycline or a derivative thereof. In such embodiments, the modified TetR, rTetR, rtTA, or Tet-On 3G transactivator protein is only capable of binding and activating the inducible promoter when the transactivator protein is bound by tetracycline or a derivative thereof. Derivatives of tetracycline are known in the art, and includes doxycycline (Dox).

Accordingly; in an exemplary embodiment, an inducible TCR or CAR expression system of the present invention comprises a first nucleic acid comprising a human phosphoglycerate kinase 1 promoter operably linked upstream to a nucleic acid sequence encoding a Tet-On 3G transactivator protein; and a second nucleic acid comprising an inducible TRE3GS promoter operably linked upstream to a nucleic acid sequence encoding a TCR or CAR, wherein the second nucleic acid is in reverse orientation to the first nucleic acid. In some embodiments expression of the TCR or CAR is induced in the presence of tetracycline or a derivative thereof (e.g., doxycycline).

In some embodiments, continuous exposure of the inducible TCR or CAR expression system of the present invention to tetracycline or a derivative thereof, results in continuous expression of a TCR or CAR. In some embodiments, expression of the TCR or CAR can be reduced or halted upon withdrawal of the induction agent, e.g.; doxycycline. In some embodiments, expression of the TCR or CAR can be fine-tuned depending on the amount of the induction agent, e.g., doxycycline, that is exposed to the inducible system. For example, a higher dose of doxycycline can induce a higher level of expression of the TCR or CAR. As such; an inducible TCR or CAR expression system of the present invention is a tunable TCR or CAR expression system, and the level of expression of the TCR or CAR is dose-dependent with respect to the dose of induction agent the inducible TCR or CAR expression system is exposed to.

In some embodiments, after withdrawal of the induction agent (e.g., doxycycline), the TCR or CAR is no longer expressed. In some embodiments; re-introduction of the induction agent (e.g., doxycycline) re-induces expression of the TCR or CAR.

T Cell Receptor

The present invention provides compositions and methods for modified immune cells or precursors thereof (e.g., modified T cells) comprising an exogenous (e.g., transgenic) T cell receptor (TCR). The present invention includes an isolated transgenic T cell receptor (TCR) for use in the modified cell of the invention. In another aspect, the invention includes an isolated nucleic acid encoding a transgenic T cell receptor (TCR) for use in the modified cell of the invention. In yet another aspect, the invention includes a genetically modified T cell comprising an exogeneous nucleic acid encoding a transgenic TCR. The TCR expression system comprises a tetracycline (Tet)-On inducible gene expression system, wherein the Tet-On inducible gene expression system comprises a reverse Tet transactivator (Tet-On 3G) protein and at least one promoter fused downstream of at least one Tet-operator sequence (PTRE3GS Inducible Promoter) that drives the expression of a transgenic TCR in the presence of doxycycline. In one embodiment, the present invention provides a modified immune cell (e.g., T cell) comprising an exogenous TCR, wherein the exogenous TCR is expressed by a Tet-On inducible system, wherein the Tet-On inducible system comprises a promoter (e.g., constitutive promoter) operably linked to a nucleic acid encoding a reverse Tet transactivator (e.g., Tet-On 3G), and an inducible promoter operably linked to a nucleic acid encoding the exogenous TCR.

In another aspect, the invention includes a method for generating a modified immune cell or precursor cell thereof (e.g., modified T cell) comprising a transgenic TCR. The method comprises stimulating a population of T cells with CD3 and/or CD28 and transducing the T cells with a Tet-On inducible gene expression system. The Tet-On inducible gene expression system comprises a reverse Tet transactivator (rtTA) fusion protein and at least one promoter fused downstream of at least one Tet-operator sequence. Then, the T cells are electroporated with Cas9 RNA or Cas9 protein and guide RNAs. The CD3$^+$ T cells are depleted and the CD3$^-$ T cells are harvested. Doxycycline is then administering to the T cells.

In one embodiment, Tet-On inducible exogenous TCR expression in T cells provides modified T cells with enhanced potency (e.g., anti-tumor activities).

A T cell receptor is a complex of membrane proteins that participate in the activation of T cells in response to the presentation of antigen. Stimulation of the TCR is triggered by major histocompatibility complex molecules (MEW) on antigen presenting cells that present antigen peptides to the T cells and bind to the TCR complexes to induce a series of intracellular signaling cascades.

The TCR is generally composed of six different membrane bound chains that form the TCR heterodimer responsible for ligand recognition, and participate in the activation of T cells in response to an antigen. TCRs exist in alpha/beta and gamma/delta forms, which are structurally similar but have distinct anatomical locations and functions. An alpha/beta TCR comprises a TCR alpha chain and a TCR beta chain. T cells expressing a TCR comprising a TCR alpha chain and a TCR beta chain are commonly referred to as alpha/beta T cells. Gamma/delta TCRs comprise a TCR gamma chain and a TCR delta chain. T cells expressing a TCR comprising a TCR gamma chain and a TCR delta chain are commonly referred to as gamma/delta T cells. A TCR of the present disclosure is a TCR comprising a TCR alpha chain and a TCR beta chain. In one embodiment, the TCR comprises a TCR alpha and beta chain, such as the nucleic acid encoding the TCR comprises a nucleic acid encoding a TCR alpha and a TCR beta chain. In another embodiment, an alpha or beta chain or both comprises at least one N-deglycosylation.

Each chain is composed of two extracellular domains, a variable and constant domain. The TCR alpha chain and the TCR beta chain are each comprised of two extracellular domains, a variable region and a constant region. The TCR alpha chain variable region and the TCR beta chain variable region are required for the affinity of a TCR to a target antigen. Each variable region comprises three hypervariable or complementarity-determining regions (CDRs) which provide for binding to a target antigen. The constant region of the TCR alpha chain and the constant region of the TCR beta chain are proximal to the cell membrane. A TCR further comprises a transmembrane region and a short cytoplasmic tail. CD3 molecules are assembled together with the TCR heterodimer. CD3 molecules comprise a characteristic sequence motif for tyrosine phosphorylation, known as immunoreceptor tyrosine-based activation motifs (ITAMs). Proximal signaling events are mediated through the CD3 molecules, and accordingly, TCR-CD3 complex interaction plays an important role in mediating cell recognition events.

In one embodiment, the TCR comprises at least one murine constant region. The constant domain is proximal to the cell membrane, followed by a transmembrane domain and a short cytoplasmic tail. The variable domain contributes to the determination of the particular antigen and MHC molecule to which the TCR has binding specificity. In turn, the specificity of a T cell for a unique antigen-MHC complex resides in the particular TCR expressed by the T cell.

Each of the constant and variable domains may include an intra-chain disulfide bond. In one embodiment, TCR comprises at least one disulfide bond. The variable domains include the highly polymorphic loops analogous to the complementarity determining regions (CDRs) of antibodies. The diversity of TCR sequences is generated via somatic rearrangement of linked variable (V), diversity (D), joining (J), and constant genes.

Functional alpha and gamma chain polypeptides are formed by rearranged V-J-C regions, whereas beta and delta chains consist of V-D-J-C regions. The extracellular constant domain includes a membrane proximal region and an immunoglobulin region.

The TCR can include a wildtype TCR, a high affinity TCR, and/or a chimeric TCR. When the TCR is modified, it may have higher affinity for the target cell antigen than a wildtype TCR. A high affinity TCR may be the result of modifications to a wild-type TCR that confers a higher affinity for a target antigen compared to the wild-type TCR. A high affinity TCR may be an affinity-matured TCR. Methods for modifying TCRs and/or the affinity-maturation of TCRs are known to those of skill in the art. Techniques for engineering and expressing TCRs include, but are not limited to, the production of TCR heterodimers which include the native disulphide bridge which connects the respective subunits (Garboczi, et al., (1996), Nature 384 (6605): 134-41; Garboczi, et al., (1996), J Immunol 157(12): 5403-10; Chang et al., (1994), PNAS USA 91: 11408-11412; Davodeau et al., (1993), J. Biol. Chem. 268(21): 15455-15460; Golden et al., (1997), J. Imm. Meth. 206: 163-169; U.S. Pat. No. 6,080,840).

In embodiments where the TCR is a chimeric TCR, the TCR may include chimeric domains, such as the TCR comprises a co-stimulatory signaling domain at a C' terminal of at least one of the chains. In other embodiment, the TCR may include a modified chain, such as a modified alpha or beta chain. Such modifications may include, but are not limited to, N-deglycosylation, altered domain (such as an engineered variable region to target a specific antigen or increase affinity), addition of one or more disulfide bonds, entire or fragment of a chain derived from a different species, and any combination thereof.

In some embodiments, the exogenous TCR is a full TCR or an antigen-binding portion or antigen-binding fragment thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable a chain and variable β chain of a TCR, sufficient to form a binding site for binding to a specific MHC-peptide complex. Generally, the variable chains of a TCR contain complementarity determining regions (CDRs) involved in recognition of the peptide, MHC and/or MHC-peptide complex.

In some embodiments, the variable domains of the TCR contain hypervariable loops, or CDRs, which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al, Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR contains a variable alpha domain ($V_a$) and/or a variable beta domain (V) or antigen-binding fragments thereof. In some embodiments, the a-chain and/or β-chain of a TCR also can contain a constant domain, a transmembrane domain and/or a short cytoplasmic tail (see, e.g., Janeway et al., Immunobiology: The Immune System in Health and Disease, 3 Ed., Current Biology Publications, p. 4:33, 1997). In some embodiments, the a-chain constant domain is encoded by the TRAC gene (IMGT nomenclature) or is a variant thereof. In some embodiments, the β-chain constant region is encoded by TRBC1 or TRBC2 genes (IMGT nomenclature) or is a variant thereof. In some embodiments, the constant domain is adjacent to the cell membrane. For example, in some cases, the extracellular portion of the TCR formed by the two chains contains two membrane-proximal constant domains, and two membrane-distal variable domains, which variable domains each contain CDRs.

It is within the level of a skilled artisan to determine or identify the various domains or regions of a TCR. In some aspects, residues of a TCR are known or can be identified according to the International Immunogenetics Information System (IMGT) numbering system (see e.g. www.imgt.org; see also, Lefranc et al. (2003) Developmental and Comparative Immunology, 2&; 55-77; and The T Cell Factsbook 2nd Edition, Lefranc and LeFranc Academic Press 2001). Using this system, the CDR1 sequences within a TCR Va chains and/or vβ chain correspond to the amino acids present between residue numbers 27-38, inclusive, the CDR2 sequences within a TCR Va chain and/or vβ chain correspond to the amino acids present between residue numbers 56-65, inclusive, and the CDR3 sequences within a TCR Va chain and/or vβ chain correspond to the amino acids present between residue numbers 105-117, inclusive. The IMGT numbering system should not be construed as limiting in any way, as there are other numbering systems known to those of skill in the art, and it is within the level of the skilled artisan to use any of the numbering systems available to identify the various domains or regions of a TCR.

In some embodiments, the TCR may be a heterodimer of two chains a and β (or optionally γ and δ) that are linked, such as by a disulfide bond or disulfide bonds. In some embodiments, the constant domain of the TCR may contain short connecting sequences in which a cysteine residue forms a disulfide bond, thereby linking the two chains of the TCR. In some embodiments, a TCR may have an additional cysteine residue in each of the a and β chains, such that the TCR contains two disulfide bonds in the constant domains. In some embodiments, each of the constant and variable domains contain disulfide bonds formed by cysteine residues.

In some embodiments, the TCR for engineering cells as described is one generated from a known TCR sequence(s), such as sequences of vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences. In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the T-cells can be a cultured T-cell hybridoma or clone. In some embodiments, the TCR or antigen-binding portion thereof can be synthetically generated from knowledge of the sequence of the TCR. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15: 169-180 and Cohen et al. (2005) J Immunol. 175:5799-5808. In some embodiments, phage display is used to isolate TCRs against a target antigen (see, e.g., Varela-Rohena et al. (2008) Nat Med. 14: 1390-1395 and Li (2005) Nat Biotechnol. 23:349-354.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments as described, the TCR can contain an introduced disulfide bond or bonds. In some embodiments, the native disulfide bonds are not present. In some embodiments, the one or more of the native cysteines (e.g. in the constant domain of the a chain and β chain) that form a native interchain disulfide bond are substituted to another residue, such as to a serine or alanine. In some embodiments, an introduced disulfide bond can be formed by mutating non-cysteine residues on the alpha and beta chains, such as in the constant domain of the a chain and β chain, to cysteine. Exemplary non-native disulfide bonds of a TCR are described in published International PCT No. WO2006/000830 and WO2006037960. In some embodiments, cysteines can be introduced at residue Thr48 of the a chain and Ser57 of the β chain, at residue Thr45 of the a chain and Ser77 of the β chain, at residue Tyr10 of the a chain and Ser17 of the β chain, at residue Thr45 of the a chain and Asp59 of the β chain and/or at residue Ser15 of the a chain and Glu15 of the β chain. In some embodiments, the presence of non-native cysteine residues (e.g. resulting in one or more non-native disulfide bonds) in a recombinant TCR can favor production of the desired recombinant TCR in a cell in which it is introduced over expression of a mismatched TCR pair containing a native TCR chain.

In some embodiments, the TCR chains contain a transmembrane domain. In some embodiments, the transmembrane domain is positively charged. In some cases, the TCR chain contains a cytoplasmic tail. In some aspects, each chain (e.g. alpha or beta) of the TCR can possess one N-terminal immunoglobulin variable domain, one immunoglobulin constant domain, a transmembrane region, and a short cytoplasmic tail at the C-terminal end. In some embodiments, a TCR, for example via the cytoplasmic tail, is associated with invariant proteins of the CD3 complex involved in mediating signal transduction. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3 chains) contain one or more immunoreceptor tyrosine-based activation motif or ITAM that are involved in the signaling capacity of the TCR complex.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). A TCR may be cell-bound or in soluble form. In some embodiments, for purposes of the provided methods, the TCR is in cell-bound form expressed on the surface of a cell. In some embodiments a dTCR contains a first polypeptide wherein a sequence corresponding to a TCR a chain variable region sequence is fused to the N terminus of a sequence corresponding to a TCR a chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native interchain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane. In some embodiments, a dTCR contains a TCR a chain containing a variable a domain, a constant a domain and a first dimerization motif attached to the C-terminus of the constant a domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR a chain and TCR β chain together.

In some embodiments, the TCR is a scTCR, which is a single amino acid strand containing an a chain and a β chain that is able to bind to MHC-peptide complexes. Typically, a scTCR can be generated using methods known to those of skill in the art, See e.g., International published PCT Nos. WO 96/13593, WO 96/18105, WO99/18129, WO04/033685, WO2006/037960, WO2011/044186; U.S. Pat. No. 7,569,664; and Schlueter, C. J. et al. J. Mol. Biol. 256, 859 (1996). In some embodiments, a scTCR contains a first segment constituted by an amino acid sequence corresponding to a TCR a chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment. In some embodiments, a scTCR contains a first segment constituted by an amino acid sequence corresponding to a TCR β chain variable region, a second segment constituted by an amino acid sequence corresponding to a TCR a chain variable region sequence fused to the N terminus of an amino acid sequence corresponding to a TCR a chain constant domain extracellular sequence, and a linker sequence linking the C terminus of the first segment to the N terminus of the second segment. In some embodiments, a scTCR contains a first segment constituted by an a chain variable region sequence fused to the N terminus of an a chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment. In some embodiments, a scTCR contains a first segment constituted by a TCR β chain variable region sequence fused to the N terminus of a β chain extracellular constant domain sequence, and a second segment constituted by an a chain variable region sequence fused to the N terminus of a sequence a chain extracellular constant and transmembrane sequence, and, optionally, a linker sequence linking the C terminus of the first segment to the N terminus of the second segment. In some embodiments, for the scTCR to bind an MHC-peptide complex, the a and β chains must be paired so that the variable region sequences thereof are orientated for such binding. Various methods of promoting pairing of an a and β in a scTCR are well known in the art.

In some embodiments, a linker sequence is included that links the α and β chains to form the single polypeptide strand. In some embodiments, the linker should have sufficient length to span the distance between the C terminus of the α chain and the N terminus of the β chain, or vice versa, while also ensuring that the linker length is not so long so that it blocks or reduces bonding of the scTCR to the target peptide-MHC complex. In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P-, wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, a scTCR contains a disulfide bond between residues of the single amino acid strand, which, in some cases, can promote stability of the pairing between the α and β regions of the single chain molecule (see e.g. U.S. Pat. No. 7,569,664). In some embodiments, the scTCR contains a covalent disulfide bond linking a residue of the immunoglobulin region of the constant domain of the α chain to a residue of the immunoglobulin region of the constant domain of the β chain of the single chain molecule. In some embodiments, the disulfide bond corresponds to the native disulfide bond present in a native dTCR. In some embodiments, the disulfide bond in a native TCR is not present. In some embodiments, the disulfide bond is an introduced non-native disulfide bond, for example, by incorporating one or more cysteines into the constant region extracellular sequences of the first and second chain regions of the scTCR polypeptide. Exemplary cysteine mutations include any as described above. In some cases, both a native and a non-native disulfide bond may be present.

In some embodiments, any of the TCRs, including a dTCR or scTCR, can be linked to signaling domains that yield an active TCR on the surface of a T cell. In some embodiments, the TCR is expressed on the surface of cells. In some embodiments, the TCR does contain a sequence corresponding to a transmembrane sequence. In some embodiments, the transmembrane domain can be a Cα or Cβ transmembrane domain. In some embodiments, the transmembrane domain can be from a non-TCR origin, for example, a transmembrane region from CD3z, CD28 or B7.1. In some embodiments, the TCR does contain a sequence corresponding to cytoplasmic sequences. In some embodiments, the TCR contains a CD3z signaling domain. In some embodiments, the TCR is capable of forming a TCR complex with CD3. In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal.

In one aspect, the invention includes a population of modified T cells comprising an electroporated RNA encoding a modified T cell receptor (TCR) comprising affinity for an antigen on a target cell, wherein the population of T cells was expanded prior to electroporation with the TCR RNA.

In another aspect, the invention includes a modified T cell comprising an exogenous nucleic acid encoding a T cell receptor (TCR) comprising affinity for an antigen on a target cell; and an electroporated nucleic acid encoding a costimulatory molecule, wherein the T cell expresses the TCR and co-stimulatory molecule. The co-stimulatory molecule may be selected from the group consisting of CD3, CD27, CD28, CD83, CD86, CD127, 4-1BB, 4-1BBL, PD-1 and PD-1L.

In one embodiment, the invention includes introducing a nucleic acid encoding a modified T cell receptor (TCR) comprising affinity for an antigen on a target cell into the expanded T cells. In this embodiment, the T cells are capable of expressing the modified TCR.

In one embodiment, the TCR comprises specificity to a target cell antigen. The target cell antigen may include any type of protein associated with a target cell. For example, the target cell antigen may be chosen to recognize a particular disease state of the target cell. Thus examples of cell surface markers that may act as ligands for the antigen binding domain of the TCR including those associated with viral, bacterial and parasitic infections, autoimmune disease and cancer cells. In certain embodiments, the target cell antigen includes any tumor associated antigen (TAA) or any viral antigen, or any fragment thereof. In some embodiments, the TCR comprises affinity to a target antigen on a target cell. The target antigen may include any type of protein, or epitope thereof, associated with the target cell. In some embodiments, the target antigen is processed and presented by MHCs. The target cell antigen may include any protein that may be processed and presented by major histocompatibility complexes. For example, the target antigen may be associated with a particular disease state. For example, the TCR may comprise affinity to a target antigen on a target cell that indicates a particular disease state of the target cell. Thus examples of cell markers that may act as targets of the TCR include those associated with viral, bacterial and parasitic infections, autoimmune disease and cancer cells. In certain embodiments, the target antigen includes any of tumor associated antigens (TAA) or any viral antigen, or any fragment thereof.

In one embodiment, the target cell antigen is a New York esophageal-1 (NY-ESO-1) peptide. NY-ESO-1 belongs to the cancer-testis (CT) antigen group of proteins. NY-ESO-1 is a highly immunogenic antigen in vitro and is presented to T cells via the MHC. CTLs recognizing the A2 presented epitope NY-ESO$_{157-165}$, SLLMWITQC (SEQ ID NO:98), have been grown from the blood and lymph nodes of myeloma patients. T cell clones specific for this epitope have been shown to kill tumor cells. A high affinity TCR recognizing the NY-ESO$_{157-165}$ epitope may recognize HLA-A2-positive, NY-ESO-1 positive cell lines (but not to cells that lack either HLA-A2 or NY-ESO). Accordingly, a TCR of the present disclosure may be a HLA-A2-restricted NY-ESO-1 (SLLMWITQC; SEQ ID NO:98)-specific TCR. In one embodiment, an NY-ESO-1 TCR of the present disclosure is a wild-type NY-ESO-1 TCR. A wild-type NY-ESO-1 TCR may include, without limitation, the 8F NY-ESO-1 TCR (also referred to herein as "8F" or "8F TCR"), and the 1G4 NY-ESO-1 TCR (also referred to herein as "1G4" or "1G4 TCR"). In one embodiment, an NY-ESO-1 TCR of the present disclosure is an affinity enhanced 1G4 TCR, also called Ly95. 1G4 TCR and affinity enhanced 1G4 TCR is described in U.S. Pat. No. 8,143,376.

An aspect of the invention provides for a modified immune cell or precursor cell thereof (e.g., modified T cell) comprising an exogenous TCR, wherein expression of the exogenous TCR is regulated by a Tet-On inducible system. For example, such a modified cell can be generated by introducing into the cell a nucleic acid comprising a Tet-On inducible gene expression system in operable linkage with a nucleic acid encoding for the exogenous TCR.

In one embodiment, a modified immune cell or precursor cell thereof (e.g., modified T cell) of the present invention comprises an 8F TCR, wherein the 8F TCR is expressed under a Tet-On inducible gene expression system (e.g., expression of the 8F TCR is regulated by the Tet-On system). For example, such a modified cell can be generated by introducing into the cell a nucleic acid comprising a Tet-On inducible gene expression system in operable linkage with a nucleic acid encoding for the 8F TCR.

Chimeric Antigen Receptor (CAR)

The present invention provides compositions and methods for modified immune cells or precursors thereof, e.g., modified T cells, comprising a chimeric antigen receptor (CAR). Thus, in some embodiments, the immune cell has been genetically modified to express the CAR. CARs of the present invention comprise an antigen binding domain, a transmembrane domain, a hinge domain, and an intracellular signaling domain.

In one aspect of the invention, the genetically modified T cell comprises a chimeric antigen receptor (CAR). The CAR comprises an antigen binding domain. The antigen binding domain can comprise an antibody or fragment thereof that binds to a target antigen. Preferably, the antigen binding domain is an scFv antibody that binds to a target antigen. The choice of antigen binding domain depends upon the type and number of antigens that are present on the surface of a target cell. For example, the antigen binding domain may be chosen to recognize an antigen that acts as a cell surface marker on a target cell associated with a particular disease state.

The antigen binding domains described herein can be combined with any of the transmembrane domains described herein, any of the intracellular domains or cytoplasmic domains described herein, or any of the other domains described herein that may be included in the CAR. A subject CAR of the present invention may also include a spacer domain as described herein. In some embodiments, each of the antigen binding domain, transmembrane domain, and intracellular domain is separated by a linker.

Antigen Binding Domain

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. Thus, in one embodiment, the antigen binding domain portion comprises a mammalian antibody or a fragment thereof.

In some instances, the antigen binding domain may be derived from the same species in which the CAR will ultimately be used. For example, for use in humans, the antigen binding domain of the CAR may comprise a human antibody as described elsewhere herein, or a fragment thereof The antigen binding domain may be operably linked to another domain of the CAR, such as the transmembrane domain or the intracellular domain, both described elsewhere herein, for expression in the cell. In one embodiment, a nucleic acid encoding the antigen binding domain is operably linked to a nucleic acid encoding a transmembrane domain and a nucleic acid encoding an intracellular domain.

The antigen binding domain of a CAR is an extracellular region of the CAR for binding to a specific target antigen including proteins, carbohydrates, and glycolipids. In some embodiments, the CAR comprises affinity to a target antigen on a target cell. The target antigen may include any type of protein, or epitope thereof, associated with the target cell. For example, the CAR may comprise affinity to a target antigen on a target cell that indicates a particular disease state of the target cell.

As described herein, a CAR of the present disclosure having affinity for a specific target antigen on a target cell may comprise a target-specific binding domain. In some embodiments, the target-specific binding domain is a murine target-specific binding domain, e.g., the target-specific binding domain is of murine origin. In some embodiments, the target-specific binding domain is a human target-specific binding domain, e.g., the target-specific binding domain is of human origin.

In some embodiments, a CAR of the present disclosure may have affinity for one or more target antigens on one or more target cells. In some embodiments, a CAR may have affinity for one or more target antigens on a target cell. In such embodiments, the CAR is a bispecific CAR, or a multispecific CAR. In some embodiments, the CAR comprises one or more target-specific binding domains that confer affinity for one or more target antigens. In some embodiments, the CAR comprises one or more target-specific binding domains that confer affinity for the same target antigen. For example, a CAR comprising one or more target-specific binding domains having affinity for the same target antigen could bind distinct epitopes of the target antigen. When a plurality of target-specific binding domains is present in a CAR, the binding domains may be arranged in tandem and may be separated by linker peptides. For example, in a CAR comprising two target-specific binding domains, the binding domains are connected to each other covalently on a single polypeptide chain, through an oligo- or polypeptide linker, an Fc hinge region, or a membrane hinge region. In some embodiments, the antigen binding domain is selected from the group consisting of an antibody, an antigen binding fragment (Fab), and a single-chain variable fragment (scFv).

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker, which connects the N-terminus of the VH with the C-terminus of the VL, or the C-terminus of the VH with the N-terminus of the VL. In some embodiments, the antigen binding domain (e.g., TAA binding domain) comprises an scFv having the configuration from N-terminus to C-terminus, VH-linker-VL. In some embodiments, the antigen binding domain comprises an scFv having the configuration from N-terminus to C-terminus, VL-linker-VH. Those of skill in the art would be able to select the appropriate configuration for use in the present invention.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. Various linker sequences are known in the art, including, without limitation, glycine serine (GS) linkers such as (GS)$_n$, (GSGGS)$_n$ (SEQ ID NO:99), (GGGS)$_n$ (SEQ ID NO:100), and (GGGGS)$_n$ (SEQ ID NO:101), where n represents an integer of at least 1. Exemplary linker sequences can comprise amino acid sequences including, without limitation, GGSG (SEQ ID NO:102), GGSGG (SEQ ID NO:103), GSGSG (SEQ ID NO:104), GSGGG (SEQ ID NO:105), GGGSG (SEQ ID NO:106), GSSSG (SEQ ID NO:107), GGGGS (SEQ ID NO:108), GGGGSGGGGSGGGGS (SEQ ID NO:109) and the like. Those of skill in the art would be able to select the appropriate linker sequence for use in the present invention. In one embodiment, an antigen binding domain of the present invention comprises a heavy chain variable region (VH) and a light chain variable region (VL), wherein the VH and VL is separated by the linker sequence having the amino acid sequence GGGGSGGGGSGGGGS (SEQ ID NO:110), which may be encoded by the nucleic acid sequence ggtggcggtggctcgggcggtggtgggtcgggtggcggcggatct (SEQ ID NO:111).

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Biol Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

In some embodiments, the antigen binding domain may be derived from the same species in which the CAR will ultimately be used. For example, for use in humans, the antigen binding domain of the CAR may comprise a human antibody or a fragment thereof.

Transmembrane Domain

With respect to the transmembrane domain, the CAR can be designed to comprise a transmembrane domain that connects the antigen binding domain of the CAR to the intracellular domain. In one embodiment, the transmembrane domain is naturally associated with one or more of the domains in the CAR. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the CAR into a cell membrane, e.g., an artificial hydrophobic sequence. Examples of the transmembrane regions of particular use in this invention include, without limitation, transmembrane domains derived from (i.e. comprise at least the transmembrane region(s) of) the alpha, beta or zeta chain of the T-cell receptor, CD28, CD3 epsilon, CD45, CD4, CD5, CD7 CD8, CD9, CD16, CD22, CD33, CD37, CD64, CD80, CD86, CD134 (OX-40), CD137 (4-1BB), CD154 (CD40L), Toll-like receptor 1 (TLR1), TLR2, TLR3, TLR4, TLR5, TLR6, TLR7, TLR8, and TLR9. In some instances, a variety of hinges can be employed as well including the Ig (immunoglobulin) hinge.

In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

The transmembrane domains described herein can be combined with any of the antigen binding domains described herein, any of the intracellular domains described herein, or any of the other domains described herein that may be included in a subject CAR.

In some embodiments, the transmembrane domain further comprises a hinge region. A subject CAR of the present invention may also include an hinge region. The hinge region of the CAR is a hydrophilic region which is located between the antigen binding domain and the transmembrane domain. In some embodiments, this domain facilitates proper protein folding for the CAR. The hinge region is an optional component for the CAR. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4).

In some embodiments, a subject CAR of the present disclosure includes a hinge region that connects the antigen binding domain with the transmembrane domain, which, in turn, connects to the intracellular domain. The hinge region is preferably capable of supporting the antigen binding domain to recognize and bind to the target antigen on the target cells (see, e.g., Hudecek et al., *Cancer Immunol. Res.* (2015) 3(2): 125-135). In some embodiments, the hinge region is a flexible domain, thus allowing the antigen binding domain to have a structure to optimally recognize the specific structure and density of the target antigens on a cell such as tumor cell (Hudecek et al., supra). The flexibility of the hinge region permits the hinge region to adopt many different conformations.

In some embodiments, the hinge region is an immunoglobulin heavy chain hinge region. In some embodiments, the hinge region is a hinge region polypeptide derived from a receptor (e.g., a CD8-derived hinge region).

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids.

For example, hinge regions include glycine polymers $(G)_n$, glycine-serine polymers (including, for example, (GS)$_n$, (GSGGS)$_n$ (SEQ ID NO: 99) and (GGGS)$_n$ (SEQ ID NO: 100), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, Rev. Computational. Chem. (1992) 2: 73-142). Exemplary hinge regions can comprise amino acid sequences including, but not limited to, GGSG (SEQ ID NO: 102), GGSGG (SEQ ID NO: 103), GSGSG (SEQ ID NO: 104), GSGGG (SEQ ID NO: 105), GGGSG (SEQ ID NO: 106), GSSSG (SEQ ID NO: 107), and the like.

In some embodiments, the hinge region is an immunoglobulin heavy chain hinge region. Immunoglobulin hinge region amino acid sequences are known in the art; see, e.g., Tan et al., Proc. Natl. Acad. Sci. USA (1990) 87(1):162-166; and Huck et al., Nucleic Acids Res. (1986) 14(4): 1779-1789. As non-limiting examples, an immunoglobulin hinge region can include one of the following amino acid sequences: DKTHT (SEQ ID NO: 112); CPPC (SEQ ID NO: 113); CPEPKSCDTPPPCPR (SEQ ID NO: 114) (see, e.g., Glaser et al., J. Biol. Chem. (2005) 280:41494-41503); ELKTPLGDTTHT (SEQ ID NO: 115); KSCDKTHTCP (SEQ ID NO: 116); KCCVDCP (SEQ ID NO: 117); KYGPPCP (SEQ ID NO: 118); EPKSCDKTHTCPPCP (SEQ ID NO: 119) (human IgG1 hinge); ERKCCVECPPCP (SEQ ID NO: 120) (human IgG2 hinge); ELKTPLGDTTH-TCPRCP (SEQ ID NO: 121) (human IgG3 hinge); SPNMVPHAHHAQ (SEQ ID NO: 122) (human IgG4 hinge); and the like.

The hinge region can comprise an amino acid sequence of a human IgG1, IgG2, IgG3, or IgG4, hinge region. In one embodiment, the hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO: 123) see, e.g., Yan et al., J. Biol. Chem. (2012) 287: 5891-5897. In one embodiment, the hinge region can comprise an amino acid sequence derived from human CD8, or a variant thereof.

In one embodiment, the transmembrane domain comprises a CD28 transmembrane domain. In another embodiment, the transmembrane domain comprises a CD8 hinge domain and a CD28 transmembrane domain. The transmembrane domain may be combined with any hinge domain and/or may comprise one or more transmembrane domains described herein.

The transmembrane domains described herein, such as a transmembrane region of alpha, beta or zeta chain of the T-cell receptor, CD28, CD3 epsilon, CD45, CD4, CD5, CD7, CD8, CD9, CD 16, CD22, CD33, CD37, CD64, CD80, CD86, CD134 (OX-40), CD137 (4-1BB), CD154 (CD40L), Toll-like receptor 1 (TLR1), TLR2, TLR3, TLR4, TLR5, TLR6, TLR7, TLR8, and TLR9, can be combined with any of the antigen binding domains described herein, any of the intracellular domains or cytoplasmic domains described herein, or any of the other domains described herein that may be included in the CAR.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

Between the extracellular domain and the transmembrane domain of the CAR, or between the intracellular domain and the transmembrane domain of the CAR, there may be incorporated a spacer domain. As used herein, the term "spacer domain" generally means any oligo- or polypeptide that functions to link the transmembrane domain to, either the extracellular domain or, the intracellular domain in the polypeptide chain. A spacer domain may comprise up to 300 amino acids, e.g., 10 to 100 amino acids, or 25 to 50 amino acids. In some embodiments, the spacer domain may be a short oligo- or polypeptide linker, e.g., between 2 and 10 amino acids in length. For example, glycine-serine doublet provides a particularly suitable linker between the transmembrane domain and the intracellular signaling domain of the subject CAR.

Intracellular Domain

A subject CAR of the present invention also includes an intracellular signaling domain. The terms "intracellular signaling domain" and "intracellular domain" are used interchangeably herein. The intracellular signaling domain of the CAR is responsible for activation of at least one of the effector functions of the cell in which the CAR is expressed (e.g., immune cell). The intracellular signaling domain transduces the effector function signal and directs the cell (e.g., immune cell) to perform its specialized function, e.g., harming and/or destroying a target cell.

The intracellular domain or otherwise the cytoplasmic domain of the CAR includes a similar or the same intracellular domain as the chimeric intracellular signaling molecule described elsewhere herein, and is responsible for activation of the cell in which the CAR is expressed. In one embodiment, the intracellular domain comprises CD3 zeta. In another embodiment, the intracellular domain comprises CD28 and CD3 zeta.

Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular signaling domain include, without limitation, the ζ chain of the T cell receptor complex or any of its homologs, e.g., η chain, FcsRIγ and β chains, MB 1 (Iga) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular signaling domain may be human CD3 zeta chain, FcyRIII, FcsRI, cytoplasmic tails of Fc receptors, an immunoreceptor tyrosine-based activation motif (ITAM) bearing cytoplasmic receptors, and combinations thereof.

In one embodiment, the intracellular domain of the CAR includes any portion of one or more co-stimulatory molecules, such as at least one signaling domain from CD3, CD8, CD27, CD28, ICOS, 4-IBB, PD-1, any derivative or variant thereof, any synthetic sequence thereof that has the same functional capability, and any combination thereof.

Other examples of the intracellular domain include a fragment or domain from one or more molecules or receptors including, but are not limited to, TCR, CD3 zeta, CD3 gamma, CD3 delta, CD3 epsilon, CD86, common FcR gamma, FcR beta (Fc Epsilon Rib), CD79a, CD79b, Fcgamma Rlla, DAP10, DAP 12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD127, CD 160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1 Id, ITGAE, CD 103, ITGAL, CD 11 a, LFA-1, ITGAM, CD lib, ITGAX, CD 11c, ITGB1, CD29, ITGB2, CD 18, LFA-1, ITGB7, TNFR2, TRANCE/RANKL, DNAM1 (CD226), SLAMF4 (CD244, 2B4), CD84, CD 96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD 162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, J. Clin. Oncol. (2015) 33(6): 651-653). Additionally, intracellular signaling domains may include signaling domains used by NK and NKT cells (see, e.g., Hermanson and Kaufman, Front. Immunol. (2015) 6: 195) such as signaling domains of NKp30 (B7-H6) (see, e.g., Zhang et al., J. Immunol. (2012) 189(5): 2290-2299), and DAP 12 (see, e.g., Topfer et al., J. Immunol. (2015) 194(7): 3201-3212), NKG2D, NKp44, NKp46, DAP10, and CD3z.

Intracellular signaling domains suitable for use in a subject CAR of the present invention include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In some embodiments, the intracellular signaling domain includes at least one (e.g., one, two, three, four, five, six, etc.) ITAM motifs as described below.

In some embodiments, the intracellular signaling domain includes DAP10/CD28 type signaling chains. In some embodiments, the intracellular signaling domain is not covalently attached to the membrane bound CAR, but is instead diffused in the cytoplasm.

Intracellular signaling domains suitable for use in a subject CAR of the present invention include immunoreceptor tyrosine-based activation motif (ITAM)-containing intracellular signaling polypeptides. In some embodiments, an ITAM motif is repeated twice in an intracellular signaling domain, where the first and second instances of the ITAM motif are separated from one another by 6 to 8 amino acids. In one embodiment, the intracellular signaling domain of a subject CAR comprises 3 ITAM motifs.

In some embodiments, intracellular signaling domains includes the signaling domains of human immunoglobulin receptors that contain immunoreceptor tyrosine based activation motifs (ITAMs) such as, but not limited to, FcgammaRI, FcgammaRIIA, FcgammaRIIC, FcgammaRIIIA, FcRL5 (see, e.g., Gillis et al., Front. Immunol. (2014) 5:254).

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12, FCER1G (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In one embodiment, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular signaling domain is derived from FCER1G (also known as FCRG; Fc epsilon receptor I gamma chain; Fc receptor gamma-chain; fc-epsilon RI-gamma; fcRgamma; fceR1 gamma; high affinity immunoglobulin epsilon receptor subunit gamma; immunoglobulin E receptor, high affinity, gamma chain; etc.). In one embodiment, the intracellular signaling domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In one embodiment, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In one embodiment, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). In one embodiment, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). In one embodiment, the intracellular signaling domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In one embodiment, an intracellular signaling domain suitable for use in an FN3 CAR of the present disclosure includes a DAP10/CD28 type signaling chain. In one embodiment, an intracellular signaling domain suitable for use in an FN3 CAR of the present disclosure includes a ZAP70 polypeptide. In some embodiments, the intracellular signaling domain includes a cytoplasmic signaling domain of TCR zeta, FcR gamma, FcR beta, CD3 gamma, CD3 delta, CD3 epsilon, CD5, CD22, CD79a, CD79b, or CD66d. In one embodiment, the intracellular signaling domain in the CAR includes a cytoplasmic signaling domain of human CD3 zeta.

While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The intracellular signaling domain includes any truncated portion of the intracellular signaling domain sufficient to transduce the effector function signal.

The intracellular signaling domains described herein can be combined with any of the antigen binding domains described herein, any of the transmembrane domains described herein, or any of the other domains described herein that may be included in the CAR.

The intracellular domains described herein can be combined with any of the antigen binding domains described herein, any of the transmembrane domains described herein, and/or any of the other domains described herein that may be included in the CAR.

In another embodiment, a spacer domain may be incorporated between the antigen binding domain and the transmembrane domain of the CAR, or between the intracellular domain and the transmembrane domain of the CAR. As used herein, the term "spacer domain" generally means any oligo- or polypeptide that functions to link the transmembrane domain to, either the antigen binding domain or, the intracellular domain in the polypeptide chain. In one embodiment, the spacer domain may comprise up to 300 amino acids, preferably 10 to 100 amino acids and most preferably 25 to 50 amino acids. In another embodiment, a short oligo- or polypeptide linker, preferably between 2 and 10 amino acids in length may form the linkage between the transmembrane domain and the intracellular domain of the CAR. An example of a linker includes a glycine-serine doublet.

Human Antibodies

It may be preferable that the antigen binding domains of the CAR comprise human antibodies or fragments thereof. Fully human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Antibodies directed against the target of choice can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as Ml 3 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Humanized Antibodies

Alternatively, in some embodiments, a non-human antibody can be humanized, where specific sequences or regions of the antibody are modified to increase similarity to an antibody naturally produced in a human. For instance, in the present invention, the antibody or fragment thereof may comprise a non-human mammalian scFv. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka etal., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan etal., J. Immunol., 169:1119-25 (2002), Caldas etal., Protein Eng., 13 (5): 353-60 (2000), Morea et al., Methods, 20(3):267-79 (2000), Baca et al., J. Biol. Chem., 272(16): 10678-84 (1997), Roguska et al., Protein Eng., 9(10):895-904 (1996), Couto et al., Cancer Res., 55 (23 Supp):5973s-5977s (1995), Couto etal., Cancer Res., 55(8): 1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann etal., Nature, 332:323-327 (1988); Verhoeyen etal., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences.

Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody. However, using certain methods of humanization, the affinity and/or specificity of binding of the antibody to the target antigen may be increased using methods of "directed evolution," as described by Wu et al., J. Mol. Biol., 294:151 (1999), the contents of which are incorporated herein by reference herein in their entirety.

Switch Receptor

The present invention provides compositions and methods for modified immune cells or precursors thereof, e.g., modified T cells, comprising a switch receptor. Thus, in some embodiments, the immune cell has been genetically modified to express the switch receptor. As used herein, the term "switch receptor" refers to a molecule designed to reduce the effect of a negative signal transduction molecule, e.g., the effect of a negative signal transduction molecule on a modified immune cell of the present invention. A switch receptor of the present invention may be designed to, in addition to reducing the effects of a negative signal transduction molecule, to convert the negative signal into a positive signal, by virtue of comprising an intracellular domain associated with the positive signal. Switch receptors designed to convert a negative signal into a positive signal are described herein. Accordingly, switch receptors comprise an extracellular domain associated with a negative signal and an intracellular domain associated with a positive signal. For example, a modified immune cell comprising a switch receptor may bind a negative signal transduction molecule in the microenvironment of the modified immune cell, and convert the effect the negative signal transduction molecule may have on the modified immune cell into a positive signal.

Tumor cells generate an immunosuppressive microenvironment that serves to protect them from immune recognition and elimination. This immunosuppressive microenvironment can limit the effectiveness of immunosuppressive therapies such as CAR-T or TCR-T cell therapy. The secreted cytokine Transforming Growth Factor β (TGFβ) directly inhibits the function of cytotoxic T cells and additionally induces regulatory T cell formation to further suppress immune responses. T cell immunosuppression due to TGFβ in the context of prostate cancers has been previously demonstrated (Donkor et al., 2011; Shalapour et al., 2015). To reduce the immunosuppressive effects of TGFβ, immune cells can be modified to express a TGFβR-IL12 switch receptor In one embodiment, a switch receptor suitable for use in the present invention is a TGFβR-IL12Rβ1 receptor. The TGFβR-IL12Rβ1 receptor converts a negative TGF-β signal into a positive IL-12 signal when expressed in a cell. In one embodiment, the TGFβR-IL12Rβ1 receptor comprises an amino acid sequence set forth below:

(SEQ ID NO: 124)
MEAAVAAPRPRLLLLVLAAAAAAAAALLPGATALQCFCHLCTKDNFTCVTD

GLCFVSVTETTDKVIHNSMCIAEIDLIPRDRPFVCAPSSKTGSVTTTYCCN

QDHCNKIELPTTVKSSPGLGPVELAAVIAGPVCFVCISLMLMVYIRAARHL

-continued
CPPLPTPCASSAIEFPGGKETWQWINPVDFQEEASLQEALVVEMSWDKGER

TEPLEKTELPEGAPELALDTELSLEDGDRCKAKM, which may be encoded by the nucleic acid sequence set forth below:

(SEQ ID NO: 125)
Atggaggcggcggtcgctgctccgcgtccccggctgctcctcctcgtgctg gcggcggcggcggcggcggcggcggcgctgctcccggggggcgacggcgtta cagtgtttctgccacctctgtacaaaagacaattttacttgtgtgacagat gggctctgctttgtctctgtcacagagaccacagacaaagttatacacaac agcatgtgtatagctgaaattgacttaattcctcgagataggccgtttgta tgtgcaccctatcaaaaactgggtctgtgactacaacatattgctgcaatc aggaccattgcaataaaatagaacttccaactactgtaaagtcatcacctg gccttggtcctgtggaactggcagctgtcattgctggaccagtgtgcttcg tctgcatctcactcatgttgatggtctatatcagggccgcacggcacctgt gcccgccgctgcccacaccctgtgccagctccgccattgagttccctggag ggaaggagacttggcagtggatcaacccagtggacttccaggaagaggcat ccctgcaggaggccctggtggtagagatgtcctgggacaaaggcgagagga ctgagcctctcgagaagacagagctacctgagggtgcccctgagctggccc tggatacagagttgtccttggaggatggagacaggtgcaaggccaagatg.

Tolerable variations of the TGFβR-IL12Rβ1 receptor will be known to those of skill in the art, while maintaining its intended biological activity (e.g., converting a negative TGF-signal into a positive IL-12 signal when expressed in a cell). Accordingly, a TGFβR-IL12Rβ1 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 9'7%, at least 98%, at least 99% sequence identity to the TGFβR-IL12Rβ1 receptor amino acid sequence set forth in SEQ ID NO:124. Accordingly, a TGFβR-IL12Rβ1 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβR-IL12Rβ1 receptor nucleic acid sequence set forth in SEQ ID NO:125.

In one embodiment, a switch receptor suitable for use in the present invention is a TGFβR-IL12Rβ2 receptor. The TGFβR-IL12Rβ2 receptor converts a negative TGF-β signal into a positive IL-12 signal when expressed in a cell. In one embodiment, the TGFβR-IL12R2 receptor comprises an amino acid sequence set forth below:

(SEQ ID NO: 126)
MGRGLLRGLWPLHIVLWTRIASTIPPHVQKSVNNDMIVTDNNGAVKFPQLC

KFCDVRFSTCDNQKSCMSNCSITSICEKPQEVCVAVWRKNDENITLETVCH

-continued
DPKLPYHDFILEDAASPKCIMKEKKKPGETFFMCSCSSDECNDNIIFSEEY

NTSNPDLLLVIFQVTGISLLPPLGVAISVIIIFYQQKVFVLLAALRPQWCS

REIPDPANSTCAKKYPIAEEKTQLPLDRLLIDWPTPEDPEPLVISEVLHQV

TPVFRHPPCSNWPQREKGIQGHQASEKDMMHSASSPPPPRALQAESRQLVD

LYKVLESRGSDPKPENPACPWTVLPAGDLPTHDGYLPSNIDDLPSHEAPLA

DSLEELEPQHISLSVFPSSSLHPLTFSCGDKLTLDQLKMRCDSLML, which may be encoded by the nucleic acid sequence set forth below:

(SEQ ID NO: 127)
atgggtcgggggctgctcaggggcctgtggccgctgcacatcgtcctgtgg acgcgtatcgccagcacgatcccaccgcacgttcagaagtcggttaataac gacatgatagtcactgacaacaacggtgcagtcaagtttccacaactgtgt aaattttgtgatgtgagattttccacctgtgacaaccagaaatcctgcatg agcaactgcagcatcacctccatctgtgagaagccacaggaagtctgtgtg gctgtatggagaaagaatgacgagaacataacactagagacagtttgccat gaccccaagctccctaccatgactttattctggaagatgctgcttctcca aagtgcattatgaaggaaaaaaaaagcctggtgagactttcttcatgtgt tcctgtagctctgatgagtgcaatgacaacatcatcttctcagaagaatat aacaccagcaatcctgacttgttgctagtcatatttcaagtgacaggcatc agcctcctgccaccactgggagttgccatatctgtcatcatcatcttctac cagcaaaaggtgtttgttctcctagcagccctcagacctcagtggtgtagc agagaaattccagatccagcaaatagcacttgcgctaagaaatatcccatt gcagaggagaagacacagctgcccttggacaggctcctgatagactggccc acgcctgaagatcctgaaccgctggtcatcagtgaagtccttcatcaagtg acccccagttttcagacatccccctgctccaactggccacaaagggaaaa ggaatccaaggtcatcaggcctctgagaaagacatgatgcacagtgcctca agcccaccacctccaagagctctccaagctgagagcagacaactggtggat ctgtacaaggtgctggagagcaggggctccgacccaaagccagaaaaccca gcctgtccctggacggtgctcccagcaggtgaccttccacccatgatggc tacttaccctccaacatagatgacctcccctcacatgaggcacctctcgct gactctctggaagaactggagcctcagcacatctccctttctgttttcccc tcaagttctcttcacccactcaccttctcctgtggtgataagctgactctg gatcagttaaagatgaggtgtgactccctcatgctc.

Tolerable variations of the TGFβR-IL12Rβ2 receptor will be known to those of skill in the art, while maintaining its intended biological activity (e.g., converting a negative TGF-β signal into a positive IL-12 signal when expressed in a cell). Accordingly, a TGFβR-IL12Rβ2 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβR-IL12Rβ2 receptor amino acid sequence set forth in SEQ ID NO:126. Accordingly, a TGFβR-IL12Rβ2 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβR-IL12R2 receptor nucleic acid sequence set forth in SEQ ID NO:127.

In one embodiment, a switch receptor suitable for use in the present invention is a PD1-CTM-CD28 receptor. The PD1-CTM-CD28 receptor converts a negative PD1 signal into a positive CD28 signal when expressed in a cell. The PD1-CTM-CD28 receptor comprises a variant of the PD1 extracellular domain, a CD28 transmembrane domain, and a CD28 cytoplasmic domain. In one embodiment, the PD1-CTM-CD28 receptor comprises an amino acid sequence set forth below:

(SEQ ID NO: 128)
MQIPQAPWPVVWAVLQLGWRPGWFLDSPDRPWNPPTFSPALLVVTEGDNAT

FTCSFSNTSESFVLNWYRMSPSNQTDKLAAFPEDRSQPGQDCRFRVTQLPN

GRDFHMSVVRARRNDSGTYLCGAISLAPKAQIKESLRAELRVTERRAEVPT

AHPSPSPRPAGQFQTLVFWVLVVVGGVLACYSLLVTVAFIIFWVRSKRSRL

LHSDYMNMTPRRPGPTRKHYQPYAPPRDFAAYRS, which may be encoded by the nucleic acid sequence set forth below:

(SEQ ID NO: 129)
ATGCAGATCCCACAGGCGCCCTGGCCAGTCGTCTGGGCGGTGCTACAACTG

GGCTGGCGGCCAGGATGGTTCTTAGACTCCCCAGACAGGCCCTGGAACCCC

CCCACCTTCTCCCCAGCCCTGCTCGTGGTGACCGAAGGGGACAACGCCACC

TTCACCTGCAGCTTCTCCAACACATCGGAGAGCTTCGTGCTAAACTGGTAC

CGCATGAGCCCCAGCAACCAGACGGACAAGCTGGCCGCCTTCCCCGAGGAC

CGCAGCCAGCCCGGCCAGGACTGCCGCTTCCGTGTCACACAACTGCCCAAC

GGGCGTGACTTCCACATGAGCGTGGTCAGGGCCCGGCGCAATGACAGCGGC

ACCTACCTCTGTGGGGCCATCTCCCTGGCCCCCAAGGCGCAGATCAAAGAG

AGCCTGCGGGCAGAGCTCAGGGTGACAGAGAGAAGGGCAGAAGTGCCCACA

GCCCACCCCAGCCCCTCACCCAGGCCAGCCGGCCAGTTCCAAACCCTGGTG

TTTTGGGTGCTGGTGGTGGTTGGTGGAGTCCTGGCTTGCTATAGCTTGCTA

GTAACAGTGGCCTTTATTATTTTCTGGGTGAGGAGTAAGAGGAGCAGGCTC

CTGCACAGTGACTACATGAACATGACTCCCCGCCGCCCCGGGCCCACCCGC

AAGCATTACCAGCCCTATGCCCCACCACGCGACTTCGCAGCCTATCGCTC

C.

Tolerable variations of the PD1-CTM-CD28 receptor will be known to those of skill in the art, while maintaining its intended biological activity (e.g., converting a negative PD1 signal into a positive CD28 signal when expressed in a cell). Accordingly, a PD1-CTM-CD28 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-CTM-CD28 receptor amino acid sequence set forth in SEQ ID NO:128. Accordingly, a PD1-CTM-CD28 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-CTM-CD28 receptor nucleic acid sequence set forth in SEQ ID NO:129.

In one embodiment, a switch receptor suitable for use in the present invention is a PD1-PTM-CD28 receptor. The PD1-PTM-CD28 receptor converts a negative PD1 signal into a positive CD28 signal when expressed in a cell. The PD1-PTM-CD28 receptor comprises a variant of the PD1 extracellular domain, a PD1 transmembrane domain, and a CD28 cytoplasmic domain. In one embodiment, the PD1-PTM-CD28 receptor comprises an amino acid sequence set forth below:

(SEQ ID NO: 130)
MQIPQAPWPVVWAVLQLGWRPGWFLDSPDRPWNPPTFSPALLVVTEGDNAT

FTCSFSNTSESFVLNWYRMSPSNQTDKLAAFPEDRSQPGQDCRFRVTQLPN

GRDFHMSVVRARRNDSGTYLCGAISLAPKLQIKESLRAELRVTERRAEVPT

AHPSPSPRPAGQFQTLVVGVVGGLLGSLVLLVWVLAVIRSKRSRLLHSDYM

NMTPRRPGPTRKHYQPYAPPRDFAAYRS, which may be encoded by the nucleic acid sequence set forth below:

(SEQ ID NO: 131)
ATGCAGATCCCACAGGCGCCCTGGCCAGTCGTCTGGGCGGTGCTACAACTG

GGCTGGCGGCCAGGATGGTTCTTAGACTCCCCAGACAGGCCCTGGAACCCC

CCCACCTTCTCCCCAGCCCTGCTCGTGGTGACCGAAGGGGACAACGCCACC

TTCACCTGCAGCTTCTCCAACACATCGGAGAGCTTCGTGCTAAACTGGTAC

CGCATGAGCCCCAGCAACCAGACGGACAAGCTGGCCGCCTTCCCCGAGGAC

CGCAGCCAGCCCGGCCAGGACTGCCGCTTCCGTGTCACACAACTGCCCAAC

GGGCGTGACTTCCACATGAGCGTGGTCAGGGCCCGGCGCAATGACAGCGGC

ACCTACCTCTGTGGGGCCATCTCCCTGGCCCCCAAGGCGCAGATCAAAGAG

AGCCTGCGGGCAGAGCTCAGGGTGACAGAGAGAAGGGCAGAAGTGCCCACA

GCCCACCCCAGCCCCTCACCCAGGCCAGCCGGCCAGTTCCAAACCCTGGTG

GTTGGTGTCGTGGGCGGCCTGCTGGGCAGCCTGGTGCTGCTAGTCTGGGTC

CTGGCCGTCATCAGGAGTAAGAGGAGCAGGCTCCTGCACAGTGACTACATG

AACATGACTCCCCGCCGCCCCGGGCCCACCCGCAAGCATTACCAGCCCTAT

GCCCCACCACGCGACTTCGCAGCCTATCGCTCC.

Tolerable variations of the PD1-PTM-CD28 receptor will be known to those of skill in the art, while maintaining its intended biological activity (e.g., converting a negative PD1 signal into a positive CD28 signal when expressed in a cell). Accordingly, a PD1-PTM-CD28 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-PTM-CD28 receptor amino acid sequence set forth in SEQ ID NO:130. Accordingly, a PD1-PTM-CD28 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-PTM-CD28 receptor nucleic acid sequence set forth in SEQ ID NO:131.

In one embodiment, a switch receptor suitable for use in the present invention is a PD1$^{A132L}$-PTM-CD28 receptor. The PD1$^{A132L}$-PTM-CD28 receptor converts a negative PD1 signal into a positive CD28 signal when expressed in a cell. A point mutation at amino acid position 132, substituting alanine with leucine (A132L), of PD1 was found to increase its affinity with PD-L1 by two fold (see, e.g., Zhang et al., Immunity (2004) 20(3), 337-347). The PD1$^{A132L}$-PTM-CD28 receptor comprises a variant of the PD1 extracellular domain that has an amino acid substitution at position 132 (A132L), a PD1 transmembrane domain, and a CD28 cytoplasmic domain. In one embodiment, the PD1$^{A132L}$-PTM-CD28 receptor comprises an amino acid sequence set forth below:

(SEQ ID NO: 132)
MQIPQAPWPVVWAVLQLGWRPGWFLDSPDRPWNPPTFSPALLVVTEGDNAT

FTCSFSNTSESFVLNWYRMSPSNQTDKLAAFPEDRSQPGQDCRFRVTQLPN

GRDFHMSVVRARRNDSGTYLCGAISLAPKLQIKESLRAELRVTERRAEVPT

AHPSPSPRPAGQFQTLVVGVVGGLLGSLVLLVWVLAVIRSKRSRLLHSDYM

NMTPRRPGPTRKHYQPYAPPRDFAAYRS, which may be encoded by the nucleic acid sequence set forth below:

(SEQ ID NO: 133)
Atgcagatcccacaggcgccctggccagtcgtctgggcggtgctacaactg ggctggcggccaggatggttcttagactccccagacaggccctggaacccc cccaccttctccccagccctgctcgtggtgaccgaaggggacaacgccacc ttcacctgcagcttctccaacacatcggagagtcgtgctaaactggtacc gcatgagcccagcaaccagacggacaagctggccgccttccccgaggacc gcagccagcccggccaggactgccgcttccgtgtcacacaactgcccaacg ggcgtgacttccacatgagcgtggtcagggcccggcgcaatgacagcggca cctacctctgtggggccatctccctggcccccaagctgcagatcaaagaga gcctgcgggcagagctcagggtgacagagagaagggcagaagtgcccacag cccacccagcccctcacccaggccagccggccagttccaaaccctggtgg ttggtgtcgtgggcggcctgctgggcagcctggtgctgctagtctgggtcc tggccgtcatcaggagtaagaggagcaggctcctgcacagtgactacatga -continued acatgactccccgccgccccgggcccaccccgcaagcattaccagccctatg ccccaccacgcgacttcgcagcctatcgc.

Tolerable variations of the PD1$^{4132L}$-PTM-CD28 receptor will be known to those of skill in the art, while maintaining its intended biological activity (e.g., converting a negative PD1 signal into a positive CD28 signal when expressed in a cell). Accordingly, a PD1$^{4132L}$-PTM-CD28 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1$^{4132L}$-PTM-CD28 receptor amino acid sequence set forth in SEQ ID NO:132. Accordingly, a PD1$^{4132L}$-PTM-CD28 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1$^{4132L}$-PTM-CD28 receptor nucleic acid sequence set forth in SEQ ID NO:133.

Other suitable switch receptors for use in the present invention are described in PCT Publication No. WO2013019615A2, the disclosure of which is incorporated herein by reference.

Nucleic Acids and Expression Vectors

The present invention provides a nucleic acid encoding a chimeric antigen receptor (CAR) having affinity for a target antigen. The present invention provides a nucleic acid encoding a T cell receptor (TCR) having affinity for a target antigen. The present invention also provides a nucleic acid encoding switch receptor.

In some embodiments, a nucleic acid of the present disclosure provides for the production of a TCR as described herein, e.g., in a mammalian cell. In some embodiments, a nucleic acid of the present disclosure provides for amplification of the TCR-encoding nucleic acid.

As described herein, a TCR of the present disclosure comprises a TCR alpha chain and a TCR beta chain. Accordingly, the present disclosure provides a nucleic acid encoding a TCR alpha chain, and a nucleic acid encoding a TCR beta chain. In some embodiments, the nucleic acid encoding a TCR alpha chain is separate from the nucleic acid encoding a TCR beta chain. In an exemplary embodiment, the nucleic acid encoding a TCR alpha chain, and the nucleic acid encoding a TCR beta chain, resides within the same nucleic acid.

In some embodiments, a nucleic acid of the present disclosure comprises a nucleic acid comprising a TCR alpha chain coding sequence and a TCR beta chain coding sequence. In some embodiments, a nucleic acid of the present disclosure comprises a nucleic acid comprising a TCR alpha chain coding sequence and a TCR beta chain coding sequence that is separated by a linker. A linker for use in the present disclosure allows for multiple proteins to be encoded by the same nucleic acid sequence (e.g., a multicistronic or bicistronic sequence), which are translated as a polyprotein that is dissociated into separate protein components. For example, a linker for use in a nucleic acid of the present disclosure comprising a TCR alpha chain coding sequence and a TCR beta chain coding sequence, allows for the TCR alpha chain and TCR beta chain to be translated as a polyprotein that is dissociated into separate TCR alpha chain and TCR beta chain components.

In some embodiments, the linker comprises a nucleic acid sequence that encodes for an internal ribosome entry site (IRES). As used herein, "an internal ribosome entry site" or "IRES" refers to an element that promotes direct internal ribosome entry to the initiation codon, such as ATG, of a protein coding region, thereby leading to cap-independent translation of the gene. Various internal ribosome entry sites are known to those of skill in the art, including, without limitation, IRES obtainable from viral or cellular mRNA sources, e.g., immunogloublin heavy-chain binding protein (BiP); vascular endothelial growth factor (VEGF); fibroblast growth factor 2; insulin-like growth factor; translational initiation factor eIF4G; yeast transcription factors TFIID and HAP4; and IRES obtainable from, e.g., cardiovirus, rhinovirus, aphthovirus, HCV, Friend murine leukemia virus (FrMLV), and Moloney murine leukemia virus (MoMLV). Those of skill in the art would be able to select the appropriate IRES for use in the present invention.

In some embodiments, the linker comprises a nucleic acid sequence that encodes for a self-cleaving peptide. As used herein, a "self-cleaving peptide" or "2A peptide" refers to an oligopeptide that allow multiple proteins to be encoded as polyproteins, which dissociate into component proteins upon translation. Use of the term "self-cleaving" is not intended to imply a proteolytic cleavage reaction. Various self-cleaving or 2A peptides are known to those of skill in the art, including, without limitation, those found in members of the Picornaviridae virus family, e.g., foot-and-mouth disease virus (FMDV), equine rhinitis A virus (ERAVO, Thosea asigna virus (TaV), and porcine tescho virus-1 (PTV-1); and carioviruses such as Theilovirus and encephalomyocarditis viruses. 2A peptides derived from FMDV, ERAV, PTV-1, and TaV are referred to herein as "F2A," "E2A," "P2A," and "T2A," respectively. Those of skill in the art would be able to select the appropriate self-cleaving peptide for use in the present invention.

In some embodiments, a linker further comprises a nucleic acid sequence that encodes a furin cleavage site. Furin is a ubiquitously expressed protease that resides in the trans-golgi and processes protein precursors before their secretion. Furin cleaves at the COOH— terminus of its consensus recognition sequence. Various furin consensus recognition sequences (or "furin cleavage sites") are known to those of skill in the art, including, without limitation, Arg-X-Lys-Arg (SEQ ID NO:134) or Arg-X-Arg-Arg (SEQ ID NO:135), X1-Arg-X-X1-Arg (SEQ ID NO:136) and Arg-X-X-Arg (SEQ ID NO:137), such as an Arg-Gln-Lys-Arg (SEQ ID NO:138), where X is any naturally occurring amino acid, and X1 represents Arg or Lys. Those of skill in the art would be able to select the appropriate Furin cleavage site for use in the present invention.

In some embodiments, the linker comprises a nucleic acid sequence encoding a combination of a Furin cleavage site and a 2A peptide. Examples include, without limitation, a linker comprising a nucleic acid sequence encoding Furin and F2A, a linker comprising a nucleic acid sequence encoding Furin and E2A, a linker comprising a nucleic acid sequence encoding Furin and P2A, a linker comprising a nucleic acid sequence encoding Furin and T2A. Those of skill in the art would be able to select the appropriate combination for use in the present invention. In such embodiments, the linker may further comprise a spacer sequence between the Furin and 2A peptide. Various spacer sequences are known in the art, including, without limitation, glycine serine (GS) spacers such as (GS)n, (GSGGS)n (SEQ ID NO:99) and (GGGS)n (SEQ ID NO:100), where n represents an integer of at least 1. Exemplary spacer sequences can comprise amino acid sequences including, without limitation, GGSG (SEQ ID NO:102), GGSGG (SEQ ID NO:103), GSGSG (SEQ ID NO:104), GSGGG (SEQ ID NO:105), GGGSG (SEQ ID NO:106), GSSSG (SEQ ID NO:107), and the like. Those of skill in the art would be able to select the appropriate spacer sequence for use in the present invention.

In an exemplary embodiment, a nucleic acid of the present disclosure comprises a nucleic acid sequence comprising a TCR alpha chain coding sequence and a TCR beta chain coding sequence that is separated by a Furin-(G4S)2-T2A (F-GS2-T2A) linker. The F-GS2-T2A linker may be encoded by the nucleic acid sequence CGTGCGAAGAGGGGCGGCGGGGGCTCCGGCGGGG-GAGGCAGTGAGGGCCGCGG CTCCCTGCTGACCTGCG-GAGATGTAGAAGAGAACCCAGGCCCC (SEQ ID NO:139), and may comprise the amino acid sequence RAKRGGGGSGGGGSEGRGSLLTCGDVEENPGP (SEQ ID NO:140). Those of skill in the art would appreciate that linkers of the present invention may include tolerable sequence variations.

In some embodiments, the present disclosure provides a nucleic acid comprising a nucleic acid sequence encoding a switch receptor as described herein. In some embodiments, a nucleic acid comprises a nucleic acid sequence encoding a switch receptor and a nucleic acid sequence encoding a TCR (e.g., 8F TCR). In one embodiment, the nucleic acid sequence encoding the switch receptor and the nucleic acid sequence encoding the TCR resides on separate nucleic acids. In one embodiment, the nucleic acid sequence encoding the switch receptor and the nucleic acid sequence encoding the TCR resides within the same nucleic acid. In such an embodiment, the nucleic acid sequence encoding the switch receptor and the nucleic acid sequence encoding the TCR is separated by a linker as described herein.

For example, a nucleic acid of the present disclosure may comprise a nucleic acid sequence encoding a switch receptor, a linker, and a nucleic acid sequence encoding a TCR. In one embodiment, the linker comprises a nucleic acid sequence encoding a 2A peptide (e.g., F2A). In an exemplary embodiment, a nucleic acid of the present disclosure may comprise a nucleic acid sequence encoding a switch receptor and a nucleic acid sequence encoding a TCR separated by a nucleic acid sequence encoding F2A. In an exemplary embodiment, the nucleic acid sequence encoding a TCR comprises a TCR alpha chain coding sequence and a TCR beta chain coding sequence separated by a nucleic acid sequence encoding F-GS2-T2A.

Accordingly, in one embodiment, a nucleic acid of the present disclosure comprises from 5' to 3': a nucleic acid sequence encoding a switch receptor, a nucleic acid sequence encoding a linker, and a nucleic acid sequence encoding a TCR. In one embodiment, a nucleic acid of the present disclosure comprises from 5' to 3': a nucleic acid sequence encoding a TCR, a nucleic acid sequence encoding a linker, and a nucleic acid sequence encoding a switch receptor. In an exemplary embodiment, a nucleic acid of the present disclosure comprises from 5' to 3': a nucleic acid sequence encoding a switch receptor, a nucleic acid sequence encoding F2A, and a nucleic acid sequence encoding a TCR. In another exemplary embodiment, a nucleic acid of the present disclosure comprises from 5' to 3': a nucleic acid sequence encoding a switch receptor, a nucleic acid sequence encoding F2A, a nucleic acid sequence encoding a TCR alpha chain, a nucleic acid sequence encoding F-GS2-T2A, and a nucleic acid sequence encoding a TCR beta chain.

In some embodiments, a nucleic acid of the present disclosure may be operably linked to a transcriptional control element, e.g., a promoter, and enhancer, etc. Suitable promoter and enhancer elements are known to those of skill in the art. Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

For expression in a bacterial cell, suitable promoters include, but are not limited to, lad, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. Proc. Natl. Acad. Sci. USA (1993) 90:7739; and Marodon et al. (2003) Blood 101:3416. As another example, a CD8 gene promoter can be used. NK cell-specific expression can be achieved by use of an NcrI (p46) promoter; see, e.g., Eckelhart et al. Blood (2011) 117:1565.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173(1): 86-93; Alpuche-Aranda et al., Proc. Natl. Acad. Sci. USA (1992) 89(21): 10079-83), a nirB promoter (Harborne et al. Mol. Micro. (1992) 6:2805-2813), and the like (see, e.g., Dunstan et al., Infect. Immun. (1999) 67:5133-5141; McKelvie et al., Vaccine (2004) 22:3243-3255; and Chatfield et al., Biotechnol. (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al., Infect. Immun. (2002) 70:1087-1096); an rpsM promoter (see, e.g., Valdivia and Falkow Mol. Microbiol. (1996). 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the EF-1 alpha promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

In some embodiments, a nucleic acid of the present disclosure further comprises a nucleic acid sequence encoding a CAR inducible expression cassette. In one embodiment, the CAR inducible expression cassette is for the production of a transgenic polypeptide product that is released upon CAR signaling. See, e.g., Chmielewski and Abken, Expert Opin. Biol. Ther. (2015) 15(8): 1145-1154; and Abken, Immunotherapy (2015) 7(5): 535-544.

A vector may be used to introduce a T cell receptor (TCR) or a chimeric antigen receptor (CAR) into an immune (e.g., T cell) as described elsewhere herein. In one aspect, the invention includes a vector comprising a nucleic acid sequence encoding a TCR. In another aspect, the invention includes a vector comprising a nucleic acid sequence encoding a CAR. A vector may be used to introduce a switch receptor into an immune cell (e.g., T cell) as described elsewhere herein. In another aspect, the invention includes a vector comprising a nucleic acid sequence encoding a switch receptor.

The vector can comprise a plasmid vector, viral vector, retrotransposon (e.g. piggyback, sleeping beauty), site directed insertion vector (e.g. CRISPR, Zn finger nucleases, TALEN), suicide expression vector, lentiviral vector, RNA vector, or other known vector in the art.

The present invention also provides a vector in which DNA of the present invention is inserted. Vectors, including those derived from retroviruses such as lentivirus, are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells, such as hepatocytes. They also have the added advantage of resulting in low immunogenicity in the subject into which they are introduced.

The expression of natural or synthetic nucleic acids is typically achieved by operably linking a nucleic acid or portions thereof to a promoter, and incorporating the construct into an expression vector. The vector is one generally capable of replication in a mammalian cell, and/or also capable of integration into the cellular genome of the mammal. Typical vectors contain transcription and translation terminators, initiation sequences, and promoters useful for regulation of the expression of the desired nucleic acid sequence.

The nucleic acid can be cloned into any number of different types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

The expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35: 2543-2549; Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648; Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617); SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

In some embodiments, an expression vector (e.g., a lentiviral vector) may be used to introduce the CAR and/or TCR and/or switch receptor into an immune cell or precursor thereof (e.g., a T cell). Accordingly, an expression vector (e.g., a lentiviral vector) of the present invention may comprise a nucleic acid encoding for a CAR and/or TCR and/or switch receptor. In some embodiments, the expression vector (e.g., lentiviral vector) will comprise additional elements that will aid in the functional expression of the CAR and/or TCR and/or switch receptor encoded therein. In some embodiments, an expression vector comprising a nucleic acid encoding for a CAR and/or TCR and/or switch receptor further comprises a mammalian promoter. In one embodiment, the vector further comprises an elongation-factor-1-alpha promoter (EF-1α promoter). Use of an EF-1α promoter may increase the efficiency in expression of downstream transgenes (e.g., a CAR and/or the dominant negative receptor and/or switch receptor encoding nucleic acid sequence). Physiologic promoters (e.g., an EF-1a promoter) may be less likely to induce integration mediated genotoxicity, and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention. In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In one embodiment, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a CAR and/or the TCR and/or switch receptor.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

Figure 7:
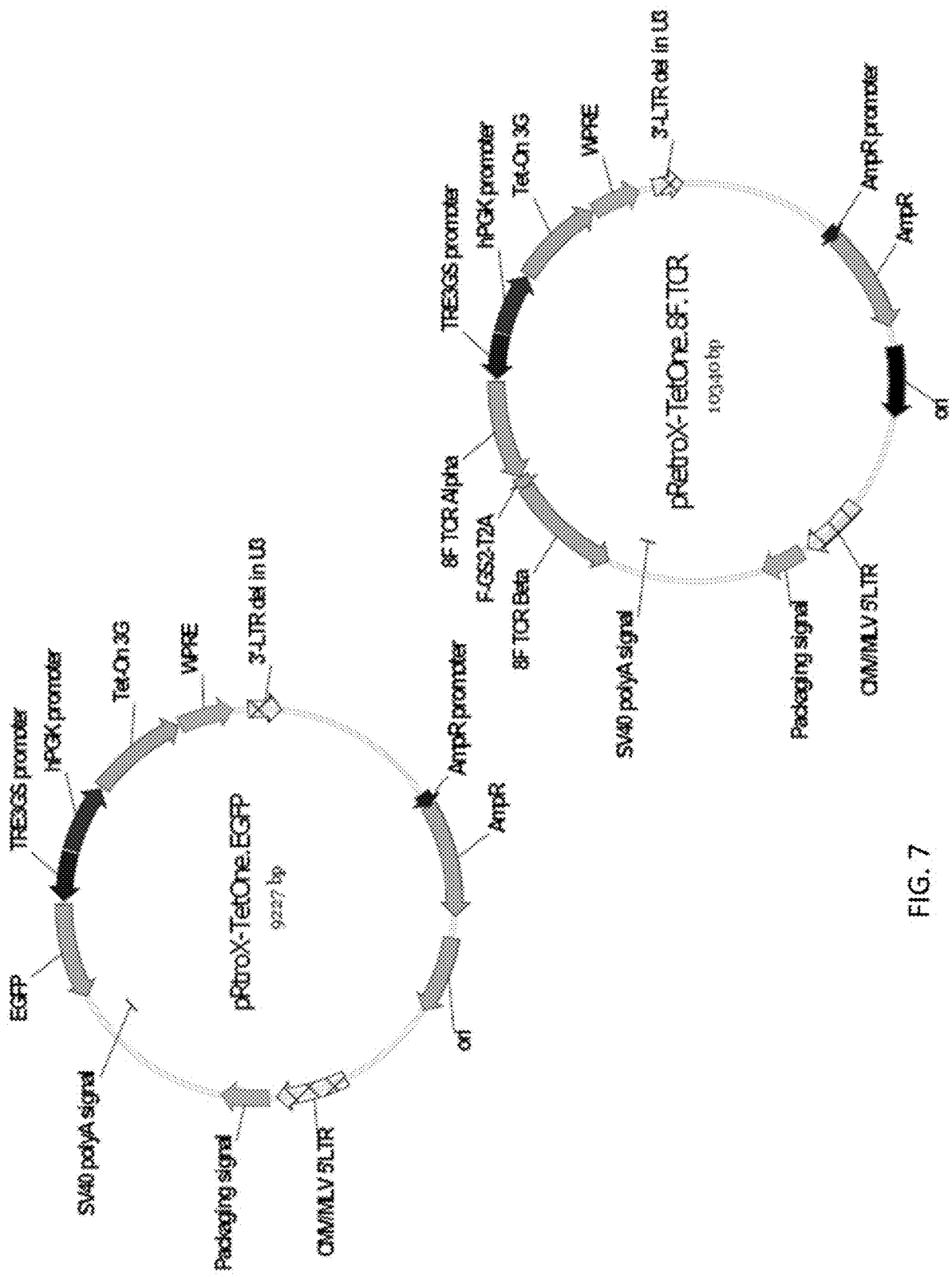
FIG. 7 is a set of images depicting vector maps for tetracycline (Tet)-On retroviral vectors for controlled gene expression of EGFP (pRetoX-TetONE.EGFP) and NY-ESO-1 TCR (8F) (pRetroX-TetONE.8F.TCR).

In an exemplary embodiment, the invention provides a vector comprising a Tet-On gene expression system, as shown in FIG. 7. As shown in FIG. 7, a pRetroX-TetOne.EGFP vector comprises the Tet-On inducible expression system. A human PGK (hPGK) promoter drives expression of Tet-On 3G (a reverse Tet transactivator protein). An inducible TRE3GS promoter drives expression of a transgene (e.g., EGFP, as depicted in the pRetroX-TetOne.EGFP vector). In the presence of doxycycline (Dox), Tet-On 3G binds specifically to PTRE3G and activates transcription of the downstream transgene (e.g., EGFP). Also shown in FIG. 7 is a pRetroX-TetOne.8F.TCR vector of the present invention. As shown, the pRetroX-TetOne.8F.TCR vector comprises the Tet-On inducible expression system that drives expression of the 8F TCR in the presence of Dox.

The "all-in-one" design of the vectors depicted in FIG. 7 (an embodiment of the present invention) allows for both the transactivator protein component and the inducible promoter component to reside on a single vector. The Tet-On 3G transactivator is expressed in the forward direction from a human phosphoglycerate kinase 1 promoter (hPGK promoter), and the exogenous TCR and/or CAR and/or switch receptor is expressed from the TRE3GS promoter in the reverse orientation. Any promoter can be used to drive expression of the transactivator protein in the forward direction, e.g., any constitutive promoter as described herein (e.g., an EF-1a promoter).

Accordingly, the present invention provides a vector comprising in a forward direction, a constitutive promoter operably linked to a nucleic acid encoding a transactivator protein, and in a reverse orientation, an inducible promoter operably linked to a nucleic acid encoding a TCR and/or CAR and/or switch receptor.

In another embodiment, the invention provides a vector comprising a Tet-On inducible system that drives expression of a CAR and/or TCR and/or switch receptor as described herein. The vector may be a self-inactivating vector. The vector may further comprise an EF-1α promoter, a rev response element (RRE), a woodchuck hepatitis virus post-transcriptional regulatory element (WPRE), and a cPPT sequence.

In one embodiment, a nucleic acid encoding a TCR/CAR and a nucleic acid encoding a switch receptor resides on the same nucleic acid. The nucleic acid encoding a TCR/CAR and the nucleic acid encoding a switch receptor may be separated by a linker as described herein (e.g., a F-GS2-T2A linker). Accordingly, an expression vector of the invention comprises a nucleic acid encoding a TCR/CAR and a nucleic acid encoding a switch receptor.

In one embodiment, the nucleic acid encoding a TCR/CAR and the nucleic acid encoding a switch receptor resides on separate nucleic acids. Accordingly, the present invention provides separate expression vectors, one expression vector comprising the nucleic acid encoding a TCR/CAR, and another expression vector comprising the nucleic acid encoding a switch receptor. In embodiments where separate expression vectors comprise the nucleic acid encoding a TCR/CAR and the nucleic acid encoding a switch receptor, the separate expression vectors can comprise the same backbone sequences. In other embodiments, the separate expression vectors comprise different backbone sequences. For example, in one embodiment, a lentiviral vector comprises the nucleic acid encoding a TCR/CAR, and a retroviral vector comprises the nucleic acid encoding a switch receptor. Each expression vector can also comprise a Tet-On inducible system as described herein. The skilled artisan would be able to determine the appropriate expression vector.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a CAR and/or TCR and/or switch receptor of the present disclosure. Methods for introducing RNA into a host cell are known in the art. See, e.g., Zhao et al. Cancer Res. (2010) 15: 9053.

Introducing RNA comprising a nucleotide sequence encoding a CAR and/or TCR and/or switch receptor of the present disclosure into a host cell can be carried out in vitro or ex vivo or in vivo. For example, a host cell (e.g., an NK cell, a cytotoxic T lymphocyte, etc.) can be electroporated in vitro or ex vivo with RNA comprising a nucleotide sequence encoding a CAR and/or TCR and/or switch receptor of the present disclosure.

The production of any of the molecules described herein can be verified by sequencing. Expression of the full length proteins may be verified using immunoblot, immunohistochemistry, flow cytometry or other technology well known and available in the art.

In order to assess expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of Generating Modified Immune Cells

The present invention provides methods for producing/generating a modified immune cell or precursor cell thereof (e.g., a modified T cell). The cells are generally engineered by introducing a nucleic acid encoding a TCR and/or CAR and/or switch receptor as described herein. Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

In some embodiments, a nucleic acid encoding a CAR and/or TCR and/or switch receptor is introduced into a cell by an expression vector. Expression vectors comprising a nucleic acid encoding a the TCR and/or CAR and/or switch receptor are provided herein. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggybak, and Integrases such as Phi31. Some other suitable expression vectors include Herpes simplex virus (HSV) and retrovirus expression vectors.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the CAR and/or TCR and/or switch receptor in the host cell. In some embodiments, the adenovirus genome is a 36 kb, linear, double stranded DNA, where a foreign DNA sequence (e.g., a nucleic acid encoding a TCR and/or CAR and/or switch receptor) may be inserted to substitute large pieces of adenoviral DNA in order to make the expression vector of the present invention (see, e.g., Danthinne and Imperiale, Gene Therapy (2000) 7(20): 1707-1714).

Another expression vector is based on an adeno associated virus, which takes advantage of the adenovirus coupled systems. This AAV expression vector has a high frequency of integration into the host genome. It can infect non-dividing cells, thus making it useful for delivery of genes into mammalian cells, for example, in tissue cultures or in vivo. The AAV vector has a broad host range for infectivity. Details concerning the generation and use of AAV vectors are described in U.S. Pat. Nos. 5,139,941 and 4,797,368.

Retrovirus expression vectors are capable of integrating into the host genome, delivering a large amount of foreign genetic material, infecting a broad spectrum of species and cell types and being packaged in special cell lines. The retrovirus vector is constructed by inserting a nucleic acid (e.g., a nucleic acid encoding a TCR and/or CAR and/or switch receptor) into the viral genome at certain locations to produce a virus that is replication defective. Though the retrovirus vectors are able to infect a broad variety of cell types, integration and stable expression of the TCR and/or CAR and/or switch receptor, requires the division of host cells.

Lentivirus vectors are derived from lentiviruses, which are complex retroviruses that, in addition to the common retroviral genes gag, pol, and env, contain other genes with regulatory or structural function (see, e.g., U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentivirus vectors have been generated by multiply attenuating the HIV virulence genes, for example, the genes env, vif, vpr, vpu and nef are deleted making the vector biologically safe. Lentivirus vectors are capable of infecting non-dividing cells and can be used for both in vivo and ex vivo gene transfer and expression, e.g., of a nucleic acid encoding a TCR and/or CAR and/or switch receptor (see, e.g., U.S. Pat. No. 5,994,136).

Expression vectors including a nucleic acid of the present disclosure can be introduced into a host cell by any means known to persons skilled in the art. The expression vectors may include viral sequences for transfection, if desired. Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and may be screened by virtue of a marker present in the vectors. Various markers that may be used are known in the art, and may include hprt, neomycin resistance, thymidine kinase, hygromycin resistance, etc. As used herein, the terms "cell," "cell line," and "cell culture" may be used interchangeably. In some embodiments, the host cell an immune cell or precursor thereof, e.g., a T cell, an NK cell, or an NKT cell.

The present invention also provides genetically engineered cells which include and stably express a TCR and/or CAR and/or switch receptor of the present disclosure. In some embodiments, the genetically engineered cells are genetically engineered T-lymphocytes (T cells), naive T cells (TN), memory T cells (for example, central memory T cells (TCM), effector memory cells (TEM)), natural killer cells (NK cells), and macrophages capable of giving rise to therapeutically relevant progeny. In one embodiment, the genetically engineered cells are autologous cells.

Modified cells (e.g., comprising a TCR and/or CAR and/or switch receptor) may be produced by stably transfecting host cells with an expression vector including a nucleic acid of the present disclosure. Additional methods to generate a modified cell of the present disclosure include, without limitation, chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells expressing a TCR and/or CAR and/or switch receptor of the present disclosure may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, e.g., Sambrook et al. (2001), Molecular Cloning: A Laboratory Manual, Cold Spring Harbor Laboratory, New York. Chemical methods for introducing an expression vector into a host cell include colloidal dispersion systems, such as macromolecule complexes, nanocapsules, microspheres, beads, and lipid-based systems including oil-in-water emulsions, micelles, mixed micelles, and liposomes.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about $-20°$ C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Moreover, the nucleic acids may be introduced by any means, such as transducing the expanded host cells, transfecting the expanded host cells, and electroporating the expanded host cells. One nucleic acid may be introduced by one method and another nucleic acid may be introduced into the host cell by a different method.

RNA

In one embodiment, the nucleic acids introduced into the host cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a chimeric membrane protein. By way of example, the template encodes an antibody, a fragment of an antibody or a portion of an antibody. By way of another example, the template comprises an extracellular domain comprising a single chain variable domain of an antibody, such as anti-CD3, and an intracellular domain of a co-stimulatory molecule. In one embodiment, the template for the RNA chimeric membrane protein encodes a chimeric membrane protein comprising an extracellular domain comprising an antigen binding domain derived from an antibody to a co-stimulatory molecule, and an intracellular domain derived from a portion of an intracellular domain of CD28 and 4-1BB.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the RNA is electroporated into the cells, such as in vitro transcribed RNA.

The disclosed methods can be applied to the modulation of host cell activity in basic research and therapy, in the fields of cancer, stem cells, acute and chronic infections, and autoimmune diseases, including the assessment of the ability of the genetically modified host cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of host cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Methods of Treatment

The modified immune cells or precursor cells thereof (e.g., modified T cells) described herein may be included in a composition for therapy. The composition may include a pharmaceutical composition and further include a pharmaceutically acceptable carrier. A therapeutically effective amount of the pharmaceutical composition comprising the modified T cells may be administered.

In one aspect, the invention includes a method for adoptive cell transfer therapy comprising administering to a subject in need thereof a modified immune cell of the present invention. In another aspect, the invention includes a method of treating a disease or condition in a subject comprising administering to a subject in need thereof a population of modified immune cells.

Also included is a method of treating a disease or condition in a subject comprising administering to a subject in need thereof a genetically modified allogeneic immune cell (e.g., T cell) comprising an exogenous nucleic acid encoding a transgenic TCR and/or CAR and/or switch receptor comprising a tetracycline (Tet)-On inducible gene expression system, wherein the Tet-On inducible gene expression system comprises a reverse Tet transactivator (rtTA) fusion protein and at least one promoter fused downstream of at least one Tet-operator sequence, wherein when doxycycline (Dox) is administered to the cell, the gene expression system is induced and the TCR and/or CAR and/or switch receptor is expressed.

Additionally included is a method of treating a disease or condition in a subject comprising administering to a subject in need thereof a genetically modified autologous immune cell (e.g., T cell) comprising an exogenous nucleic acid encoding a transgenic TCR and/or CAR and/or switch receptor comprising a tetracycline (Tet)-On inducible gene expression system, wherein the Tet-On inducible gene expression system comprises a reverse Tet transactivator (rtTA) fusion protein and at least one promoter fused downstream of at least one Tet-operator sequence, wherein when doxycycline (Dox) is administered to the cell, the gene expression system is induced and the TCR and/or CAR and/or switch receptor is expressed.

A method of treating cancer is provided by the present invention. In some embodiments, the method comprises administering to a subject in need thereof a modified immune cell (e.g., T cell) comprising an inducible TCR or CAR expression system as described elsewhere herein.

In one embodiment, a method of treating cancer in a subject in need thereof comprises administering to the subject a combination comprising a modified immune cell comprising an inducible TCR or CAR expression system, and doxycycline. In some embodiments, the modified immune cell (e.g., T cell) is co-administered with the doxycycline.

In some embodiments, the modified immune cell (e.g., T cell) is contacted with doxycycline prior to administration into the subject. In such embodiments, the modified cell is "pre-induced" prior to administration into the subject. In some embodiments, continuous administration of doxycycline to the patient after administration of a pre-induced modified cell allows for continuous expression of the TCR or CAR. In such cases, immune cell (e.g., T cell) exhaustion may occur. In some embodiments, the pre-induced modified cell (e.g., T cell) expresses the TCR or CAR for a period of time within the patient, and due to non-continuous administration of doxycycline, expression of the TCR or CAR will reduce and/or halt. In some embodiments, subsequent administration of doxycycline to the patient will re-induce expression of the TCR or CAR. In cases where doxycycline is subsequently administered to re-induce expression of the TCR or CAR, the doxycycline can be metabolized by the patient by normal processes. Once the doxycycline is fully metabolized, expression of the TCR or CAR may be reduced and/or halted.

The described procedure can be repeated multiple times to "re-treat" subjects without having to re-administer modified immune cells. For example, in subjects with a relapsed cancer (e.g., the cancer survived initial treatment with modified cells), re-administration of doxycycline can target the relapsed cancer.

The present invention also provides a method of treating cancer in a subject in need thereof comprising administering a combination of TCR redirected T cells comprising an inducible TCR expression system, and doxycycline. Accordingly, in one embodiment, a method of treating cancer in a subject in need thereof comprises administering to the subject a combination comprising a universal T cell receptor (TCR) redirected T cell and doxycycline, wherein the T cell comprises an insertion and/or deletion in one or more gene loci each encoding an endogenous protein selected from the group consisting of TRAC, TRBC, B2M, and CIITA, wherein the insertion and/or deletion is capable of down-regulating expression of the endogenous protein; and an inducible TCR expression system comprising: a first nucleic acid comprising a human phosphoglycerate kinase 1 promoter operably linked upstream to a nucleic acid sequence encoding a Tet-On 3G transactivator protein; and a second nucleic acid comprising an inducible TRE3GS promoter operably linked upstream to a nucleic acid sequence encoding an exogenous TCR, wherein the second nucleic acid is in reverse orientation to the first nucleic acid, wherein the doxycycline induces expression of the exogenous TCR.

In another embodiment, a method of treating cancer in a subject in need thereof comprises administering to the subject a combination comprising a universal T cell receptor (TCR) redirected T cell and doxycycline, wherein the T cell comprises an insertion and/or deletion in one or more gene loci each encoding an endogenous protein selected from the group consisting of TRAC, TRBC, B2M, and CIITA, wherein the insertion and/or deletion is capable of down-regulating expression of the endogenous protein; a switch receptor; and an inducible TCR expression system comprising: a first nucleic acid comprising a human phosphoglycerate kinase 1 promoter operably linked upstream to a nucleic acid sequence encoding a Tet-On 3G transactivator protein; and a second nucleic acid comprising an inducible TRE3GS promoter operably linked upstream to a nucleic acid sequence encoding an exogenous TCR, wherein the second nucleic acid is in reverse orientation to the first nucleic acid, wherein the doxycycline induces expression of the exogenous TCR.

Also provided is a method of preventing T cell exhaustion in a subject in need thereof comprising administering to the subject a combination comprising a universal T cell receptor (TCR) redirected T cell and doxycycline, wherein the T cell comprises an insertion and/or deletion in one or more gene loci each encoding an endogenous protein selected from the group consisting of TRAC, TRBC, B2M, and CIITA, wherein the insertion and/or deletion is capable of down-regulating expression of the endogenous protein; a switch receptor; and an inducible TCR expression system comprising: a first nucleic acid comprising a human phosphoglycerate kinase 1 promoter operably linked upstream to a nucleic acid sequence encoding a Tet-On 3G transactivator protein; and a second nucleic acid comprising an inducible TRE3GS promoter operably linked upstream to a nucleic acid sequence encoding an exogenous TCR, wherein the second nucleic acid is in reverse orientation to the first nucleic acid, wherein the doxycycline induces expression of the exogenous TCR.

As described herein, the doxycycline can be used to pre-induce the universal TCR directed T cell. As described herein, the doxycycline can be used to re-induce the universal TCR directed T cell.

The modified T cells generated as described herein possess T cell function. Further, the modified T cells can be administered to a mammal, preferably a human, to suppress an immune reaction, such as those common to autoimmune diseases such as diabetes, psoriasis, rheumatoid arthritis, multiple sclerosis, GVHD, enhancing allograft tolerance induction, transplant rejection, and the like. In addition, the cells of the present invention can be used for the treatment of any condition in which a diminished or otherwise inhibited immune response, especially a cell-mediated immune response, is desirable to treat or alleviate the disease. In one aspect, the invention includes treating a condition, such as an autoimmune disease, in a subject, comprising administering to the subject a therapeutically effective amount of a pharmaceutical composition comprising a population of modified T cells.

Examples of autoimmune disease include but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

The modified T cells generated as described herein can also be expanded and used to treat inflammatory disorders. Examples of inflammatory disorders include but are not limited to, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

In another embodiment, the T cells described herein may be used for the manufacture of a medicament for the treatment of an immune response in a subject in need thereof. In another embodiment, the invention includes the modified cell described herein for use in a method of treating an immune response in a subject in need thereof.

The cells of the present invention can be administered to an animal, preferably a mammal, even more preferably a human, to treat a cancer. In addition, the cells of the present invention can be used for the treatment of any condition related to a cancer, especially a cell-mediated immune response against a tumor cell(s), where it is desirable to treat or alleviate the disease. Examples of cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. Compositions and methods of the present invention can be used to treat any type of tumor, including but not limited to a solid tumor or a non-solid tumor.

In certain embodiments, the subject is provided a secondary treatment. Secondary treatments include but are not limited to chemotherapy, radiation, surgery, and medications.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

The cells of the invention to be administered may be autologous, allogeneic or xenogenic with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

The cells described herein can also be administered using any number of matrices. The present invention utilizes such matrices within the novel context of acting as an artificial lymphoid organ to support, maintain, or modulate the immune system, typically through modulation of T cells. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized, as such these patents are incorporated herein by reference in their entirety. Matrices comprise features commonly associated with being biocompatible when administered to a mammalian host. Matrices may be formed from natural and/or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release of seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable sub stance.

Sources of Immune Cells

Prior to expansion, a source of immune cells is obtained from a subject for ex vivo manipulation. Sources of target cells for ex vivo manipulation may also include, e.g., autologous or heterologous donor blood, cord blood, or bone marrow. For example, the source of immune cells may be from the subject to be treated with the modified immune cells of the invention, e.g., the subject's blood, the subject's cord blood, or the subject's bone marrow. Non-limiting examples of subjects include humans, dogs, cats, mice, rats, and transgenic species thereof. Preferably, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some aspects, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), a stem cell memory T cell, a lymphoid progenitor cell, a hematopoietic stem cell, a natural killer cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

In some embodiments, the methods include isolating immune cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some aspects, a washing step is accomplished by tangential flow filtration (TFF) according to the manufacturer's instructions. In some embodiments, the cells are resuspended in a variety of biocompatible buffers after washing. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker+) or express high levels (marker$^{high}$) of one or more particular markers, such as surface markers, or that are negative for (marker) or express relatively low levels (marker$^{low}$) of one or more markers. For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD 127, and/or CD62L and/or depleted of (e.g., negatively selected for) cells that are positive for or express high surface levels of CD45RA. In some embodiments, cells are enriched for or depleted of cells positive or expressing high surface levels of CD 122, CD95, CD25, CD27, and/or IL7-Ra (CD 127). In some examples, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNABEADS® M-450 CD3/CD28 T Cell Expander).

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such sub-populations. In some embodiments, combining TCM-enriched CD8+ T cells and CD4+ T cells further enhances efficacy.

In embodiments, memory T cells are present in both CD62L+ and CD62L-subsets of CD8+ peripheral blood lymphocytes. PBMC can be enriched for or depleted of CD62L-CD8+ and/or CD62L+CD8+ fractions, such as using anti-CD8 and anti-CD62L antibodies. In some embodiments, a CD4+ T cell population and a CD8+ T cell sub-population, e.g., a sub-population enriched for central memory (TCM) cells. In some embodiments, the enrichment for central memory T (TCM) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for TCM cells is carried out by depletion of cells expressing CD4, CD 14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD 14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+ T helper cells are sorted into naive, central memory, and effector cells by identifying cell populations that have cell surface antigens. CD4+ lymphocytes can be obtained by standard methods. In some embodiments, naive CD4+ T lymphocytes are CD45RO-, CD45RA+, CD62L+, CD4+ T cells. In some embodiments, central memory CD4+ cells are CD62L+ and CD45RO+. In some embodiments, effector CD4+ cells are CD62L- and CD45RO. In one example, to enrich for CD4+ cells by negative selection, a monoclonal antibody cocktail typically includes antibodies to CD14, CD20, CD1 1b, CD16, HLA-DR, and CD8. In some embodiments, the antibody or binding partner is bound to a solid support or matrix, such as a magnetic bead or paramagnetic bead, to allow for separation of cells for positive and/or negative selection.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In another embodiment, T cells are isolated from peripheral blood by lysing the red blood cells and depleting the monocytes, for example, by centrifugation through a PERCOLL™ gradient. Alternatively, T cells can be isolated from an umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

Expansion of Immune Cells

Whether prior to or after modification of cells to express a CAR and/or TCR and/or switch receptor, the cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005. For example, the immune cells of the invention may be expanded by contact with a surface having attached thereto an agent that stimulates a CD3/TCR complex associated signal and a ligand that stimulates a co-stimulatory molecule on the surface of the immune cells. In particular, immune cell populations may be stimulated by contact with an anti-CD3 antibody, or an antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the immune cells, a ligand that binds the accessory molecule is used. For example, immune cells can be contacted with an anti-CD3 antibody and an anti-CD28 antibody, under conditions appropriate for stimulating proliferation of the immune cells. Examples of an anti-CD28 antibody include 9.3, B-T3, XR-CD28 (Diaclone, Besancon, France) and these can be used in the invention, as can other methods and reagents known in the art (see, e.g., ten Berge et al., Transplant Proc. (1998) 30(8): 3975-3977; Haanen et al., J. Exp. Med. (1999) 190(9): 1319-1328; and Garland et al., J. Immunol. Methods (1999) 227(1-2): 53-63).

Expanding the immune cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the immune cells expand in the range of about 20 fold to about 50 fold.

Following culturing, the immune cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The immune cell medium may be replaced during the culture of the immune cells at any time. Preferably, the immune cell medium is replaced about every 2 to 3 days. The immune cells are then harvested from the culture apparatus whereupon the immune cells can be used immediately or cryopreserved to be stored for use at a later time. In one embodiment, the invention includes cryopreserving the expanded immune cells. The cryopreserved immune cells are thawed prior to introducing nucleic acids into the immune cell.

In another embodiment, the method comprises isolating immune cells and expanding the immune cells. In another embodiment, the invention further comprises cryopreserving the immune cells prior to expansion. In yet another embodiment, the cryopreserved immune cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of immune cells comprises the addition to the cellular growth factors, such as those described in U.S. Pat. No. 5,199,942, or other factors, such as flt3-L, IL-1, IL-3 and c-kit ligand. In one embodiment, expanding the immune cells comprises culturing the immune cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for immune cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of immune cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the immune cells may include an agent that can co-stimulate the immune cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the immune cells expand in the range of about 20 fold to about 50 fold, or more by culturing the electroporated population. In one embodiment, human T regulatory cells are expanded via anti-CD3 antibody coated KT64.86 artificial antigen presenting cells (aAPCs). Methods for expanding and activating immune cells can be found in U.S. Pat. Nos. 7,754,482, 8,722,400, and 9,555, 105, contents of which are incorporated herein in their entirety.

In one embodiment, the method of expanding the immune cells can further comprise isolating the expanded immune cells for further applications. In another embodiment, the method of expanding can further comprise a subsequent electroporation of the expanded immune cells followed by culturing. The subsequent electroporation may include introducing a nucleic acid encoding an agent, such as a transducing the expanded immune cells, transfecting the expanded immune cells, or electroporating the expanded immune cells with a nucleic acid, into the expanded population of immune cells, wherein the agent further stimulates the immune cell. The agent may stimulate the immune cells, such as by stimulating further expansion, effector function, or another immune cell function.

Gene Edited Immune Cells

The present disclosure provides gene edited modified cells. In some embodiments, a modified cell (e.g., a modified cell comprising a tunable TCR or CAR expression system) of the present disclosure is genetically edited to disrupt the expression of one or more endogenously expressed genes. In some embodiments, the gene-edited immune cells (e.g., T cells) have a reduction, deletion, elimination, knockout or disruption in expression of one or more endogenously expressed genes.

In some embodiments, the modified cell of the present disclosure is genetically edited to disrupt the expression of one or more of an endogenous gene selected from the group consisting of T Cell Receptor Alpha Constant (TRAC), T cell Receptor Beta Constant (TRBC), Beta-2-Microglobulin (B2M), Class II Major Histocompatibility Complex Transactivator (CIITA), and Programmed Cell Death 1 (PD1).

In certain embodiments a standardized therapy is used in which allogeneic therapeutic cells are pre-manufactured, characterized in detail, and available for immediate administration to patients. By allogeneic it is meant that the cells are obtained from individuals belonging to the same species but are genetically dissimilar. In immune-competent hosts allogeneic cells are rapidly rejected, a process termed host versus graft rejection, and this substantially limits the efficacy of the transferred cells. In immune-incompetent hosts, allogeneic cells are able to engraft, but their endogenous T-cell receptors (TCR) specificities may recognize the host tissue as foreign, resulting in graft versus host disease, which can lead to serious tissue damage and death. Without being bound to any theory, disrupting the expression of TRAC and/or TRBC results in 1) reduced endogenous TCR and exogenous TCR (e.g., an NY-ESO-1 TCR) mispairing, thus reducing the risk of autoreactivity; and 2) enhances exogenous TCR expression on the cell surface by reducing mispairing with endogenous TCR, thus increasing efficacy of the modified cells. Beta-2 microglobulin, also known as B2M, is the light chain of MHC class I molecules, and as such an integral part of the major histocompatibility complex. Mice models deficient for beta-2 microglobulin have shown that B2M is necessary for cell surface expression of MHC class I and stability of the peptide binding groove. CIITA protein acts as a positive regulator of class II major histocompatibility complex gene transcription, including B2M gene transcription, and is often referred to as the "master control factor" for the expression of these genes.

In other embodiments, the modified cell of the present disclosure is genetically edited to disrupt the expression of endogenous PDCD1 gene products (Programmed Death 1 receptor; PD-1). Disrupting the expression of endogenous PD-1 (PD1) may create "checkpoint" resistant modified cells, resulting in increased tumor control. Checkpoint resistant modified cells may also be created by disrupting the expression of, for example, without limitation, the Adenosine A2A receptor (A2AR), B7-H3 (CD276), B7-H4 (VTCN1), the B and T Lymphocyte Attenuator protein (BTLA/CD272), CD96, the Cytotoxic T-Lymphocyte Associated protein 4 (CTLA-4/CD152), Indoleamine 2,3-dioxygenase (IDO), the Killer-cell Immunoglobulin-like Receptor (KIR), the Lymphocyte Activation Gene-3 (LAG3), the T cell immunoreceptor with Ig and ITIM domains (TIGIT), T-cell Immunoglobulin domain and Mucin domain 3 (TIM-3), or the V-domain Ig suppressor of T cell activation (VISTA).

Accordingly, the modified cell of the present invention is genetically edited to disrupt the expression of any of the endogenous genes described herein. Accordingly, in some embodiments, a modified cell (e.g., a modified cell comprising a tunable TCR or CAR expression system) of the present invention is genetically edited to disrupt the expression of one or more of the endogenous genes described herein.

In embodiments where one or more of TRAC, TRBC, B2M, and CIITA are disrupted, a universal immune cell is produced. As used herein, the term "universal immune cell" or "universal T cell" refers to allogeneic immune cells and T cells that are pre-modified/pre-manufactured for administration into any patient.

Accordingly, provided herein is a method of generating a population of universal T cell receptor (TCR) directed T cells, the method comprising: a) stimulating a population of isolated T cells, thereby generating a population of stimulated T cells; b) introducing into the population of stimulated T cells a nucleic acid comprising an inducible TCR expression system comprising: a first nucleic acid comprising a human phosphoglycerate kinase 1 promoter operably linked upstream to a nucleic acid sequence encoding a Tet-On 3G transactivator protein; and a second nucleic acid comprising an inducible TRE3GS promoter operably linked upstream to a nucleic acid sequence encoding an exogenous TCR, wherein the second nucleic acid is in reverse orientation to the first nucleic acid, thereby generating a population of modified T cells; c) introducing into the population of modified T cells one or more polypeptides and/or nucleic acids capable of downregulating expression of an endogenous protein selected from the group consisting of TRAC, TRBC, B2M, and CIITA, thereby generating a population of gene edited modified T cells; d) depleting CD3+ T cells from the population of gene edited modified T cells and isolating a population of CD3− gene edited modified T cells; and e) contacting the population of CD3− gene edited modified T cells with doxycycline to induce expression of the exogenous TCR, thereby generating a population of universal TCR directed T cells.

Methods for depleting CD3+ T cells from a population of CD3+ and CD3− T cells are known in the art. For example, where stimulation of T cells comprises contacting the T cells with magnetic beads coated with anti-CD3 and/or anti-CD28 antibodies, subsequent removal of the magnetic beads can remove CD3+ T cells from the population.

Various gene editing technologies are known to those skilled in the art. Gene editing technologies include, without limitation, homing endonucleases, zinc-finger nucleases (ZFNs), transcription activator-like effector (TALE) nucleases (TALENs), and clustered regularly interspaced short palindromic repeats (CRISPR)-CRISPR-associated protein 9 (Cas9). Homing endonucleases generally cleave their DNA substrates as dimers, and do not have distinct binding and cleavage domains. ZFNs recognize target sites that consist of two zinc-finger binding sites that flank a 5- to 7-base pair (bp) spacer sequence recognized by the FokI cleavage domain. TALENs recognize target sites that consist of two TALE DNA-binding sites that flank a 12- to 20-bp spacer sequence recognized by the FokI cleavage domain. The Cas9 nuclease is directed by a guide RNA (gRNA) to a targetsequence located immediately upstream of a compatible protospacer adjacent motif (PAM). Accordingly, one of skill in the art would be able to select the appropriate gene editing technology for the present invention.

In some aspects, the disruption is carried out by gene editing using an RNA-guided nuclease system such as a CRISPR-Cas system (e.g. CRISPR-Cas9 system) specific for the gene (e.g., TRAC, TRBC, CIITA, B2M, PD1) being disrupted. In some embodiments, an agent containing a Cas9 and a guide RNA (gRNA) is introduced into the cell. In some embodiments, the agent is or comprises a ribonucleoprotein (RNP) complex of a Cas9 polypeptide and a gRNA (Cas9/gRNA RNP). In some embodiments, the agent comprises a nucleic acid (e.g. plasmid) comprising a Cas9 and a gRNA.

In some embodiment, the introduction includes contacting the agent or portion thereof with the cells, in vitro, which can include cultivating or incubating the cell and agent for up to 24, 36 or 48 hours or 3, 4, 5, 6, 7, or 8 days. In some embodiments, the introduction further can include effecting delivery of the agent into the cells. In various embodiments, the methods, compositions and cells according to the present disclosure utilize direct delivery of ribonucleoprotein (RNP) complexes of Cas9 and gRNA to cells, for example by electroporation. In some embodiments, the RNP complexes include a gRNA that has been modified to include a 3' poly-A tail and a 5' Anti-Reverse Cap Analog (ARCA) cap.

The CRISPR/Cas9 system is a facile and efficient system for inducing targeted genetic alterations. Target recognition by the Cas9 protein requires a 'seed' sequence within the guide RNA (gRNA) and a conserved di-nucleotide containing protospacer adjacent motif (PAM) sequence upstream of the gRNA-binding region. The CRISPR/Cas9 system can thereby be engineered to cleave virtually any DNA sequence by redesigning the gRNA in cell lines (such as 293T cells), primary cells, and/or TCR T cells. The CRISPR/Cas9 system can simultaneously target multiple genomic loci by co-expressing a single Cas9 protein with two or more gRNAs, making this system suited for multiple gene editing or synergistic activation of target genes.

The Cas9 protein and guide RNA form a complex that identifies and cleaves target sequences. Cas9 is comprised of six domains: REC I, REC II, Bridge Helix, PAM interacting, HNH, and RuvC. The REC I domain binds the guide RNA, while the Bridge helix binds to target DNA. The HNH and RuvC domains are nuclease domains. Guide RNA is engineered to have a 5' end that is complementary to the target DNA sequence. Upon binding of the guide RNA to the Cas9 protein, a conformational change occurs activating the protein. Once activated, Cas9 searches for target DNA by binding to sequences that match its protospacer adjacent motif (PAM) sequence. A PAM is a two or three nucleotide base sequence within one nucleotide downstream of the region complementary to the guide RNA. In one non-limiting example, the PAM sequence is 5'-NGG-3'. When the Cas9 protein finds its target sequence with the appropriate PAM, it melts the bases upstream of the PAM and pairs them with the complementary region on the guide RNA. Then the RuvC and HNH nuclease domains cut the target DNA after the third nucleotide base upstream of the PAM.

One non-limiting example of a CRISPR/Cas system used to inhibit gene expression, CRISPRi, is described in U.S. Patent Appl. Publ. No. US20140068797. CRISPRi induces permanent gene disruption that utilizes the RNA-guided Cas9 endonuclease to introduce DNA double stranded breaks which trigger error-prone repair pathways to result in frame shift mutations. A catalytically dead Cas9 lacks endonuclease activity. When coexpressed with a guide RNA, a DNA recognition complex is generated that specifically interferes with transcriptional elongation, RNA polymerase binding, or transcription factor binding. This CRISPRi system efficiently represses expression of targeted genes.

CRISPR/Cas gene disruption occurs when a guide nucleic acid sequence specific for a target gene and a Cas endonuclease are introduced into a cell and form a complex that enables the Cas endonuclease to introduce a double strand break at the target gene. In certain embodiments, the CRISPR/Cas system comprises an expression vector, such as, but not limited to, a pAd5F35-CRISPR vector. In other embodiments, the Cas expression vector induces expression of Cas9 endonuclease. Other endonucleases may also be used, including but not limited to, Cas12a (Cpf1), T7, Cas3, Cas8a, Cas8b, Cas10d, Cse1, Csy1, Csn2, Cas4, Cas10, Csm2, Cmr5, Fok1, other nucleases known in the art, and any combinations thereof.

In certain embodiments, inducing the Cas expression vector comprises exposing the cell to an agent that activates an inducible promoter in the Cas expression vector. In such embodiments, the Cas expression vector includes an inducible promoter, such as one that is inducible by exposure to an antibiotic (e.g., by tetracycline or a derivative of tetracycline, for example doxycycline). Other inducible promoters known by those of skill in the art can also be used. The inducing agent can be a selective condition (e.g., exposure to an agent, for example an antibiotic) that results in induction of the inducible promoter. This results in expression of the Cas expression vector.

Guide RNA (gRNA), also referred to as "short guide RNA" or "sgRNA", provides both targeting specificity and scaffolding/binding ability for the Cas9 nuclease. The gRNA can be a synthetic RNA composed of a targeting sequence and scaffold sequence derived from endogenous bacterial crRNA and tracrRNA. gRNA is used to target Cas9 to a specific genomic locus in genome engineering experiments. Guide RNAs can be designed using standard tools well known in the art. As used herein, the term "guide RNA" or "gRNA" refer to any nucleic acid that directs an RNA-guided nuclease such as a Cas9 to a target sequence (e.g., a genomic or episomal sequence) in a cell. It will be understood to those with skill in the art that gRNA sequences may be recited with a thymine or "T" nucleotide in place of a uracil or "U" nucleotide.

The guide RNA is specific for a genomic region of interest and targets that region for Cas endonuclease-induced double strand breaks. The target sequence of the guide RNA sequence may be within a loci of a gene or within a non-coding region of the genome. In certain embodiments, the guide nucleic acid sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40 or more nucleotides in length.

As used herein, a "modular" or "dual RNA" guide comprises more than one, and typically two, separate RNA molecules, such as a CRISPR RNA (crRNA) and a trans-activating crRNA (tracrRNA), which are usually associated with one another, for example by duplexing. gRNAs and their component parts are described throughout the literature (see, e.g., Briner et al. Mol. Cell, 56(2), 333-339 (2014), which is incorporated by reference).

As used herein, a "unimolecular gRNA," "chimeric gRNA," or "single guide RNA (sgRNA)" comprises a single RNA molecule. The sgRNA may be a crRNA and tracrRNA linked together. For example, the 3' end of the crRNA may be linked to the 5' end of the tracrRNA. A crRNA and a tracrRNA may be joined into a single unimolecular or chimeric gRNA, for example, by means of a four nucleotide (e.g., GAAA) "tetraloop" or "linker" sequence bridging complementary regions of the crRNA (at its 3' end) and the tracrRNA (at its 5' end).

Additional details regarding guide RNA structure and function, including the gRNA/Cas9 complex for genome editing may be found in, at least, Mali et al. Science, 339(6121), 823-826 (2013); Jiang et al. Nat. Biotechnol. 31(3). 233-239 (2013); and Jinek et al. Science, 337(6096), 816-821 (2012); which are incorporated by reference herein.

As used herein, a "guide sequence" or "targeting sequence" refers to the nucleotide sequence of a gRNA, whether unimolecular or modular, that is fully or partially complementary to a target sequence in the genome of a cell where editing is desired. Guide sequences are typically 10-30 nucleotides in length, preferably 16-24 nucleotides in length (for example, 16, 17, 18, 19, 20, 21, 22, 23 or 24 nucleotides in length), and are at or near the 5' terminus of a gRNA.

As used herein, a "target domain" or "target polynucleotide sequence" or "target sequence" is the DNA sequence in a genome of a cell that is complementary to the guide sequence of the gRNA.

In the context of formation of a CRISPR complex, "target sequence" refers to a sequence to which a guide sequence is designed to have some complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In certain embodiments, a target sequence is located in the nucleus or cytoplasm of a cell. In other embodiments, the target sequence may be within an organelle of a eukaryotic cell, for example, mitochondrion or nucleus. Typically, in the context of a CRISPR system, formation of a CRISPR complex (comprising a guide sequence hybridized to a target sequence and complexed with one or more Cas proteins) results in cleavage of one or both strands in or near (e.g., within about 1, 2, 3, 4, 5, 6, 7, 8, 9, 10, 20, 50 or more base pairs) the target sequence. As with the target sequence, it is believed that complete complementarity is not needed, provided this is sufficient to be functional.

In certain embodiments, one or more vectors driving expression of one or more elements of a CRISPR system are introduced into a host cell, such that expression of the elements of the CRISPR system direct formation of a CRISPR complex at one or more target sites. For example, a Cas nuclease, a crRNA, and a tracrRNA could each be operably linked to separate regulatory elements on separate vectors. Alternatively, two or more of the elements expressed from the same or different regulatory elements may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In certain embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron).

In certain embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Additional domains that may form part of a fusion protein comprising a CRISPR enzyme are described in U.S. Patent Appl. Publ. No. US20110059502, incorporated herein by reference. In certain embodiments, a tagged CRISPR enzyme is used to identify the location of a target sequence.

Conventional viral and non-viral based gene transfer methods can be used to introduce nucleic acids in mammalian and non-mammalian cells or target tissues. Such methods can be used to administer nucleic acids encoding components of a CRISPR system to cells in culture, or in a host organism. Non-viral vector delivery systems include DNA plasmids, RNA (e.g., a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell (Anderson, 1992, Science 256:808-813; and Yu, et al., 1994, Gene Therapy 1:13-26).

In some embodiments, the CRISPR/Cas is derived from a type II CRISPR/Cas system. In other embodiments, the CRISPR/Cas system is derived from a Cas9 nuclease. Exemplary Cas9 nucleases that may be used in the present invention include, but are not limited to, *S. pyogenes* Cas9 (SpCas9), *S. aureus* Cas9 (SaCas9), *S. thermophilus* Cas9 (StCas9), *N. meningitidis* Cas9 (NmCas9), *C. jejuni* Cas9 (Cj Cas9), and *Geobacillus* Cas9 (GeoCas9).

In general, Cas proteins comprise at least one RNA recognition and/or RNA binding domain. RNA recognition and/or RNA binding domains interact with the guiding RNA. Cas proteins can also comprise nuclease domains (i.e., DNase or RNase domains), DNA binding domains, helicase domains, RNAse domains, protein-protein interaction domains, dimerization domains, as well as other domains. The Cas proteins can be modified to increase nucleic acid binding affinity and/or specificity, alter an enzymatic activity, and/or change another property of the protein. In certain embodiments, the Cas-like protein of the fusion protein can be derived from a wild type Cas9 protein or fragment thereof. In other embodiments, the Cas can be derived from modified Cas9 protein. For example, the amino acid sequence of the Cas9 protein can be modified to alter one or more properties (e.g., nuclease activity, affinity, stability, and so forth) of the protein. Alternatively, domains of the Cas9 protein not involved in RNA-guided cleavage can be eliminated from the protein such that the modified Cas9 protein is smaller than the wild type Cas9 protein. In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-stranded break in DNA. (Jinek, et al., 2012, Science, 337:816-821). In certain embodiments, the Cas9-derived protein can be modified to contain only one functional nuclease domain (either a RuvC-like or a HNH-like nuclease domain). For example, the Cas9-derived protein can be modified such that one of the nuclease domains is deleted or mutated such that it is no longer functional (i.e., the nuclease activity is absent). In some embodiments in which one of the nuclease domains is inactive, the Cas9-derived protein is able to introduce a nick into a double-stranded nucleic acid (such protein is termed a "nickase"), but not cleave the double-stranded DNA. In any of the above-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art.

In one non-limiting embodiment, a vector drives the expression of the CRISPR system. The art is replete with suitable vectors that are useful in the present invention. The vectors to be used are suitable for replication and, optionally, integration in eukaryotic cells. Typical vectors contain transcription and translation terminators, initiation sequences, and promoters useful for regulation of the expression of the desired nucleic acid sequence. The vectors of the present invention may also be used for nucleic acid standard gene delivery protocols. Methods for gene delivery are known in the art (U.S. Pat. Nos. 5,399,346, 5,580,859 & 5,589,466, incorporated by reference herein in their entireties).

Further, the vector may be provided to a cell in the form of a viral vector. Viral vector technology is well known in the art and is described, for example, in Sambrook et al. (4th Edition, Molecular Cloning: A Laboratory Manual, Cold Spring Harbor Laboratory, New York, 2012), and in other virology and molecular biology manuals. Viruses, which are useful as vectors include, but are not limited to, retroviruses, adenoviruses, adeno-associated viruses, herpes viruses, Sindbis virus, gammaretrovirus and lentiviruses. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193).

In some embodiments, guide RNA(s) and Cas9 can be delivered to a cell as a ribonucleoprotein (RNP) complex (e.g., a Cas9/RNA-protein complex). RNPs are comprised of purified Cas9 protein complexed with gRNA and are well known in the art to be efficiently delivered to multiple types of cells, including but not limited to stem cells and immune cells (Addgene, Cambridge, Mass., Mirus Bio LLC, Madison, Wis.). In some embodiments, the Cas9/RNA-protein complex is delivered into a cell by electroporation.

In some embodiments, a gene edited modified cell of the present disclosure is edited using CRISPR/Cas9 to disrupt one or more endogenous genes in a modified cell (e.g., a modified T cell). In some embodiments, CRISPR/Cas9 is used to disrupt one or more of endogenous TRAC, TRBC, B2M, and/or CIITA. In certain exemplary embodiments, CRISPR/Cas9 is used to disrupt one or more of endogenous TRAC, TRBC, B2M, CIITA, and/or PD1 loci, thereby resulting in the downregulation of TRAC, TRBC, B2M, CIITA, and/or PD1. Suitable gRNAs for use in disrupting one or more of endogenous TRAC, TRBC, B2M, CIITA, and/or PD1 is set forth in FIGS. 26 and 27.

Accordingly, a method of genetically editing a modified cell of the present disclosure comprises introducing into the cell one or more nucleic acids capable of downregulating gene expression of one or more endogenous genes selected from TRAC, TRBC, B2M, CIITA, and PD1. In one embodiment, a method of genetically editing a modified cell of the present disclosure comprises introducing into the cell one or more nucleic acids capable of downregulating gene expression of one or more endogenous genes selected from TRAC, TRBC, B2M, and CIITA. In one embodiment, a method of genetically editing a modified cell of the present invention comprises introducing into the cell one or more nucleic acids capable of downregulating gene expression of endogenous TRAC. In one embodiment, a method of genetically editing a modified cell of the present invention comprises introducing into the cell one or more nucleic acids capable of downregulating gene expression of endogenous TRBC. In one embodiment, a method of genetically editing a modified cell of the present invention comprises introducing into the cell one or more nucleic acids capable of downregulating gene expression of endogenous B2M. In one embodiment, a method of genetically editing a modified cell of the present invention comprises introducing into the cell one or more nucleic acids capable of downregulating gene expression of endogenous CIITA. In one embodiment, a method of genetically editing a modified cell of the present invention comprises introducing into the cell one or more nucleic acids capable of downregulating gene expression of endogenous PD1.

In one embodiment, a method of generating a modified immune cell or precursor cell thereof, comprising: introducing into the immune cell a nucleic acid comprising a tunable T cell receptor (TCR) or chimeric antigen receptor (CAR) expression system comprising: a first nucleic acid comprising a constitutive promoter operably linked to a nucleic acid sequence encoding a transactivator protein; and a second nucleic acid comprising an inducible promoter operably linked to a nucleic acid sequence encoding an exogenous TCR or CAR, wherein the second nucleic acid is in reverse orientation to the first nucleic acid, wherein expression of the exogenous TCR or CAR is induced by the presence of an induction agent; and introducing into the immune cell one or more polypeptides and/or nucleic acids capable of downregulating expression of an endogenous protein.

In one embodiment, a method of generating a modified immune cell or precursor cell thereof, comprising: introducing into the immune cell a nucleic acid comprising a tunable T cell receptor (TCR) or chimeric antigen receptor (CAR) expression system comprising: a first nucleic acid comprising a constitutive promoter operably linked to a nucleic acid sequence encoding a transactivator protein; and a second nucleic acid comprising an inducible promoter operably linked to a nucleic acid sequence encoding an exogenous TCR or CAR, wherein the second nucleic acid is in reverse orientation to the first nucleic acid, wherein expression of the exogenous TCR or CAR is induced by the presence of an induction agent; introducing into the immune cell a nucleic acid encoding a switch receptor; and introducing into the immune cell one or more polypeptides and/or nucleic acids capable of downregulating expression of an endogenous protein.

In one embodiment, a method of generating a modified immune cell or precursor cell thereof, comprising: introducing into the immune cell a nucleic acid comprising a tunable T cell receptor (TCR) or chimeric antigen receptor (CAR) expression system comprising: a first nucleic acid comprising a human phosphoglycerate kinase 1 promoter operably linked upstream to a nucleic acid sequence encoding a Tet-On 3G transactivator protein; and a second nucleic acid comprising an inducible TRE3GS promoter operably linked upstream to a nucleic acid sequence encoding an exogenous TCR or CAR, wherein the second nucleic acid is in reverse orientation to the first nucleic acid, wherein expression of the exogenous TCR or CAR is induced by the presence of an induction agent; and introducing into the immune cell one or more polypeptides and/or nucleic acids capable of downregulating expression of an endogenous protein.

In one embodiment, a method of generating a modified immune cell or precursor cell thereof, comprising: introducing into the immune cell a nucleic acid comprising a tunable T cell receptor (TCR) or chimeric antigen receptor (CAR) expression system comprising: a first nucleic acid comprising a human phosphoglycerate kinase 1 promoter operably linked upstream to a nucleic acid sequence encoding a Tet-On 3G transactivator protein; and a second nucleic acid comprising an inducible TRE3GS promoter operably linked upstream to a nucleic acid sequence encoding an exogenous TCR or CAR, wherein the second nucleic acid is in reverse orientation to the first nucleic acid, wherein expression of the exogenous TCR or CAR is induced by the presence of an induction agent; introducing into the immune cell a nucleic acid encoding a switch receptor; and introducing into the immune cell one or more polypeptides and/or nucleic acids capable of downregulating expression of an endogenous protein.

In an exemplary embodiment, the one or more polypeptides and/or nucleic acids capable of downregulating expression of an endogenous protein downregulate the expression of one or more endogenous proteins selected from the group consisting of TRAC, TRBC, B2M, CIITA, and PD1.

In an exemplary embodiment, each of the one or more polypeptides and/or nucleic acids capable of downregulating expression comprises a CRISPR-related system. In some embodiments, the CRISPR-related system is a CRISPR nuclease and a guide RNA.

In an exemplary embodiment, the guide RNA comprises a guide sequence that is sufficiently complementary with a target sequence of the endogenous gene selected from TRAC, TRBC, B2M, CIITA, and PD1.

In some embodiments, the target sequence is within the TRAC gene and the guide RNA comprises a nucleic acid sequence set forth in any one of SEQ ID NOs: 85-97. In some embodiments, the target sequence is within the TRBC gene and the guide RNA comprises a nucleic acid sequence set forth in any one of SEQ ID NOs: 1-24. In some embodiments, the target sequence is within the B2M gene and the guide RNA comprises a nucleic acid sequence set forth in any one of SEQ ID NOs: 73-84. In some embodiments, the target sequence is within the CIITA gene and the guide RNA comprises a nucleic acid sequence set forth in any one of SEQ ID NOs: 25-48. In some embodiments, the target sequence is within the PD1 gene and the guide RNA comprises a nucleic acid sequence set forth in any one of SEQ ID NOs: 49-72.

In some aspects, the provided compositions and methods include those in which at least or greater than about 50%, 60%, 65%, 70%, 75%, 80%, 85%, 90% or 95% of immune cells in a composition of immune cells contain the desired genetic modification. For example, about 50%, 60%, 65%, 70%, 75%, 80%, 85%, 90% or 95% of immune cells in a composition of cells into which an agent (e.g. gRNA/Cas9) for knockout or genetic disruption of endogenous gene (e.g., TRAC, TRBC, B2M, CIITA, PD1) was introduced contain the genetic disruption; do not express the targeted endogenous polypeptide, do not contain a contiguous and/or functional copy of the targeted gene. In some embodiments, the methods, compositions and cells according to the present disclosure include those in which at least or greater than about 50%, 60%, 65%, 70%. 75%, 80%, 85%, 90% or 95% of cells in a composition of cells into which an agent (e.g. gRNA/Cas9) for knockout or genetic disruption of a targeted gene was introduced do not express the targeted polypeptide, such as on the surface of the immune cells. In some embodiments, at least or greater than about 50%, 60%, 65%, 70%, 75%, 80%, 85%, 90% or 95% of cells in a composition of cells into which an agent (e.g. gRNA/Cas9) for knockout or genetic disruption of the targeted gene was introduced are knocked out in both alleles, i.e. comprise a biallelic deletion, in such percentage of cells.

In some embodiments, provided are compositions and methods in which the Cas9-mediated cleavage efficiency (% indel) in or near the targeted gene (e.g. within or about within 100 base pairs, within or about within 50 base pairs, or within or about within 25 base pairs or within or about within 10 base pairs upstream or downstream of the cut site) is at least or greater than about 50%, 60%, 65%, 70%, 75%, 80%, 85%, 90% or 95% in cells of a composition of cells into which an agent (e.g. gRNA/Cas9) for knockout or genetic disruption of a targeted gene has been introduced.

In some embodiments, the provided cells, compositions and methods results in a reduction or disruption of signals delivered via the endogenous in at least or greater than about 50%, 60%, 65%, 70%, 75%, 80%, 85%, 90% or 95% of cells in a composition of cells into which an agent (e.g. gRNA/Cas9) for knockout or genetic disruption of a targeted gene was introduced.

In some embodiments, compositions according to the provided disclosure that comprise cells engineered with a recombinant receptor and comprise the reduction, deletion, elimination, knockout or disruption in expression of an endogenous receptor (e.g. genetic disruption of TRAC, TRBC, B2M, CIITA, and/or PD1) retain the functional property or activities of the receptor compared to the receptor expressed in engineered cells of a corresponding or reference composition, which comprises the receptor but does not comprise the genetic disruption of a gene or express the polypeptide, when assessed under the same conditions. In some embodiments, the engineered cells of the provided compositions retain a functional property or activity compared to a corresponding or reference composition comprising engineered cells in which such are engineered with the recombinant receptor but do not comprise the genetic disruption or express the targeted polypeptide when assessed under the same conditions. In some embodiments, the cells retain cytotoxicity, proliferation, survival or cytokine secretion compared to such a corresponding or reference composition.

In some embodiments, the immune cells in the composition retain a phenotype of the immune cell or cells compared to the phenotype of cells in a corresponding or reference composition when assessed under the same conditions. In some embodiments, cells in the composition include naive cells, effector memory cells, central memory cells, stem central memory cells, effector memory cells, and long-lived effector memory cells. In some embodiments, the percentage of T cells, or T cells expressing the recombinant receptor (e.g. TCR or CAR), and comprising the genetic disruption of a targeted gene (e.g., TRAC, TRBC, B2M, CIITA, PD1) exhibit a non-activated, long-lived memory or central memory phenotype that is the same or substantially the same as a corresponding or reference population or composition of cells engineered with the recombinant receptor but not containing the genetic disruption. In some embodiments, such property, activity or phenotype can be measured in an in vitro assay, such as by incubation of the cells in the presence of an antigen targeted by the TCR or CAR, a cell expressing the antigen and/or an antigen-receptor activating substance. In some embodiments, any of the assessed activities, properties or phenotypes can be assessed at various days following electroporation or other introduction of the agent, such as after or up to 3, 4, 5, 6, 7 days. In some embodiments, such activity, property or phenotype is retained by at least 80%, 85%, 90%, 95% or 100% of the cells in the composition compared to the activity of a corresponding composition containing cells engineered with the recombinant receptor but not comprising the genetic disruption of the targeted gene when assessed under the same conditions.

As used herein, reference to a "corresponding composition" or a "corresponding population of immune cells" (also called a "reference composition" or a "reference population of cells") refers to immune cells (e.g., T cells) obtained, isolated, generated, produced and/or incubated under the same or substantially the same conditions, except that the immune cells or population of immune cells were not introduced with the agent. In some aspects, except for not containing introduction of the agent, such immune cells are treated identically or substantially identically as immune cells that have been introduced with the agent, such that any one or more conditions that can influence the activity or properties of the cell, including the upregulation or expression of the inhibitory molecule, is not varied or not substantially varied between the cells other than the introduction of the agent.

Methods and techniques for assessing the expression and/or levels of T cell markers are known in the art. Antibodies and reagents for detection of such markers are well known in the art, and readily available. Assays and methods for detecting such markers include, but are not limited to, flow cytometry, including intracellular flowsytometry, ELISA, ELISPOT, cytometric bead array or other multiplex methods, Western Blot and other immunoaffinity-based methods. In some embodiments, antigen receptor (e.g. TCR or CAR)-expressing cells can be detected by flow cytometry or other immunoaffinity based method for expression of a marker unique to such cells, and then such cells can be co-stained for another T cell surface marker or markers.

In some embodiments, the cells, compositions and methods provide for the deletion, knockout, disruption, or reduction in expression of the target gene in immune cells (e.g. T cells) to be adoptively transferred (such as cells engineered to express an exogenous TCR or CAR). In some embodiments, the methods are performed ex vivo on primary cells, such as primary immune cells (e.g. T cells) from a subject. In some aspects, methods of producing or generating such genetically engineered T cells include introducing into a population of cells containing immune cells (e.g. T cells) one or more nucleic acid encoding a recombinant receptor (e.g. exogenous TCR or CAR) and an agent or agents that is capable of disrupting, a gene that encode the endogenous receptor to be targeted. As used herein, the term "introducing" encompasses a variety of methods of introducing DNA into a cell, either in vitro or in vivo, such methods including transformation, transduction, transfection (e.g. electroporation), and infection. Vectors are useful for introducing DNA encoding molecules into cells. Possible vectors include plasmid vectors and viral vectors. Viral vectors include retroviral vectors, lentiviral vectors, or other vectors such as adenoviral vectors or adeno-associated vectors.

The population of cells containing T cells can be cells that have been obtained from a subject, such as obtained from a peripheral blood mononuclear cells (PBMC) sample, an unfractionated T cell sample, a lymphocyte sample, a white blood cell sample, an apheresis product, or a leukapheresis product. In some embodiments, T cells can be separated or selected to enrich T cells in the population using positive or negative selection and enrichment methods. In some embodiments, the population contains CD4+, CD8+ or CD4+ and CD8+ T cells. In some embodiments, the step of introducing the nucleic acid encoding a genetically engineered antigen receptor and the step of introducing the agent (e.g. Cas9/gRNA/RNP) can occur simultaneously or sequentially in any order. In some embodiments, subsequent to introduction of the exogenous receptor and one or more gene editing agents (e.g. Cas9/gRNA/RNP), the cells are cultured or incubated under conditions to stimulate expansion and/or proliferation of cells.

Thus, provided are cells, compositions and methods that enhance immune cell, such as T cell, function in adoptive cell therapy, including those offering improved efficacy, such as by increasing activity and potency of administered genetically engineered cells, while maintaining persistence or exposure to the transferred cells over time. In some embodiments, the genetically engineered cells, exhibit increased expansion and/or persistence when administered in vivo to a subject, as compared to certain available methods. In some embodiments, the provided immune cells exhibit increased persistence when administered in vivo to a subject. In some embodiments, the persistence of genetically engineered immune cells, in the subject upon administration is greater as compared to that which would be achieved by alternative methods, such as those involving administration of cells genetically engineered by methods in which T cells were not introduced with an agent that reduces expression of or disrupts a gene encoding an endogenous receptor. In some embodiments, the persistence is increased at least or about at least 1.5-fold, 2-fold, 3-fold, 4-fold, 5-fold, 6-fold, 7-fold, 8-fold, 9-fold, 10-fold, 20-fold, 30-fold, 50-fold, 60-fold, 70-fold, 80-fold, 90-fold, 100-fold or more.

In some embodiments, the degree or extent of persistence of administered cells can be detected or quantified after administration to a subject. For example, in some aspects, quantitative PCR (qPCR) is used to assess the quantity of cells expressing the exogenous receptor (e.g., TCR or CAR) in the blood or serum or organ or tissue (e.g., disease site) of the subject. In some aspects, persistence is quantified as copies of DNA or plasmid encoding the exogenous receptor per microgram of DNA, or as the number of receptor-expressing cells per microliter of the sample, e.g., of blood or serum, or per total number of peripheral blood mononuclear cells (PBMCs) or white blood cells or T cells per microliter of the sample. In some embodiments, flow cytometric assays detecting cells expressing the receptor generally using antibodies specific for the receptors also can be performed. Cell-based assays may also be used to detect the number or percentage of functional cells, such as cells capable of binding to and/or neutralizing and/or inducing responses, e.g., cytotoxic responses, against cells of the disease or condition or expressing the antigen recognized by the receptor. In any of such embodiments, the extent or level of expression of another marker associated with the exogenous receptor (e.g. exogenous TCR or CAR) can be used to distinguish the administered cells from endogenous cells in a subject.

Pharmaceutical Compositions

Pharmaceutical compositions of the present invention may comprise the modified immune cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The cells of the invention to be administered may be autologous, allogeneic or xenogeneic with respect to the subject undergoing therapy.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

Also provided are populations of immune cells of the invention, compositions containing such cells and/or enriched for such cells, such as in which cells expressing the recombinant receptor make up at least 50%, 60%, 70%, 80%, 90%, 91%, 92%, 93%, 94%, 95%, 96%, 97%, 98%, 99%, or more of the total cells in the composition or cells of a certain type such as regulatory T cells. Among the compositions are pharmaceutical compositions and formulations for administration, such as for adoptive cell therapy. Also provided are therapeutic methods for administering the cells and compositions to subjects, e.g., patients.

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

It can generally be stated that a pharmaceutical composition comprising the modified immune cells described herein may be administered at a dosage of $10^4$ to $10^9$ cells/kg body weight, in some instances $10^5$ to $10^6$ cells/kg body weight, including all integer values within those ranges. Immune cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

The administration of the modified immune cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

Experimental Examples

The invention is now described with reference to the following Examples. These Examples are provided for the purpose of illustration only, and the invention is not limited to these Examples, but rather encompasses all variations that are evident as a result of the teachings provided herein.

Materials and Methods:

The materials and methods employed in these experiments are now described.

Primary Human Lymphocytes.

Primary human CD4 and CD8 T cells were isolated from healthy volunteer donors following leukapheresis by negative selection using RosetteSep kits (Stem Cell Technologies, Vancouver BC, Canada). All specimens were collected under a University Institutional Review Board-approved protocol, and written informed consent was obtained from each donor. Primary lymphocytes were stimulated with anti-CD3/CD28 Dynabeads (Life Technologies, Grand Island, N.Y.,).

Design and Construction of CRISPRs.

Cas9 DNA was synthesized by PCR based on the publications (Cong et al. (2013) Science 339, 819-823; Slaymaker et al. (2016) Science 351, 84-88) and cloned into RNA in vitro transcription (IVT) vector pD-A vector7. gRNAs were selected using web based CRISPR algorithms (crisprdotmitdotedu and chopchopdotrcdotfasdotharvarddotedu). Higher score gRNA sequences for five gene loci (TRAC, TRBC, B2M, CIITA and PD-1) were selected (FIG. 26 & FIG. 27). sgRNAs were designed as reported (Ren et al. (2016) *Clinical Cancer Research*, clincanres-1300) for gBlock synthesis. The selected sgRNAs were PCR amplified, digested with XhoI/EcoRI and cloned into pD-A IVT vector. The in vitro transcribed Cas9 mRNA and sgRNA were generated and stored as described (Ren et al. (2016) *Clinical Cancer Research*, clincanres-1300).

Construction of Tetracycline (Tet)-on Inducible Gene Expression System.

The pRetroX-TetOne 3G vector (Takara Bio Inc.) was first digested with EcoRI and BstZ17I. The EGFP or NY-ESO-1 TCR (8F TCR) was PCR amplified from pGEM-EGFP and pTRP.8F TCR to introduce EcoRI and BstZ17I at 5' and 3' ends respectively and cloned into pRetroX-TetOne 3G vector to generate pRetroX-TetONE.EGFP and pRetroX-TetONE.8F TCR (FIG. 7).

Flow Cytometry.

The following monoclonal antibodies and reagents were used with the indicated specificity and the appropriate isotype controls. From BD Biosciences (San Jose, Calif.): APC-conjugated anti-CD3 (555335), FITC-anti-CD8 (555366), PE-anti-CD8 (555635), PE-anti-CD107a (555801), and PE-anti-beta-2 microglobulin (551337), FITC-anti-HLA-I (555552), APC-anti-PD-1 (114102), (Pasadena, Calif.): PE-anti-Vb13.1 (From Beckman Coulter). Data were acquired on a Fortessa (BD Biosciences, San Jose, Calif.) and data were analyzed with FlowJo version 7.6.1 (Tree Star, Inc., Ashland, Oreg.).

Enrichment CD3neg T Cells.

Cells washed with Auto MACS buffer were incubated for 30 min with CD3 microbeads (Miltenyi Biotec, 130-050-101, Auburn, Calif.) at 4° C. After being washed twice, the cells were passed through an LD column (Miltenyi Biotec, Auburn, Calif.), and the flow-through fraction was collected for further use.

ELISA Assays.

Target cells were washed and suspended at $1 \times 10^6$ cells/ml in R10 medium. Next, 100 µl of each target cell type was added in triplicate to a 96-well round-bottom plate (Corning). Effector T cells were washed and re-suspended at $1 \times 10^6$ cells/ml in R10 medium, and then 100 µl of T cells was combined with the target cells in the indicated wells. The plates were incubated at 37° C. for 18 to 24 hours. After the incubation, the supernatant was harvested and subjected to an ELISA (eBioscience).

Cd107A Staining.

Cells were plated at an E:T of 1:1 ($1 \times 10^5$ effectors: $1 \times 10^5$ targets) in 160 µl of R10 medium in a 96-well plate. Next, 20 µl of phycoerythrin-labeled anti-CD107a Ab was added, and the plate was incubated at 37° C. for 1 hour before the addition of Golgi Stop (2 µl of Golgi Stop in 3 ml of R10 medium, 20 µl/well; BD Biosciences, 51-2092KZ) and incubation for another 2.5 hours. Then, 5 µl of FITC-anti-CD8 and 5 µl of APC-anti-CD3 were added for incubation at 37° C. for 30 min. After the incubation, the samples were washed with FACS buffer and analyzed by flow cytometry.

Luciferase-Based CTL Assay.

Nalm6-CBG tumor cells were generated and employed in a modified version of a luciferase-based CTL assay8. Briefly, click beetle green luciferase (CBG)-T2A-eGFP was lentivirally transduced into Nalm6 tumor cells and sorted for GFP expression. The resulting Nalm6-CBG cells were resuspended at $1 \times 10^5$ cells/ml in R10 medium and incubated with different ratios of T cells (e.g., 30:1, 15:1, etc.) overnight at 37° C. Then, 100 µl of the mixture was transferred to a 96-well white illuminometer plate. Next, 100 µl of substrate was added, and the luminescence was immediately determined. The results are reported as percent killing based on the luciferase activity in the wells with tumor cells but no T cells (% killing=100−((RLU from well with effector and target cell coculture)/(RLU from well with target cells)× 100)).

The results of the experiments are now described.

Example 1: High Gene Disruption Efficiency sgRNAs were Selected for TRAC, TRBC, B2M, CIITA and PD-1

Figure 6A:
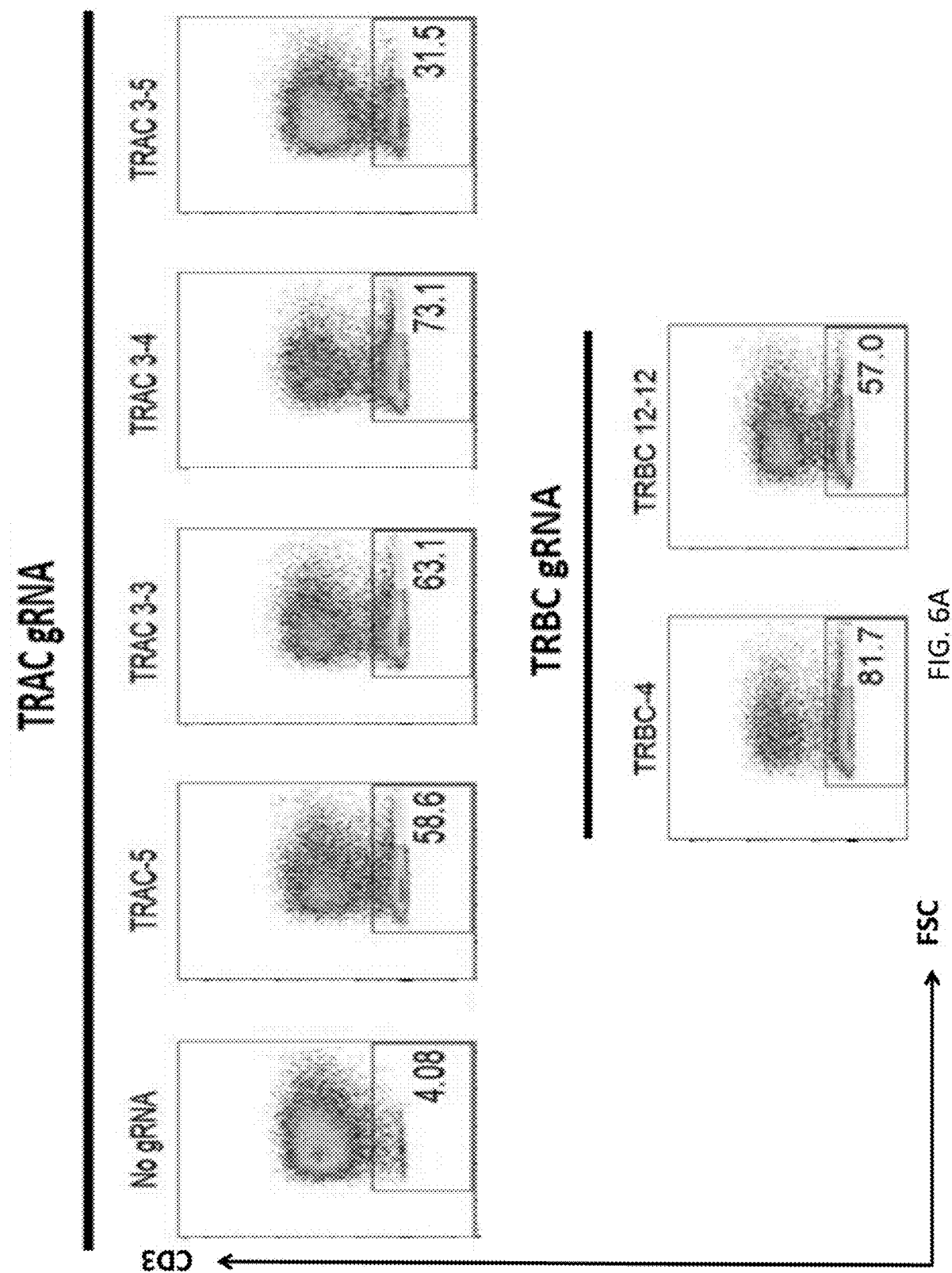
FIGS. 6A-6B are a series of plots illustrating gene disruption efficiency in T cells for selected, and cloned sgRNAs with high efficiency targeting: TRAC, TRBC, PD-1, B2M and CIITA.
Figure 6B:
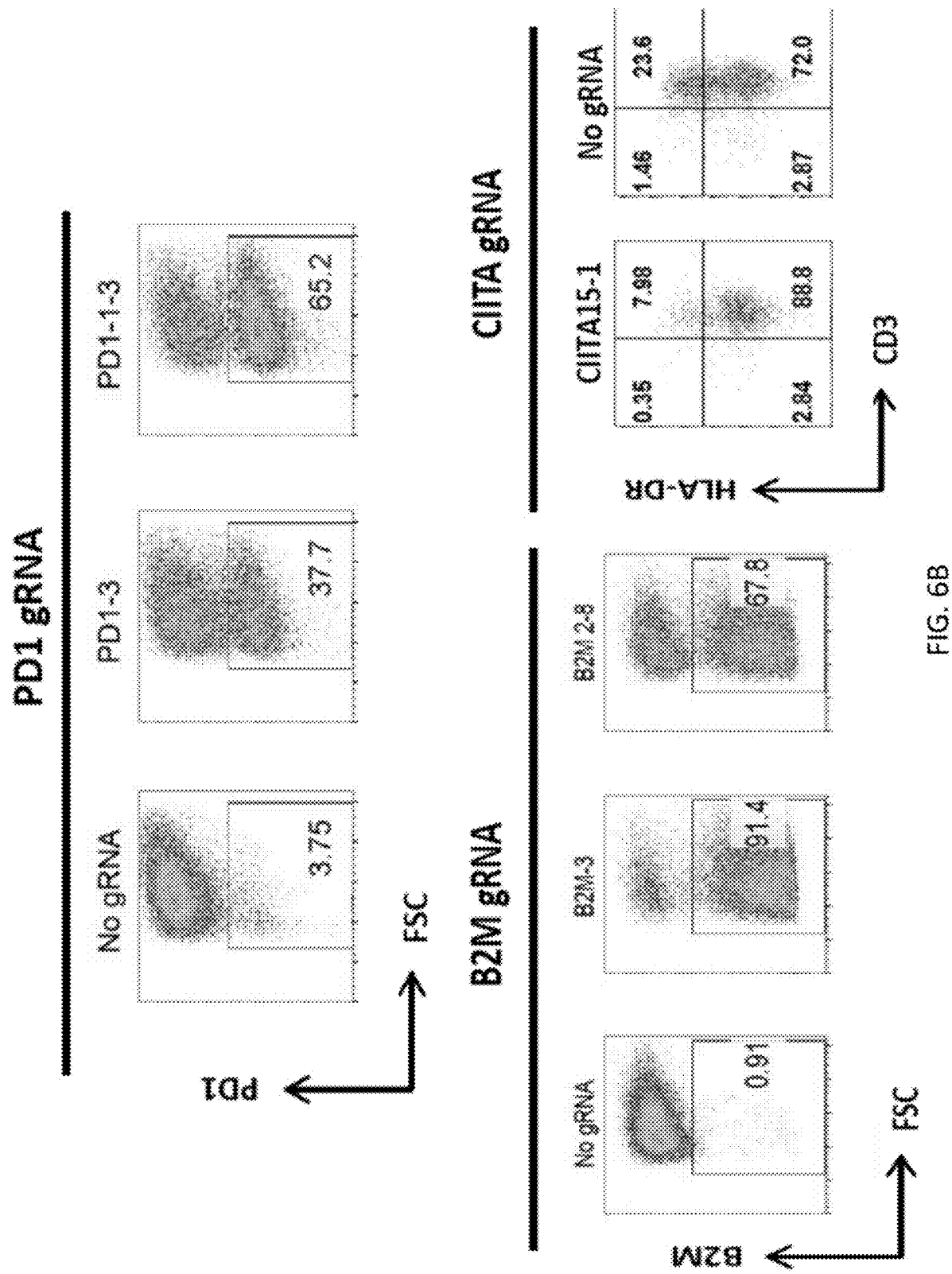

Twenty-four T cell receptor beta constant (TRBC), 24 class II, major histocompatibility complex transactivator (CIITA), 24 programmed cell death protein 1(PD-1), 12 beta-2-microglobulin (B2m), and 13 T cell receptor alpha constant (TRAC) gRNAs (FIGS. 26-27) were tested in stimulated T cells to screen for high efficiency gene disruption (FIGS. 1, 2A-2B, 3, 4A-4C, & 5A-5C). gRNAs with high gene disruption efficiency were selected and cloned into pD-A IVT vector (FIGS. 6A-6B & FIG. 28).

Figure 8:
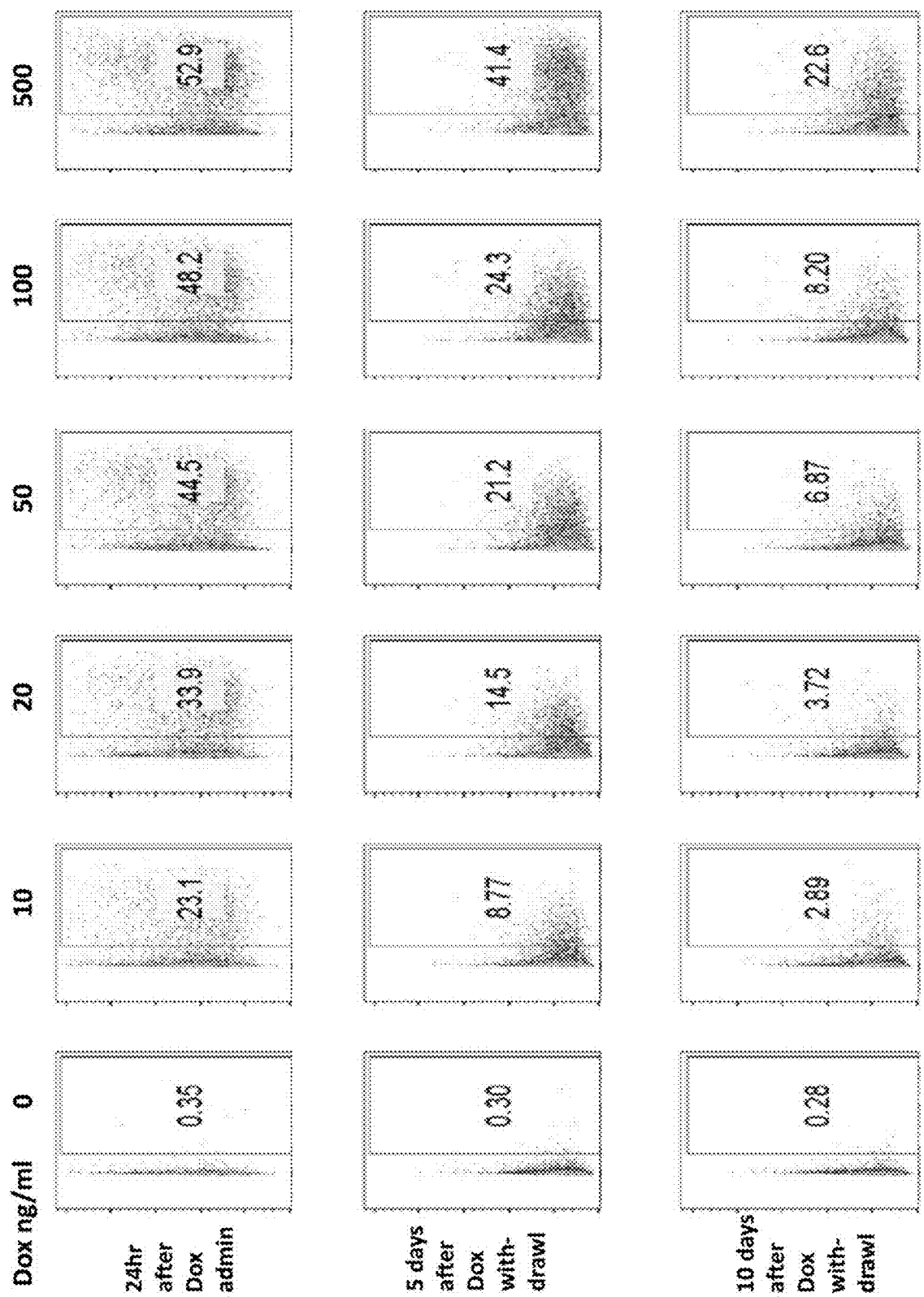
FIG. 8 is a series of plots illustrating EGFP expression of pRetoX-TetONE. EGFP transferred GP2-293 cells were doxycycline (Dox) dependent. Dox dose dependent EGFP expression is shown.
Figure 9:
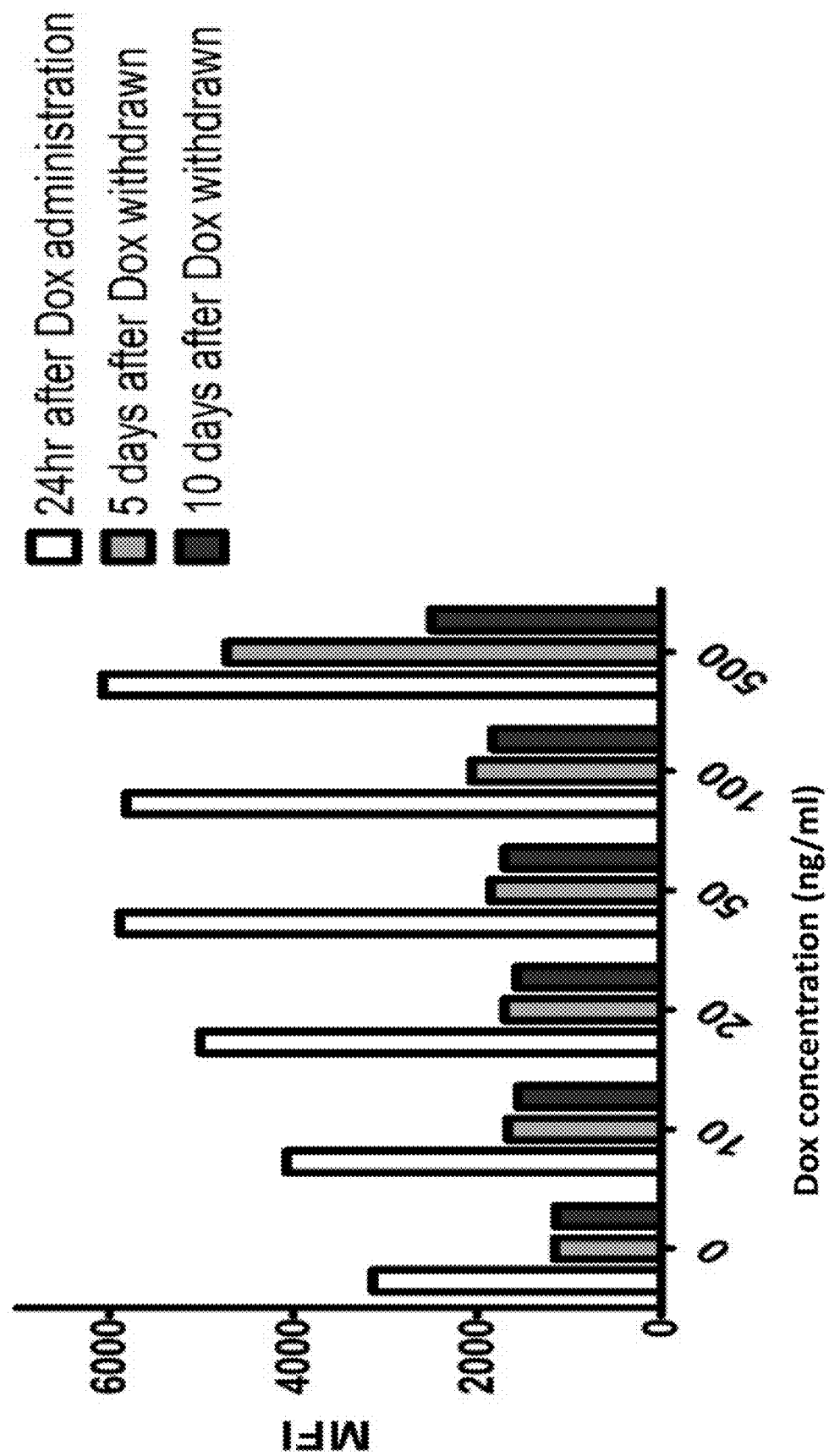
FIG. 9 is a bar graph depicting the Mean Fluorescence Intensity (MFI) of EGFP expression of pRetoX-TetONE.EGFP transferred GP2-293 cells as shown in FIG. 8.
Figure 10:
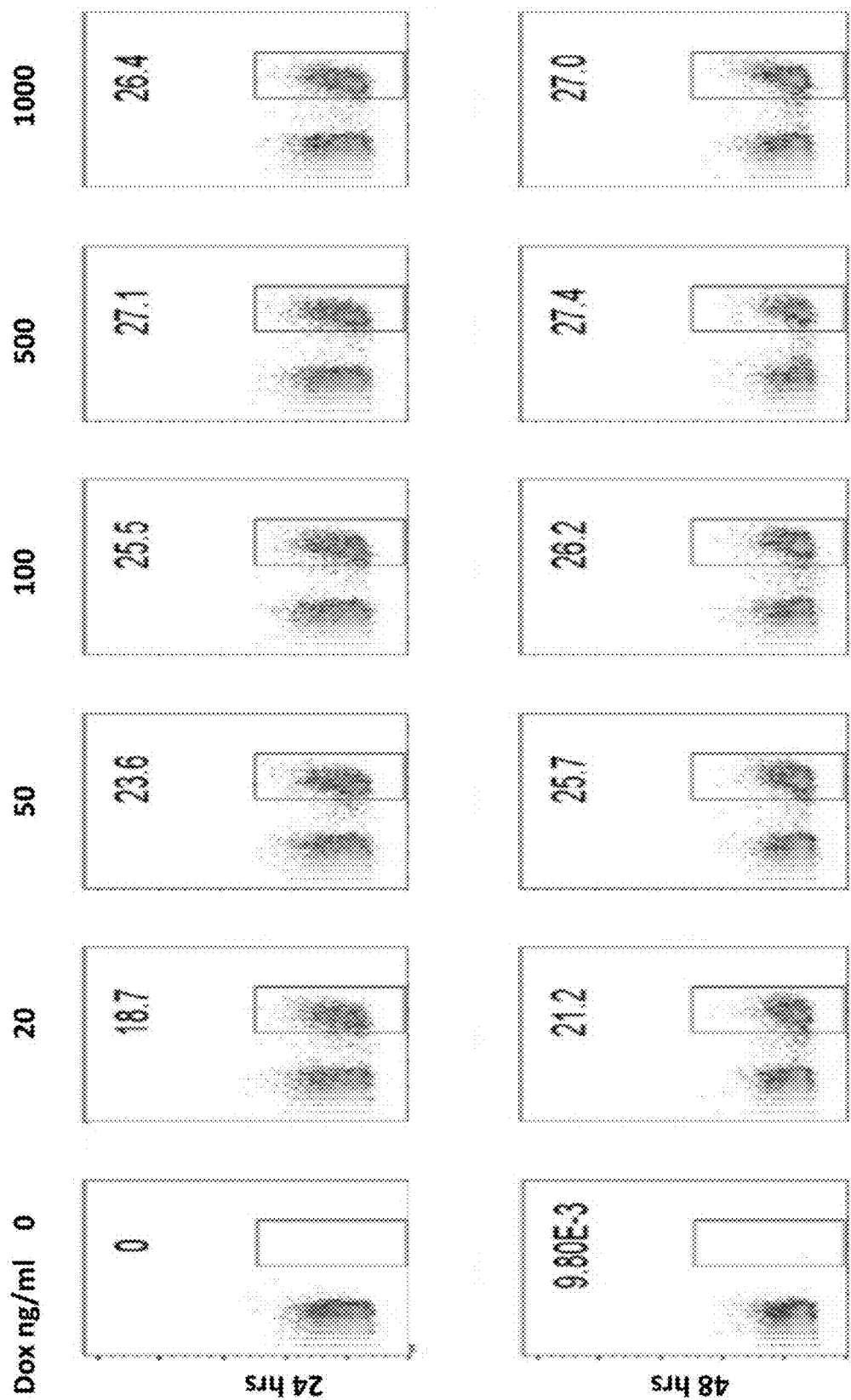
FIG. 10 is a series of plots illustrating EGFP expression of pRetoX-TetONE.EGFP transduced T cells was doxycycline (Dox) dependent. Dox dose dependent EGFP expression is shown.
Figure 11:
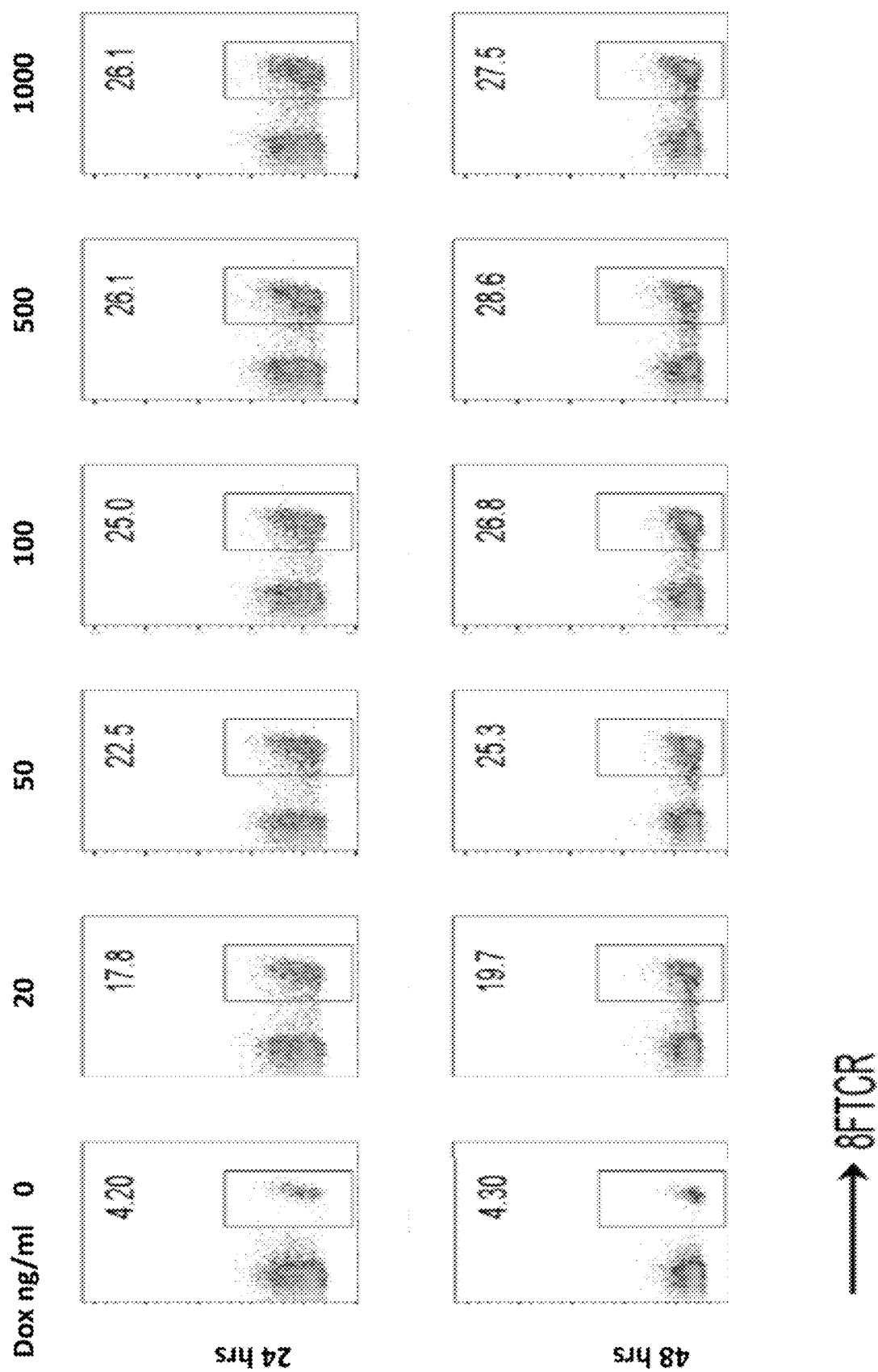
FIG. 11 is a series of plots illustrating transgenic TCR (NY-ESO-1 8F TCR (vb8)) expression of pRetoX-TetONE.8.TCR transduced T cells was doxycycline (Dox) dependent. Dox dose dependent TCR expression is shown.
Figure 12:
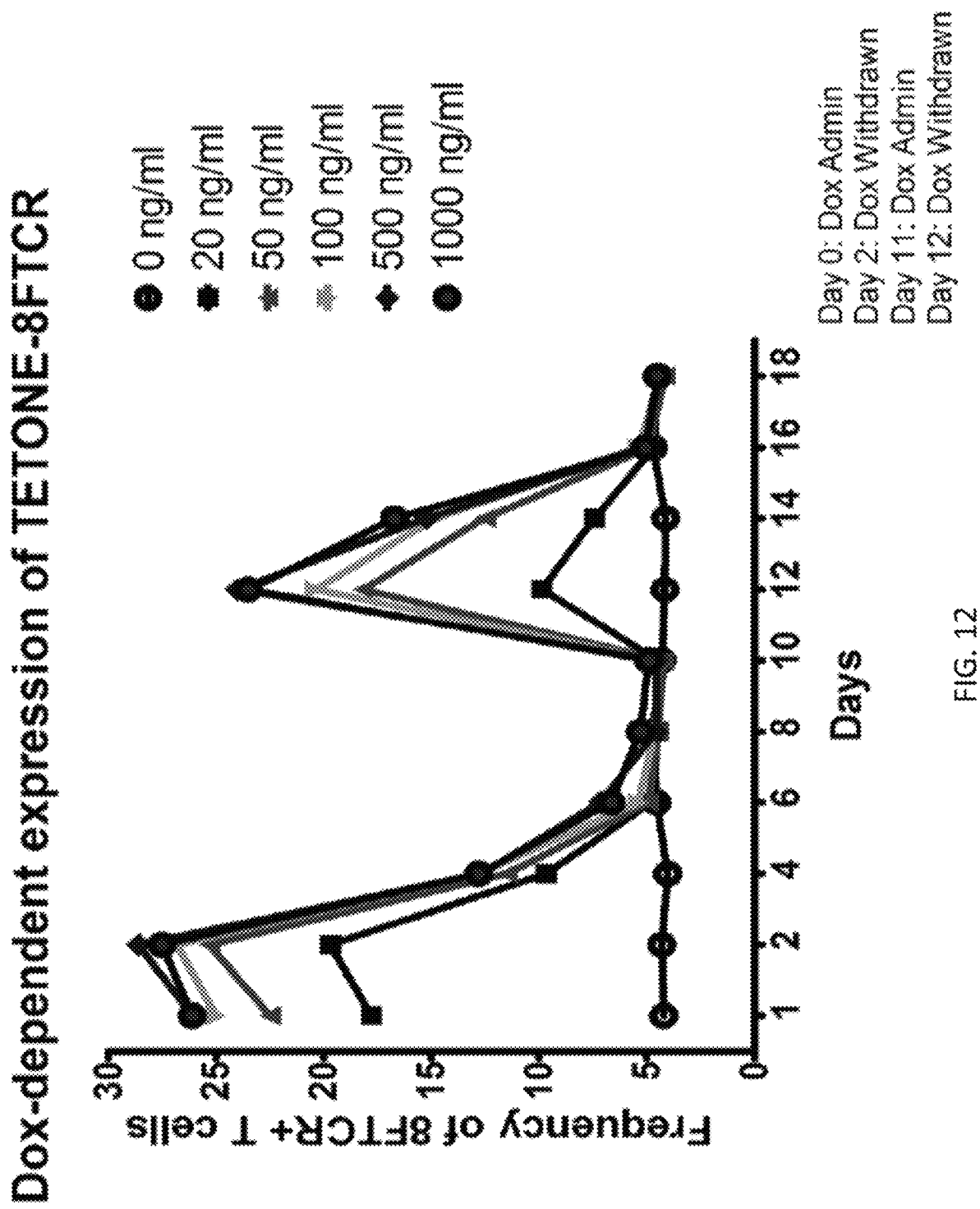
FIG. 12 is a graph illustrating expression of TETONE-8FTCR is dox-dependent. Various doses of Dox were administered to T cells that were transduced by TETONE-8FTCR retrovirus. Expression of 8FTCR was induced by Dox administration on Day 0, and was turned off gradually after Dox withdrawn on Day 2. A second administration of Dox on Day 11 also induced 8FTCR expression, which was shut down after Dox was withdrawn on Day 12.
Figure 13:
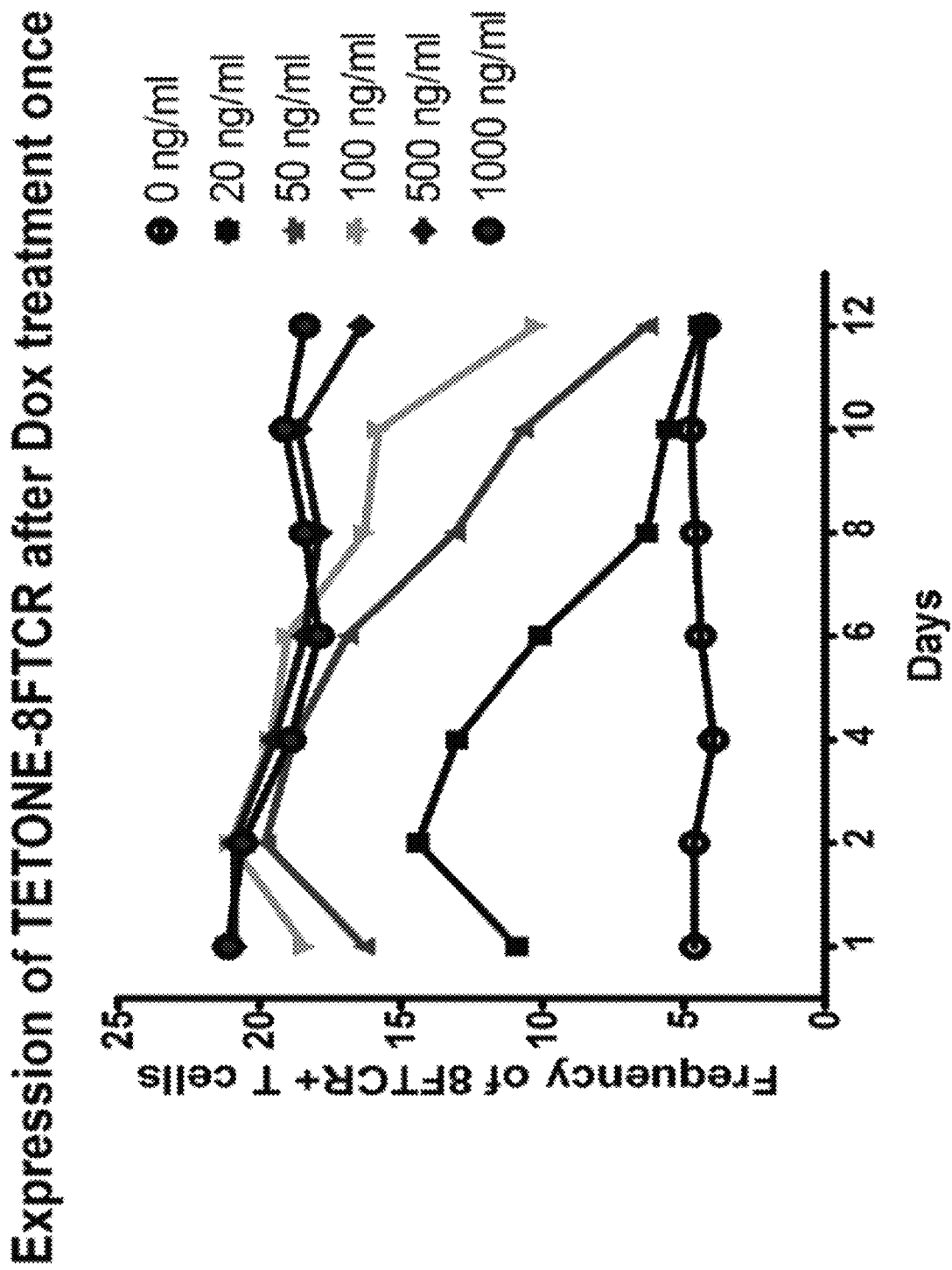
FIG. 13 is a graph illustrating residual Dox in the medium can sustain the expression of TETONE-8FTCR if not washed out. Expression of TETONE-8FTCR was monitored after one time Dox treatment on Day 0. Cells were kept cultured in the medium containing doxycycline throughout the experiment.
Figure 14:
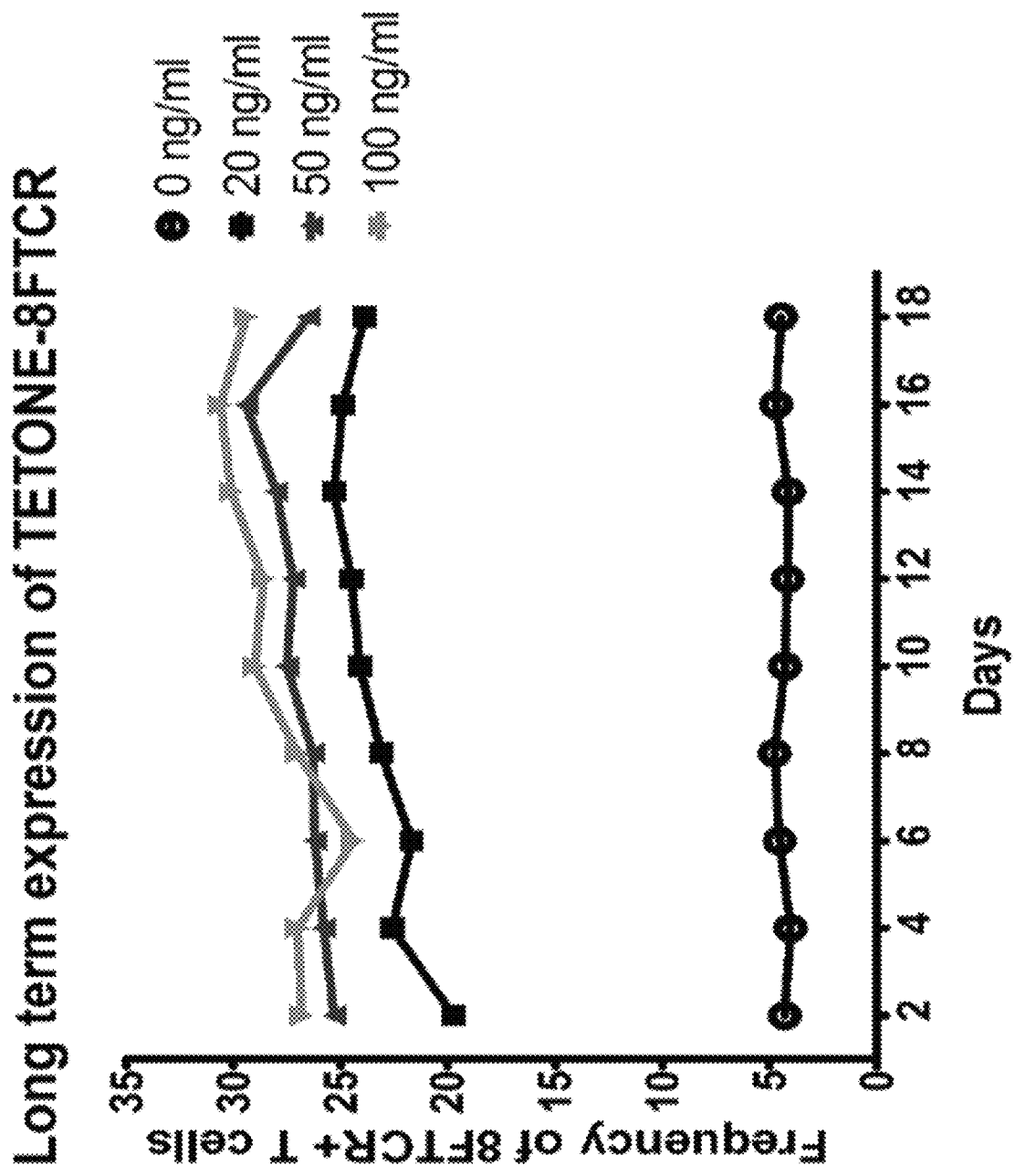
FIG. 14 is a graph illustrating expression of TETONE-8FTCR is sustained by repeated administration of Dox. Dox was administered every other day from Day 0.
Figure 15:
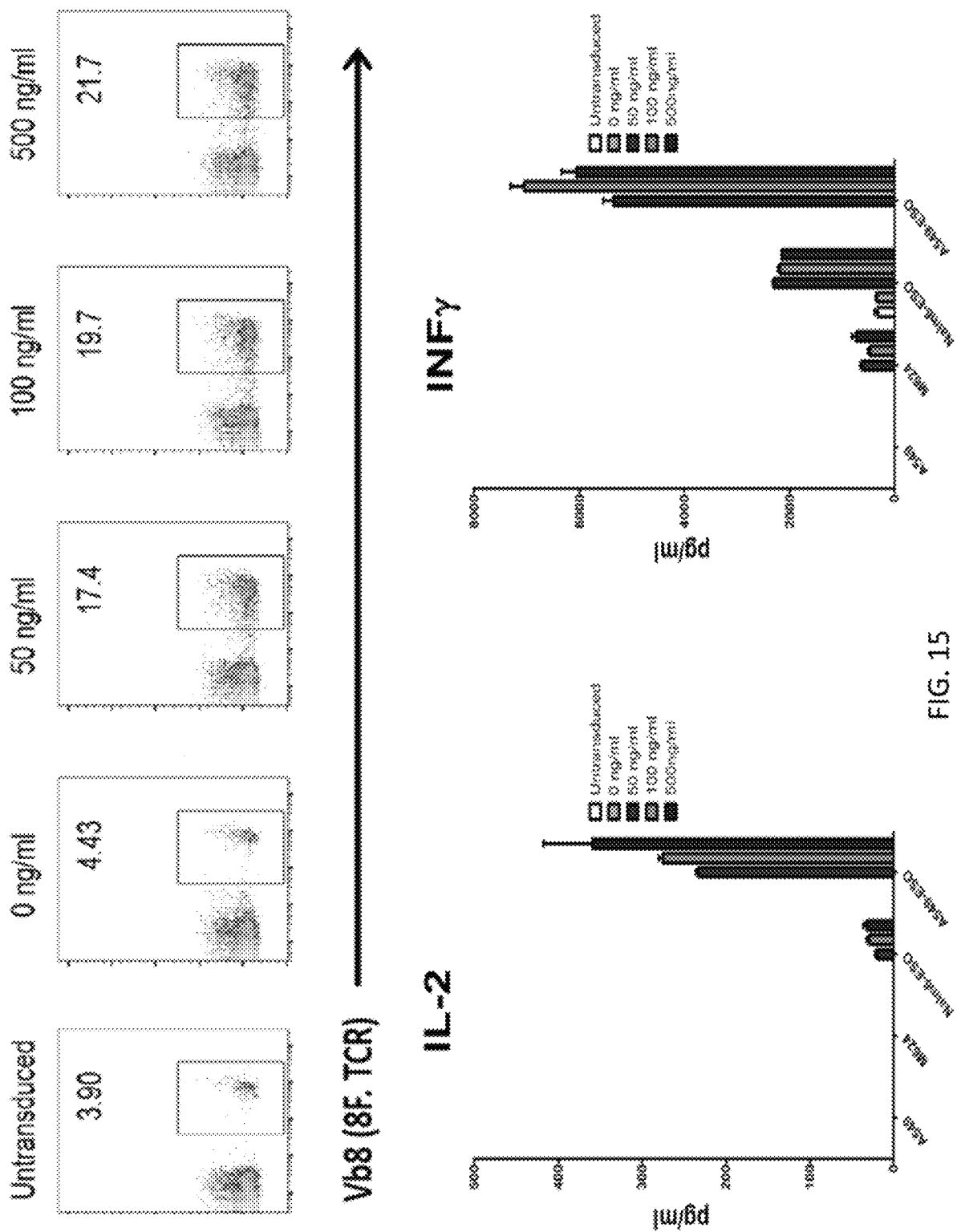
FIG. 15 is a series of plots illustrating pRetoX-TetONE.8.TCR transduced T cells were cultured in the present of different concentration of Dox for 24 h. TCR expression (vb8) was detected by flow cytometry (upper panel) and the T cells were stimulated by NY-ESO-1/HLA-A2 positive cell lines, M624, Nalm6-ESO and A549-ESO (A549 was used as NY-ESO-1/HLA-A2 negative control) for 24 hours to detect cytokine (IL2 and IFN-gamma) secretion of the stimulated T cells.
Figure 16:
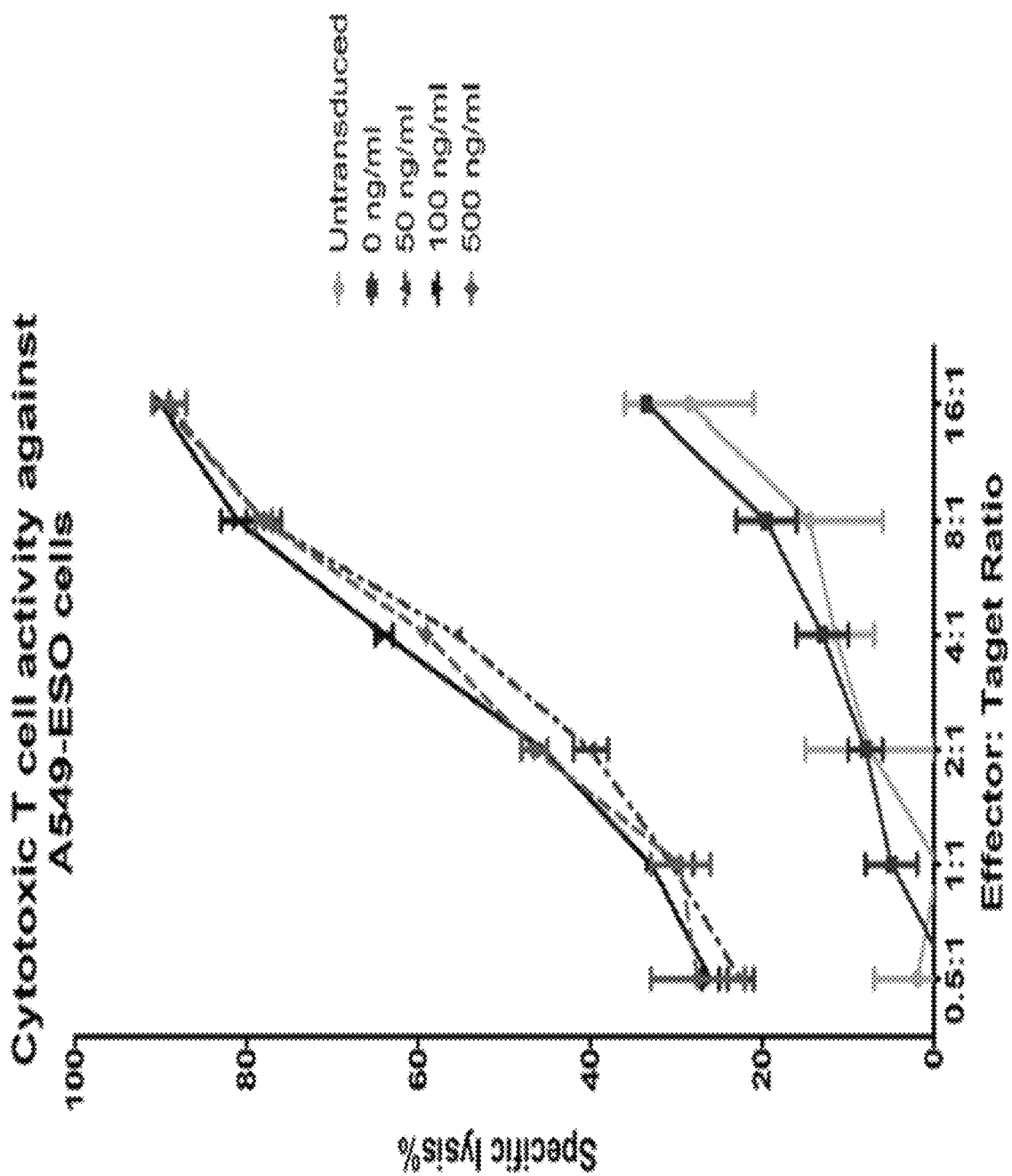
FIG. 16 is a graph illustrating pRetoX-TetONE.8.TCR transduced T cells were cultured in the presence of different concentration of Dox for 24 hours and the lytic activity of the T cells were tested against an NY-ESO-1/HLA-A2 positive cell line, and A549-ESO in a Luciferase-based CTL assay.

Example 2: Expression of a Transgenic TCR is Induced Using a Tetracycline (Tet)-on System A tetracycline (Tet)-On retroviral vector system was used to construct EGFP (pRetoX-TetONE.EGFP) and a NY-ESO-1 TCR (pRetoX-TetONE.8.TCR) (FIG. 7). First, the system was tested by transducing Tet-On EGFP into GP2-293 cell line. There was no GFP expression if no Dox was present in the culture (FIG. 8). EGFP could be induced after Dox was added to the cultures and EGFP expression was positively correlated with the dose of Dox added to the cultures (FIGS. 8 & 9). Next, T cells were transduced with Tet-On EGFP (FIG. 10). Similar to GP2-293 transduced cells, there was no GFP expression when Dox was not present in the culture (FIG. 8). EGFP could be induced after Dox was added to the cultures and EGFP expression was positively correlated with the dose of Dox added to the cultures. When T cells were transduced with Tet-On NY-ESO-1 TCR, only background TCR (endogenous TCR, 4-5%) was detected if there was no Dox present in the culture (FIG. 11). However, increased TCR expression could be induced after Dox was added to the cultures and TCR expression was positively correlated with the dose of Dox added to the cultures. The induced TCR expression decreased once Dox was withdrawn and the induced expression of TCR decreased to background levels 6 days after adding Dox (FIG. 12). Without washing out the added Dox, the induced expression of TCR persisted much longer, especially when high concentrations of Dox were used (FIG. 13). Longer term induced TCR expression could be maintained if Dox was continuously supplied, even at low concentrations (FIG. 14). Moreover, the anti-tumor activities, such as cytokine production (IL-2 and IFN-gamma, FIG. 15) and lytic activity (FIG. 16) of Tet-On NY-ESO-1

TCR transduced T cells, upon Dox induction and tumor stimulation, were also positively correlated with the dose of Dox added to the cultures.

Figure 19:
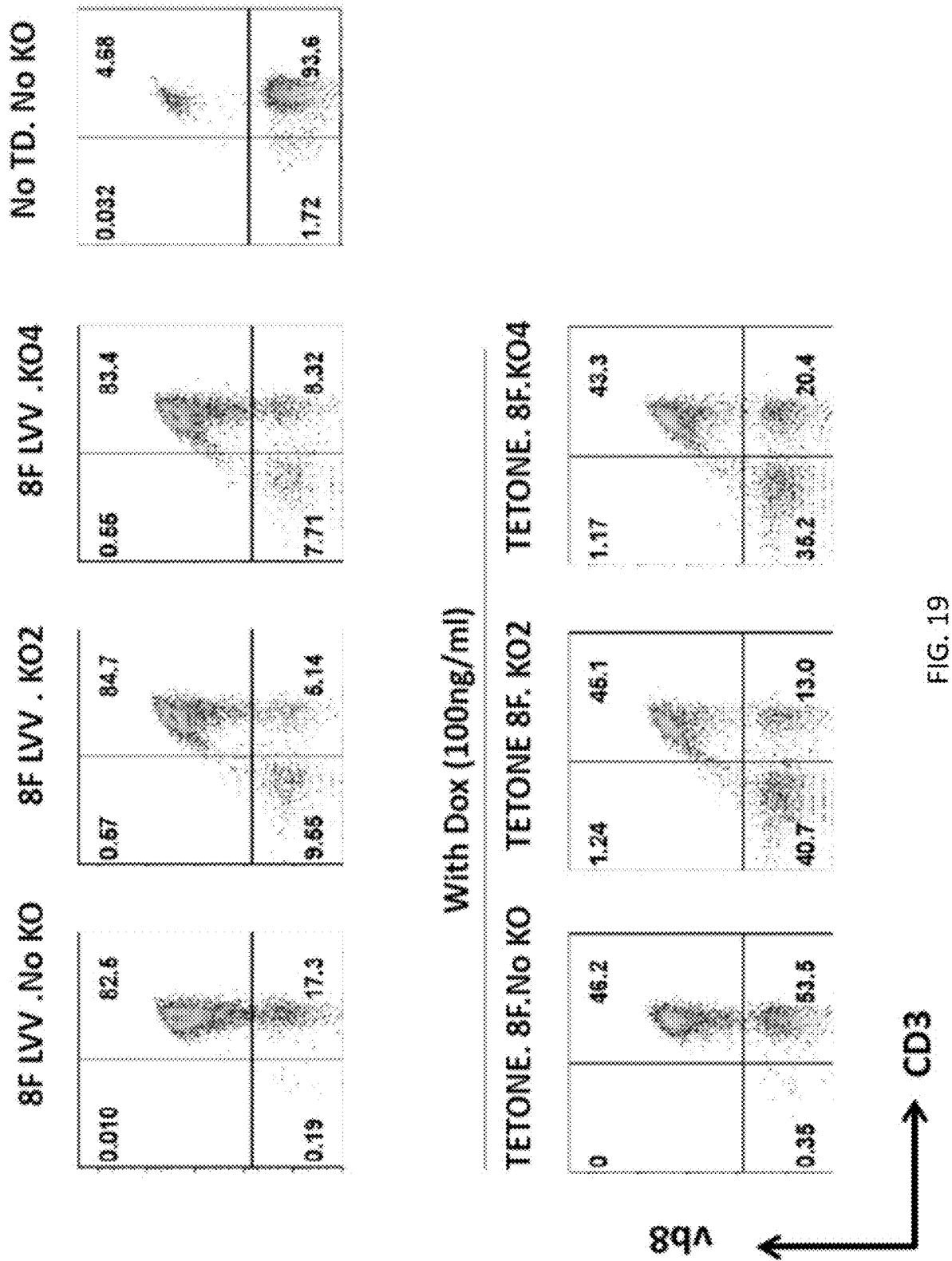
FIG. 19 is a series of plots illustrating vb8 and CD3 expression was examined for lentiviral vector transduced T cells (upper panel) and pRetoX-TetONE.8.TCR transduced with Dox (lower panel). No TD, non-transduced; No KO, non-CRISPR/CAS9 gene editing; 8F RVV, pRetroX.TetONE.8F.TCR (TETONE.8F); KO2, TRAC and TRBC gene disruption; KO4, TRAC, TRBC, B2M and CIITA gene disruption; 8F LVV, pTRP.8F.TCR (8FTCR LVV).
Figure 20:
FIG. 20 is a series of plots illustrating lentiviral vector pTRP.8F.TCR transduced T cells (LVV) or pRetoX-TetONE.8.TCR transduced T cells (TETON RVV) were electroporated with CRISPR/CAS9 for multiplex gene disruption of TRAC and TRBC (KO2) or TRAC, TRBC B2M and CIITA (KO4). CD3 and B2M and were detected at day 8 post stimulation. NO TD, Non transduced T cells. NO KO, Non CRISPR gene editing T cells.

Example 3: CD3⁻ T Cells with Inducible Transgenic TCR Expression are Generated Using Tetracycline (Tet)-on System A procedure for generating universal TCR transduced T cells was developed as shown in FIG. 17. 8F NY-ESO-1 TCR lentiviral transduced T cells with CRISPR/CAS9 double (TRAC and TRBC) or quadruple (TRAC, TRBC, B2M and CIITA) gene disruption were generated in parallel as T cell potency controls. As shown in FIG. 18, 54.5% transgenic TCR was detected when pRetoX-TetONE.8.TCR (RVV TETONE) transduced T cells were induced by 100 ng/ml Dox for 24 hours compared with 82.5% vb8 for pTRP.8F.TCR lentiviral transduced T cells. After the pRetoX-TetONE.8.TCR transduced T cells were electroporated with CAS9/gRNA for double (1(02) or quadruple (KO4) gene disruption, 45.1% and 43.3% vb8+/Cd3+ T cells could be detected upon 24 hour 100 ng/ml Dox induction, compared with 46.2% for non-CRISPR gene edited, Dox induced T cells (FIG. 19). Gene disruption efficiency was examined by flow cytometry detection of CD3 and B2M. High efficient gene disruption was confirmed for both double gene ablation and quadruple gene disruption, as evidenced by over 70% gene knockout for TCR/CD3 or B2M (FIG. 20).

Figure 21:
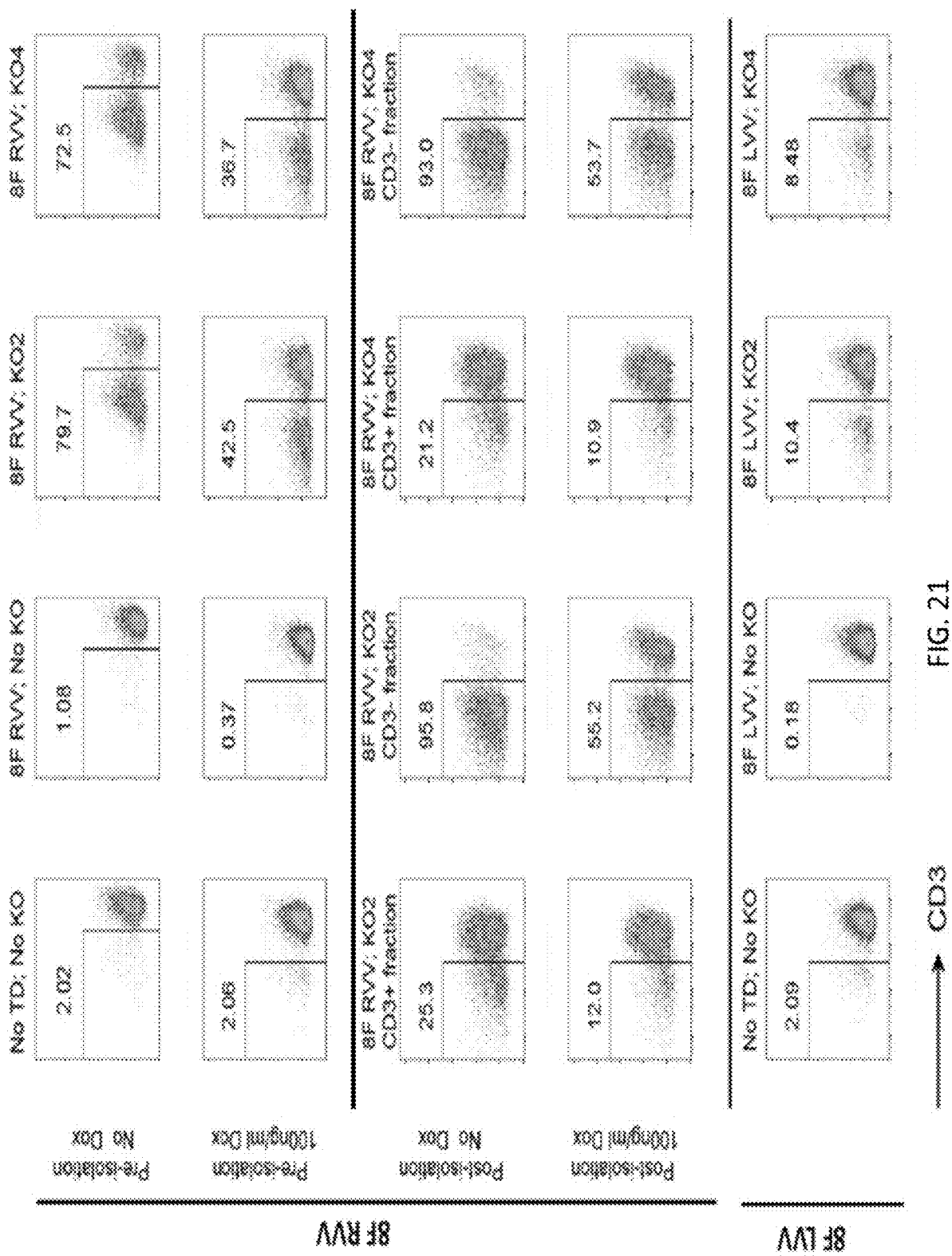
FIG. 21 is a series of plots illustrating CD3 expression was examined for: 1.) CD3 pre-sorted T cells of pRetoX-TetONE.8.TCR transduced, with or without Dox (upper panel); 2.) CD3+ or CD3− fractions of the sorted T cells before (Post-isolation, No Dox) and after adding Dox (Post-isolation, 100 ng/ml Dox) (middle panel) and, 3.) Non-sorted lentiviral vector transduced T cells. No TD, non-transduced; No KO, non-CRISPR/CAS9 gene editing; 8F RVV, pRetroX.TetONE.8F.TCR (TETONE-8FTCR RVV); KO2, TRAC and TRBC gene disruption; KO4, TRAC, TRBC, B2M and CIITA gene disruption; 8F LVV, pTRP.8F.TCR (8FTCR LVV).
Figure 22:
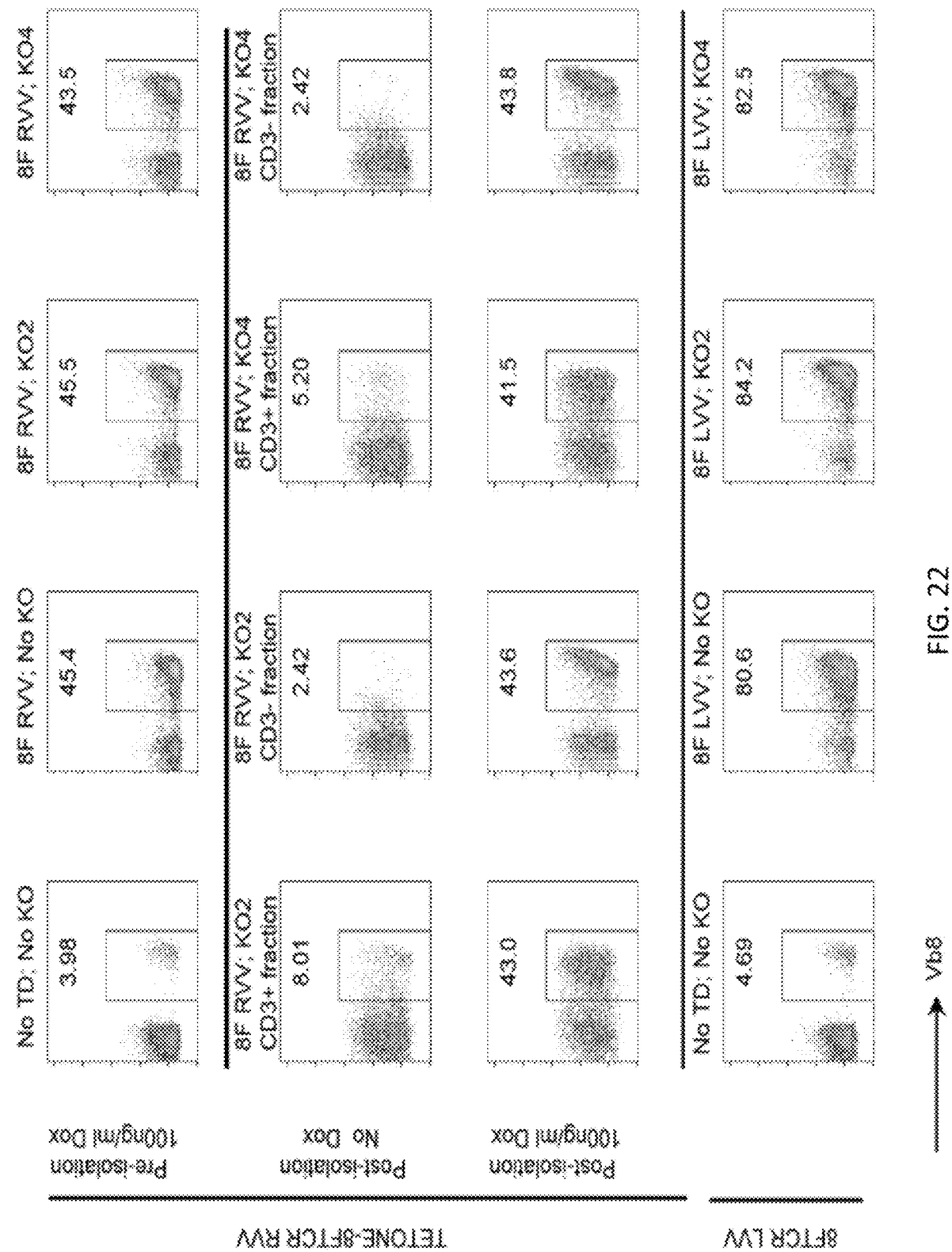
FIG. 22 is a series of plots illustrating vb8 expression was examined for: 1.) CD3 pre-sorted T cells of pRetoX-TetONE.8.TCR transduced, with Dox (upper panel); 2.) CD3+ or CD3− fractions of the sorted T cells before (Post-isolation, No Dox) and after adding Dox (Post-isolation, 100 ng/ml Dox) (middle panel) and, 3.) Non-sorted lentiviral vector transduced T cells. No TD, non-transduced; No KO, non-CRISPR/CAS9 gene editing; 8F RVV, pRetroX.TetONE.8F.TCR (TETONE-8FTCR RVV); KO2, TRAC and TRBC gene disruption; KO4, TRAC, TRBC, B2M and CIITA gene disruption; 8F LVV, pTRP.8F.TCR (8FTCR LVV).
Figure 23:
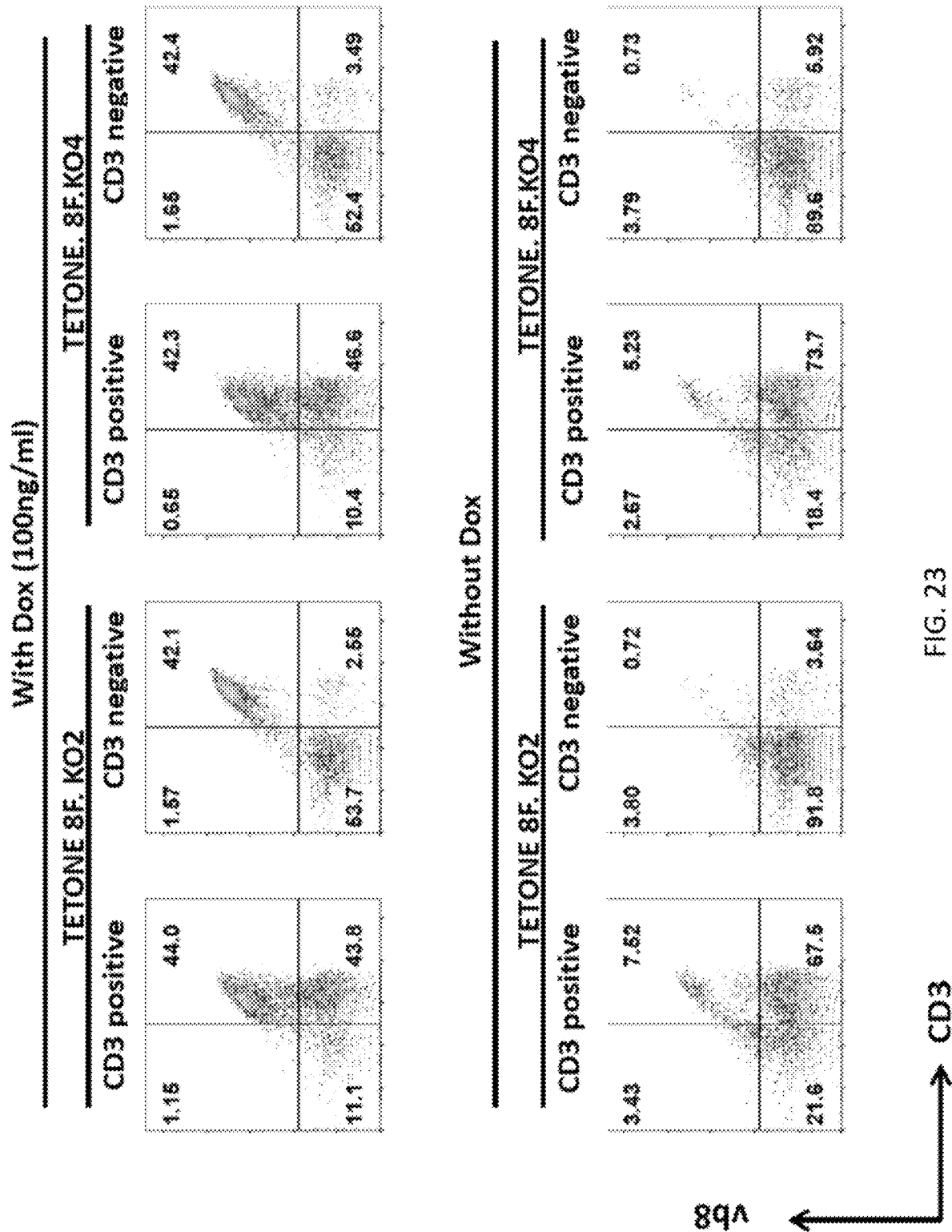
FIG. 23 is a series of plots illustrating vb8 and CD3 expression was examined for CD3+ or CD3− fractions of the sorted T cells with (upper panel) without Dox (lower panel) 8F RVV, pRetroX.TetONE.8F.TCR (TETONE-8FTCR RVV); KO2, TRAC and TRBC gene disruption; KO4, TRAC, TRBC, B2M and CIITA gene disruption.

Example 4: Generating TCR Transduced T Cells that are Free from Endogenous TCR Associated CD3 Expression To generate universal TCR T cells that were free from endogenous TCR associated CD3 expression, 8 days post stimulation, both CD3 positive and CD3 negative T cells were harvested from T cells that were transduced with pRetoX-TetONE.8.TCR (8F RVV) and electroporated for CRISPR double (KO2) or quadruple (KO4), using Miltenyi CD3 MicroBeads for CD3 negative selection. As shown in FIG. 21, CD3 negative T cells could be enriched. By adding Dox to the separated T cells (Post-isolation) to induce the expression of the transduced TCR, CD3 could be induced to express (FIGS. 21, 22 & 23).

Example 5: Enhanced Function of Universal TCR T Cells

Figure 24C:
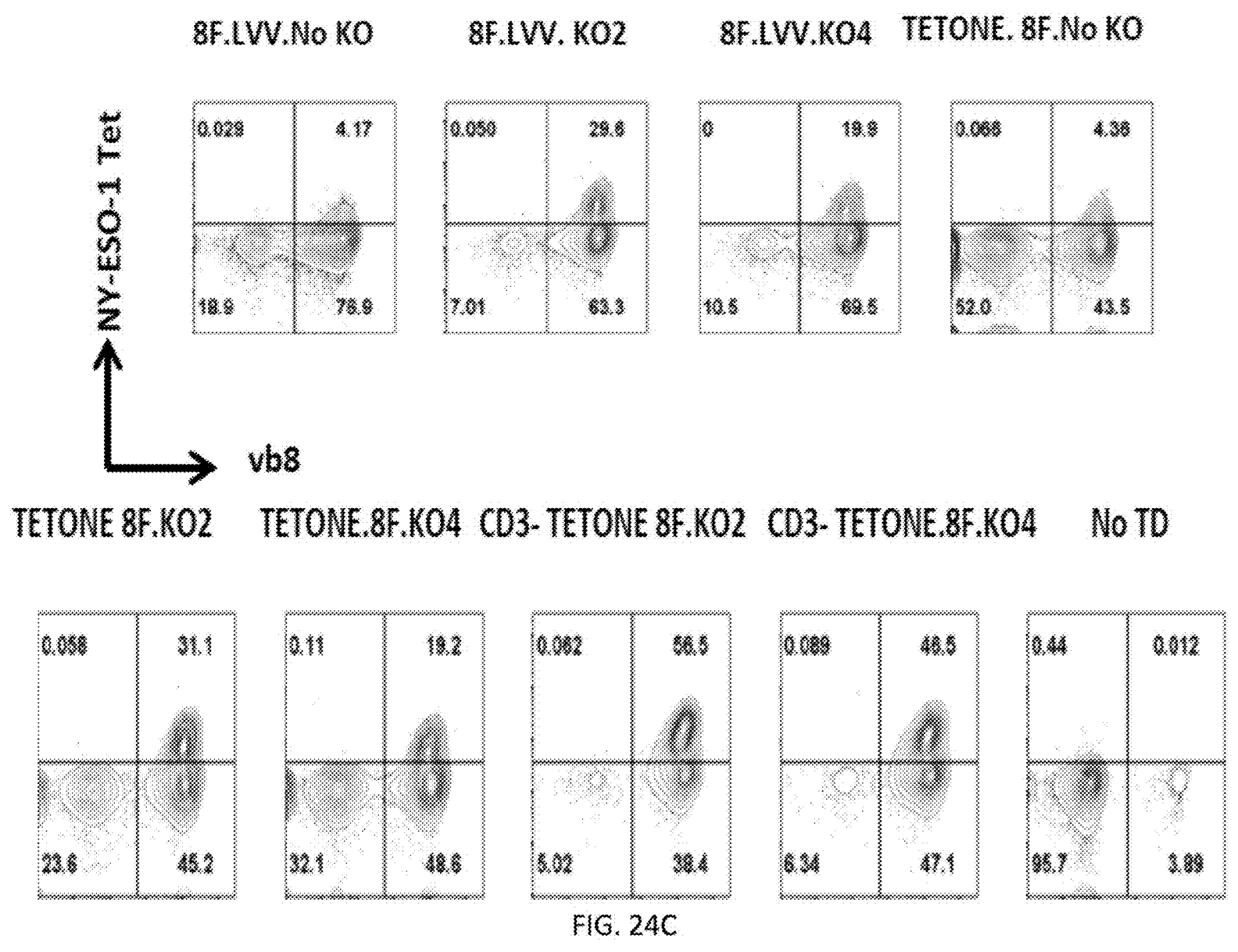
Figure 25C:
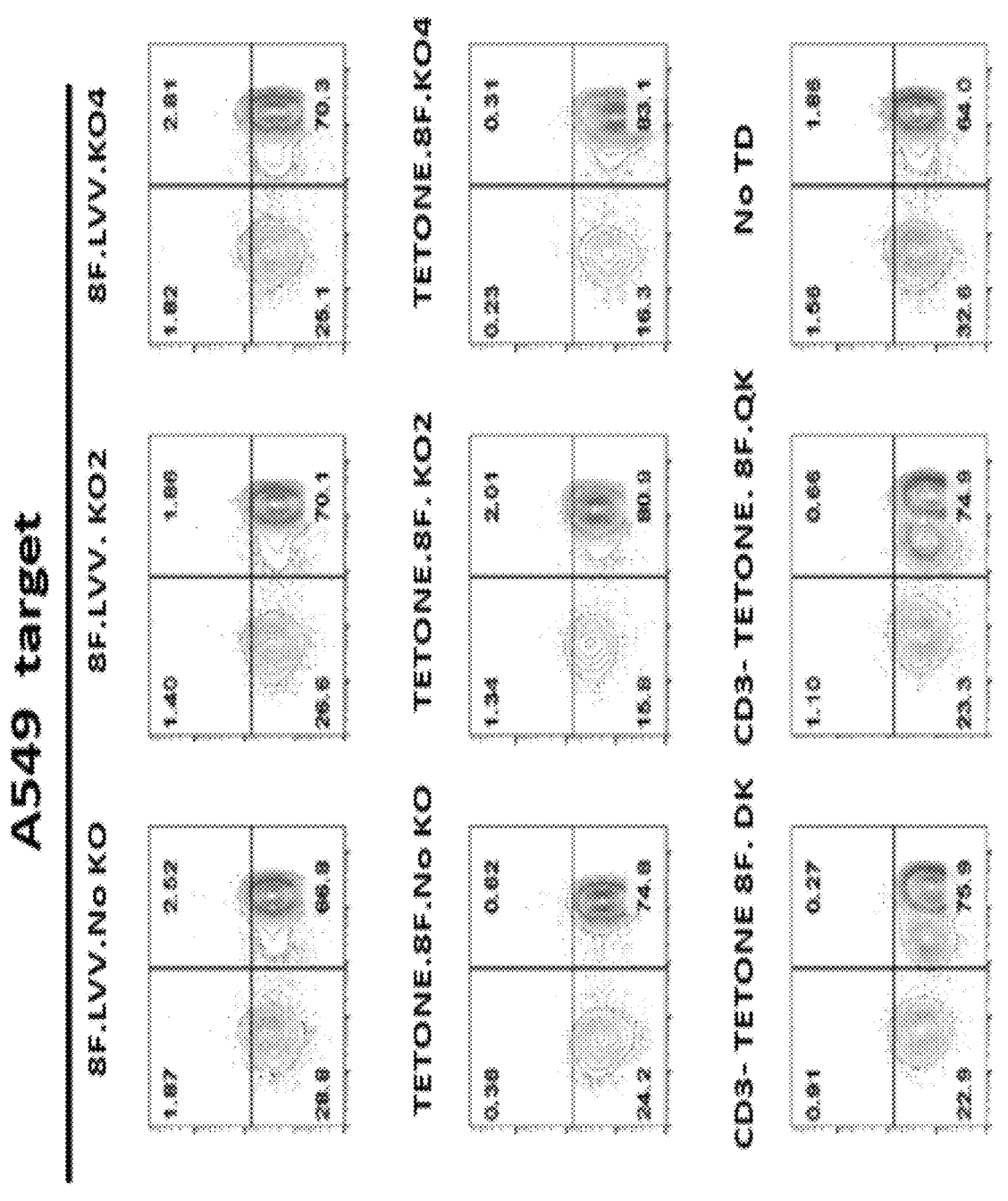

Universal TCR T cells generated using the tetracycline (Tet)-On system, CRISPR gene editing, and CD3 depletion, were tested for antitumor activity. Using regular NY-ESO-1 TCR lentiviral transduced/CRISPR gene edited T cells and tetracycline (Tet)-On system transduced CRISPR gene editing (without CD3 depletion), NY-ESO-1 tetramer binding assay by flow cytometry showed significantly increased tetramer staining for the universal TCR T cells (CD3– TETONE.8F.KO2& CD3– TETONE.8F.KO4), as well as significantly increased tetramer binding of CD4 T cells (CD8 negative population) (FIGS. 24A-24C). After 4 hours stimulation of the T cells with NY-ESO-1/HLA-A2 positive tumor line A549-ESO and Nalm6-ESO, CD107a staining was significantly increased for the universal TCR T cells (CD3– TETONE.8F.KO2& CD3– TETONE.8F.KO4), compared with regular NY-ESO-1 TCR lentiviral transduced/ CRISPR gene edited T cells and tetracycline (Tet)-On system transduced CRISPR gene editing (without CD3 depletion) T cells (FIGS. 25A-25C).

Example 6: Function of Tet-On-8FTCR Transduced T Cells In Vivo

Figure 29:
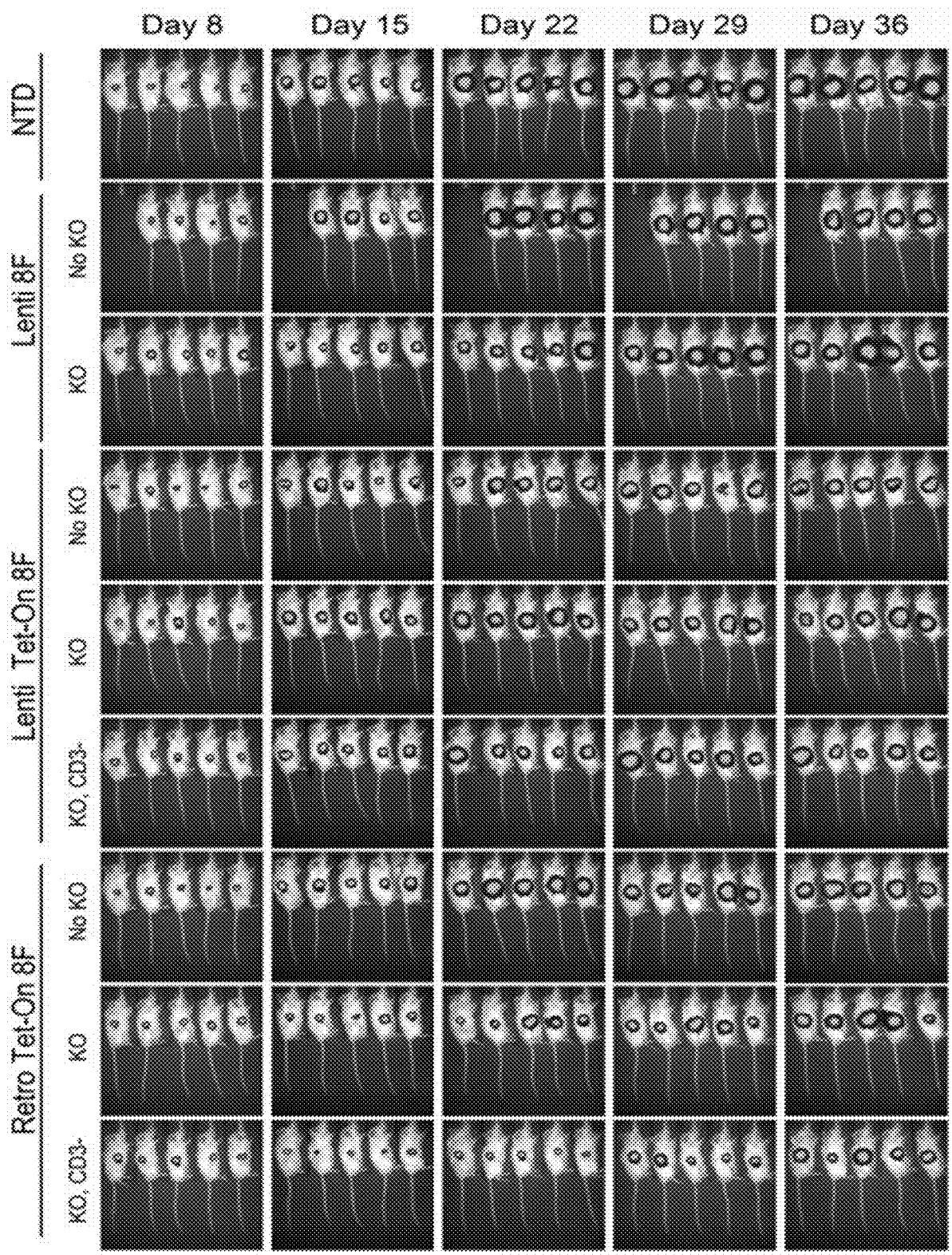
FIG. 29 depicts bioluminescence imaging of tumors in different groups over time as indicated.
Figure 30:
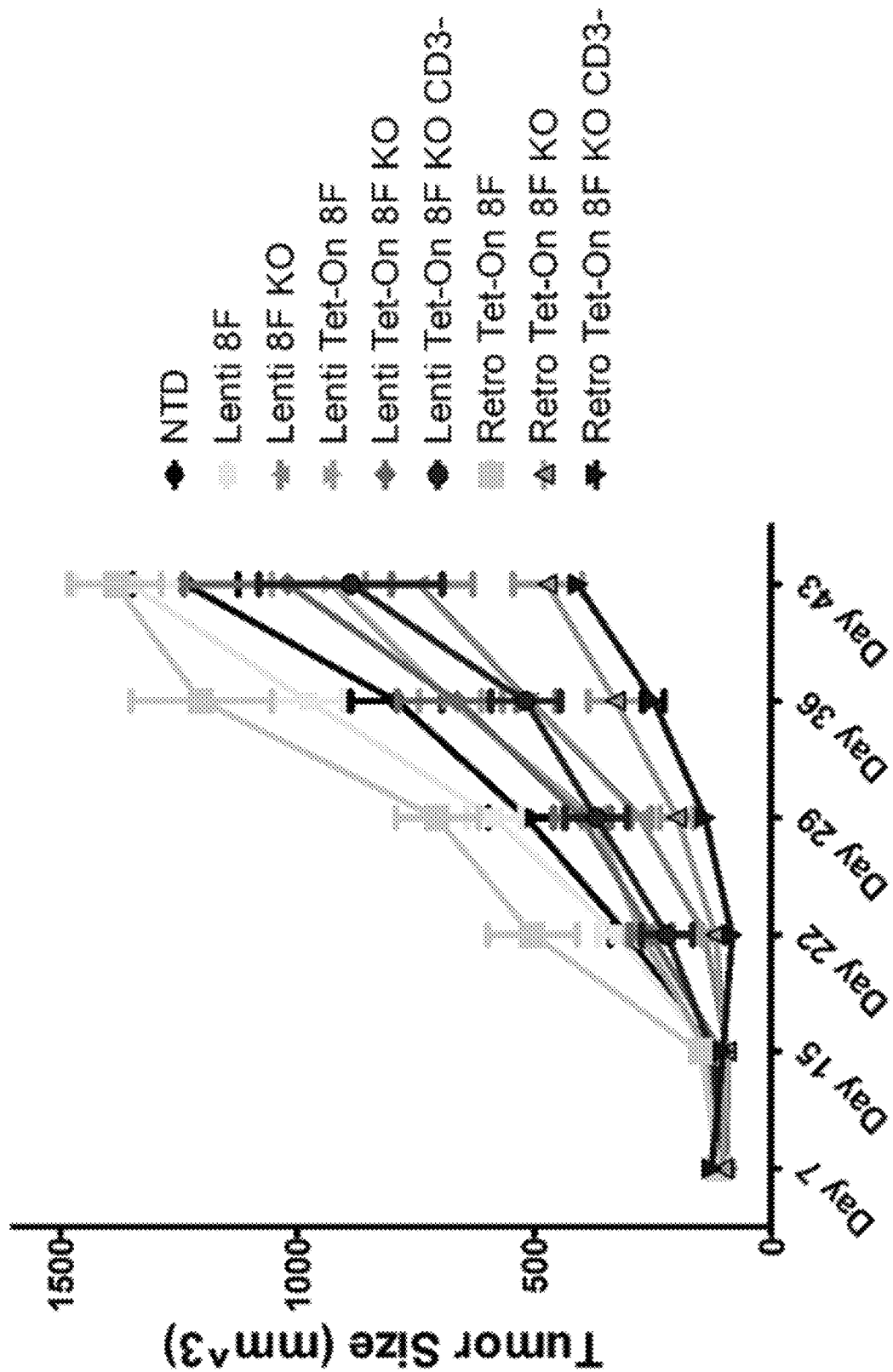
FIG. 30 is a graph showing caliper measurements of tumor sizes in different groups over time as indicated.

Five million A549ESO cells were injected subcutaneously into mice to establish xenograft tumors. Ten million transduced T cells were injected intravenously eight days later when tumor size reached about 100 mm³. Doxycycline-containing chow was continuously supplied in order to induce 8FTCR expression in the Lenti Tet-On 8F and Retro Tet-On 8F groups. Bioluminescence imaging showed that Retro Tet-On 8F KO and KO CD3– groups had higher anti-tumor activities than other groups (FIG. 29). Caliper measurements showed that the Retro Tet-On 8F KO CD3– group had the highest tumor control capacity, followed by the Retro Tet-On 8F KO group, and the Lenti 8F KO group (FIG. 30).

Figure 31:
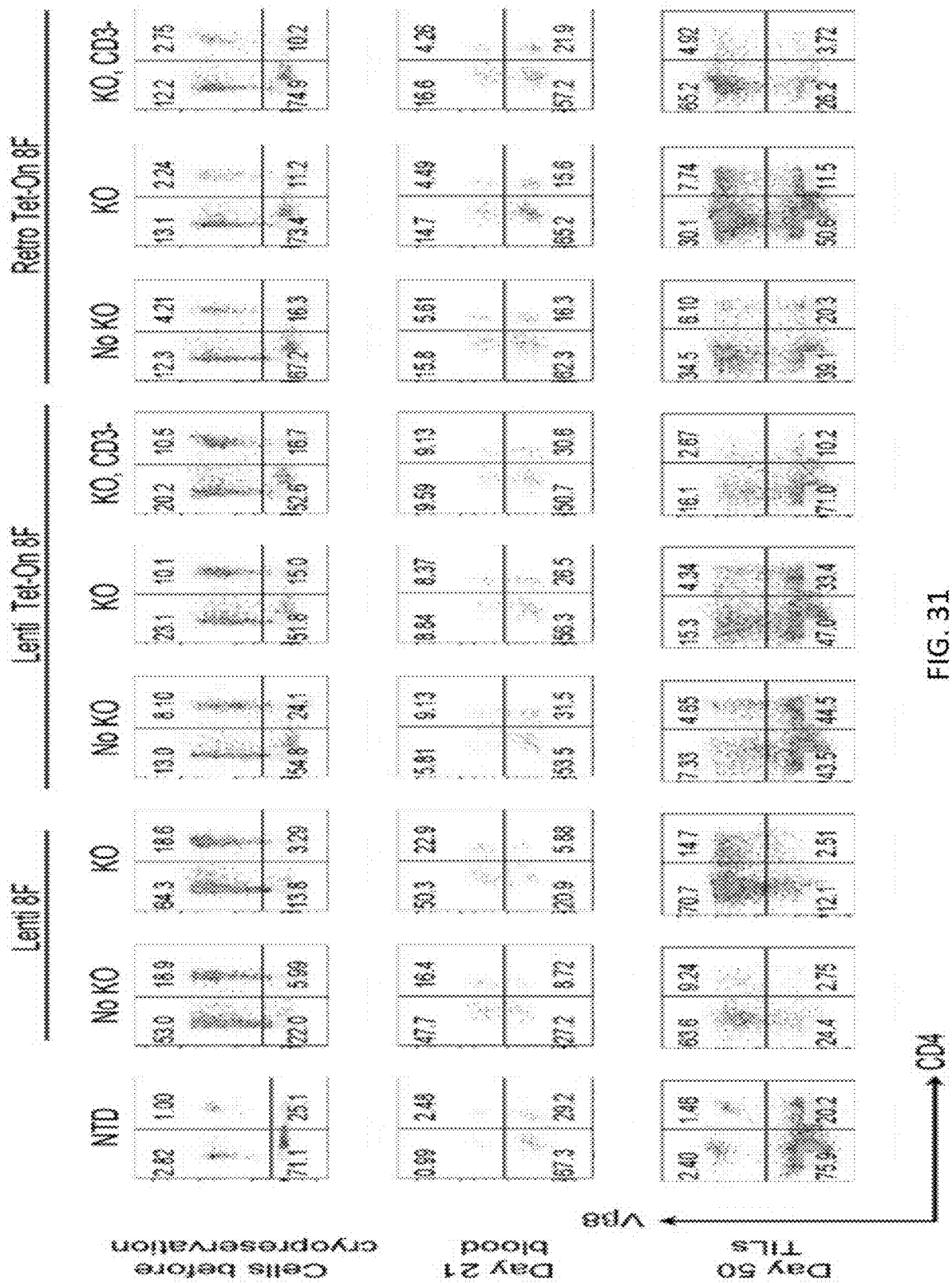
FIG. 31 depicts plots demonstrating frequencies of 8FTCR+ T cells prior to cryopreservation, in blood at day 21, and in tumor infiltrating leukocytes (TILs) at day 50.
Figure 32C:
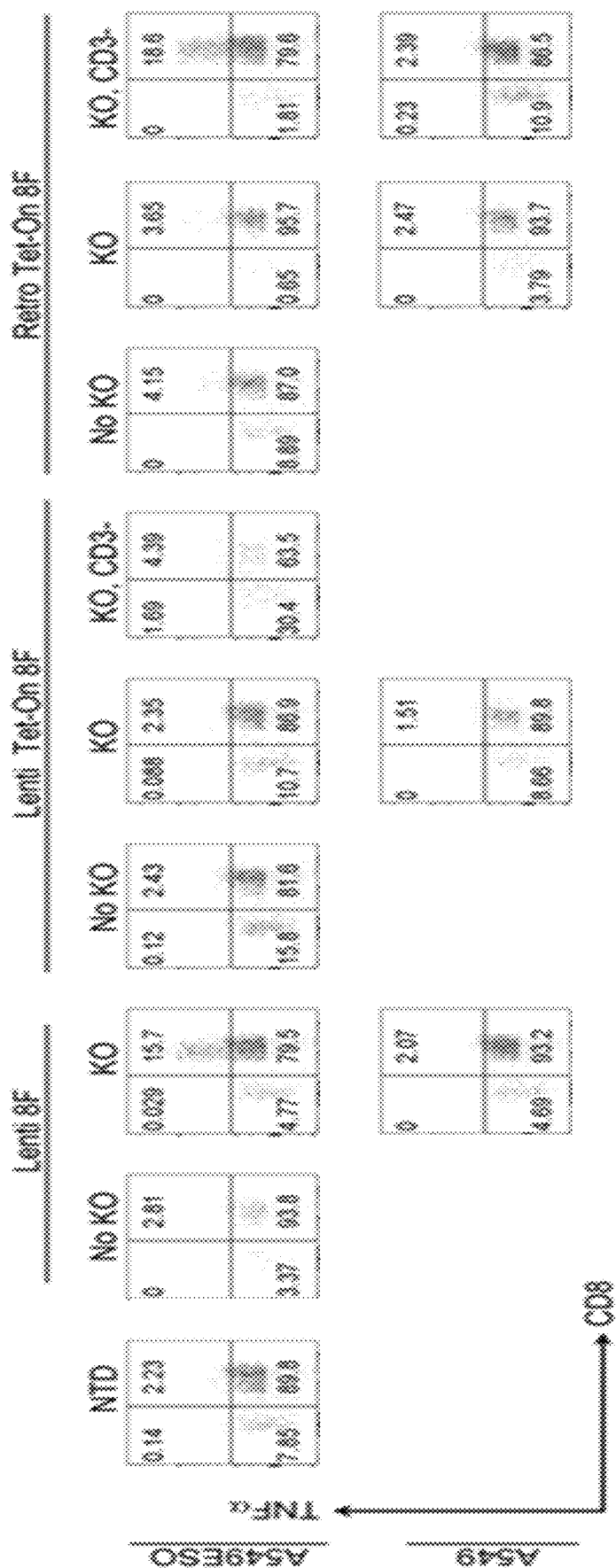
Figures 32D, 32E:
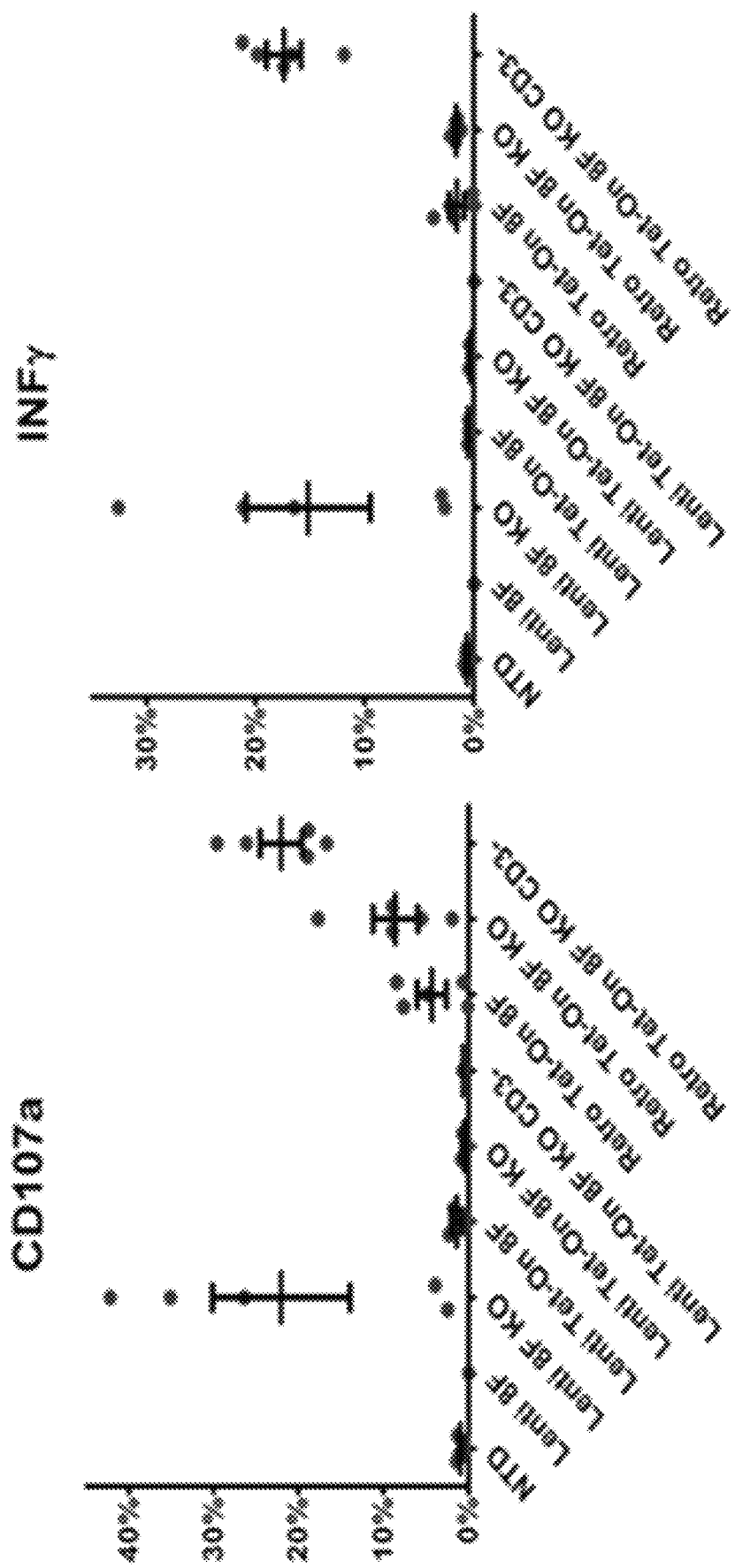
Figure 32F:
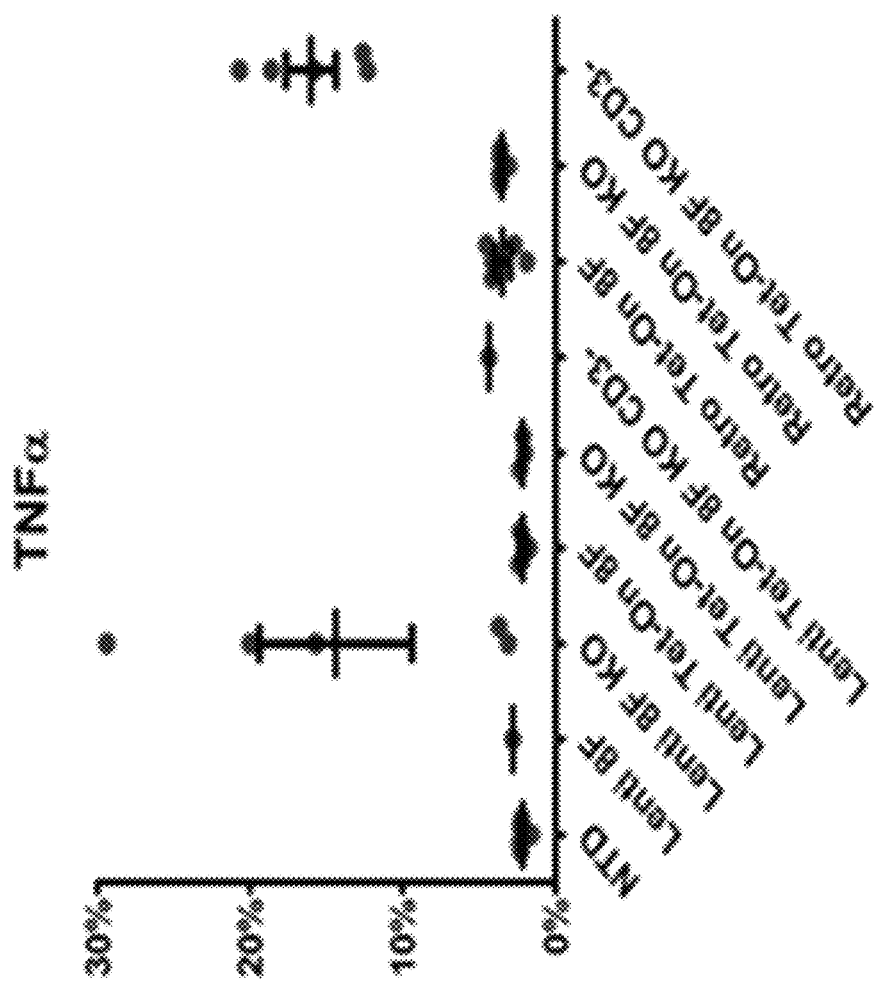

Tumor infiltrating leukocytes (TILs) were isolated from tumors at Day 50 post-inoculation of tumor cells. Frequencies of 8FTCR+ cells were examined in T cells prior to cryopreservation, in blood at Day 21, and in TILs at Day 50. The frequencies of 8FTCR+ cells in blood and TILs were maintained in the Lenti 8F and Lenti Tet-On 8F groups. The frequency is significantly increased in Retro Tet-On 8F groups (No KO: from 16.5% to 40.6%; KO: from 15.3% to 37.8%; KO CD3-: from 15% to 70.1%) (FIG. 31). Without being bound by any theory, this suggests that Retro Tet-On 8F transduced T cells were more proliferative than other T cells in response to tumor stimulation.

TILs were co-cultured with A549 or A549ESO in order to investigate if the TILs have specific activities, including the expression of CD107a, INFγ, and TNFα. A549 cells did not elicit responses. The Retro Tet-On 8F KO CD3– group and the Retro Tet-On 8F KO group showed the highest induction of CD107a, INFγ, and TNFα by A549ESO (FIGS. 32A-32F), demonstrating that the TILs have specific activities toward the tumor cells.

Figure 33:
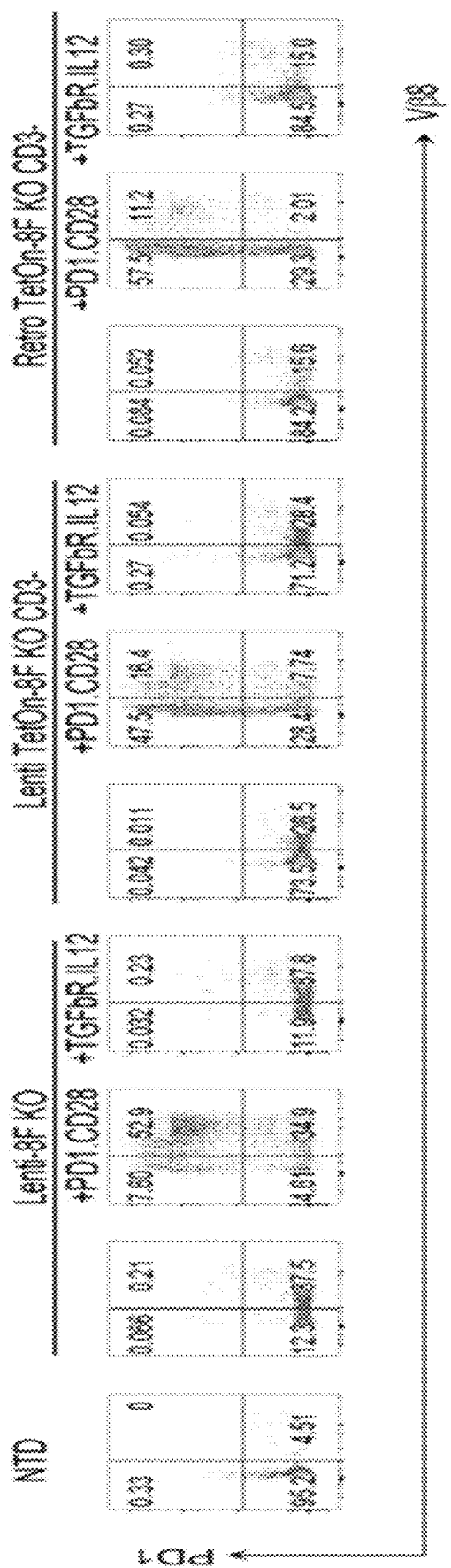
FIG. 33 depicts plots showing the expression of Vβ8 and PD1 in transduced T cells as indicated.

Example 7: Improvement of Tet-On-8FTCR Function by Combining with PD1-CD28 or TGFbR-IL12 Switch Receptors T cells were co-transduced using 8FTCR (lentivirus), TetON-8FTCR (lentivirus) or TetON-8F (retrovirus) together with PD1-CD28 or TGFbR-IL12 switch receptors (retrovirus). Endogenous TCR was depleted in the TetOn-8F groups (labeled with 'CD3-' in FIGS. 33 and 34). The expression of Vβ8 and PD1 is shown in FIG. 33. T cells were co-cultured with various tumor lines: A549 line (does not express NY-ESO-1 and served as a negative control); A549ESO line (forced expression of NY-ESO-1); A549ESO_PDL1 line (forced expression of NY-ESO-1 and PD-L1). Exogenous TGFβ was added to the culture medium of labeled samples in order to examine if they could activate the TGFbR-IL12 switch receptor.

Figure 34:
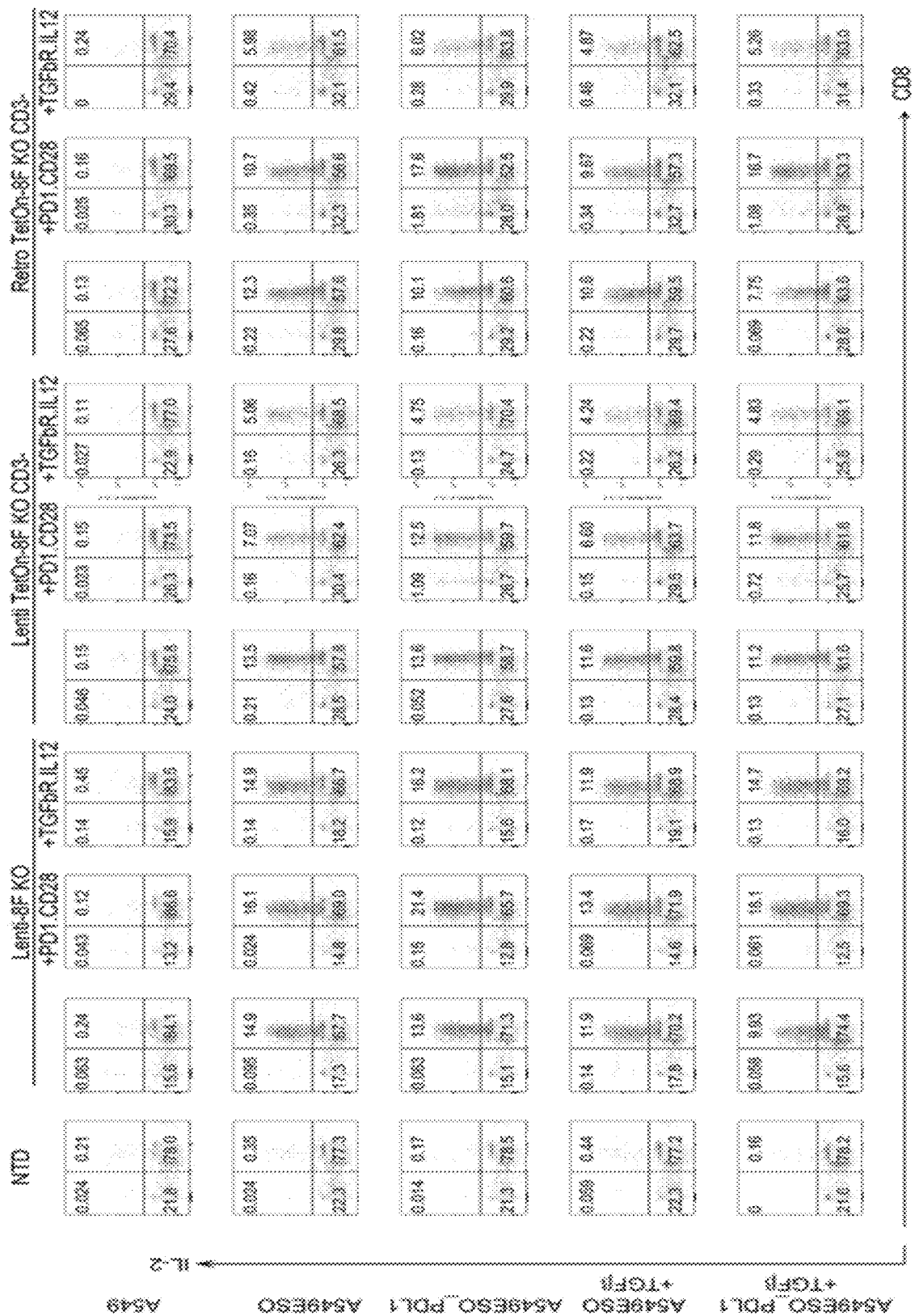
FIG. 34 depicts plots showing the frequency of IL-2+ T cells in different groups as indicated.

When co-cultured with A549ESO_PDL1 cells, T cells expressing 8FTCR alone showed reduced frequency of IL-2 producing cells compared with coculturing with A549 cells (FIG. 34). T cells co-expressing 8FTCR and PD1-CD28 switch receptor had increased frequency of IL-2 produced when co-cultured with A549ESO_PDL1 cells compared with A549 cells (FIG. 34), indicating that PD-L1 ligand expressed in tumor cells can activate the PD1-CD28 switch receptor in T cells.

Figure 35:
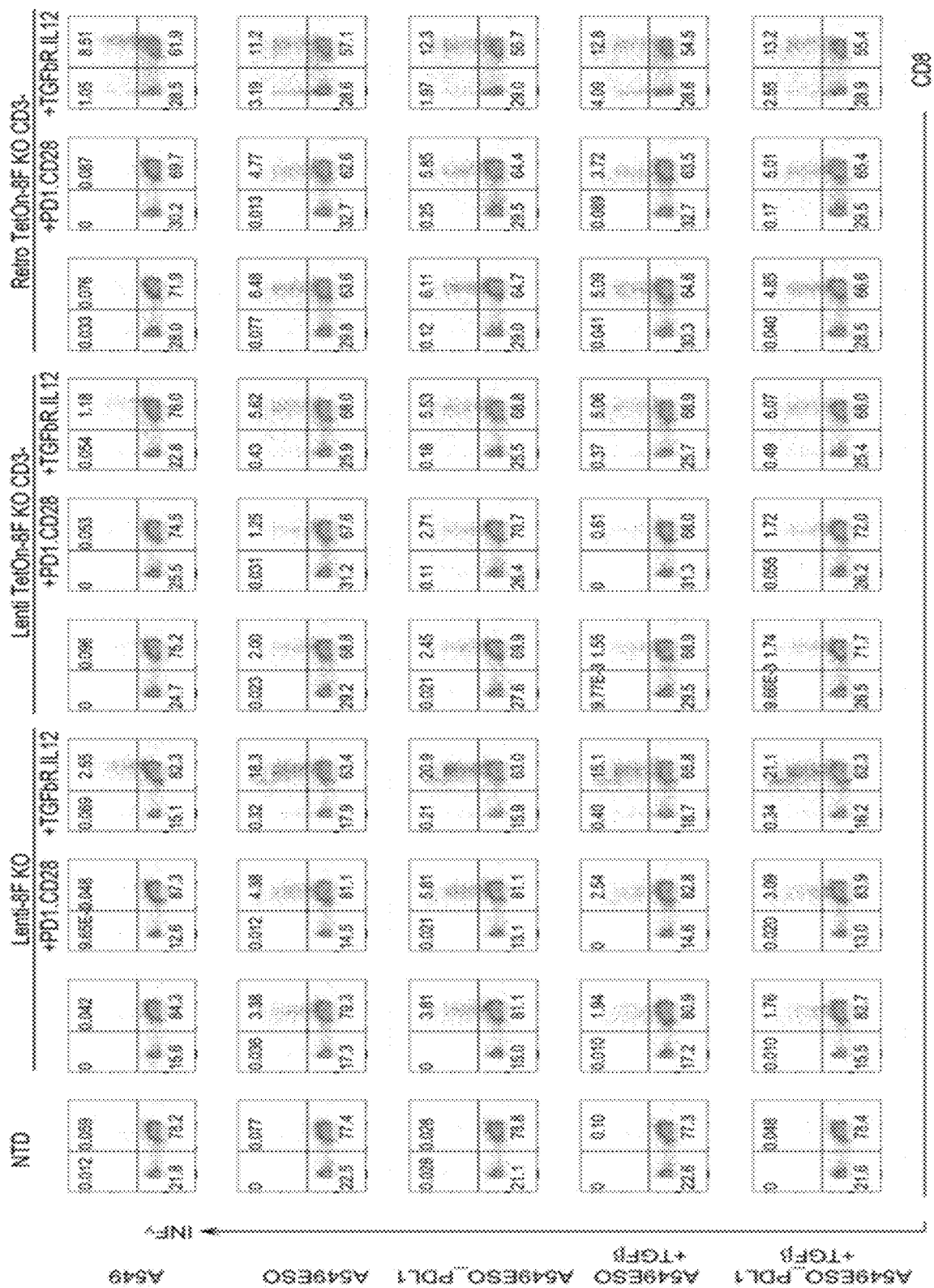
FIG. 35 depicts plots showing the frequency of IFNγ+ T cells in different groups as indicated.

When exogenous TGFβ was present in the medium, T cells expressing 8FTCR alone showed reduced frequency of INFγ producing cells (FIG. 35). T cells co-expressing 8FTCR and the TGFbR-IL12 switch receptor showed increased frequency of INFγ production (FIG. 35), indicating that TGFβ can activate the TGFbR-IL12 switch receptor in T cells.

Figure 36A:
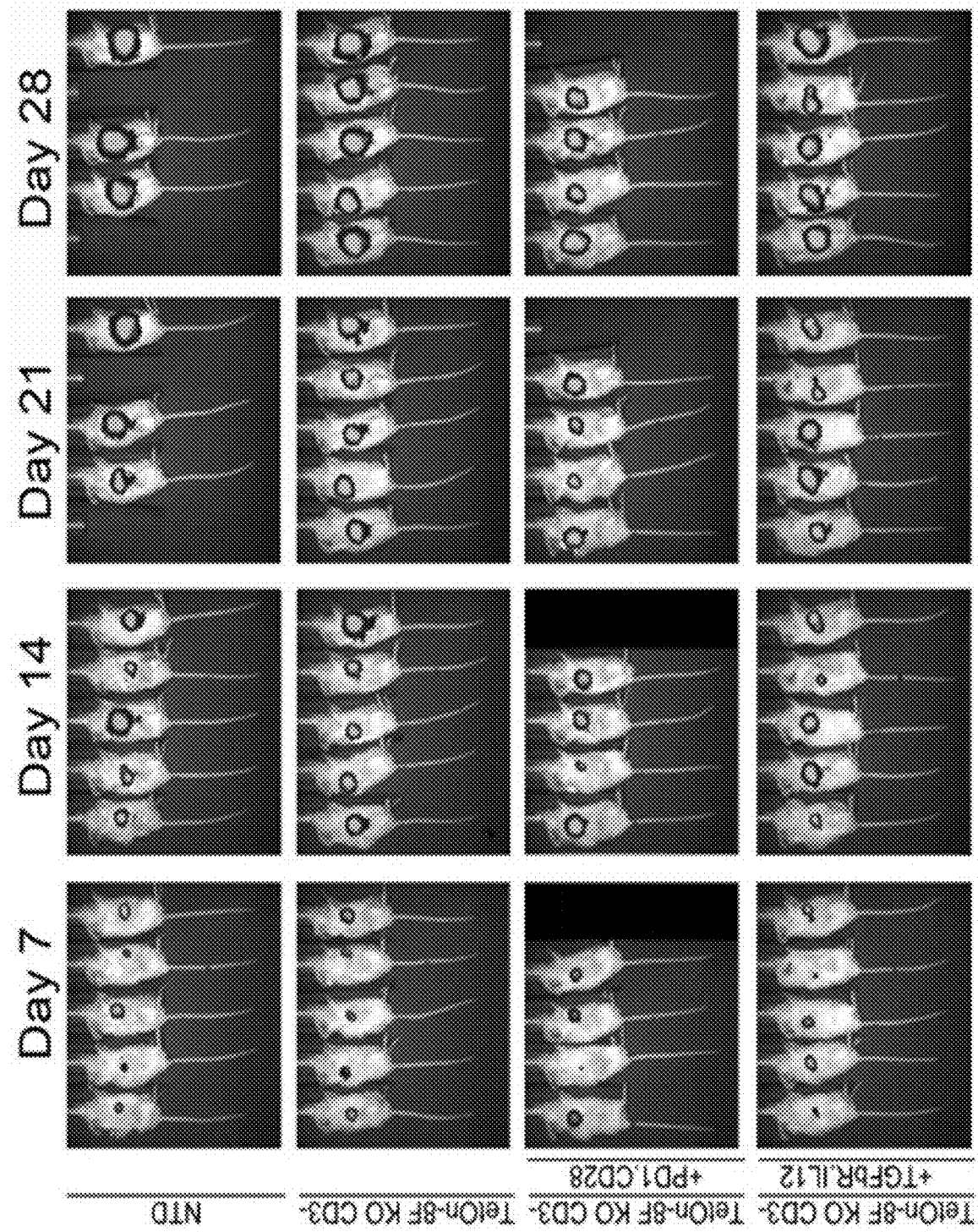
FIGS. 36A-36B depict bioluminescence imaging of tumors in different groups over time as indicated: images of mice (FIG. 36A), and graph depicting quantification (FIG. 36B).
Figure 36B:
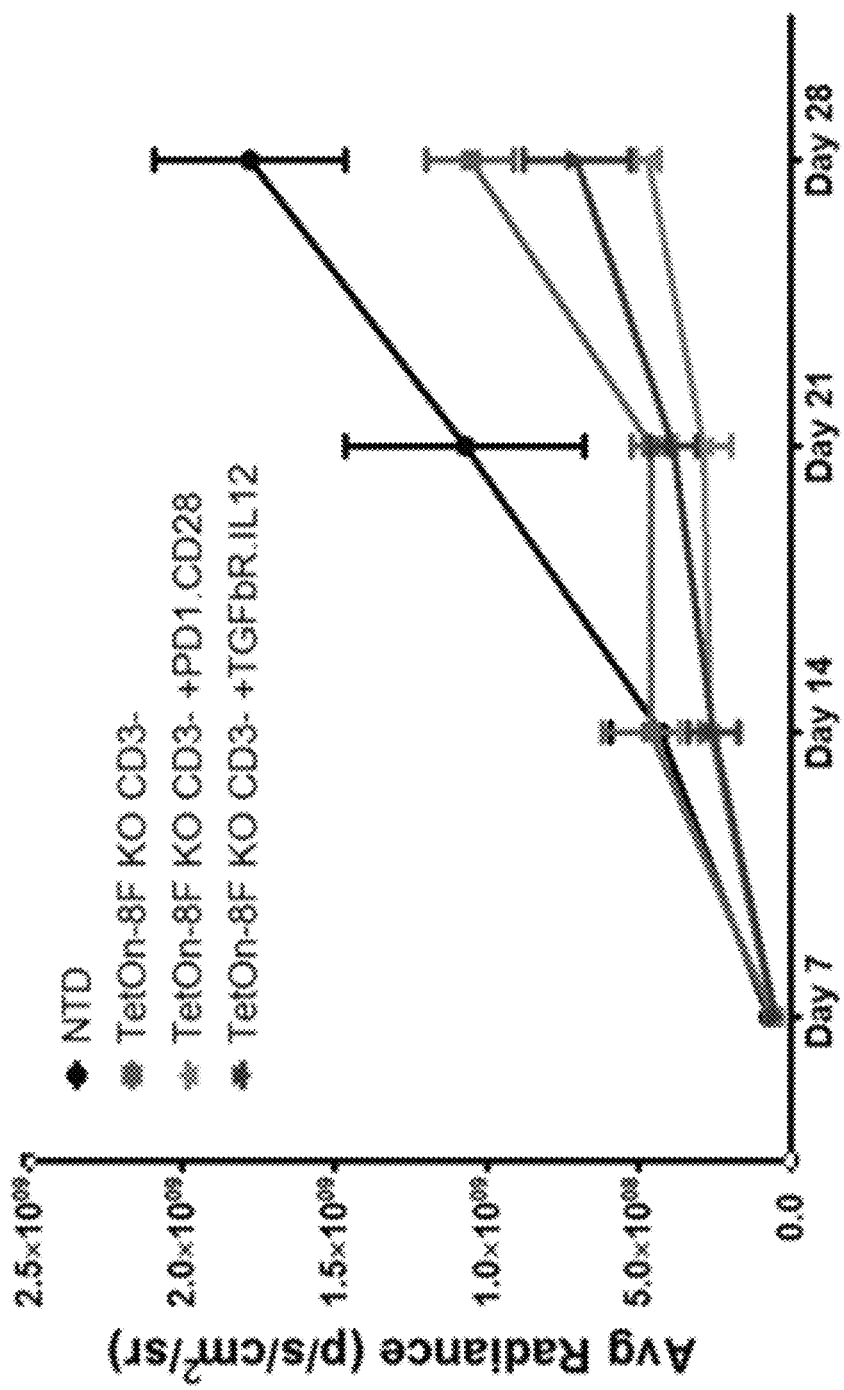

Five million A549ESO cells were injected subcutaneously into mice to establish xenograft tumors. Eight million Retro-TetOn-8FTCR+ T cells were injected intravenously eight days later when tumor size reached about 100 mm$^3$. Doxycycline-containing chow was continuously supplied in order to induce 8FTCR expression. Bioluminescence imaging showed that 8FTCR+PD1-CD28 and 8FTCR+ TGFbR-IL12 switch receptor groups had higher anti-tumor activities than 8FTCR alone (FIGS. 36A and 36B).

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating a disease or condition in a subject with adoptive cell transfer therapy comprising administering to the subject a population of modified immune cells comprising:

a genetically modified immune cell comprising an exogenous nucleic acid encoding an exogenous receptor, wherein the exogenous receptor selectively binds to one or more antigens, the exogenous nucleic acid further comprising an inducible gene expression system, wherein when an induction agent is periodically administered to the cell, the gene expression system is periodically induced and the exogenous receptor is periodically expressed on the surface of the genetically modified immune cell thereby counteracting immune cell exhaustion;

wherein the genetically modified immune cell is selected from the group consisting of a T cell, a natural killer cell (NK cell), a natural killer T cell, a lymphoid progenitor cell, a hematopoietic stem cell, a stem cell, a macrophage, and a dendritic cell; and wherein the disease or condition is selected from the group consisting of an infectious disease, an autoimmune disease, an inflammatory disorder, and a cancer.

2. The method of claim 1, wherein the inducible gene expression system comprises:

(a) a first nucleic acid comprising a constitutive promoter operably linked to a nucleic acid sequence encoding a transactivator protein; and (b) a second nucleic acid comprising an inducible promoter operably linked to the exogenous nucleic acid sequence encoding the exogenous receptor, wherein the second nucleic acid is in reverse orientation to the first nucleic acid.

3. The method of claim 2, wherein the transactivator protein is selected from the group consisting of a reverse Tet repressor (rTetR), a reverse tetracycline-controlled transactivator protein (rtTA), and a Tet-On 3G transactivator protein.

4. The method of claim 2, wherein the inducible promoter comprises one or more repeats of the Tet operator sequence.

5. The method of claim 2, wherein the inducible promoter is a TRE3GS promoter.

6. The method of claim 2, wherein the constitutive promoter drives constitutive expression of the transactivator protein, and wherein the constitutive promoter is selected from the group consisting of a human phosphoglycerate kinase 1 (PGK1 promoter), and a human elongation factor 1 alpha (EF1α) promoter.

7. The method of claim 1, wherein the induction agent is tetracycline, doxycycline or an analog thereof.

8. The method of claim 1, wherein expression of the exogenous receptor is in a dose-dependent manner with respect to the amount of the induction agent present.

9. The method of claim 1, wherein withdrawal of the induction agent results in a reduction in the expression of the exogenous receptor.

10. The method of claim 1, wherein the exogenous receptor is a T cell receptor (TCR) selected from the group consisting of a wild-type TCR, a high affinity TCR, and a chimeric TCR.

11. The method of claim 1, wherein the exogenous receptor is a chimeric antigen receptor (CAR) comprising an antigen-binding domain, a transmembrane domain, and an intracellular domain,
wherein the antigen-binding domain is selected from the group consisting of an antibody, an scFv, and a Fab;
wherein the transmembrane domain is selected from the group consisting of an artificial hydrophobic sequence and transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, CD134, CD137, and CD154;
wherein the intracellular domain comprises at least one co-stimulatory domain selected from the group consisting of co-stimulatory domains of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS, NKG2C, and B7-H3; and/or
wherein the intracellular domain comprises an intracellular domain selected from the group consisting of cytoplasmic signaling domains of a human CD3 zeta chain, FcγRIII, FcεRI, a cytoplasmic tail of an Fc receptor, an immunoreceptor tyrosine-based activation motif (ITAM) bearing cytoplasmic receptors, TCR zeta, FcR gamma, FcR beta, CD3 gamma, CD3 delta, CD3 epsilon, CD5, CD22, CD79a, CD79b, and CD66d.

12. The method of claim 11, wherein the CAR further comprises a hinge domain, wherein the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of CD8, and any combination thereof.

13. The method of claim 1, wherein the genetically modified immune cell is an allogeneic or autologous human T cell.

14. The method of claim 1, wherein the genetically modified immune cell further comprises an insertion and/or deletion in one or more gene loci each encoding an endogenous immune protein selected from the group consisting of TRAC, TRBC, B2M, CIITA, PD1, and PDL1, wherein the insertion and/or deletion is capable of downregulating expression of the endogenous immune protein.

15. The method of claim 1, wherein the genetically modified immune cell further comprises a switch receptor selected from the group consisting of PD1-CTM-CD28, PD1-PTM-CD28, PD1A132L-PTM-CD28, TGFβR-IL12Rβ1 and TGFβR-IL12Rβ2.

16. A method of treating a cancer in a subject in need thereof, the method comprising administering to the subject a pharmaceutical composition comprising:
a genetically modified immune cell comprising an exogenous nucleic acid encoding an exogenous receptor, wherein the exogenous receptor selectively binds to a tumor antigen expressed on a tumor, the exogenous nucleic acid further comprising an inducible gene expression system, wherein when an induction agent is periodically administered to the cell, the gene expression system is periodically induced and the exogenous receptor is periodically expressed on the surface of the genetically modified immune cell thereby counteracting immune cell exhaustion;
wherein the genetically modified immune cell is selected from the group consisting of a T cell, a natural killer cell (NK cell), a natural killer T cell, a lymphoid progenitor cell, a hematopoietic stem cell, a stem cell, a macrophage, and a dendritic cell.

17. The method of claim 16, further comprising administering an induction agent to the subject, thereby inducing expression of the exogenous receptor in the subject.

18. The method of claim 17, wherein the genetically modified immune cell is contacted with the induction agent prior to administration of the pharmaceutical composition to the subject.

19. A method of preventing T cell exhaustion in a subject in need thereof, the method comprising administering to the subject a pharmaceutical composition comprising:
a genetically modified immune cell comprising an exogenous nucleic acid encoding an exogenous receptor, wherein the exogenous receptor selectively binds to a tumor antigen expressed on a tumor, the exogenous nucleic acid further comprising an inducible gene expression system, wherein when an induction agent is periodically administered to the cell, the gene expression system is periodically induced and the exogenous receptor is periodically expressed on the surface of the genetically modified immune cell; and
an induction agent, wherein the induction agent induces expression of the exogenous receptor at a tumor site in the subject.

20. The method of claim 19, wherein the genetically modified immune cell is contacted with the induction agent prior to administration of the pharmaceutical composition to the subject.

21. The method of claim 19, wherein periodically administering the induction agent comprises:
a step of continual administration of the induction agent to the subject to induce expression of the exogenous receptor at a tumor site within the subject,
a step of withholding administration of the induction agent to the subject to reduce expression of the exogenous receptor within the subject, thereby preventing T cell exhaustion, and/or
a step of re-administering the induction agent to the subject to re-induce expression of the exogenous receptor within the subject.

22. The method of claim 19, wherein the induction agent is tetracycline, doxycycline or an analog thereof.

* * * * *